(12) United States Patent
Villa et al.

(10) Patent No.: US 11,629,198 B2
(45) Date of Patent: Apr. 18, 2023

(54) FUSION PROTEINS AND ANTIBODIES TARGETING HUMAN RED BLOOD CELL ANTIGENS

(71) Applicant: The Trustees of the University of Pennsylvania, Philadelphia, PA (US)

(72) Inventors: Carlos H. Villa, Philadelphia, PA (US); Vladimir R. Muzykantov, Bryn Athyn, PA (US); Donald L. Siegel, Landsdale, PA (US); Colin Greineder, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 278 days.

(21) Appl. No.: 16/768,822

(22) PCT Filed: Dec. 5, 2018

(86) PCT No.: PCT/US2018/064089
§ 371 (c)(1),
(2) Date: Jun. 1, 2020

(87) PCT Pub. No.: WO2019/113224
PCT Pub. Date: Jun. 13, 2019

(65) Prior Publication Data
US 2021/0171652 A1   Jun. 10, 2021

Related U.S. Application Data

(60) Provisional application No. 62/594,909, filed on Dec. 5, 2017.

(51) Int. Cl.
*C07K 16/28* (2006.01)
*C07K 14/745* (2006.01)
*A61K 38/00* (2006.01)

(52) U.S. Cl.
CPC ...... *C07K 16/2896* (2013.01); *C07K 14/7455* (2013.01); *A61K 38/00* (2013.01); *C07K 2317/34* (2013.01); *C07K 2317/55* (2013.01); *C07K 2317/622* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,916,071 A | 4/1990 | Hung et al. | |
| 5,229,367 A | 7/1993 | Perretti et al. | |
| 5,480,869 A | 1/1996 | Wei et al. | |
| 6,180,370 B1 * | 1/2001 | Queen | A61P 31/12 |
| | | | 435/69.6 |
| 7,816,449 B2 | 10/2010 | Menovcik et al. | |
| 9,517,257 B2 * | 12/2016 | Hubbell | A61K 39/0008 |
| 2006/0136184 A1 | 6/2006 | Gustafsson et al. | |
| 2011/0033450 A1 | 2/2011 | Thullier et al. | |
| 2014/0032186 A1 | 1/2014 | Gustafsson et al. | |
| 2016/0347830 A1 | 12/2016 | Behrens et al. | |

FOREIGN PATENT DOCUMENTS

| | | |
|---|---|---|
| WO | WO 2011/126808 | 10/2011 |
| WO | WO 2013/046704 | 4/2013 |
| WO | WO 2013/049493 | 4/2013 |
| WO | WO 2015/012924 | 1/2015 |
| WO | WO 2017/023358 | 2/2017 |

OTHER PUBLICATIONS

Villa, Carlos Hipolito, et al. "Coupling Therapeutics to Human Erythrocytes Demonstrates Target-Dependent Effects on Red Cell Physiology While Preserving Efficacy." Blood 128.22 (2016): 701. (Year: 2016).*
Kudo, Daisuke, et al. Critical Care 25.1 (2021): 1-11 (Year: 2021).*
Okamoto, Takayuki et al. Critical care research and practice vol. 2012 (2012): 614545. doi:10.1155/2012/614545 (Year: 2012).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Andris et al., Variable Region Gene Segment Utilization In Rhesus Monkey Hybridomas Producing Human Red Blood Cell-Specific Antibodies: Predominance of the VH4 Family but not VH4-21(V4-34), Molecular Immunology, vol. 34(3):237-253, Feb. 1997.
Akbarzadeh et al, Liposome: classification, preparation, and applications, Nanoscale Research Letters, vol. 8(1):102, Feb. 2013.
Ballas et al., Rheological properties of antibody-coated red cells, Transfusion, vol. 24(2): 124-129, Mar. 1984.
Baskurt et al., Data reduction methods for ektacytometry in clinical hemorheology, Clinical Hemorheology and Microcirculation, vol. 54(1):99-107, Jan. 2013.
Blancher et al., Characterization of a macaque anti-Rhl7-like monoclonal antibody, Vox Sanguinis, vol. 75(1):58-62, Sep. 1998.
Bourgeaux et al., Drug-loaded erythrocytes: on the road toward marketing approval, Drug Design, Development and Theory, vol. 10:665-76, Feb. 2016.
Brody et al., Deformation and flow of red blood cells in a synthetic lattice: evidence for an active cytoskeleton, Biophysical Journal, vol. 68(6):2224-32, Jun. 1995.
Bruce et al., Changes in the blood group Wright antigens are associated with a mutation at amino acid 658 in human erythrocyte band 3: a site of interaction between band 3 and glycophorin A under certain conditions, Blood, vol. 85(2):541-7, Jan. 1995.

(Continued)

*Primary Examiner* — Michael Szperka
*Assistant Examiner* — Lia E Taylor
(74) *Attorney, Agent, or Firm* — Howson & Howson LLP

(57) ABSTRACT

Compositions and methods are provided for loading cargoes onto red blood cells. Provided herein are novel antibodies, fragments, fusion proteins and other conjugates which specifically bind red blood cells via RHCE or Band 3.

26 Claims, 42 Drawing Sheets

Specification includes a Sequence Listing.

(56) References Cited

OTHER PUBLICATIONS

Burton et al., Modelling the structure of the red cell membrane, Biochemistry and cell biology = Biochimie et biologie cellulaire, vol. 89(2):200-15, Apr. 2011.

Carnemolla et al., Targeting thrombomodulin to circulating red blood cells augments its protective effects in models of endotoxemia and ischemia-reperfusion injury, FASEB Journal, vol. 31(2):761-770, Feb. 2017.

Carnemolla et al., Quantitative analysis of thrombomodulin-mediated conversion of protein C to APC: translation from in vitro to in vivo, Journal of Immunological Methods, vol. 384(1-2):21-4, Oct. 2012.

Chasis et al., Erythrocyte membrane rigidity induced by glycophorin A-ligand interaction. Evidence for a ligand-induced association between glycophorin A and skeletal proteins, vol. 75(6):1919-1926, Jun. 1985.

Chasis et al., Signal transduction by glycophorin A: role of extracellular and cytoplasmic domains in a modulatable process, Journal of Cell Biology, vol. 107(4):1351-1357, Oct. 1998.

Chien et al., Principles and Techniques for Assessing Erythrocyte Deformability, Red Cell Rheology, 71-79, 1978.

Chou et al., The Rh and RhAG blood group systems, Immunohematology, vol. 26(4):178-186, Nov. 4, 2010.

Chu et al., Reversible binding of hemoglobin to band 3 constitutes the molecular switch that mediates O2 regulation of erythrocyte properties, Blood, vol. 128(23):2708-2716, Dec. 2016.

Czerwinski et al., Production of large repertoires of macaque mAbs to human RBCs using phage display, Transfusion, vol. 39(S10):92S, Apr. 1999.

Ding et al., Anchoring fusion thrombomodulin to the endothelial lumen protects against injury-induced lung thrombosis and inflammation, American Journal of Respiratory and Critical Care Medicine, vol. 180(3):247-56, Aug. 2009.

Dubel et al., Isolation of IgG antibody Fv-DNA from various mouse and rat hybridoma cell lines using the polymerase chain reaction with a simple set of primers, Journal of Immunology Methods, vol. 175:89-95, Sep. 1994.

Fay et al., Cellular softening mediates leukocyte demargination and trafficking, thereby increasing clinical blood counts. PNAS U.S.A. vol. 113(8):1987-1992, Feb. 2016.

Ferru et al., Regulation of membrane-cytoskeletal interactions by tyrosine phosphorylation of erythrocyte band 3, Blood. vol. 117(22):5998-6006, Jun. 2011.

Fesnak et al., Engineered T cells: the promise and challenges of cancer immunotherapy, Nature Reviews. Cancer, vol. 16(9):566-581, Aug. 2016.

Flatt et al., Study of the D—phenotype reveals erythrocyte membrane alterations in the absence of RHCE, British Journal of Haematology, vol. 158(2):262-273, Jul. 2012.

GenBank Accession No. AAC02646.1, Feb. 1998, https://www.ncbi.nlm.nih.gov/protein/AAC02646.1.

Ganguly et al., Blood clearance and activity of erythrocyte-coupled fibrinolytics, Journal of Pharmacology and Experimental Therapeutics, vol. 312(3): 1106-1113, Mar. 2005.

Gao et al., Monoclonal antibody humanness score and its applications, BMC Biotechnology, vol. 13:55, Jul. 2013.

Gersh et al., Flow-dependent channel formation in clots by an erythrocyte-bound fibrinolytic agent, Blood, vol. 117(18):4964-4967, May 2011.

Glodek et al., Ligation of complement receptor 1 increases erythrocyte membrane deformability, Blood, vol. 116(26):6063-6071, Dec. 2010.

Godal et al., The normal range of osmotic fragility of red blood cells, Scandinavian Journal of Haematology, vol. 25(2):107-12, Aug. 1980.

Gottstein et al., Generation and characterization of recombinant vascular targeting agents from hybridoma cell lines, Biotechniques, vol. 30(1):190-200, Jan. 2001.

Greineder et al., ICAM-1-targeted thrombomodulin mitigates tissue-factor driven inflammatory thrombosis in a human endothelialized microfluidic model, Blood Advances, vol. 1(18):1452-1465, Aug. 2017.

Grimm et al., Memory of tolerance and induction of regulatory T cells by erythrocyte-targeted antigens, Scientific Reports, vol. 5:15907, Oct. 2015.

Gruswitz et al., Function of human Rh based on structure of RhCG at 2.1 A.,PNAS U.S.A,, vol. 107(21):9638-9643, May 2010.

Head et al., Expression of phosphatidylserine (PS) on wild-type and Gerbich variant erythrocytes following glycophorin-C (GPC) ligation, British Journal of Haematology, vol. 129(1): 130-137, Apr. 2005.

Head et al., Ligation of CD47 mediates phosphatidylserine expression on erythrocytes and a concomitant loss of viability in vitro, British Journal of Haematology, vol. 130(5):788-790, Sep. 2005.

Huang et al., Human red blood cell Wright antigens: a genetic and evolutionary perspective on glycophorin A-band 3 interaction, Blood, vol. 87(9):3942-3947, May 1996.

Hunault-Berger et al., A Phase 2 study of L-asparaginase encapsulated in erythrocytes in elderly patients with Philadelphia chromosome negative acute lymphoblastic leukemia: The GRASPALL/GRAALL-SA2-2008 study, American Journal of Hematology, vol. 90(9):811-818, Sep. 2015.

Ihler et al., Enzymatic degradation of uric acid by uricase-loaded human erythrocytes, The Journal of Clinical Investigation, vol. 56(3):595-602, Sep. 1975.

Ihler et al., Enzyme loading of erythrocytes, PNAS U.S.A., vol. 70(9):2663-6, Sep. 1973.

Jo et al., Liposomes as carriers of hydrophilic small molecule drugs: strategies to enhance encapsulation and delivery, Colloids and Surfaces, B., Biointerfaces, vol. 1;123:345-63, Nov. 2014.

Joktranta et al., Biotinylation of monoclonal antibodies prevents their ability to activate the classical pathway of complement, Journal of Immunology, vol. 151(4):2124-31, Aug. 1993.

Kalfa et al., Rac GTPases regulate the morphology and deformability of the erythrocyte cytoskeleton, Blood, vol. 108(12):3637-3645, Dec. 2006.

Kalia et al., Advances in Bioconjugation, Current Organic Chemistry, vol. 14(2):138-147, Jan. 2010.

Khoory et al. Ligation of Glycophorin A Generates Reactive Oxygen Species Leading to Decreased Red Blood Cell Function, PLoS One, vol. 11(1):e0141206., Jan. 2016.

Kina et al., The monoclonal antibody TER-119 recognizes a molecule associated with glycophorin A and specifically marks the late stages of murine erythroid lineage, British Journal of Haematology, vol. 109(2):280-287, May 2000.

Knowles et al., Cooperative action between band 3 and glycophorin A in human erythrocytes: immobilization of band 3 induced by antibodies to glycophorin A., Biophysical Journal, vol. 66(5):1726-1732, May 1994.

Kontos et al., Improving protein pharmacokinetics by engineering erythrocyte affinity, Molecular Pharmaceutics, vol. 7(6):2141-2147, Dec. 2010.

Kontos et al., Engineering antigens for in situ erythrocyte binding induces T-cell deletion, PNAS U.S.A., vol. 110(1):E60-68, Jan. 2013.

Leuzzi et al., Positive effect of erythrocyte-delivered dexamethasone in ataxia-telangiectasia, Neurology Neuroimmunilogy & Neuroinflammation, vol. 2(3):e98, Apr. 2015.

Levi, M., Recombinant soluble thrombomodulin: coagulation takes another chance to reduce sepsis mortality, Journal of Thrombosis and Haemostasis, vol. 13(4):505-507, Apr. 2015.

Lizcano et al., Erythrocyte sialoglycoproteins engage Siglec-9 on neutrophils to suppress activation, Blood, vol. 129(23):3100-3110, Jun. 2017.

Lomas-Francis et al., The blood group antigen factsbook: Elsevier/Academic Press, Sep. 2012.

Lorentz et al., Engineered binding to erythrocytes induces immunological tolerance to E. coli asparaginase, Science Advances, vol. 1(6):e1500112, Jul. 2015.

(56) References Cited

OTHER PUBLICATIONS

Magnani, M., Erythrocytes as carriers for drugs: the transition from the laboratory to the clinic is approaching, Expert Opinion on Biological Therapy, vol. 12(2):137-138, Jan. 2012.

Meinderts et al., Human and murine splenic neutrophils are potent phagocytes of IgG-opsonized red blood cells, Blood Adv, May 26, 2017;1(14):875-886.

Merrifield, R. B., Solid Phase Peptide Synthesis. I. The Synthesis of a Tetrapeptide, Journal of the American Chemical Society, vol. 85:2149, Jul. 1963.

Murciano et al., Prophylactic fibrinolysis through selective dissolution of nascent clots by tPA-carrying erythrocytes, Nature Biotechnology, vol. 21(8):891-896, Aug. 2003.

Nguyen et al., Regulation of phosphatidylserine exposure in red blood cells, Cellular physiology and biochemistry: international journal of experimental cellular physiology, biochemistry, and pharmacology, vol. 28(5):847-856, Dec. 2011.

Nwe et al., Growing applications of "click chemistry" for bioconjugation in contemporary biomedical research, Cancer Biotherapy & Radiopharmaceuticals, vol. 24(3): 289-302, Jun. 2009.

Pan et al., The Effect of Polymeric Nanoparticles on Biocompatibility of Carrier Red Blood Cells, PLoS One, vol. 11(3):e0152074, Mar. 2016.

Pasvol et al., Inhibition of malarial parasite invasion by monoclonal antibodies against glycophorin A correlates with reduction in red cell membrane deformability, Blood, vol. 74(5):1836-1843, Oct. 1989.

Paulitschke et al., Perturbation of red blood cell membrane rigidity by extracellular ligands, Blood, vol. 86(1):342-348, Jul. 1995.

Poole, J., The Diego blood group system—an update, Immunohematology, vol. 15(4), Dec. 1999.

Radcliffe et al., Multiple gene products from a single vector: 'self-cleaving' 2A peptides, Gene Therapy, vol. 11:1673-1674, May 2004.

Ripoche et al., Human Rhesus-associated glycoprotein mediates facilitated transport of NH(3) into red blood cells, PNAS U.S.A., vol. 101(49):17222-17227, Dec. 2004.

Roback, J.D., Technical Manual: American Association of Blood Banks (AABB), Sep. 2014.

Rojewski et al., Tissue distribution of blood group membrane proteins beyond red cells: evidence from cDNA libraries, Transfus Apher Sci., vol. 35(1):71-82, Aug. 2006.

Sahoo et al., Nanoparticle Attachment to Erythrocyte Via the Glycophorin A Targeted ERY1 Ligand Enhances Binding without Impacting Cellular Function, Pharmaceutical Research, vol. 33(5):1191-1203, May 2016.

Schofield et al., Defective anion transport activity of the abnormal band 3 in hereditary ovalocytic red blood cells, Nature, vol. 355(6363):836-838, Feb. 1992.

Shi et al., Engineered red blood cells as carriers for systemic delivery of a wide array of functional probes, PNAS U.S.A., vol. 111(28):10131-10136, May 2014.

Shields et al., Effects of intracellular Ca2+ and proteolytic digestion of the membrane skeleton on the mechanical properties of the red blood cell membrane. Biochim Biophys Acta, vol. 905(1): 181-194, Nov. 1987.

Sosale et al., Cell rigidity and shape override CD47's "self"-signaling in phagocytosis by hyperactivating myosin-II, Blood, vol. 125(3):542-552, Jan. 2015.

Spitzer et al., ScFv-mediated in vivo targeting of DAF to erythrocytes inhibits lysis by complement, Molecular Immunology, vol. 40:911-919, Feb. 2004.

Stewart et al., Solid Phase Peptide Synthesis, Freeman, pp. 27-62, 1969.

Thompson et al., A comprehensive comparison of multiple sequence alignments Nucleic Acids Research, vol. 27(13):2682-2690, Jul. 1990.

Villa et al., Erythrocytes as Carriers for Drug Delivery in Blood Transfusion and Beyond, Transfusion Medicine Reviews, vol. 31(1):26-35, Aug. 2017.

Villa et al., Delivery of drugs bound to erythrocytes: new avenues for an old intravascular carrier, Therapeutic Delivery, vol. 6(7):795-826, Jul. 2015.

Villa et al., Biocompatible coupling of therapeutic fusion proteins to human erythrocytes, Blood Adv, Feb. 13, 2018;2(3):165-176.

Wakamiya et al., Asparaginase entrapped in red blood cells: action and survival, Science, vol. 193(4254), Aug. 1976.

Watts et al., Comparative rheology of the adhesion of platelets and leukocytes from flowing blood: why are platelets so small? American Journal of Physiology. Hearth and Circulatory Physiology, vol. 304(11):H1483-1494, Jun. 2013.

Wautter et al., Increased adhesion to endothelial cells of erythrocytes from patients with polycythemia vera is mediated by laminin alpha5 chain and Lu/BCAM, Blood, vol. 110(3):894-901, Aug. 2007.

Westhoff, C.M., Deciphering the function of the Rh family of proteins, Transfusion, vol. 45(2 Suppl):117S-121S, Aug. 2005.

Zaitsev et al., Targeting recombinant thrombomodulin fusion protein to red blood cells provides multifaceted thromboprophylaxis, Blood, vol. 119(20):4779-4785, May 2012.

Zaitsev et al., Sustained thromboprophylaxis mediated by an RBC-targeted pro-urokinase zymogen activated at the site of clot formation, Blood, vol. 115(25):5241-5248, Jun. 2010.

International Search Report and Written Opinion dated Apr. 8, 2019, issued in International Patent Application No. PCT/US2018/064089.

* cited by examiner

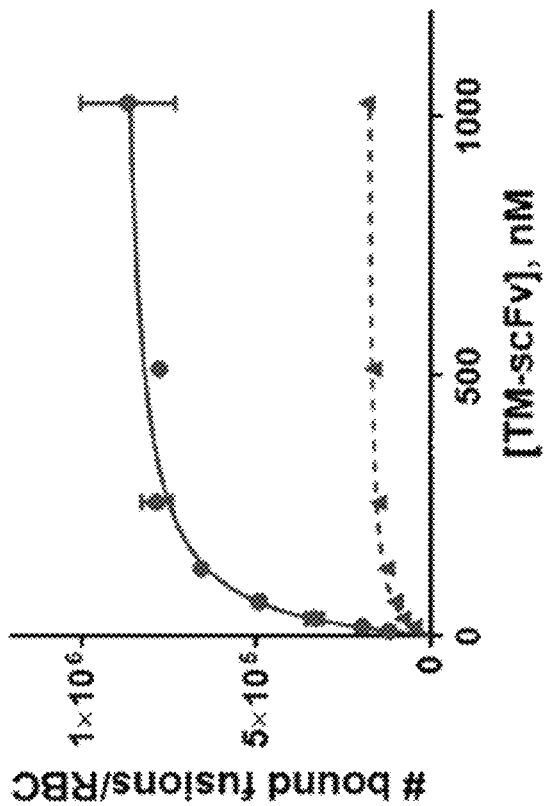
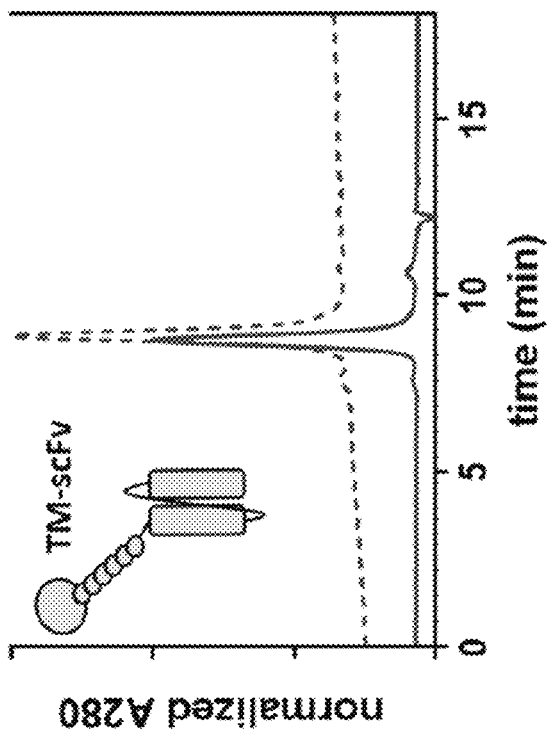
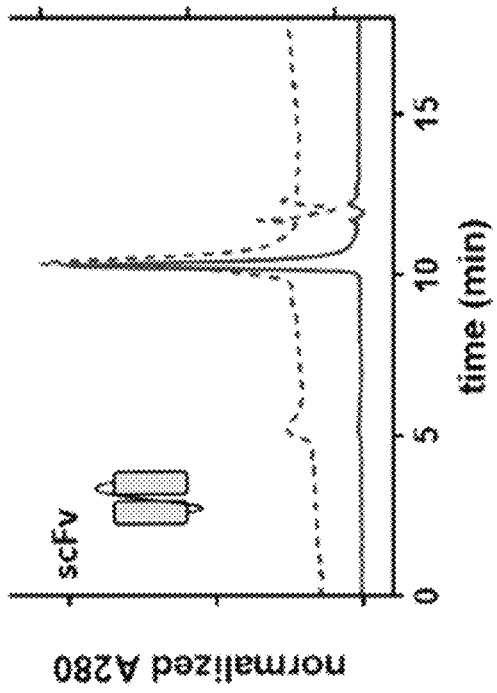
FIG. 1A
FIG. 1B
FIG. 1C

RhD/RhCE

Band3

GPA

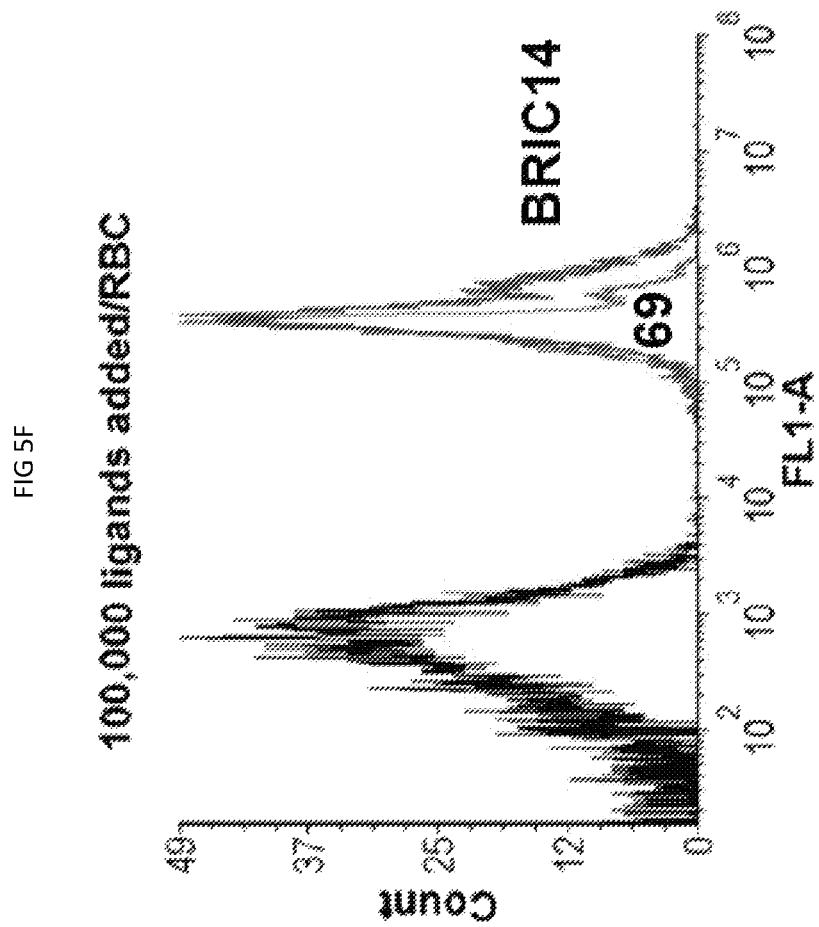

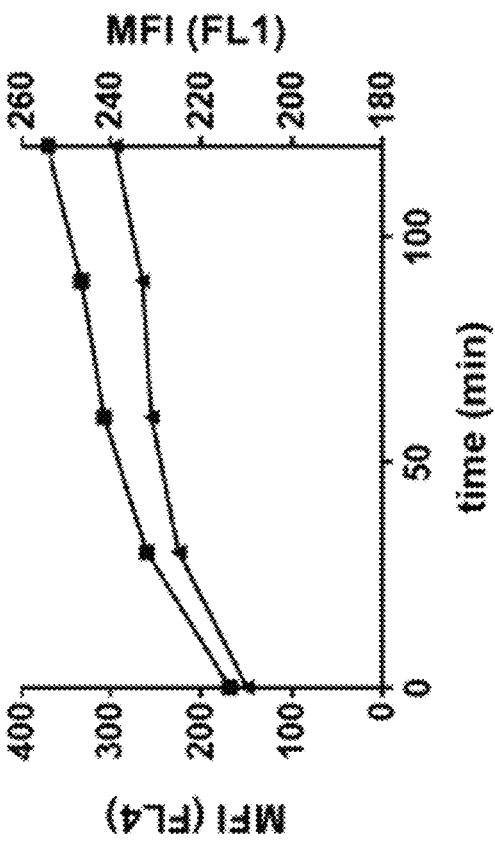
FIG. 9B
FIG. 9C
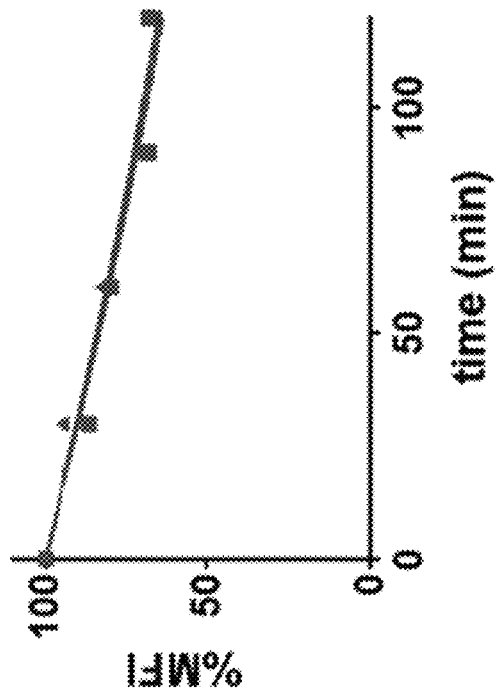
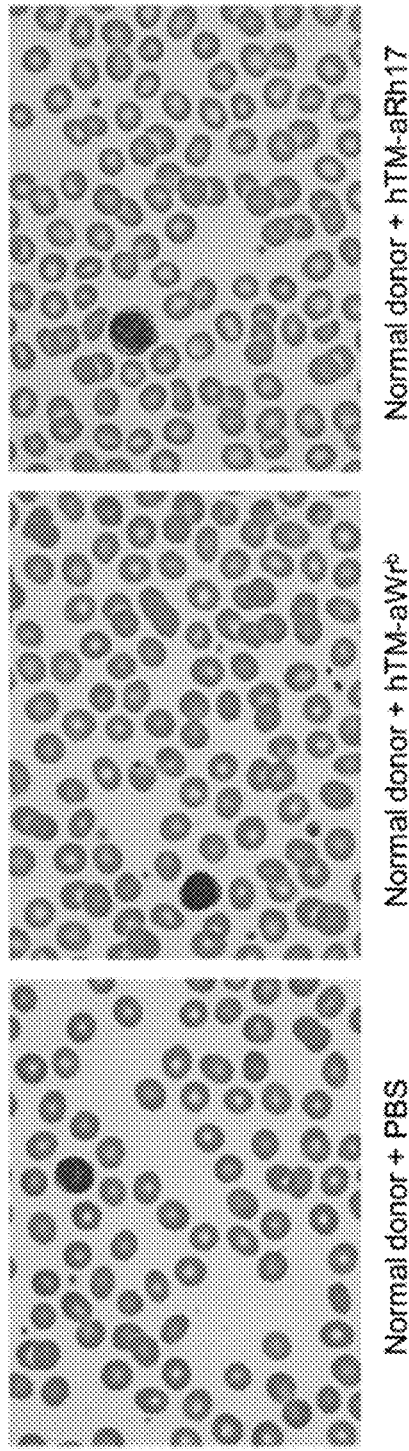
FIG. 10

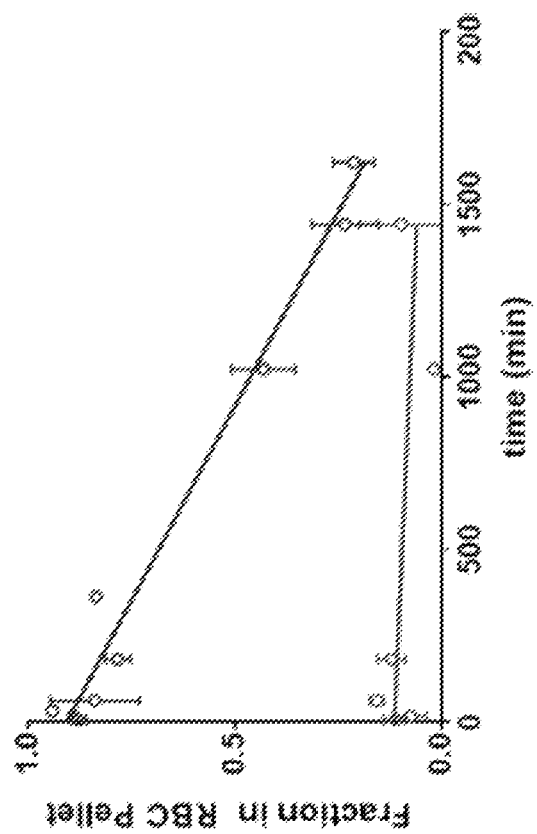
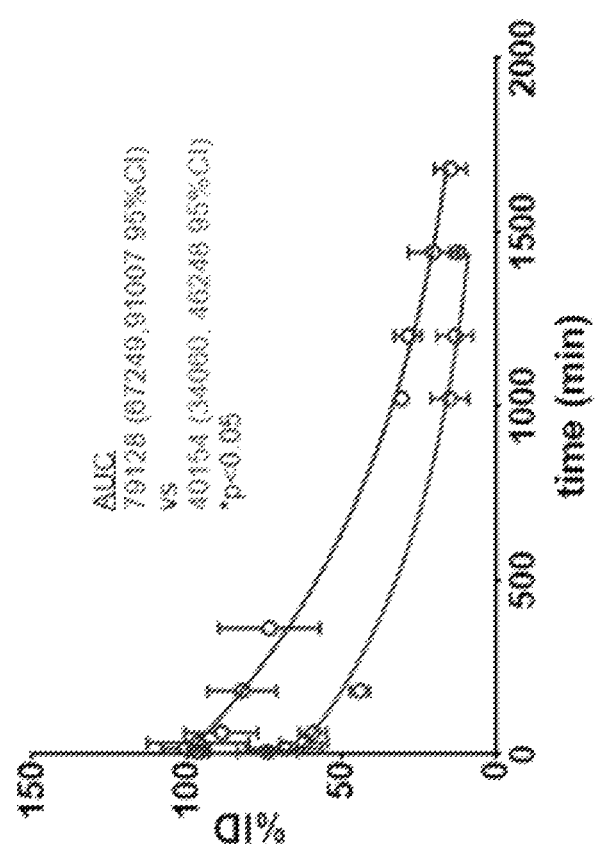
FIG 19C
FIG 19B

SEQUENCE LISTING

```
<160> NUMBER OF SEQ ID NOS: 367

<210> SEQ ID NO 1
<211> LENGTH: 8
<212> TYPE: PRT
<213> ORGANISM: Homo sapiens

<400> SEQUENCE: 1

Gly Ala Ser Ile Ser Asn Tyr Trp
1               5

<210> SEQ ID NO 2
<211> LENGTH: 8
<212> TYPE: PRT
<213> ORGANISM: Homo sapiens

<400> SEQUENCE: 2

Ile Asp Gly Ser Thr Tyr Ser Thr
1               5

<210> SEQ ID NO 3
<211> LENGTH: 21
<212> TYPE: PRT
<213> ORGANISM: Homo sapiens

<400> SEQUENCE: 3

Ala Arg Glu Gly Gln Asp Pro Leu Ala Pro Thr Leu Ala Thr Ser Gly
1               5                   10                  15

Ser Gly Leu Asp Ser
            20

<210> SEQ ID NO 4
<211> LENGTH: 6
<212> TYPE: PRT
<213> ORGANISM: Homo sapiens

<400> SEQUENCE: 4

Glu Asn Val Asn Asn Tyr
1               5

<210> SEQ ID NO 5
<211> LENGTH: 3
<212> TYPE: PRT
<213> ORGANISM: Homo sapiens

<400> SEQUENCE: 5

Ala Ala Ser
1

<210> SEQ ID NO 6
<211> LENGTH: 9
<212> TYPE: PRT
<213> ORGANISM: Homo sapiens
```

<400> SEQUENCE: 6

Gln His Ser Tyr Gly Thr Pro Leu Thr
1               5

<210> SEQ ID NO 7
<211> LENGTH: 8
<212> TYPE: PRT
<213> ORGANISM: Homo sapiens

<400> SEQUENCE: 7

Gly Ala Ser Ile Ser Asn Tyr Trp
1               5

<210> SEQ ID NO 8
<211> LENGTH: 8
<212> TYPE: PRT
<213> ORGANISM: Homo sapiens

<400> SEQUENCE: 8

Ile Asp Gly Ser Thr Tyr Ser Thr
1               5

<210> SEQ ID NO 9
<211> LENGTH: 21
<212> TYPE: PRT
<213> ORGANISM: Homo sapiens

<400> SEQUENCE: 9

Ala Arg Glu Gly Gln Asp Pro Leu Ala Pro Thr Leu Ala Thr Ser Gly
1               5                   10                  15

Ser Gly Leu Asp Ser
            20

<210> SEQ ID NO 10
<211> LENGTH: 6
<212> TYPE: PRT
<213> ORGANISM: Homo sapiens

<400> SEQUENCE: 10

Gln Asp Ile Tyr Ser Asn
1               5

<210> SEQ ID NO 11
<211> LENGTH: 3
<212> TYPE: PRT
<213> ORGANISM: Homo sapiens

<400> SEQUENCE: 11

Gly Ala Ser
1

<210> SEQ ID NO 12
<211> LENGTH: 9
<212> TYPE: PRT
<213> ORGANISM: Homo sapiens

<400> SEQUENCE: 12

Gln Glu Val His Arg Asn Pro Phe Thr
1               5

<210> SEQ ID NO 13
<211> LENGTH: 8
<212> TYPE: PRT

```
<213> ORGANISM: Homo sapiens

<400> SEQUENCE: 13

Gly Ala Pro Ile Ser Asn Tyr Trp
1               5

<210> SEQ ID NO 14
<211> LENGTH: 8
<212> TYPE: PRT
<213> ORGANISM: Homo sapiens

<400> SEQUENCE: 14

Ile Asp Gly Ser Ile Tyr Thr Thr
1               5

<210> SEQ ID NO 15
<211> LENGTH: 21
<212> TYPE: PRT
<213> ORGANISM: Homo sapiens

<400> SEQUENCE: 15

Ala Arg Glu Gly Gln Asn Pro Leu Val Pro Thr Tyr Gly Ser Thr Gly
1               5                   10                  15

Phe Gly Leu Asp Phe
            20

<210> SEQ ID NO 16
<211> LENGTH: 6
<212> TYPE: PRT
<213> ORGANISM: Homo sapiens

<400> SEQUENCE: 16

Gln Gly Ile Ser Ser Trp
1               5

<210> SEQ ID NO 17
<211> LENGTH: 3
<212> TYPE: PRT
<213> ORGANISM: Homo sapiens

<400> SEQUENCE: 17

Lys Ala Ser
1

<210> SEQ ID NO 18
<211> LENGTH: 9
<212> TYPE: PRT
<213> ORGANISM: Homo sapiens

<400> SEQUENCE: 18

Gln Gln Tyr Ser Ser Ser Pro Arg Thr
1               5

<210> SEQ ID NO 19
<211> LENGTH: 128
<212> TYPE: PRT
<213> ORGANISM: Homo sapiens

<400> SEQUENCE: 19

Glu Val Gln Leu Leu Glu Ser Gly Pro Gly Leu Val Lys Pro Ser Glu
1               5                   10                  15

Thr Leu Ser Leu Thr Cys Gly Val Ser Gly Ala Ser Ile Ser Asn Tyr
            20                  25                  30
```

Trp Trp Ser Trp Ile Arg Gln Ser Pro Gly Lys Gly Leu Glu Trp Ile
            35                  40                  45

Gly Glu Ile Asp Gly Ser Thr Tyr Ser Thr His Tyr Asn Pro Ser Leu
 50                  55                  60

Lys Gly Arg Val Thr Ile Ser Lys Asp Ala Ser Lys Asn Gln Leu Ser
 65                  70                  75                  80

Leu Arg Leu Thr Ser Val Thr Ala Ala Asp Thr Ala Val Tyr Tyr Cys
                85                  90                  95

Ala Arg Glu Gly Gln Asp Pro Leu Ala Pro Thr Leu Ala Thr Ser Gly
                100                 105                 110

Ser Gly Leu Asp Ser Trp Gly Arg Gly Leu Val Val Ser Val Ser Ser
            115                 120                 125

<210> SEQ ID NO 20
<211> LENGTH: 109
<212> TYPE: PRT
<213> ORGANISM: Homo sapiens

<400> SEQUENCE: 20

Ala Ala Glu Leu Gln Met Thr Gln Ser Pro Ser Ser Leu Ser Ala Ser
 1               5                   10                  15

Leu Gly Asp Arg Val Thr Ile Thr Cys Arg Ala Ser Glu Asn Val Asn
                20                  25                  30

Asn Tyr Leu His Trp Tyr Gln Gln Lys Pro Gly Lys Ala Pro Lys Leu
            35                  40                  45

Leu Ile Tyr Ala Ala Ser Thr Leu Gln Ser Gly Val Pro Ser Arg Phe
 50                  55                  60

Ser Gly Ser Gly Ser Gly Thr Asp Phe Thr Leu Thr Ile Ser Ser Leu
 65                  70                  75                  80

Gln Pro Glu Asp Val Ala Thr Tyr Tyr Cys Gln His Ser Tyr Gly Thr
                85                  90                  95

Pro Leu Thr Phe Gly Gly Gly Thr Lys Val Glu Ile Lys
                100                 105

<210> SEQ ID NO 21
<211> LENGTH: 128
<212> TYPE: PRT
<213> ORGANISM: Homo sapiens

<400> SEQUENCE: 21

Glu Val Gln Leu Leu Glu Ser Gly Pro Gly Leu Gly Lys Pro Ser Glu
 1               5                   10                  15

Thr Leu Ser Leu Thr Cys Gly Val Ser Gly Ala Ser Ile Ser Asn Tyr
                20                  25                  30

Trp Trp Ser Trp Ile Arg Gln Ser Pro Gly Lys Gly Leu Glu Trp Ile
            35                  40                  45

Gly Glu Ile Asp Gly Ser Thr Tyr Ser Thr His Tyr Asn Pro Ser Leu
 50                  55                  60

Lys Gly Arg Val Thr Ile Ser Lys Asp Ala Ser Lys Asn Gln Leu Ser
 65                  70                  75                  80

Leu Arg Leu Thr Ser Val Thr Ala Ala Asp Thr Ala Val Tyr Tyr Cys
                85                  90                  95

Ala Arg Glu Gly Gln Asp Pro Leu Ala Pro Thr Leu Ala Thr Ser Gly
                100                 105                 110

Ser Gly Leu Asp Ser Trp Gly Arg Gly Leu Val Val Thr Val Ser Ser
            115                 120                 125

<210> SEQ ID NO 22
<211> LENGTH: 109
<212> TYPE: PRT
<213> ORGANISM: Homo sapiens

<400> SEQUENCE: 22

Ala Ala Glu Leu Gln Met Thr Gln Ser Pro Ser Ala Leu Ser Ala Ser
1               5                   10                  15

Val Gly Asp Arg Val Thr Ile Ser Cys Arg Ala Ser Gln Asp Ile Tyr
            20                  25                  30

Ser Asn Leu Ala Trp Tyr Gln Gln Lys Pro Gly Lys Ala Pro Lys Leu
        35                  40                  45

Leu Ile Tyr Gly Ala Ser Arg Leu Gln Ser Gly Ile Pro Ser Arg Phe
    50                  55                  60

Ser Ala Ser Gly Ala Gly Thr Glu Phe Thr Leu Thr Ile Ser Gly Leu
65                  70                  75                  80

Gln Pro Glu Asp Ser Ala Val Tyr Tyr Cys Gln Glu Val His Arg Asn
                85                  90                  95

Pro Phe Thr Phe Gly Pro Gly Thr Lys Leu Asp Ile Lys
            100                 105

<210> SEQ ID NO 23
<211> LENGTH: 128
<212> TYPE: PRT
<213> ORGANISM: Homo sapiens

<400> SEQUENCE: 23

Glu Val Gln Leu Leu Glu Ser Gly Pro Gly Leu Leu Lys Pro Ser Glu
1               5                   10                  15

Thr Leu Ser Leu Thr Cys Ala Val Ser Gly Ala Pro Ile Ser Asn Tyr
            20                  25                  30

Trp Trp Ser Trp Ile Arg Gln Ser Pro Gly Lys Gly Leu Glu Trp Ile
        35                  40                  45

Gly Glu Ile Asp Gly Ser Ile Tyr Thr Thr Tyr Tyr Asn Pro Ser Leu
    50                  55                  60

Lys Ser Arg Val Ala Ile Ser Lys Asp Thr Ser Lys Asn Arg Leu Ser
65                  70                  75                  80

Leu Lys Leu Thr Ser Val Thr Ala Ala Asp Thr Ala Val Tyr Tyr Cys
                85                  90                  95

Ala Arg Glu Gly Gln Asn Pro Leu Val Pro Thr Tyr Gly Ser Thr Gly
            100                 105                 110

Phe Gly Leu Asp Phe Trp Gly His Gly Leu Ala Val Thr Val Ser Ser
        115                 120                 125

<210> SEQ ID NO 24
<211> LENGTH: 107
<212> TYPE: PRT
<213> ORGANISM: Homo sapiens

<400> SEQUENCE: 24

Ala Ala Glu Leu Thr Gln Ser Pro Ser Ser Leu Ser Ala Ser Val Gly
1               5                   10                  15

Asp Arg Val Thr Ile Thr Cys Gln Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly

```
              50                  55                  60
Ser Gly Ser Gly Thr Asp Phe Thr Leu Thr Ile Ser Ser Leu Gln Ser
 65                  70                  75                  80

Glu Asp Phe Ala Thr Tyr Tyr Cys Gln Gln Tyr Ser Ser Ser Pro Arg
                 85                  90                  95

Thr Phe Gly Gln Gly Thr Lys Val Glu Ile Lys
            100                 105

<210> SEQ ID NO 25
<211> LENGTH: 384
<212> TYPE: DNA
<213> ORGANISM: Homo sapiens

<400> SEQUENCE: 25
gaggtgcagc tgctcgagtc aggtccagga ctggtgaagc cttcggagac cctgtccctc      60
acctgcggtg tctctggtgc ctccatcagt aattactggt ggagttggat ccgccagtcc     120
ccagggaagg gactggagtg gattggggag atcgatggta gtacttatag cacccactac     180
aacccctccc tcaagggtcg agtcaccatt tcaaaagacg cgtccaagaa tcagttgtcc     240
ctgaggctga cctctgtgac cgccgcggac acggccgtgt attattgtgc gagagaggga     300
caggatcctt tagcgcctac ccttgccacg tcgggttcgg ggttggattc ctggggccga     360
gggctcgtcg tctccgtctc ctcc                                            384

<210> SEQ ID NO 26
<211> LENGTH: 330
<212> TYPE: DNA
<213> ORGANISM: Homo sapiens

<400> SEQUENCE: 26
gcggccgagc tccagatgac ccagtctcca tcctccctat ctgcatcgct gggagacaga      60
gtcaccatca cttgcagggc aagtgagaac gttaacaact atttacattg gtatcagcag     120
aaaccaggga agcccctaa gctcctgatc tatgctgcat ccactttgca aagtggggtc     180
ccatcaaggt tcagcggcag tggatctggg acagatttca ctctcaccat cagcagcctg     240
cagcctgaag atgttgcaac ttattactgt cagcatagtt atggtacccc gctcactttc     300
ggcggaggga ccaaggtgga gatcaaacga                                      330

<210> SEQ ID NO 27
<211> LENGTH: 384
<212> TYPE: DNA
<213> ORGANISM: Homo sapiens

<400> SEQUENCE: 27
gaggtgcagc tgctcgagtc aggcccagga ctggggaagc cttcggagac cctgtccctc      60
acctgcggtg tctctggtgc ctccatcagc aattactggt ggagctggat ccgccagtcc     120
ccagggaagg gactggagtg gattggggag atcgatggta gtacttatag cacccactac     180
aacccctccc tcaagggtcg agtcaccatt tcaaaagacg cgtccaagaa tcagttgtcc     240
ctgaggctga cctctgtgac cgccgcggac acggccgtgt attattgtgc gagagaggga     300
caggatcctt tagcgcctac ccttgccacg tcgggttcgg ggctggattc ctggggccga     360
ggcctcgtcg tcaccgtctc ctcc                                            384

<210> SEQ ID NO 28
<211> LENGTH: 330
<212> TYPE: DNA
```

<213> ORGANISM: Homo sapiens

<400> SEQUENCE: 28

```
gcggccgagc tccagatgac ccagtctcca tctgccttgt ctgcatctgt aggagacaga    60
gtcaccatct cttgccgggc aagtcaggac atttatagta atttagcgtg gtatcaacag   120
aaaccaggga agcccctaa gctcctgatc tatggcgcat ccagattgca aagtgggatt   180
ccctctcggt tcagtgctag cggagctggg acagaattca ctctcaccat cagcggcctg   240
caacctgaag attctgcagt atattactgt caagaggttc atcgtaaccc attcactttc   300
ggccccggga ccaaactgga tatcaaacga                                    330
```

<210> SEQ ID NO 29
<211> LENGTH: 384
<212> TYPE: DNA
<213> ORGANISM: Homo sapiens

<400> SEQUENCE: 29

```
gaggtgcagc tgctcgagtc gggcccagga ctgctgaagc catcggagac cctgtccctc    60
acctgcgctg tctctggtgc ccccatcagt aactactggt ggagttggat tcgtcagtcc   120
ccagggaagg gactggagtg gattggggag atcgatggta gtatatatac tacctactac   180
aaccccctccc tcaagagtcg agtcgccatt tcaaaggaca cgtccaagaa ccggctgtcc   240
ctgaaactga cctctgtgac cgccgcggac acggccgtct attattgtgc gagagagggc   300
cagaaccctc tagtgcctac atatggttcg acgggattcg gattggattt ctggggccat   360
ggactcgccg tcaccgtctc gtca                                          384
```

<210> SEQ ID NO 30
<211> LENGTH: 324
<212> TYPE: DNA
<213> ORGANISM: Homo sapiens

<400> SEQUENCE: 30

```
gcggccgagc tcacccagtc tccatcttcc ttgtctgcat ctgtaggaga cagagtcacc    60
atcacttgcc aagccagtca gggtattagc agctggttag cctggtatca gcagaaacca   120
gggaaagccc ctaagctcct gatctataag gcatccagtt tgcaaagtgg ggtcccatca   180
aggttcagcg gcagtggatc tgggacagat ttcactctca ccatcagcag cctgcagtct   240
gaagattttg caacttatta ctgtcaacag tatagcagta gccctcggac gttcggccaa   300
gggaccaagg tggaaatcaa acga                                          324
```

<210> SEQ ID NO 31
<211> LENGTH: 9
<212> TYPE: PRT
<213> ORGANISM: Homo sapiens

<400> SEQUENCE: 31

Gly Asp Ser Ile Ser Ser Gly Leu Gly
1               5

<210> SEQ ID NO 32
<211> LENGTH: 9
<212> TYPE: PRT
<213> ORGANISM: Homo sapiens

<400> SEQUENCE: 32

Gly Gly Ser Leu Ser Gly Gly Tyr Asp
1               5

<210> SEQ ID NO 33
<211> LENGTH: 9
<212> TYPE: PRT
<213> ORGANISM: Homo sapiens

<400> SEQUENCE: 33

Gly Tyr Ser Leu Ser Ser Ala Tyr Gly
1               5

<210> SEQ ID NO 34
<211> LENGTH: 9
<212> TYPE: PRT
<213> ORGANISM: Homo sapiens

<400> SEQUENCE: 34

Gly Ser Ser Leu Ser Ser Ala Tyr Gly
1               5

<210> SEQ ID NO 35
<211> LENGTH: 9
<212> TYPE: PRT
<213> ORGANISM: Homo sapiens

<400> SEQUENCE: 35

Gly Asp Ser Ile Ser Ser Gly Tyr Gly
1               5

<210> SEQ ID NO 36
<211> LENGTH: 9
<212> TYPE: PRT
<213> ORGANISM: Homo sapiens

<400> SEQUENCE: 36

Gly Tyr Ser Ile Ser Ser Gly Tyr Gly
1               5

<210> SEQ ID NO 37
<211> LENGTH: 9
<212> TYPE: PRT
<213> ORGANISM: Homo sapiens

<400> SEQUENCE: 37

Gly Tyr Ser Ile Ser Ser Gly Tyr Gly
1               5

<210> SEQ ID NO 38
<211> LENGTH: 9
<212> TYPE: PRT
<213> ORGANISM: Homo sapiens

<400> SEQUENCE: 38

Gly Ser Ser Leu Ser Ser Ala Tyr Gly
1               5

<210> SEQ ID NO 39
<211> LENGTH: 9
<212> TYPE: PRT
<213> ORGANISM: Homo sapiens

<400> SEQUENCE: 39

Gly Gly Ser Ile Ser Gly Gly Tyr Asp
1               5

```
<210> SEQ ID NO 40
<211> LENGTH: 9
<212> TYPE: PRT
<213> ORGANISM: Homo sapiens

<400> SEQUENCE: 40

Gly Ser Ser Leu Ser Ser Ala Tyr Gly
1               5

<210> SEQ ID NO 41
<211> LENGTH: 9
<212> TYPE: PRT
<213> ORGANISM: Homo sapiens

<400> SEQUENCE: 41

Gly Gly Ser Ile Ser Gly Gly Tyr Asp
1               5

<210> SEQ ID NO 42
<211> LENGTH: 9
<212> TYPE: PRT
<213> ORGANISM: Homo sapiens

<400> SEQUENCE: 42

Gly Tyr Ser Ile Ser Ser Gly Tyr Gly
1               5

<210> SEQ ID NO 43
<211> LENGTH: 9
<212> TYPE: PRT
<213> ORGANISM: Homo sapiens

<400> SEQUENCE: 43

Gly Asn Ser Ile Ser Ser Gly Tyr Gly
1               5

<210> SEQ ID NO 44
<211> LENGTH: 9
<212> TYPE: PRT
<213> ORGANISM: Homo sapiens

<400> SEQUENCE: 44

Gly Gly Ser Ile Asn Gly Gly Tyr Asp
1               5

<210> SEQ ID NO 45
<211> LENGTH: 9
<212> TYPE: PRT
<213> ORGANISM: Homo sapiens

<400> SEQUENCE: 45

Gly Gly Ser Ile Ser Gly Gly Tyr Asp
1               5

<210> SEQ ID NO 46
<211> LENGTH: 9
<212> TYPE: PRT
<213> ORGANISM: Homo sapiens

<400> SEQUENCE: 46

Gly Asp Ser Ile Ser Ser Gly Tyr Gly
1               5

<210> SEQ ID NO 47
<211> LENGTH: 9
```

```
<212> TYPE: PRT
<213> ORGANISM: Homo sapiens

<400> SEQUENCE: 47

Gly Ser Ser Leu Ser Ser Ala Tyr Gly
1               5

<210> SEQ ID NO 48
<211> LENGTH: 9
<212> TYPE: PRT
<213> ORGANISM: Homo sapiens

<400> SEQUENCE: 48

Gly Tyr Ser Ile Ser Ser Gly Tyr Gly
1               5

<210> SEQ ID NO 49
<211> LENGTH: 9
<212> TYPE: PRT
<213> ORGANISM: Homo sapiens

<400> SEQUENCE: 49

Gly Phe Ser Ile Ser Ser Asp Tyr Gly
1               5

<210> SEQ ID NO 50
<211> LENGTH: 8
<212> TYPE: PRT
<213> ORGANISM: Homo sapiens

<400> SEQUENCE: 50

Tyr Ser Ile Ser Ser Gly Tyr Gly
1               5

<210> SEQ ID NO 51
<211> LENGTH: 9
<212> TYPE: PRT
<213> ORGANISM: Homo sapiens

<400> SEQUENCE: 51

Gly Ser Ser Leu Ser Ser Ala Tyr Gly
1               5

<210> SEQ ID NO 52
<211> LENGTH: 9
<212> TYPE: PRT
<213> ORGANISM: Homo sapiens

<400> SEQUENCE: 52

Gly Ser Ser Leu Ser Ser Ala Tyr Gly
1               5

<210> SEQ ID NO 53
<211> LENGTH: 8
<212> TYPE: PRT
<213> ORGANISM: Homo sapiens

<400> SEQUENCE: 53

Gly Gly Ser Ile Ser Ser Ala Ser
1               5

<210> SEQ ID NO 54
<211> LENGTH: 9
<212> TYPE: PRT
<213> ORGANISM: Homo sapiens
```

<400> SEQUENCE: 54

Gly Ser Ser Leu Ser Ser Ala Tyr Gly
1               5

<210> SEQ ID NO 55
<211> LENGTH: 9
<212> TYPE: PRT
<213> ORGANISM: Homo sapiens

<400> SEQUENCE: 55

Gly Ser Ser Leu Ser Ser Ala Tyr Gly
1               5

<210> SEQ ID NO 56
<211> LENGTH: 9
<212> TYPE: PRT
<213> ORGANISM: Homo sapiens

<400> SEQUENCE: 56

Ser Leu Ser Leu Ser Ser Gly Phe Ala
1               5

<210> SEQ ID NO 57
<211> LENGTH: 9
<212> TYPE: PRT
<213> ORGANISM: Homo sapiens

<400> SEQUENCE: 57

Gly Asn Ser Ile Ser Ser Ala Tyr Gly
1               5

<210> SEQ ID NO 58
<211> LENGTH: 9
<212> TYPE: PRT
<213> ORGANISM: Homo sapiens

<400> SEQUENCE: 58

Gly Gly Ser Leu Ser Gly Gly Tyr Asp
1               5

<210> SEQ ID NO 59
<211> LENGTH: 9
<212> TYPE: PRT
<213> ORGANISM: Homo sapiens

<400> SEQUENCE: 59

Gly Ser Ser Leu Ser Ser Ala Tyr Gly
1               5

<210> SEQ ID NO 60
<211> LENGTH: 9
<212> TYPE: PRT
<213> ORGANISM: Homo sapiens

<400> SEQUENCE: 60

Gly Ser Ser Leu Ser Ser Ala Tyr Gly
1               5

<210> SEQ ID NO 61
<211> LENGTH: 9
<212> TYPE: PRT
<213> ORGANISM: Homo sapiens

<400> SEQUENCE: 61

```
Gly Tyr Ser Leu Ser Ser Ala Tyr Gly
1               5

<210> SEQ ID NO 62
<211> LENGTH: 9
<212> TYPE: PRT
<213> ORGANISM: Homo sapiens

<400> SEQUENCE: 62

Gly Gly Ser Leu Ser Gly Gly Tyr Asp
1               5

<210> SEQ ID NO 63
<211> LENGTH: 9
<212> TYPE: PRT
<213> ORGANISM: Homo sapiens

<400> SEQUENCE: 63

Gly Tyr Ser Ile Ser Ser Gly Phe Ala
1               5

<210> SEQ ID NO 64
<211> LENGTH: 8
<212> TYPE: PRT
<213> ORGANISM: Homo sapiens

<400> SEQUENCE: 64

Ile Gly Gly Ser Arg Gly Asn Thr
1               5

<210> SEQ ID NO 65
<211> LENGTH: 8
<212> TYPE: PRT
<213> ORGANISM: Homo sapiens

<400> SEQUENCE: 65

Ile Tyr Asp Ser Arg Trp Thr Thr
1               5

<210> SEQ ID NO 66
<211> LENGTH: 8
<212> TYPE: PRT
<213> ORGANISM: Homo sapiens

<400> SEQUENCE: 66

Ile Gly Gly Ser Arg Asp Asn Val
1               5

<210> SEQ ID NO 67
<211> LENGTH: 8
<212> TYPE: PRT
<213> ORGANISM: Homo sapiens

<400> SEQUENCE: 67

Ile Gly Gly Ser Arg Asp Asn Thr
1               5

<210> SEQ ID NO 68
<211> LENGTH: 8
<212> TYPE: PRT
<213> ORGANISM: Homo sapiens

<400> SEQUENCE: 68

Ile Gly Gly Ser Arg Gly Thr Thr
```

```
<210> SEQ ID NO 69
<211> LENGTH: 8
<212> TYPE: PRT
<213> ORGANISM: Homo sapiens

<400> SEQUENCE: 69

Ile Gly Gly Ser Arg Asp Asn Thr
1               5

<210> SEQ ID NO 70
<211> LENGTH: 8
<212> TYPE: PRT
<213> ORGANISM: Homo sapiens

<400> SEQUENCE: 70

Ile Gly Gly Ser Arg Gly Asn Thr
1               5

<210> SEQ ID NO 71
<211> LENGTH: 8
<212> TYPE: PRT
<213> ORGANISM: Homo sapiens

<400> SEQUENCE: 71

Ile Gly Gly Ser Arg Asp Asn Thr
1               5

<210> SEQ ID NO 72
<211> LENGTH: 8
<212> TYPE: PRT
<213> ORGANISM: Homo sapiens

<400> SEQUENCE: 72

Ile Tyr Asp Ser Arg Gly Thr Thr
1               5

<210> SEQ ID NO 73
<211> LENGTH: 8
<212> TYPE: PRT
<213> ORGANISM: Homo sapiens

<400> SEQUENCE: 73

Ile Gly Gly Ser Arg Asp Asn Thr
1               5

<210> SEQ ID NO 74
<211> LENGTH: 8
<212> TYPE: PRT
<213> ORGANISM: Homo sapiens

<400> SEQUENCE: 74

Ile Tyr Asp Ser Arg Gly Thr Thr
1               5

<210> SEQ ID NO 75
<211> LENGTH: 8
<212> TYPE: PRT
<213> ORGANISM: Homo sapiens

<400> SEQUENCE: 75

Ile Gly Gly Ser Arg Gly Asn Ala
1               5
```

```
<210> SEQ ID NO 76
<211> LENGTH: 8
<212> TYPE: PRT
<213> ORGANISM: Homo sapiens

<400> SEQUENCE: 76

Ile Gly Gly Ser Arg Ser Asn Thr
1               5

<210> SEQ ID NO 77
<211> LENGTH: 8
<212> TYPE: PRT
<213> ORGANISM: Homo sapiens

<400> SEQUENCE: 77

Ile Tyr Gly Ser Arg Gly Thr Thr
1               5

<210> SEQ ID NO 78
<211> LENGTH: 8
<212> TYPE: PRT
<213> ORGANISM: Homo sapiens

<400> SEQUENCE: 78

Ile Tyr Asp Ser Arg Gly Thr Thr
1               5

<210> SEQ ID NO 79
<211> LENGTH: 8
<212> TYPE: PRT
<213> ORGANISM: Homo sapiens

<400> SEQUENCE: 79

Ile Gly Gly Ser Arg Gly Asn Thr
1               5

<210> SEQ ID NO 80
<211> LENGTH: 8
<212> TYPE: PRT
<213> ORGANISM: Homo sapiens

<400> SEQUENCE: 80

Ile Gly Gly Ser Arg Asp Asn Thr
1               5

<210> SEQ ID NO 81
<211> LENGTH: 8
<212> TYPE: PRT
<213> ORGANISM: Homo sapiens

<400> SEQUENCE: 81

Phe Gly Gly Ser Arg Gly Asn Thr
1               5

<210> SEQ ID NO 82
<211> LENGTH: 8
<212> TYPE: PRT
<213> ORGANISM: Homo sapiens

<400> SEQUENCE: 82

Ile Gly Gly Ser Arg Gly Asn Thr
1               5

<210> SEQ ID NO 83
```

```
<211> LENGTH: 8
<212> TYPE: PRT
<213> ORGANISM: Homo sapiens

<400> SEQUENCE: 83

Ile Gly Gly Ser Arg Gly Asn Thr
1               5

<210> SEQ ID NO 84
<211> LENGTH: 8
<212> TYPE: PRT
<213> ORGANISM: Homo sapiens

<400> SEQUENCE: 84

Ile Gly Gly Ser Arg Asp Asn Thr
1               5

<210> SEQ ID NO 85
<211> LENGTH: 8
<212> TYPE: PRT
<213> ORGANISM: Homo sapiens

<400> SEQUENCE: 85

Ile Gly Gly Ser Arg Asp Asn Thr
1               5

<210> SEQ ID NO 86
<211> LENGTH: 8
<212> TYPE: PRT
<213> ORGANISM: Homo sapiens

<400> SEQUENCE: 86

Ile Ser Gly Ser Gly Ser Pro Thr
1               5

<210> SEQ ID NO 87
<211> LENGTH: 8
<212> TYPE: PRT
<213> ORGANISM: Homo sapiens

<400> SEQUENCE: 87

Ile Gly Gly Ser Arg Asp Asn Thr
1               5

<210> SEQ ID NO 88
<211> LENGTH: 8
<212> TYPE: PRT
<213> ORGANISM: Homo sapiens

<400> SEQUENCE: 88

Ile Gly Gly Ser Arg Asp Asn Thr
1               5

<210> SEQ ID NO 89
<211> LENGTH: 8
<212> TYPE: PRT
<213> ORGANISM: Homo sapiens

<400> SEQUENCE: 89

Ile Gly Gly Ser Arg Asp Asn Val
1               5

<210> SEQ ID NO 90
<211> LENGTH: 8
<212> TYPE: PRT
```

<213> ORGANISM: Homo sapiens

<400> SEQUENCE: 90

Ile Gly Gly Ser Arg Gly Thr Thr
1               5

<210> SEQ ID NO 91
<211> LENGTH: 8
<212> TYPE: PRT
<213> ORGANISM: Homo sapiens

<400> SEQUENCE: 91

Ile Tyr Asp Ser Arg Gly Thr Thr
1               5

<210> SEQ ID NO 92
<211> LENGTH: 8
<212> TYPE: PRT
<213> ORGANISM: Homo sapiens

<400> SEQUENCE: 92

Ile Gly Gly Asn Arg Asp Asn Thr
1               5

<210> SEQ ID NO 93
<211> LENGTH: 8
<212> TYPE: PRT
<213> ORGANISM: Homo sapiens

<400> SEQUENCE: 93

Ile Gly Gly Ser Arg Asp Asn Thr
1               5

<210> SEQ ID NO 94
<211> LENGTH: 8
<212> TYPE: PRT
<213> ORGANISM: Homo sapiens

<400> SEQUENCE: 94

Ile Gly Gly Ser Arg Asp Asn Val
1               5

<210> SEQ ID NO 95
<211> LENGTH: 8
<212> TYPE: PRT
<213> ORGANISM: Homo sapiens

<400> SEQUENCE: 95

Ile Tyr Asp Ser Arg Gly Thr Thr
1               5

<210> SEQ ID NO 96
<211> LENGTH: 8
<212> TYPE: PRT
<213> ORGANISM: Homo sapiens

<400> SEQUENCE: 96

Ile Gly Gly Ser Arg Asp Asn Thr
1               5

<210> SEQ ID NO 97
<211> LENGTH: 14
<212> TYPE: PRT
<213> ORGANISM: Homo sapiens

```
<400> SEQUENCE: 97

Ala Arg Arg Ala Pro Tyr Trp Gly Tyr Ser Tyr Leu Asp Tyr
1               5                   10

<210> SEQ ID NO 98
<211> LENGTH: 13
<212> TYPE: PRT
<213> ORGANISM: Homo sapiens

<400> SEQUENCE: 98

Ala Arg Arg Gly Gly Tyr Gly Ala Ser Tyr Phe Asp Leu
1               5                   10

<210> SEQ ID NO 99
<211> LENGTH: 13
<212> TYPE: PRT
<213> ORGANISM: Homo sapiens

<400> SEQUENCE: 99

Val Arg Arg Ala Thr Tyr Gly Asn Ser Tyr Phe Asp Ser
1               5                   10

<210> SEQ ID NO 100
<211> LENGTH: 13
<212> TYPE: PRT
<213> ORGANISM: Homo sapiens

<400> SEQUENCE: 100

Ala Gln Arg Gly Ala Tyr Gly Tyr Ser Tyr Phe Asp Tyr
1               5                   10

<210> SEQ ID NO 101
<211> LENGTH: 13
<212> TYPE: PRT
<213> ORGANISM: Homo sapiens

<400> SEQUENCE: 101

Ala Arg Asp Ser Gly Tyr Ser Phe Arg Tyr Phe Asp Phe
1               5                   10

<210> SEQ ID NO 102
<211> LENGTH: 13
<212> TYPE: PRT
<213> ORGANISM: Homo sapiens

<400> SEQUENCE: 102

Ala Arg Asp Gly Gly Tyr Gly Ser Arg Tyr Met Asp Ser
1               5                   10

<210> SEQ ID NO 103
<211> LENGTH: 13
<212> TYPE: PRT
<213> ORGANISM: Homo sapiens

<400> SEQUENCE: 103

Ala Arg Asp Ser Gly Tyr Asn Thr Arg Tyr Phe Asp Tyr
1               5                   10

<210> SEQ ID NO 104
<211> LENGTH: 13
<212> TYPE: PRT
<213> ORGANISM: Homo sapiens

<400> SEQUENCE: 104
```

Ala Gln Arg Gly Ala Tyr Gly Tyr Ser Tyr Phe Asp Tyr
1               5                   10

<210> SEQ ID NO 105
<211> LENGTH: 13
<212> TYPE: PRT
<213> ORGANISM: Homo sapiens

<400> SEQUENCE: 105

Ala Arg Arg Ala Gly Tyr Gly Ser Ala Tyr Phe Asp Tyr
1               5                   10

<210> SEQ ID NO 106
<211> LENGTH: 13
<212> TYPE: PRT
<213> ORGANISM: Homo sapiens

<400> SEQUENCE: 106

Ala Arg Arg Gly Ala Phe Gly Asn Ser Tyr Phe Asp Tyr
1               5                   10

<210> SEQ ID NO 107
<211> LENGTH: 13
<212> TYPE: PRT
<213> ORGANISM: Homo sapiens

<400> SEQUENCE: 107

Ala Arg Arg Ala Gly Tyr Gly Ser Ala Tyr Phe Asp Tyr
1               5                   10

<210> SEQ ID NO 108
<211> LENGTH: 13
<212> TYPE: PRT
<213> ORGANISM: Homo sapiens

<400> SEQUENCE: 108

Ala Arg Asp Gly Gly Tyr Gly Glu Arg Tyr Leu Glu Phe
1               5                   10

<210> SEQ ID NO 109
<211> LENGTH: 13
<212> TYPE: PRT
<213> ORGANISM: Homo sapiens

<400> SEQUENCE: 109

Ala Arg Asp Trp Gly Tyr Gly Tyr Arg Tyr Leu Asp Tyr
1               5                   10

<210> SEQ ID NO 110
<211> LENGTH: 13
<212> TYPE: PRT
<213> ORGANISM: Homo sapiens

<400> SEQUENCE: 110

Ala Lys Arg Val Gly Tyr Gly Asn Ser Tyr Phe Asp Ser
1               5                   10

<210> SEQ ID NO 111
<211> LENGTH: 13
<212> TYPE: PRT
<213> ORGANISM: Homo sapiens

<400> SEQUENCE: 111

Ala Arg Arg Ala Gly Tyr Gly Ser Ala Tyr Phe Asp Tyr
1               5                   10

<210> SEQ ID NO 112
<211> LENGTH: 14
<212> TYPE: PRT
<213> ORGANISM: Homo sapiens

<400> SEQUENCE: 112

Ala Arg Arg Ala Pro Tyr Trp Gly Tyr Ser Tyr Leu Asp Tyr
1               5                   10

<210> SEQ ID NO 113
<211> LENGTH: 13
<212> TYPE: PRT
<213> ORGANISM: Homo sapiens

<400> SEQUENCE: 113

Ala Gln Arg Gly Ala Tyr Gly Tyr Ser Tyr Phe Asp Tyr
1               5                   10

<210> SEQ ID NO 114
<211> LENGTH: 13
<212> TYPE: PRT
<213> ORGANISM: Homo sapiens

<400> SEQUENCE: 114

Ala Arg Asp Ser Gly Tyr Ser Arg Arg Trp Val Asp Tyr
1               5                   10

<210> SEQ ID NO 115
<211> LENGTH: 13
<212> TYPE: PRT
<213> ORGANISM: Homo sapiens

<400> SEQUENCE: 115

Ala Arg Asp Trp Gly Tyr Gly Tyr Arg Tyr Phe Asp Phe
1               5                   10

<210> SEQ ID NO 116
<211> LENGTH: 13
<212> TYPE: PRT
<213> ORGANISM: Homo sapiens

<400> SEQUENCE: 116

Ala Arg Asp Ser Gly Tyr Asn Thr Arg Tyr Phe Asp Tyr
1               5                   10

<210> SEQ ID NO 117
<211> LENGTH: 13
<212> TYPE: PRT
<213> ORGANISM: Homo sapiens

<400> SEQUENCE: 117

Ala Gln Arg Gly Ala Tyr Gly Tyr Ser Tyr Phe Asp Tyr
1               5                   10

<210> SEQ ID NO 118
<211> LENGTH: 13
<212> TYPE: PRT
<213> ORGANISM: Homo sapiens

<400> SEQUENCE: 118

Ala Gln Arg Gly Ala Tyr Gly Tyr Ser Tyr Phe Asp Tyr
1               5                   10

```
<210> SEQ ID NO 119
<211> LENGTH: 13
<212> TYPE: PRT
<213> ORGANISM: Homo sapiens

<400> SEQUENCE: 119

Ala Arg Arg Gly Gly Tyr Gly Asn Arg Tyr Phe Asp Tyr
1               5                   10

<210> SEQ ID NO 120
<211> LENGTH: 13
<212> TYPE: PRT
<213> ORGANISM: Homo sapiens

<400> SEQUENCE: 120

Ala Gln Arg Gly Ala Tyr Gly Tyr Ser Tyr Phe Asp Tyr
1               5                   10

<210> SEQ ID NO 121
<211> LENGTH: 13
<212> TYPE: PRT
<213> ORGANISM: Homo sapiens

<400> SEQUENCE: 121

Ala Gln Arg Gly Ala Tyr Gly Tyr Ser Tyr Phe Asp Tyr
1               5                   10

<210> SEQ ID NO 122
<211> LENGTH: 13
<212> TYPE: PRT
<213> ORGANISM: Homo sapiens

<400> SEQUENCE: 122

Val Thr Ile His Gly Tyr Arg Asn Trp Tyr Leu Asp His
1               5                   10

<210> SEQ ID NO 123
<211> LENGTH: 13
<212> TYPE: PRT
<213> ORGANISM: Homo sapiens

<400> SEQUENCE: 123

Ala Arg Asp Ser Gly Tyr Ser Phe Arg Tyr Phe Asp Phe
1               5                   10

<210> SEQ ID NO 124
<211> LENGTH: 13
<212> TYPE: PRT
<213> ORGANISM: Homo sapiens

<400> SEQUENCE: 124

Ala Arg Arg Gly Gly Tyr Gly Ala Ser Tyr Phe Asp Leu
1               5                   10

<210> SEQ ID NO 125
<211> LENGTH: 13
<212> TYPE: PRT
<213> ORGANISM: Homo sapiens

<400> SEQUENCE: 125

Ala Gln Arg Gly Ala Tyr Gly Tyr Ser Tyr Phe Asp Tyr
1               5                   10

<210> SEQ ID NO 126
<211> LENGTH: 13
```

```
<212> TYPE: PRT
<213> ORGANISM: Homo sapiens

<400> SEQUENCE: 126

Ala Gln Arg Gly Ala Tyr Gly Tyr Ser Tyr Phe Asp Tyr
1               5                   10

<210> SEQ ID NO 127
<211> LENGTH: 13
<212> TYPE: PRT
<213> ORGANISM: Homo sapiens

<400> SEQUENCE: 127

Val Arg Arg Ala Thr Tyr Gly Asn Ser Tyr Phe Asp Ser
1               5                   10

<210> SEQ ID NO 128
<211> LENGTH: 13
<212> TYPE: PRT
<213> ORGANISM: Homo sapiens

<400> SEQUENCE: 128

Ala Arg Arg Val Gly Tyr Gly Ala Thr Tyr Phe Asp Leu
1               5                   10

<210> SEQ ID NO 129
<211> LENGTH: 13
<212> TYPE: PRT
<213> ORGANISM: Homo sapiens

<400> SEQUENCE: 129

Ala Arg Arg Gly Ala Tyr Gly Asn Ser Tyr Phe Asp Phe
1               5                   10

<210> SEQ ID NO 130
<211> LENGTH: 6
<212> TYPE: PRT
<213> ORGANISM: Homo sapiens

<400> SEQUENCE: 130

Gln Ser Ile Gly Ser Ser
1               5

<210> SEQ ID NO 131
<211> LENGTH: 6
<212> TYPE: PRT
<213> ORGANISM: Homo sapiens

<400> SEQUENCE: 131

Gln Ser Ile Gly Ser His
1               5

<210> SEQ ID NO 132
<211> LENGTH: 6
<212> TYPE: PRT
<213> ORGANISM: Homo sapiens

<400> SEQUENCE: 132

Gln Ser Val Gly Ser His
1               5

<210> SEQ ID NO 133
<211> LENGTH: 6
<212> TYPE: PRT
<213> ORGANISM: Homo sapiens
```

<400> SEQUENCE: 133

Gln Ser Val Gly Ser Ser
1               5

<210> SEQ ID NO 134
<211> LENGTH: 6
<212> TYPE: PRT
<213> ORGANISM: Homo sapiens

<400> SEQUENCE: 134

Gln Ser Val Gly Ser Asn
1               5

<210> SEQ ID NO 135
<211> LENGTH: 6
<212> TYPE: PRT
<213> ORGANISM: Homo sapiens

<400> SEQUENCE: 135

Gln Ser Ile Gly Thr Ser
1               5

<210> SEQ ID NO 136
<211> LENGTH: 6
<212> TYPE: PRT
<213> ORGANISM: Homo sapiens

<400> SEQUENCE: 136

Gln Ser Val Gly Ser Arg
1               5

<210> SEQ ID NO 137
<211> LENGTH: 6
<212> TYPE: PRT
<213> ORGANISM: Homo sapiens

<400> SEQUENCE: 137

Gln Ser Leu Gly Ser Arg
1               5

<210> SEQ ID NO 138
<211> LENGTH: 6
<212> TYPE: PRT
<213> ORGANISM: Homo sapiens

<400> SEQUENCE: 138

Gln Ser Ile Gly Thr Asn
1               5

<210> SEQ ID NO 139
<211> LENGTH: 6
<212> TYPE: PRT
<213> ORGANISM: Homo sapiens

<400> SEQUENCE: 139

Glu Ser Val Gly Ser Ser
1               5

<210> SEQ ID NO 140
<211> LENGTH: 6
<212> TYPE: PRT
<213> ORGANISM: Homo sapiens

<400> SEQUENCE: 140

Gln Thr Val Gly Arg Asn
1               5

<210> SEQ ID NO 141
<211> LENGTH: 6
<212> TYPE: PRT
<213> ORGANISM: Homo sapiens

<400> SEQUENCE: 141

Gln Ser Ile Gly Ser Ser
1               5

<210> SEQ ID NO 142
<211> LENGTH: 6
<212> TYPE: PRT
<213> ORGANISM: Homo sapiens

<400> SEQUENCE: 142

Gln Ser Ile Gly Ser Ser
1               5

<210> SEQ ID NO 143
<211> LENGTH: 6
<212> TYPE: PRT
<213> ORGANISM: Homo sapiens

<400> SEQUENCE: 143

Gln Ser Val Ser Ser Arg
1               5

<210> SEQ ID NO 144
<211> LENGTH: 6
<212> TYPE: PRT
<213> ORGANISM: Homo sapiens

<400> SEQUENCE: 144

Gln Ser Val Gly Ser Asn
1               5

<210> SEQ ID NO 145
<211> LENGTH: 6
<212> TYPE: PRT
<213> ORGANISM: Homo sapiens

<400> SEQUENCE: 145

Gln Ser Ile Gly Thr Asn
1               5

<210> SEQ ID NO 146
<211> LENGTH: 6
<212> TYPE: PRT
<213> ORGANISM: Homo sapiens

<400> SEQUENCE: 146

Gln Thr Val Gly Arg Asn
1               5

<210> SEQ ID NO 147
<211> LENGTH: 6
<212> TYPE: PRT
<213> ORGANISM: Homo sapiens

<400> SEQUENCE: 147

Gln Ser Val Gly Thr Asn

```
1               5

<210> SEQ ID NO 148
<211> LENGTH: 6
<212> TYPE: PRT
<213> ORGANISM: Homo sapiens

<400> SEQUENCE: 148

Gln Ser Val Gly Ser Asn
1               5

<210> SEQ ID NO 149
<211> LENGTH: 6
<212> TYPE: PRT
<213> ORGANISM: Homo sapiens

<400> SEQUENCE: 149

Gln Ser Val Gly Ser Asn
1               5

<210> SEQ ID NO 150
<211> LENGTH: 6
<212> TYPE: PRT
<213> ORGANISM: Homo sapiens

<400> SEQUENCE: 150

Gln Ser Val Gly Ser Tyr
1               5

<210> SEQ ID NO 151
<211> LENGTH: 6
<212> TYPE: PRT
<213> ORGANISM: Homo sapiens

<400> SEQUENCE: 151

Gln Ser Val Gly Ser Ser
1               5

<210> SEQ ID NO 152
<211> LENGTH: 6
<212> TYPE: PRT
<213> ORGANISM: Homo sapiens

<400> SEQUENCE: 152

Gln Ser Val Gly Ser Ser
1               5

<210> SEQ ID NO 153
<211> LENGTH: 6
<212> TYPE: PRT
<213> ORGANISM: Homo sapiens

<400> SEQUENCE: 153

Gln Ser Ile Gly Ser Asn
1               5

<210> SEQ ID NO 154
<211> LENGTH: 6
<212> TYPE: PRT
<213> ORGANISM: Homo sapiens

<400> SEQUENCE: 154

Gln Ser Leu Gly Gly Arg
1               5
```

<210> SEQ ID NO 155
<211> LENGTH: 6
<212> TYPE: PRT
<213> ORGANISM: Homo sapiens

<400> SEQUENCE: 155

Gln Ser Ile Gly Thr Ser
1               5

<210> SEQ ID NO 156
<211> LENGTH: 6
<212> TYPE: PRT
<213> ORGANISM: Homo sapiens

<400> SEQUENCE: 156

Gln Ser Ile Gly Thr Asn
1               5

<210> SEQ ID NO 157
<211> LENGTH: 6
<212> TYPE: PRT
<213> ORGANISM: Homo sapiens

<400> SEQUENCE: 157

Gln Ser Val Gly Ser Asn
1               5

<210> SEQ ID NO 158
<211> LENGTH: 6
<212> TYPE: PRT
<213> ORGANISM: Homo sapiens

<400> SEQUENCE: 158

Gln Thr Val Gly Arg Asn
1               5

<210> SEQ ID NO 159
<211> LENGTH: 6
<212> TYPE: PRT
<213> ORGANISM: Homo sapiens

<400> SEQUENCE: 159

Gln Ser Leu Gly Ser Arg
1               5

<210> SEQ ID NO 160
<211> LENGTH: 6
<212> TYPE: PRT
<213> ORGANISM: Homo sapiens

<400> SEQUENCE: 160

Gln Ser Val Gly Ser Tyr
1               5

<210> SEQ ID NO 161
<211> LENGTH: 6
<212> TYPE: PRT
<213> ORGANISM: Homo sapiens

<400> SEQUENCE: 161

Gln Ser Val Gly Ser Asn
1               5

<210> SEQ ID NO 162

```
<211> LENGTH: 6
<212> TYPE: PRT
<213> ORGANISM: Homo sapiens

<400> SEQUENCE: 162

Gln Ser Val Gly Ser Asn
1               5

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000
```

-continued

<210> SEQ ID NO 173
<400> SEQUENCE: 173
000

<210> SEQ ID NO 174
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179
<400> SEQUENCE: 179
000

<210> SEQ ID NO 180
<400> SEQUENCE: 180
000

<210> SEQ ID NO 181
<400> SEQUENCE: 181
000

<210> SEQ ID NO 182
<400> SEQUENCE: 182
000

<210> SEQ ID NO 183
<400> SEQUENCE: 183
000

<210> SEQ ID NO 184

```
<400> SEQUENCE: 184
000

<210> SEQ ID NO 185
<400> SEQUENCE: 185
000

<210> SEQ ID NO 186
<400> SEQUENCE: 186
000

<210> SEQ ID NO 187
<400> SEQUENCE: 187
000

<210> SEQ ID NO 188
<400> SEQUENCE: 188
000

<210> SEQ ID NO 189
<400> SEQUENCE: 189
000

<210> SEQ ID NO 190
<400> SEQUENCE: 190
000

<210> SEQ ID NO 191
<400> SEQUENCE: 191
000

<210> SEQ ID NO 192
<400> SEQUENCE: 192
000

<210> SEQ ID NO 193
<400> SEQUENCE: 193
000

<210> SEQ ID NO 194
<400> SEQUENCE: 194
000

<210> SEQ ID NO 195
<400> SEQUENCE: 195
```

000

<210> SEQ ID NO 196
<211> LENGTH: 10
<212> TYPE: PRT
<213> ORGANISM: Homo sapiens

<400> SEQUENCE: 196

Gln Gln Tyr Asn Asp Leu Leu Pro Leu Thr
1               5                   10

<210> SEQ ID NO 197
<211> LENGTH: 10
<212> TYPE: PRT
<213> ORGANISM: Homo sapiens

<400> SEQUENCE: 197

Gln Gln Tyr Asn Asp Leu Leu Pro Leu Thr
1               5                   10

<210> SEQ ID NO 198
<211> LENGTH: 10
<212> TYPE: PRT
<213> ORGANISM: Homo sapiens

<400> SEQUENCE: 198

Gln Gln Tyr Asn Asp Leu Leu Pro Leu Thr
1               5                   10

<210> SEQ ID NO 199
<211> LENGTH: 10
<212> TYPE: PRT
<213> ORGANISM: Homo sapiens

<400> SEQUENCE: 199

Gln Gln Tyr Asn Asp Phe Phe Pro Leu Thr
1               5                   10

<210> SEQ ID NO 200
<211> LENGTH: 10
<212> TYPE: PRT
<213> ORGANISM: Homo sapiens

<400> SEQUENCE: 200

Gln Gln Tyr Asn Asp Leu Leu Pro Leu Thr
1               5                   10

<210> SEQ ID NO 201
<211> LENGTH: 10
<212> TYPE: PRT
<213> ORGANISM: Homo sapiens

<400> SEQUENCE: 201

Gln Gln Tyr Asn Asp Leu Leu Pro Leu Thr
1               5                   10

<210> SEQ ID NO 202
<211> LENGTH: 10
<212> TYPE: PRT
<213> ORGANISM: Homo sapiens

<400> SEQUENCE: 202

Gln Gln Tyr Asn Asp Leu Leu Pro Leu Thr
1               5                   10

<210> SEQ ID NO 203
<211> LENGTH: 10
<212> TYPE: PRT
<213> ORGANISM: Homo sapiens

<400> SEQUENCE: 203

Gln Gln Tyr Asn Asp Phe Pro Pro Leu Thr
1               5                   10

<210> SEQ ID NO 204
<211> LENGTH: 10
<212> TYPE: PRT
<213> ORGANISM: Homo sapiens

<400> SEQUENCE: 204

Gln Gln Tyr Asn Asp Leu Leu Pro Leu Thr
1               5                   10

<210> SEQ ID NO 205
<211> LENGTH: 10
<212> TYPE: PRT
<213> ORGANISM: Homo sapiens

<400> SEQUENCE: 205

Gln Gln Tyr Asn Asp Leu Leu Pro Leu Thr
1               5                   10

<210> SEQ ID NO 206
<211> LENGTH: 12
<212> TYPE: PRT
<213> ORGANISM: Homo sapiens

<400> SEQUENCE: 206

Cys Gln Gln Tyr Asn Asp Leu Leu Pro Leu Thr Phe
1               5                   10

<210> SEQ ID NO 207
<211> LENGTH: 9
<212> TYPE: PRT
<213> ORGANISM: Homo sapiens

<400> SEQUENCE: 207

His Gln Ser Ser Ser Phe Pro Trp Thr
1               5

<210> SEQ ID NO 208
<211> LENGTH: 9
<212> TYPE: PRT
<213> ORGANISM: Homo sapiens

<400> SEQUENCE: 208

Gln Gln Ser Ser Ser Phe Pro Phe Thr
1               5

<210> SEQ ID NO 209
<211> LENGTH: 12
<212> TYPE: PRT
<213> ORGANISM: Homo sapiens

<400> SEQUENCE: 209

Cys Gln Gln Tyr Asn Asp Leu Leu Pro Leu Thr Phe
1               5                   10

```
<210> SEQ ID NO 210
<211> LENGTH: 10
<212> TYPE: PRT
<213> ORGANISM: Homo sapiens

<400> SEQUENCE: 210

Gln Gln Tyr Asn Asp Leu Leu Pro Leu Thr
1               5                   10

<210> SEQ ID NO 211
<211> LENGTH: 10
<212> TYPE: PRT
<213> ORGANISM: Homo sapiens

<400> SEQUENCE: 211

Gln Gln Tyr Asn Asp Leu Leu Pro Leu Thr
1               5                   10

<210> SEQ ID NO 212
<211> LENGTH: 10
<212> TYPE: PRT
<213> ORGANISM: Homo sapiens

<400> SEQUENCE: 212

Gln Gln Tyr Asn Asp Leu Leu Pro Leu Thr
1               5                   10

<210> SEQ ID NO 213
<211> LENGTH: 10
<212> TYPE: PRT
<213> ORGANISM: Homo sapiens

<400> SEQUENCE: 213

Gln Gln Tyr Asn Asp Leu Leu Pro Leu Thr
1               5                   10

<210> SEQ ID NO 214
<211> LENGTH: 9
<212> TYPE: PRT
<213> ORGANISM: Homo sapiens

<400> SEQUENCE: 214

Gln Gln Thr Asn Thr Phe Pro Trp Thr
1               5

<210> SEQ ID NO 215
<211> LENGTH: 10
<212> TYPE: PRT
<213> ORGANISM: Homo sapiens

<400> SEQUENCE: 215

Gln Gln Tyr Asn Asp Leu Leu Pro Leu Thr
1               5                   10

<210> SEQ ID NO 216
<211> LENGTH: 10
<212> TYPE: PRT
<213> ORGANISM: Homo sapiens

<400> SEQUENCE: 216

Gln Gln Tyr Asn Asp Leu Leu Pro Leu Thr
1               5                   10

<210> SEQ ID NO 217
<211> LENGTH: 10
```

```
<212> TYPE: PRT
<213> ORGANISM: Homo sapiens

<400> SEQUENCE: 217

His Gln Tyr Asn Asp Leu Leu Pro Leu Thr
1               5                   10

<210> SEQ ID NO 218
<211> LENGTH: 10
<212> TYPE: PRT
<213> ORGANISM: Homo sapiens

<400> SEQUENCE: 218

Gln Gln Tyr Asn Asp Leu Leu Pro Leu Thr
1               5                   10

<210> SEQ ID NO 219
<211> LENGTH: 10
<212> TYPE: PRT
<213> ORGANISM: Homo sapiens

<400> SEQUENCE: 219

Gln Gln Tyr Asn Asp Phe Leu Pro Leu Thr
1               5                   10

<210> SEQ ID NO 220
<211> LENGTH: 10
<212> TYPE: PRT
<213> ORGANISM: Homo sapiens

<400> SEQUENCE: 220

Gln Gln Tyr Asn Asp Phe Leu Pro Leu Thr
1               5                   10

<210> SEQ ID NO 221
<211> LENGTH: 10
<212> TYPE: PRT
<213> ORGANISM: Homo sapiens

<400> SEQUENCE: 221

Gln Gln Tyr Asn Asp Leu Leu Pro Leu Thr
1               5                   10

<210> SEQ ID NO 222
<211> LENGTH: 10
<212> TYPE: PRT
<213> ORGANISM: Homo sapiens

<400> SEQUENCE: 222

Gln Gln Tyr Asn Asp Leu Leu Pro Leu Thr
1               5                   10

<210> SEQ ID NO 223
<211> LENGTH: 10
<212> TYPE: PRT
<213> ORGANISM: Homo sapiens

<400> SEQUENCE: 223

Gln Gln Tyr Asn Asp Phe Phe Pro Leu Thr
1               5                   10

<210> SEQ ID NO 224
<211> LENGTH: 10
<212> TYPE: PRT
<213> ORGANISM: Homo sapiens
```

<400> SEQUENCE: 224

Gln Gln Tyr Asn Asp Leu Leu Pro Leu Thr
1               5                   10

<210> SEQ ID NO 225
<211> LENGTH: 10
<212> TYPE: PRT
<213> ORGANISM: Homo sapiens

<400> SEQUENCE: 225

Gln Gln Tyr Asn Asp Phe Leu Pro Leu Thr
1               5                   10

<210> SEQ ID NO 226
<211> LENGTH: 10
<212> TYPE: PRT
<213> ORGANISM: Homo sapiens

<400> SEQUENCE: 226

Gln Gln Tyr Asn Asp Phe Leu Pro Leu Thr
1               5                   10

<210> SEQ ID NO 227
<211> LENGTH: 10
<212> TYPE: PRT
<213> ORGANISM: Homo sapiens

<400> SEQUENCE: 227

Gln Gln Tyr Asn Asp Leu Leu Pro Leu Thr
1               5                   10

<210> SEQ ID NO 228
<211> LENGTH: 10
<212> TYPE: PRT
<213> ORGANISM: Homo sapiens

<400> SEQUENCE: 228

Gln Gln Tyr Asn Asp Leu Leu Pro Leu Thr
1               5                   10

<210> SEQ ID NO 229
<211> LENGTH: 122
<212> TYPE: PRT
<213> ORGANISM: Homo sapiens

<400> SEQUENCE: 229

Glu Val Gln Leu Leu Glu Ser Gly Pro Gly Leu Val Lys Pro Ser Glu
1               5                   10                  15

Thr Leu Ser Leu Thr Cys Ala Val Ser Gly Asp Ser Ile Ser Ser Gly
            20                  25                  30

Leu Gly Trp Ser Trp Ile Arg Gln Thr Pro Gly Lys Gly Leu Glu Trp
        35                  40                  45

Ile Gly Tyr Ile Gly Gly Ser Arg Gly Asn Thr Asn Tyr Asn Pro Ser
    50                  55                  60

Phe Lys Ser Arg Val Thr Ile Ser Arg Asp Thr Ser Lys Asn Gln Phe
65                  70                  75                  80

Ser Leu Arg Leu Ser Ser Met Thr Ala Ala Asp Thr Ala Val Tyr Tyr
                85                  90                  95

Cys Ala Arg Arg Ala Pro Tyr Trp Gly Tyr Ser Tyr Leu Asp Tyr Trp
            100                 105                 110

```
Gly Gln Gly Val Leu Val Thr Val Ser Ser
        115                 120

<210> SEQ ID NO 230
<211> LENGTH: 121
<212> TYPE: PRT
<213> ORGANISM: Homo sapiens

<400> SEQUENCE: 230

Glu Val Gln Leu Leu Glu Ser Gly Pro Gly Leu Val Lys Pro Ser Glu
1               5                   10                  15

Thr Leu Ser Leu Thr Cys Ala Val Ser Gly Gly Ser Leu Ser Gly Gly
            20                  25                  30

Tyr Asp Trp Ser Trp Ile Arg Gln Ser Ser Arg Lys Gly Leu Glu Trp
        35                  40                  45

Ile Gly Tyr Ile Tyr Asp Ser Arg Trp Thr Thr Asn Tyr Asn Pro Ser
    50                  55                  60

Leu Lys Lys Arg Val Thr Ile Ser Ile Asp Thr Ser Lys Asn Gln Phe
65                  70                  75                  80

Ser Leu Asn Leu Lys Ser Val Thr Ala Ala Asp Thr Ala Val Tyr Tyr
                85                  90                  95

Cys Ala Arg Arg Gly Gly Tyr Gly Ala Ser Tyr Phe Asp Leu Trp Gly
            100                 105                 110

Gln Gly Val Leu Val Thr Val Ser Ser
        115                 120

<210> SEQ ID NO 231
<211> LENGTH: 121
<212> TYPE: PRT
<213> ORGANISM: Homo sapiens

<400> SEQUENCE: 231

Glu Val Gln Leu Leu Glu Ser Gly Pro Gly Leu Val Lys Pro Ser Glu
1               5                   10                  15

Thr Leu Ser Leu Thr Cys Ala Val Ser Gly Tyr Ser Leu Ser Ser Ala
            20                  25                  30

Tyr Gly Trp Asn Trp Ile Arg Gln Ser Pro Gly Lys Gly Leu Glu Trp
        35                  40                  45

Ile Gly Ser Ile Gly Gly Ser Arg Asp Asn Val Asn Tyr Asn Pro Ser
    50                  55                  60

Leu Lys Arg Arg Val Thr Ile Ser Lys Asp Thr Ser Thr Asn His Phe
65                  70                  75                  80

Ser Leu Arg Leu Ser Ser Val Thr Ala Ala Asp Thr Ala Val Tyr Tyr
                85                  90                  95

Cys Val Arg Arg Ala Thr Tyr Gly Asn Ser Tyr Phe Asp Ser Trp Gly
            100                 105                 110

Gln Gly Val Gln Val Thr Val Ser Ser
        115                 120

<210> SEQ ID NO 232
<211> LENGTH: 121
<212> TYPE: PRT
<213> ORGANISM: Homo sapiens

<400> SEQUENCE: 232

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
```

```
                  20                  25                  30

Tyr Gly Trp Asn Trp Ile Arg Gln Pro Pro Gly Lys Gly Leu Glu Trp
            35                  40                  45

Ile Gly Ser Ile Gly Gly Ser Arg Asp Asn Thr Asn Tyr Asn Pro Ser
 50                  55                  60

Leu Lys Arg Arg Val Thr Ile Ser Lys Asp Thr Ser Lys Asn Gln Phe
 65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
               100                 105                 110

Gln Gly Val Leu Val Ala Val Ser Ser
               115                 120

<210> SEQ ID NO 233
<211> LENGTH: 121
<212> TYPE: PRT
<213> ORGANISM: Homo sapiens

<400> SEQUENCE: 233

Glu Val Gln Leu Leu Glu Ser Gly Pro Gly Leu Val Lys Pro Ser Glu
 1               5                  10                  15

Thr Leu Ser Leu Thr Cys Ala Val Ser Gly Asp Ser Ile Ser Ser Gly
                20                  25                  30

Tyr Gly Trp His Trp Ile Arg Gln Val Pro Gly Arg Gly Leu Glu Trp
            35                  40                  45

Ile Gly Ser Ile Gly Gly Ser Arg Gly Thr Thr Asn Tyr Asn Pro Ser
 50                  55                  60

Leu Lys Ser Arg Val Thr Ile Ser Glu Asp Thr Ser Lys Asn Gln Phe
 65                  70                  75                  80

Ser Leu Ser Leu Arg Ser Val Ser Ala Ala Asp Thr Ala Val Tyr Phe
                85                  90                  95

Cys Ala Arg Asp Ser Gly Tyr Ser Phe Arg Tyr Phe Asp Phe Trp Gly
               100                 105                 110

Gln Gly Val Leu Val Thr Val Ser Ser
               115                 120

<210> SEQ ID NO 234
<211> LENGTH: 121
<212> TYPE: PRT
<213> ORGANISM: Homo sapiens

<400> SEQUENCE: 234

Glu Val Gln Leu Leu Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
                20                  25                  30

Tyr Gly Trp Asn Trp Ile Arg Gln Pro Pro Gly Lys Gly Leu Glu Trp
            35                  40                  45

Ile Gly Ser Ile Gly Gly Ser Arg Asp Asn Thr Asn Tyr Asn Pro Ser
 50                  55                  60

Leu Lys Ser Arg Val Thr Leu Ser Lys Asp Thr Ser Lys Asn His Phe
 65                  70                  75                  80

Ser Leu Arg Leu Arg Ser Val Thr Ala Ala Asp Thr Ala Val Tyr Tyr
                85                  90                  95

Cys Ala Arg Asp Gly Gly Tyr Gly Ser Arg Tyr Met Asp Ser Trp Gly
```

100                 105                 110

Gln Gly Val Leu Val Ala Val Ser Ser
        115                 120

<210> SEQ ID NO 235
<211> LENGTH: 121
<212> TYPE: PRT
<213> ORGANISM: Homo sapiens

<400> SEQUENCE: 235

Glu Val Gln Leu Leu Glu Ser Gly Pro Gly Leu Val Arg Pro Ser Glu
1               5                   10                  15

Thr Leu Ser Leu Thr Cys Ala Val Ser Gly Tyr Ser Ile Ser Ser Gly
            20                  25                  30

Tyr Gly Trp His Trp Ile Arg Gln Pro Pro Gly Lys Gly Leu Glu Ser
        35                  40                  45

Leu Gly Tyr Ile Gly Gly Ser Arg Gly Asn Thr Asn Tyr Asn Pro Ser
    50                  55                  60

Leu Lys Ser Arg Val Thr Ile Ser Thr Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Ser Gly Tyr Asn Thr Arg Tyr Phe Asp Tyr Trp Gly
            100                 105                 110

Gln Gly Val Leu Val Thr Val Ser Ser
        115                 120

<210> SEQ ID NO 236
<211> LENGTH: 121
<212> TYPE: PRT
<213> ORGANISM: Homo sapiens

<400> SEQUENCE: 236

Glu Val Gln Leu Gln Leu Pro Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Ser Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Ala Val Ser Ser
        115                 120

<210> SEQ ID NO 237
<211> LENGTH: 121
<212> TYPE: PRT
<213> ORGANISM: Homo sapiens

<400> SEQUENCE: 237

Glu Val Gln Leu Leu Glu Ser Gly Pro Gly Leu Val Lys Pro Ser Glu
1               5                   10                  15

```
Thr Leu Ser Leu Thr Cys Ala Val Ser Gly Ser Ile Gly Gly
            20                  25                  30

Tyr Asp Trp Ser Trp Ile Arg Gln Ser Pro Gly Lys Gly Leu Glu Trp
        35                  40                  45

Ile Gly Tyr Ile Tyr Asp Ser Arg Gly Thr Thr Asn Tyr Asn Pro Ser
 50                  55                  60

Leu Arg Lys Arg Val Ala Ile Ser Ile Asp Thr Ser Arg Asn Gln Phe
65                   70                  75                  80

Ser Leu Asn Leu Arg Ser Leu Thr Ala Ala Asp Thr Ala Val Tyr Tyr
                85                  90                  95

Cys Ala Arg Arg Ala Gly Tyr Gly Ser Ala Tyr Phe Asp Tyr Trp Gly
            100                 105                 110

Gln Gly Val Leu Val Thr Val Ser Ser
        115                 120

<210> SEQ ID NO 238
<211> LENGTH: 121
<212> TYPE: PRT
<213> ORGANISM: Homo sapiens

<400> SEQUENCE: 238

Glu Val Gln Leu Leu Glu Ser Gly Pro Gly Leu Val Lys Pro Ser Glu
1               5                   10                  15

Thr Leu Ser Leu Thr Cys Ala Val Ser Gly Ser Ser Leu Ser Ser Ala
            20                  25                  30

Tyr Gly Trp Asn Trp Ile Arg Gln Ala Pro Gly Lys Arg Leu Glu Trp
        35                  40                  45

Ile Gly Phe Ile Gly Gly Ser Arg Asp Asn Thr Asn Tyr Asn Pro Ser
 50                  55                  60

Leu Arg Ser Arg Val Thr Ile Ser Lys Asp Thr Ser Lys Asn His Phe
65                   70                  75                  80

Ser Leu Lys Leu Thr Ser Val Thr Ala Ala Asp Thr Ala Val Tyr Phe
                85                  90                  95

Cys Ala Arg Arg Gly Ala Phe Gly Asn Ser Tyr Phe Asp Tyr Trp Gly
            100                 105                 110

Gln Gly Val Pro Val Thr Val Ser Ser
        115                 120

<210> SEQ ID NO 239
<211> LENGTH: 121
<212> TYPE: PRT
<213> ORGANISM: Homo sapiens

<400> SEQUENCE: 239

Glu Val Gln Leu Leu Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Asp Trp Ser Trp Ile Arg Gln Ser Pro Gly Lys Gly Leu Glu Trp
        35                  40                  45

Ile Gly Tyr Ile Tyr Asp Ser Arg Gly Thr Thr Asn Tyr Asn Pro Ser
 50                  55                  60

Leu Arg Lys Arg Val Thr Ile Ser Ile Asp Thr Ser Arg Asn Gln Phe
65                   70                  75                  80

Ser Leu Lys Leu Arg Ser Leu Thr Ala Ala Asp Thr Ala Val Tyr Tyr
                85                  90                  95
```

```
Cys Ala Arg Arg Ala Gly Tyr Gly Ser Ala Tyr Phe Asp Tyr Trp Gly
                100                 105                 110

Gln Gly Val Leu Val Thr Val Ser Ser
        115                 120

<210> SEQ ID NO 240
<211> LENGTH: 121
<212> TYPE: PRT
<213> ORGANISM: Homo sapiens

<400> SEQUENCE: 240

Glu Val Gln Leu Leu Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Gly Trp Thr Trp Ile Arg Gln Pro Pro Gly Lys Gly Leu Glu Trp
        35                  40                  45

Ile Gly Tyr Ile Gly Gly Ser Arg Gly Asn Ala Asn Tyr Asn Pro Ser
    50                  55                  60

Leu Lys Ser Arg Val Thr Ile Ser Lys Asp Thr Ser Lys Asn Gln Phe
65                  70                  75                  80

Ser Leu Lys Leu Thr Ser Val Thr Ala Ala Asp Thr Ala Val Tyr Tyr
                85                  90                  95

Cys Ala Arg Asp Gly Gly Tyr Gly Glu Arg Tyr Leu Glu Phe Trp Gly
                100                 105                 110

Gln Gly Ala Leu Val Thr Val Ser Ser
        115                 120

<210> SEQ ID NO 241
<211> LENGTH: 121
<212> TYPE: PRT
<213> ORGANISM: Homo sapiens

<400> SEQUENCE: 241

Glu Val Gln Leu Leu Glu Ser Gly Pro Gly Leu Val Arg Pro Ser Glu
1               5                   10                  15

Thr Leu Ser Leu Thr Cys Thr Val Ser Gly Asn Ser Ile Ser Ser Gly
            20                  25                  30

Tyr Gly Trp Asn Trp Ile Arg Gln Pro Pro Gly Lys Gly Leu Glu Leu
        35                  40                  45

Ile Gly Tyr Ile Gly Gly Ser Arg Ser Asn Thr Asn Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Trp Gly Tyr Gly Tyr Arg Tyr Leu Asp Tyr Trp Gly
                100                 105                 110

Gln Gly Val Leu Val Thr Val Ser Ser
        115                 120

<210> SEQ ID NO 242
<211> LENGTH: 121
<212> TYPE: PRT
<213> ORGANISM: Homo sapiens

<400> SEQUENCE: 242
```

Glu Val Gln Leu Leu Glu Ser Gly Pro Gly Leu Val Lys Pro Ser Glu
1               5                   10                  15

Thr Leu Ser Leu Thr Cys Ala Val Ser Gly Gly Ser Ile Asn Gly Gly
            20                  25                  30

Tyr Asp Trp Thr Trp Ile Arg Gln Ser Pro Gly Lys Gly Leu Gln Trp
        35                  40                  45

Ile Gly Trp Ile Tyr Gly Ser Arg Gly Thr Thr Asn Tyr Asn Pro Ser
50                  55                  60

Leu Arg Asn Arg Val Thr Ile Ser Ile Asp Thr Ser Arg Asn Gln Phe
65                  70                  75                  80

Ser Leu Arg Leu Ser Ser Leu Thr Ala Ala Asp Thr Ala Val Tyr Tyr
            85                  90                  95

Cys Ala Lys Arg Val Gly Tyr Gly Asn Ser Tyr Phe Asp Ser Trp Gly
            100                 105                 110

Gln Gly Val Leu Val Thr Val Ser Ser
            115                 120

<210> SEQ ID NO 243
<211> LENGTH: 121
<212> TYPE: PRT
<213> ORGANISM: Homo sapiens

<400> SEQUENCE: 243

Glu Val Gln Leu Leu Glu Ser Gly Pro Gly Leu Val Lys Pro Ser Glu
1               5                   10                  15

Thr Leu Ser Leu Thr Cys Ala Val Ser Gly Gly Ser Ile Ser Gly Gly
            20                  25                  30

Tyr Asp Trp Ser Trp Ile Arg Gln Ser Pro Gly Lys Gly Leu Glu Trp
        35                  40                  45

Ile Gly Tyr Ile Tyr Asp Ser Arg Gly Thr Thr Asn Tyr Asn Pro Ser
50                  55                  60

Leu Arg Lys Arg Val Thr Ile Ser Ile Asp Thr Ser Arg Asn Gln Phe
65                  70                  75                  80

Ser Leu Lys Leu Arg Ser Leu Thr Ala Ala Asp Thr Ala Val Tyr Tyr
            85                  90                  95

Cys Ala Arg Arg Ala Gly Tyr Gly Ser Ala Tyr Phe Asp Tyr Trp Gly
            100                 105                 110

Gln Gly Val Leu Val Thr Val Ser Ser
            115                 120

<210> SEQ ID NO 244
<211> LENGTH: 122
<212> TYPE: PRT
<213> ORGANISM: Homo sapiens

<400> SEQUENCE: 244

Glu Val Gln Leu Leu Glu Ser Gly Pro Gly Leu Val Lys Pro Ser Glu
1               5                   10                  15

Thr Leu Ser Leu Thr Cys Ala Val Ser Gly Asp Ser Ile Ser Ser Gly
            20                  25                  30

Tyr Gly Trp Ser Trp Ile Arg Gln Thr Pro Gly Lys Gly Leu Glu Trp
        35                  40                  45

Ile Gly Tyr Ile Gly Gly Ser Arg Gly Asn Thr Asn Tyr Asn Pro Ser
50                  55                  60

Leu Lys Ser Arg Val Thr Ile Ser Lys Asp Thr Ser Lys Asn Gln Phe
65                  70                  75                  80

```
Ser Leu Lys Leu Ser Ser Val Thr Ala Ala Asp Thr Ala Val Tyr Tyr
                85                  90                  95

Cys Ala Arg Arg Ala Pro Tyr Trp Gly Tyr Ser Tyr Leu Asp Tyr Trp
            100                 105                 110

Gly Gln Gly Val Leu Val Thr Val Ser Ser
        115                 120

<210> SEQ ID NO 245
<211> LENGTH: 121
<212> TYPE: PRT
<213> ORGANISM: Homo sapiens

<400> SEQUENCE: 245

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Ser Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Ala Val Ser Ser
        115                 120

<210> SEQ ID NO 246
<211> LENGTH: 121
<212> TYPE: PRT
<213> ORGANISM: Homo sapiens

<400> SEQUENCE: 246

Glu Val Gln Leu Leu Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Gly Trp Gly Trp Ile Arg Gln Ser Pro Gly Lys Gly Leu Glu Trp
        35                  40                  45

Ile Gly Tyr Phe Gly Gly Ser Arg Gly Asn Thr Asn Tyr Asn Pro Ser
    50                  55                  60

Leu Lys Ser Arg Val Thr Ile Ser Gln Asp Thr Ser Lys Asn Gln Phe
65                  70                  75                  80

Ser Leu Lys Leu Lys Ser Val Thr Ala Ala Asp Thr Gly Ile Tyr Tyr
                85                  90                  95

Cys Ala Arg Asp Ser Gly Tyr Ser Arg Arg Trp Val Asp Tyr Trp Gly
            100                 105                 110

Gln Gly Val Leu Val Thr Val Ser Ser
        115                 120

<210> SEQ ID NO 247
<211> LENGTH: 121
<212> TYPE: PRT
<213> ORGANISM: Homo sapiens
<220> FEATURE:
```

```
<221> NAME/KEY: misc_feature
<222> LOCATION: (95)..(95)
<223> OTHER INFORMATION: Xaa can be any naturally occurring amino acid

<400> SEQUENCE: 247

Glu Val Gln Leu Leu Glu Ser Gly Pro Gly Leu Val Lys Pro Leu Glu
1               5                   10                  15

Thr Leu Ser Leu Thr Cys Asp Val Ser Gly Phe Ser Ile Ser Ser Asp
            20                  25                  30

Tyr Gly Trp Ser Trp Ile Arg Gln Pro Pro Gly Lys Gly Leu Glu Leu
        35                  40                  45

Ile Gly Tyr Ile Gly Gly Ser Arg Gly Asn Thr Asn Tyr Asn Pro Ser
50                  55                  60

Leu Lys Ser Arg Val Thr Ile Ser Arg Asp Thr Ser Lys Asn Gln Phe
65                  70                  75                  80

Ser Leu Lys Leu Thr Ser Val Thr Ala Ala Asp Thr Ala Val Xaa Tyr
                85                  90                  95

Cys Ala Arg Asp Trp Gly Tyr Gly Tyr Arg Tyr Phe Asp Phe Trp Gly
            100                 105                 110

Gln Gly Val Leu Val Thr Val Ser Ser
        115                 120

<210> SEQ ID NO 248
<211> LENGTH: 121
<212> TYPE: PRT
<213> ORGANISM: Homo sapiens

<400> SEQUENCE: 248

Glu Val Gln Leu Leu Glu Ser Gly Pro Gly Leu Val Arg Pro Ser Glu
1               5                   10                  15

Thr Leu Ser Leu Thr Cys Ala Val Ser Gly Tyr Ser Ile Ser Ser Gly
            20                  25                  30

Tyr Gly Trp His Trp Ile Arg Gln Pro Pro Gly Lys Gly Leu Glu Ser
        35                  40                  45

Leu Gly Tyr Ile Gly Gly Ser Arg Gly Asn Thr Asn Tyr Asn Pro Ser
50                  55                  60

Leu Lys Ser Arg Val Thr Ile Ser Thr Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Ser Gly Tyr Asn Thr Arg Tyr Phe Asp Tyr Trp Gly
            100                 105                 110

Gln Gly Val Leu Val Thr Val Ser Ser
        115                 120

<210> SEQ ID NO 249
<211> LENGTH: 121
<212> TYPE: PRT
<213> ORGANISM: Homo sapiens

<400> SEQUENCE: 249

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45
```

Ile Gly Ser Ile Gly Gly Ser Arg Asp Asn Thr Asn Tyr Asn Pro Ser
 50                  55                  60

Leu Lys Arg Arg Val Thr Ile Ser Lys Asp Thr Ser Lys Asn Gln Phe
 65                  70                  75                  80

Ser Leu Lys Leu Lys Ser Val Thr Ala Ala Asp Thr Ala Val Tyr Tyr
                 85                  90                  95

Cys Ala Gln Arg Gly Ala Tyr Gly Tyr Ser Tyr Phe Asp Tyr Trp Gly
                100                 105                 110

Gln Gly Val Leu Val Ala Val Ser Ser
                115                 120

<210> SEQ ID NO 250
<211> LENGTH: 121
<212> TYPE: PRT
<213> ORGANISM: Homo sapiens

<400> SEQUENCE: 250

Glu Val Gln Leu Leu Glu Ser Gly Pro Gly Leu Val Lys Pro Ser Glu
 1               5                  10                  15

Thr Leu Ser Leu Thr Cys Thr Val Ser Gly Ser Ser Leu Ser Ser Ala
                 20                  25                  30

Tyr Gly Trp Asn Trp Ile Arg Gln Pro Pro Gly Lys Gly Leu Glu Trp
             35                  40                  45

Ile Gly Ser Ile Gly Gly Ser Arg Asp Asn Thr Asn Tyr Asn Pro Ser
 50                  55                  60

Leu Lys Arg Arg Val Thr Ile Ser Lys Asp Thr Ser Lys Asn Gln Phe
 65                  70                  75                  80

Ser Leu Lys Leu Lys Ser Val Thr Ala Ala Asp Thr Ala Val Tyr Tyr
                 85                  90                  95

Cys Ala Gln Arg Gly Ala Tyr Gly Tyr Ser Tyr Phe Asp Tyr Trp Gly
                100                 105                 110

Gln Gly Val Leu Val Ala Val Ser Ser
                115                 120

<210> SEQ ID NO 251
<211> LENGTH: 120
<212> TYPE: PRT
<213> ORGANISM: Homo sapiens

<400> SEQUENCE: 251

Glu Val Gln Leu Leu Glu Ser Gly Pro Gly Leu Val Arg Pro Ser Glu
 1               5                  10                  15

Thr Leu Ser Val Thr Cys Asp Val Ser Gly Gly Ser Ile Ser Ser Ala
                 20                  25                  30

Ser Trp Ser Trp Ile Arg Gln Ala Pro Gly Lys Arg Leu Glu Trp Ile
             35                  40                  45

Gly Ala Ile Ser Gly Ser Gly Ser Pro Thr Asn Val Asn Pro Ser Leu
 50                  55                  60

Lys Ser Arg Val Thr Leu Ser Val Asp Thr Ser Lys Asn Gln Leu Ser
 65                  70                  75                  80

Leu Lys Leu Arg Ser Met Thr Ala Ala Asp Thr Ala Val Tyr Tyr Cys
                 85                  90                  95

Ala Arg Arg Gly Gly Tyr Gly Asn Arg Tyr Phe Asp Tyr Trp Gly Gln
                100                 105                 110

Gly Val Ala Val Thr Val Ser Ser
                115                 120

<210> SEQ ID NO 252
<211> LENGTH: 121
<212> TYPE: PRT
<213> ORGANISM: Homo sapiens

<400> SEQUENCE: 252

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Ser Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Thr Val Ser Ser
        115                 120

<210> SEQ ID NO 253
<211> LENGTH: 121
<212> TYPE: PRT
<213> ORGANISM: Homo sapiens

<400> SEQUENCE: 253

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Ser Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Ala Val Ser Ser
        115                 120

<210> SEQ ID NO 254
<211> LENGTH: 121
<212> TYPE: PRT
<213> ORGANISM: Homo sapiens

<400> SEQUENCE: 254

Glu Val Gln Leu Leu Glu Ser Gly Pro Gly Leu Val Lys Pro Ser Glu
1               5                   10                  15

Thr Leu Ser Leu Thr Cys Ala Val Ser Ser Leu Ser Leu Ser Ser Gly
            20                  25                  30

Phe Ala Trp Ser Trp Ile Arg Gln Pro Pro Gly Glu Gly Leu Glu Trp

```
                35                  40                  45

Ile Gly Ser Ile Gly Gly Ser Arg Asp Asn Val Asn Tyr Asn Pro Ser
 50                  55                  60

Leu Lys Ser Arg Val Thr Ile Ser Lys Asp Thr Ser Lys Asn Gln Phe
 65                  70                  75                  80

Ser Leu Arg Leu Arg Ser Val Thr Ala Ala Asp Thr Ala Val Tyr Tyr
                 85                  90                  95

Cys Val Thr Ile His Gly Tyr Arg Asn Trp Tyr Leu Asp His Trp Gly
                100                 105                 110

Gln Gly Val Leu Val Thr Val Ser Thr
                115                 120
```

<210> SEQ ID NO 255
<211> LENGTH: 121
<212> TYPE: PRT
<213> ORGANISM: Homo sapiens

<400> SEQUENCE: 255

```
Glu Val Gln Leu Leu Glu Ser Gly Pro Gly Leu Val Lys Pro Ser Glu
  1               5                  10                  15

Thr Leu Ser Leu Thr Cys Ala Val Ser Gly Asn Ser Ile Ser Ser Ala
                 20                  25                  30

Tyr Gly Trp His Trp Ile Arg Gln Val Pro Gly Lys Gly Leu Glu Trp
                 35                  40                  45

Ile Gly Ser Ile Gly Gly Ser Arg Gly Thr Thr Asn Tyr Asn Pro Ser
 50                  55                  60

Leu Lys Ser Arg Gly Thr Ile Ser Glu Asp Thr Ser Lys Asn Gln Phe
 65                  70                  75                  80

Ser Leu Arg Leu Arg Ser Val Ser Ala Ala Asp Thr Ala Val Tyr Phe
                 85                  90                  95

Cys Ala Arg Asp Ser Gly Tyr Ser Phe Arg Tyr Phe Asp Phe Trp Gly
                100                 105                 110

Arg Gly Val Leu Val Thr Val Ser Ser
                115                 120
```

<210> SEQ ID NO 256
<211> LENGTH: 121
<212> TYPE: PRT
<213> ORGANISM: Homo sapiens

<400> SEQUENCE: 256

```
Glu Val Gln Leu Leu Glu Ser Gly Pro Gly Leu Val Arg Pro Ser Glu
  1               5                  10                  15

Thr Leu Ser Leu Thr Cys Ala Val Ser Gly Gly Ser Leu Ser Gly Gly
                 20                  25                  30

Tyr Asp Trp Ser Trp Ile Arg Gln Ser Pro Arg Lys Gly Leu Glu Trp
                 35                  40                  45

Ile Gly Tyr Ile Tyr Asp Ser Arg Gly Thr Thr Asn Tyr Asn Pro Ser
 50                  55                  60

Leu Lys Arg Arg Val Thr Ile Ser Ile Asp Thr Ser Lys Asn Gln Phe
 65                  70                  75                  80

Ser Leu Asn Leu Lys Ser Val Thr Ala Ala Asp Thr Ala Val Tyr Tyr
                 85                  90                  95

Cys Ala Arg Arg Gly Gly Tyr Gly Ala Ser Tyr Phe Asp Leu Trp Gly
                100                 105                 110

Gln Gly Val Leu Val Thr Val Ser Ser
```

115                 120

<210> SEQ ID NO 257
<211> LENGTH: 121
<212> TYPE: PRT
<213> ORGANISM: Homo sapiens

<400> SEQUENCE: 257

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Asn Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Ala Val Ser Ser
        115                 120

<210> SEQ ID NO 258
<211> LENGTH: 121
<212> TYPE: PRT
<213> ORGANISM: Homo sapiens

<400> SEQUENCE: 258

Glu Val Gln Leu Leu Glu Ser Gly Pro Gly Leu Val Lys Pro Ser Glu
1               5                   10                  15

Thr Leu Ser Leu Thr Cys Thr Val Ser Gly Ser Ser Leu Ser Ser Ala
            20                  25                  30

Tyr Gly Trp Asn Trp Ile Arg Gln Pro Pro Gly Lys Gly Leu Glu Trp
        35                  40                  45

Ile Gly Ser Ile Gly Gly Ser Arg Asp Asn Thr Asn Tyr Asn Pro Ser
    50                  55                  60

Leu Lys Arg Arg Val Thr Ile Ser Lys Asp Thr Ser Lys Asn Gln Phe
65                  70                  75                  80

Ser Leu Lys Leu Lys Ser Val Thr Ala Ala Asp Thr Ala Val Tyr Tyr
                85                  90                  95

Cys Ala Gln Arg Gly Ala Tyr Gly Tyr Ser Tyr Phe Asp Tyr Trp Gly
            100                 105                 110

Gln Gly Val Leu Val Ala Val Ser Ser
        115                 120

<210> SEQ ID NO 259
<211> LENGTH: 121
<212> TYPE: PRT
<213> ORGANISM: Homo sapiens

<400> SEQUENCE: 259

Glu Val Gln Leu Leu Glu Trp Gly Pro Gly Leu Val Lys Pro Ser Glu
1               5                   10                  15

Thr Leu Ser Leu Thr Cys Ala Val Ser Gly Tyr Ser Leu Ser Ser Ala
            20                  25                  30

```
Tyr Gly Trp Asn Trp Ile Arg Gln Ser Pro Gly Lys Gly Leu Glu Trp
        35                  40                  45

Ile Gly Ser Ile Gly Gly Ser Arg Asp Asn Val Asn Tyr Asn Pro Ser
 50                  55                  60

Leu Lys Arg Arg Val Thr Ile Ser Lys Asp Thr Ser Thr Asn His Phe
65                  70                  75                  80

Ser Leu Arg Leu Ser Ser Val Thr Ala Ala Asp Thr Ala Val Tyr Tyr
                85                  90                  95

Cys Val Arg Arg Ala Thr Tyr Gly Asn Ser Tyr Phe Asp Ser Trp Gly
                100                 105                 110

Gln Gly Val Gln Val Thr Val Ser Ser
        115                 120

<210> SEQ ID NO 260
<211> LENGTH: 121
<212> TYPE: PRT
<213> ORGANISM: Homo sapiens

<400> SEQUENCE: 260

Glu Val Gln Leu Leu Glu Ser Gly Pro Gly Leu Val Lys Pro Ser Glu
1               5                   10                  15

Thr Leu Ser Leu Thr Cys Ala Val Ser Gly Gly Ser Leu Ser Gly Gly
                20                  25                  30

Tyr Asp Trp Tyr Trp Ile Arg Gln Ser Pro Arg Lys Gly Leu Glu Tyr
        35                  40                  45

Ile Gly Tyr Ile Tyr Asp Ser Arg Gly Thr Thr Asn Tyr Asn Pro Ser
 50                  55                  60

Leu Lys Asn Arg Val Thr Ile Ser Ile Asp Thr Ser Lys Asn His Phe
65                  70                  75                  80

Ser Leu Asn Leu Lys Ser Val Thr Ala Ala Asp Thr Ala Val Tyr Tyr
                85                  90                  95

Cys Ala Arg Arg Val Gly Tyr Gly Ala Thr Tyr Phe Asp Leu Trp Gly
                100                 105                 110

Gln Gly Val Leu Val Thr Val Ser Ser
        115                 120

<210> SEQ ID NO 261
<211> LENGTH: 121
<212> TYPE: PRT
<213> ORGANISM: Homo sapiens

<400> SEQUENCE: 261

Glu Val Gln Leu Leu Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
                20                  25                  30

Phe Ala Trp Asn Trp Ile Arg Gln Thr Pro Gly Lys Gly Leu Glu Trp
        35                  40                  45

Ile Gly Tyr Ile Gly Gly Ser Arg Asp Asn Thr Asn Tyr Asn Pro Ser
 50                  55                  60

Leu Lys Ser Arg Val Thr Ile Ser Lys Asp Thr Ser Lys Asn Gln Phe
65                  70                  75                  80

Ser Leu Lys Leu Thr Ser Met Thr Ala Ala Asp Thr Ala Met Tyr Tyr
                85                  90                  95

Cys Ala Arg Arg Gly Ala Tyr Gly Asn Ser Tyr Phe Asp Phe Trp Gly
                100                 105                 110
```

-continued

Gln Gly Val Pro Val Thr Val Ser Ser
        115                 120

<210> SEQ ID NO 262
<211> LENGTH: 108
<212> TYPE: PRT
<213> ORGANISM: Homo sapiens

<400> SEQUENCE: 262

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Ile Gly Ser Ser
            20                  25                  30

Leu Ala Trp Tyr Gln Gln Arg Pro Gly Gln Ala Pro Lys Leu Leu Val
        35                  40                  45

His Ser Ala Tyr Phe Arg Ala Ala Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Leu Lys
            100                 105

<210> SEQ ID NO 263
<211> LENGTH: 108
<212> TYPE: PRT
<213> ORGANISM: Homo sapiens

<400> SEQUENCE: 263

Ala Ala Glu Leu Thr Gln Ser Pro Ala Thr Leu Ser Leu Phe Pro Gly
1               5                   10                  15

Glu Thr Ala Thr Leu Ser Cys Arg Ala Ser Gln Ser Ile Gly Ser His
            20                  25                  30

Leu Ala Trp Tyr Gln Gln Lys Pro Gly Gln Ala Pro Lys Leu Leu Val
        35                  40                  45

His Ser Val Ser Phe Arg Ala Thr Gly Ile Pro Asp Arg Phe Arg Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 264
<211> LENGTH: 110
<212> TYPE: PRT
<213> ORGANISM: Homo sapiens

<400> SEQUENCE: 264

Ala Ala Glu Leu Thr Leu Thr Gln Ser Pro Ala Thr Leu Ser Leu Ser
1               5                   10                  15

Pro Gly Glu Thr Ala Thr Leu Ser Cys Arg Ala Ser Gln Ser Val Gly
            20                  25                  30

Ser His Leu Ala Trp Tyr Gln Gln Lys Pro Gly Gln Ala Pro Lys Leu
        35                  40                  45

```
Leu Val His Ser Ala Tyr Phe Arg Ala Thr Gly Ile Pro Asp Arg Phe
 50                  55                  60

Ser Gly Ser Gly Ser Arg Thr Asp Phe Thr Leu Thr Ile Ser Ser Leu
 65                  70                  75                  80

Glu Pro Glu Asp Val Gly Val Tyr His Cys Gln Gln Tyr Asn Asp Leu
                 85                  90                  95

Leu Pro Leu Thr Phe Gly Gly Gly Thr Lys Val Glu Ile Lys
            100                 105                 110

<210> SEQ ID NO 265
<211> LENGTH: 108
<212> TYPE: PRT
<213> ORGANISM: Homo sapiens

<400> SEQUENCE: 265

Ala Ala Glu Leu Thr Gln Ser Pro Ala Thr Leu Ser Leu Ser Pro Gly
 1               5                  10                  15

Glu Thr Ala Thr Leu Ser Cys Arg Ala Ser Gln Ser Val Gly Ser Ser
                 20                  25                  30

Leu Ala Trp Tyr Gln Gln Lys Pro Gly Gln Ala Pro Lys Leu Leu Val
             35                  40                  45

His Ser Ile Ser Val Arg Ala Thr Gly Ile Pro Asp Arg Phe Ser Gly
 50                  55                  60

Ser Gly Ser Arg Thr Asp Phe Thr Leu Thr Ile Thr Ser Leu Glu Pro
 65                  70                  75                  80

Glu Asp Val Gly Val Tyr His Cys Gln Gln Tyr Asn Asp Phe Pro
                 85                  90                  95

Leu Thr Phe Gly Gly Gly Thr Lys Val Glu Ile Lys
            100                 105

<210> SEQ ID NO 266
<211> LENGTH: 110
<212> TYPE: PRT
<213> ORGANISM: Homo sapiens

<400> SEQUENCE: 266

Ala Ala Glu Leu Val Met Thr Gln Ser Pro Ala Thr Leu Ser Leu Ser
 1               5                  10                  15

Pro Gly Glu Thr Ala Thr Leu Ser Cys Arg Ala Ser Gln Ser Val Gly
                 20                  25                  30

Ser Asn Leu Ala Trp Tyr Gln Gln Lys Pro Gly Gln Ala Pro Lys Leu
             35                  40                  45

Leu Val His Ser Ala Tyr Phe Arg Ala Thr Gly Ile Pro Asp Arg Phe
 50                  55                  60

Ser Gly Ser Gly Ser Arg Thr Asp Phe Thr Leu Thr Ile Ser Ser Leu
 65                  70                  75                  80

Glu Pro Glu Asp Val Gly Val Tyr His Cys Gln Gln Tyr Asn Asp Leu
                 85                  90                  95

Leu Pro Leu Thr Phe Gly Gly Gly Thr Lys Val Glu Ile Asn
            100                 105                 110

<210> SEQ ID NO 267
<211> LENGTH: 108
<212> TYPE: PRT
<213> ORGANISM: Homo sapiens

<400> SEQUENCE: 267

Ala Ala Glu Leu Thr Gln Ser Pro Ala Thr Leu Ser Leu Ser Pro Gly
```

```
               1               5                  10                  15
            Glu Ala Ala Thr Leu Ser Cys Arg Ala Ser Gln Ser Ile Gly Thr Ser
                           20                  25                  30
            Leu Ala Trp Tyr Gln Gln Lys Pro Gly Gln Ala Pro Arg Leu Leu Val
                           35                  40                  45
            His Ser Ala Tyr Phe Arg Ala Thr Gly Ile Ala Asp Arg Phe Ser Gly
                       50                  55                  60
            Ser Gly Ser Arg Thr Asp Phe Thr Leu Thr Ile Ser Ser Leu Glu Pro
            65                  70                  75                  80
            Glu Asp Val Gly Val Tyr Tyr Cys Gln Gln Tyr Asn Asp Leu Leu Pro
                               85                  90                  95
            Leu Thr Phe Gly Gly Gly Thr Lys Val Glu Ile Lys
                           100                 105

<210> SEQ ID NO 268
<211> LENGTH: 108
<212> TYPE: PRT
<213> ORGANISM: Homo sapiens

<400> SEQUENCE: 268

Ala Ala Glu Leu Thr Gln Ser Pro Ala Thr Leu Ser Leu Ser Pro Gly
            1               5                  10                  15
            Glu Arg Ala Thr Leu Ser Cys Arg Ala Ser Gln Ser Val Gly Ser Arg
                           20                  25                  30
            Leu Ala Trp Tyr Gln Gln Lys Pro Gly Gln Ala Pro Arg Leu Leu Ile
                           35                  40                  45
            Tyr Gly Ala Ser Ser Arg Ala Thr Gly Ile Pro Asp Arg Phe Ser Gly
                       50                  55                  60
            Ser Gly Ser Arg Thr Asp Phe Thr Leu Thr Ile Ser Ser Leu Glu Pro
            65                  70                  75                  80
            Glu Asp Val Gly Val Tyr His Cys Gln Gln Tyr Asn Asp Leu Leu Pro
                               85                  90                  95
            Leu Thr Phe Gly Gly Gly Thr Lys Val Glu Ile Lys
                           100                 105

<210> SEQ ID NO 269
<211> LENGTH: 110
<212> TYPE: PRT
<213> ORGANISM: Homo sapiens

<400> SEQUENCE: 269

Ala Ala Glu Leu Thr Leu Thr Gln Ser Pro Ala Thr Leu Ser Leu Ser
            1               5                  10                  15
            Pro Gly Glu Thr Ala Thr Leu Ser Cys Arg Ala Ser Gln Ser Leu Gly
                           20                  25                  30
            Ser Arg Leu Ala Trp Tyr Gln Gln Lys Pro Gly Gln Pro Arg Leu
                           35                  40                  45
            Leu Ile Tyr Gly Ala Ser Thr Arg Ala Thr Gly Ile Pro Asp Arg Phe
                       50                  55                  60
            Ser Gly Ser Gly Ser Arg Thr Asp Phe Thr Leu Thr Ile Ser Ser Leu
            65                  70                  75                  80
            Glu Pro Glu Asp Val Gly Val Tyr His Cys Gln Gln Tyr Asn Asp Phe
                               85                  90                  95
            Pro Pro Leu Thr Phe Gly Gly Gly Thr Lys Val Glu Ile Lys
                           100                 105                 110
```

```
<210> SEQ ID NO 270
<211> LENGTH: 108
<212> TYPE: PRT
<213> ORGANISM: Homo sapiens

<400> SEQUENCE: 270

Ala Ala Glu Leu Thr Gln Ser Pro Ala Thr Leu Ser Leu Ala Pro Gly
1               5                   10                  15

Glu Thr Ala Thr Leu Ser Cys Arg Ala Ser Gln Ser Ile Gly Thr Asn
            20                  25                  30

Leu Ala Trp Tyr His Gln Lys Pro Gly Gln Pro Pro Lys Leu Leu Val
        35                  40                  45

His Thr Ala Tyr Val Arg Ala Thr Gly Ile Pro Asn Arg Phe Ser Gly
    50                  55                  60

Ser Gly Ser Arg Thr Asp Phe Thr Leu Thr Ile Asn Ser Leu Gln Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Ile Asp Ile Lys
            100                 105

<210> SEQ ID NO 271
<211> LENGTH: 108
<212> TYPE: PRT
<213> ORGANISM: Homo sapiens

<400> SEQUENCE: 271

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Glu Ser Val Gly Ser Ser
            20                  25                  30

Leu Ala Trp Tyr His Gln Lys Pro Gly Gln Ala Pro Arg Leu Leu Val
        35                  40                  45

His Ser Ala Ser Phe Arg Ala Thr Gly Ile Pro Asp Arg Phe Ser Gly
    50                  55                  60

Ser Gly Ser Arg Thr Glu Phe Thr Leu Thr Val Ser Ser Leu Glu Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 272
<211> LENGTH: 108
<212> TYPE: PRT
<213> ORGANISM: Homo sapiens

<400> SEQUENCE: 272

Ala Ala Glu Leu Thr Gln Ser Pro Ala Thr Leu Ser Val Ser Pro Gly
1               5                   10                  15

Glu Ala Ala Thr Leu Ser Cys Arg Ala Ser Gln Thr Val Gly Arg Asn
            20                  25                  30

Leu Ala Trp Tyr Gln Gln Lys Pro Gly Gln Ala Pro Lys Leu Leu Val
        35                  40                  45

His Ser Ala His Phe Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80
```

```
Glu Asp Ala Gly Ile Tyr His Cys Gln Gln Tyr Asn Asp Leu Leu Pro
                85                  90                  95
Leu Thr Phe Gly Gly Gly Thr Lys Val Glu Ile Lys
            100                 105
```

<210> SEQ ID NO 273
<211> LENGTH: 107
<212> TYPE: PRT
<213> ORGANISM: Homo sapiens

<400> SEQUENCE: 273

```
Ala Ala Glu Leu Thr Gln Ser Pro Ala Phe Arg Ser Val Thr Leu Lys
1               5                   10                  15
Glu Lys Val Thr Ile Thr Cys Gln Ala Ser Gln Ser Ile Gly Ser Ser
            20                  25                  30
Leu His Trp Tyr Gln Gln Lys Pro Asp Gln Ser Pro Lys Leu Leu Ile
            35                  40                  45
Lys Phe Ala Ser Gln Ser Ile Ser Gly Val Pro Ser Arg Phe Ser Gly
        50                  55                  60
Ser Gly Tyr Gly Thr Asp Phe Thr Leu Thr Ile Asn Ser Leu Glu Ala
65                  70                  75                  80
Glu Asp Ala Ala Thr Tyr Tyr Cys His Gln Ser Ser Ser Phe Pro Trp
                85                  90                  95
Thr Phe Gly Gln Gly Thr Lys Val Glu Ile Lys
            100                 105
```

<210> SEQ ID NO 274
<211> LENGTH: 107
<212> TYPE: PRT
<213> ORGANISM: Homo sapiens

<400> SEQUENCE: 274

```
Ala Ala Glu Leu Thr Gln Ser Pro Ala Phe Arg Ser Val Thr Leu Lys
1               5                   10                  15
Glu Lys Val Thr Ile Thr Cys Gln Ala Ser Gln Ser Ile Gly Ser Ser
            20                  25                  30
Leu His Trp Tyr Gln Gln Lys Pro Asp Gln Ser Pro Lys Leu Leu Ile
            35                  40                  45
Lys Tyr Ala Ser Gln Ser Ile Ser Gly Val Pro Ser Arg Phe Ser Gly
        50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys Gln Gln Ser Ser Ser Phe Pro Phe
                85                  90                  95
Thr Phe Gly Pro Gly Thr Lys Leu Asp Ile Lys
            100                 105
```

<210> SEQ ID NO 275
<211> LENGTH: 110
<212> TYPE: PRT
<213> ORGANISM: Homo sapiens

<400> SEQUENCE: 275

```
Ala Ala Glu Leu Thr Leu Thr Gln Ser Pro Ala Thr Leu Ser Leu Ser
1               5                   10                  15
Pro Gly Glu Arg Ala Thr Leu Ser Cys Arg Ala Ser Gln Ser Val Ser
            20                  25                  30
```

-continued

Ser Arg Leu Ala Trp Tyr Gln Gln Lys Pro Gly Gln Ala Pro Arg Leu
          35                  40                  45

Leu Ile Tyr Asp Ala Ser Ser Arg Val Thr Gly Ile Pro Asp Arg Phe
 50                  55                  60

Ser Gly Ser Gly Ser Gly Thr Asp Phe Thr Leu Thr Ile Ser Ser Leu
 65                  70                  75                  80

Glu Pro Glu Asp Val Gly Val Tyr His Cys Gln Gln Tyr Asn Asp Leu
                 85                  90                  95

Leu Pro Leu Thr Phe Gly Gly Gly Thr Lys Val Glu Ile Lys
            100                 105                 110

<210> SEQ ID NO 276
<211> LENGTH: 108
<212> TYPE: PRT
<213> ORGANISM: Homo sapiens

<400> SEQUENCE: 276

Ala Ala Glu Leu Thr Gln Ser Pro Ala Thr Leu Ser Leu Ser Pro Gly
 1               5                  10                  15

Glu Thr Ala Thr Leu Ser Cys Arg Ala Ser Gln Ser Val Gly Ser Asn
             20                  25                  30

Leu Ala Trp Tyr Gln Gln Lys Pro Gly Gln Ala Pro Lys Leu Leu Val
         35                  40                  45

His Ser Gly Ser Val Arg Ala Thr Gly Ile Pro Asp Arg Phe Ser Gly
 50                  55                  60

Ser Gly Ser Arg Thr Asp Phe Thr Leu Ile Ile Ser Ser Leu Glu Pro
 65                  70                  75                  80

Glu Asp Val Gly Val Tyr His Cys Gln Gln Tyr Asn Asp Leu Leu Pro
                 85                  90                  95

Leu Thr Phe Gly Gly Gly Thr Lys Val Glu Ile Lys
            100                 105

<210> SEQ ID NO 277
<211> LENGTH: 110
<212> TYPE: PRT
<213> ORGANISM: Homo sapiens

<400> SEQUENCE: 277

Ala Ala Glu Leu Thr Leu Thr Gln Ser Pro Ala Thr Leu Ser Leu Ala
 1               5                  10                  15

Pro Gly Glu Thr Ala Thr Leu Ser Cys Arg Ala Ser Gln Ser Ile Gly
             20                  25                  30

Thr Asn Leu Ala Trp Tyr His Gln Lys Pro Gly Gln Ser Pro Lys Leu
         35                  40                  45

Leu Val His Ser Ala Tyr Val Arg Ala Thr Gly Ile Pro Asp Arg Phe
 50                  55                  60

Ser Gly Ser Gly Ser Arg Thr Asp Phe Thr Leu Thr Ile Asn Ser Leu
 65                  70                  75                  80

Gln Pro Glu Asp Val Gly Val Tyr His Cys Gln Gln Tyr Asn Asp Leu
                 85                  90                  95

Leu Pro Leu Thr Phe Gly Gly Gly Thr Lys Val Glu Ile Lys
            100                 105                 110

<210> SEQ ID NO 278
<211> LENGTH: 110
<212> TYPE: PRT
<213> ORGANISM: Homo sapiens -continued

<400> SEQUENCE: 278

Ala Ala Glu Leu Thr Leu Thr Gln Ser Pro Ala Thr Leu Ser Leu Ser
1               5                   10                  15

Pro Gly Glu Thr Ala Thr Leu Ser Cys Arg Ala Ser Gln Thr Val Gly
            20                  25                  30

Arg Asn Leu Ala Trp Tyr Gln Gln Arg Pro Gly Gln Ala Pro Asn Leu
        35                  40                  45

Leu Val His Ser Ala Tyr Phe Arg Ala Thr Gly Ile Pro Asp Arg Phe
    50                  55                  60

Ser Gly Ser Gly Ser Gly Thr Asp Phe Thr Leu Thr Ile Ser Ser Leu
65                  70                  75                  80

Glu Pro Glu Asp Ala Gly Val Tyr His Cys Gln Gln Tyr Asn Asp Leu
                85                  90                  95

Leu Pro Leu Thr Phe Gly Gly Gly Thr Lys Val Glu Ile Lys
            100                 105                 110

<210> SEQ ID NO 279
<211> LENGTH: 108
<212> TYPE: PRT
<213> ORGANISM: Homo sapiens

<400> SEQUENCE: 279

Ala Ala Glu Leu Thr Gln Ser Pro Ala Thr Leu Ser Leu Ala Pro Gly
1               5                   10                  15

Glu Thr Ala Thr Leu Ser Cys Arg Ala Ser Gln Ser Val Gly Thr Asn
            20                  25                  30

Leu Ala Trp Tyr His Gln Lys Pro Gly Gln Pro Pro Lys Leu Leu Val
        35                  40                  45

His Ser Ala Tyr Val Arg Ala Thr Gly Ile Pro Asp Arg Phe Ser Gly
    50                  55                  60

Ser Gly Ser Arg Thr Asp Phe Thr Leu Thr Ile Asn Ser Leu Gln Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Ile Asp Ile Lys
            100                 105

<210> SEQ ID NO 280
<211> LENGTH: 107
<212> TYPE: PRT
<213> ORGANISM: Homo sapiens

<400> SEQUENCE: 280

Ala Ala Glu Leu Thr Gln Ser Pro Ala Phe Arg Ser Val Ser Leu Lys
1               5                   10                  15

Glu Thr Val Thr Leu Thr Cys Gln Ala Ser Gln Ser Val Gly Ser Asn
            20                  25                  30

Leu His Trp Tyr Gln Gln Lys Pro Ala Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Thr Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Thr Asn Thr Phe Pro Trp
                85                  90                  95

Thr Phe Gly Gln Gly Thr Arg Val Glu Ile Lys
            100                 105

<210> SEQ ID NO 281
<211> LENGTH: 108
<212> TYPE: PRT
<213> ORGANISM: Homo sapiens

<400> SEQUENCE: 281

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Lys Leu Leu Val
        35                  40                  45

His Ser Ala Tyr Phe Arg Ala Thr Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 282
<211> LENGTH: 108
<212> TYPE: PRT
<213> ORGANISM: Homo sapiens

<400> SEQUENCE: 282

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Tyr
            20                  25                  30

Leu Ala Trp Tyr Gln Gln Lys Pro Gly Gln Ala Pro Lys Leu Leu Val
        35                  40                  45

His Gly Ala Tyr Phe Arg Ala Ala Gly Ile Pro Asp Arg Phe Thr Gly
    50                  55                  60

Ser Gly Ser Arg Thr Asp Phe Thr Leu Thr Ile Ser Ser Leu Glu Pro
65                  70                  75                  80

Glu Asp Val Gly Ile Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 283
<211> LENGTH: 108
<212> TYPE: PRT
<213> ORGANISM: Homo sapiens

<400> SEQUENCE: 283

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Ser
            20                  25                  30

Leu Ala Trp Tyr Gln Gln Lys Pro Gly Gln Ala Pro Lys Leu Leu Val
        35                  40                  45

His Ser Ala Tyr Phe Arg Ala Thr Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys His Gln Tyr Asn Asp Leu Leu Pro
                85                  90                  95

Leu Thr Phe Gly Gly Gly Thr Lys Val Glu Ile Lys
            100                 105

<210> SEQ ID NO 284
<211> LENGTH: 108
<212> TYPE: PRT
<213> ORGANISM: Homo sapiens

<400> SEQUENCE: 284

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Ser
            20                  25                  30

Leu Ala Trp Tyr Gln Gln Lys Pro Gly Gln Ala Pro Lys Leu Leu Val
        35                  40                  45

His Ser Ala Tyr Phe Arg Ala Thr Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 285
<211> LENGTH: 110
<212> TYPE: PRT
<213> ORGANISM: Homo sapiens

<400> SEQUENCE: 285

Ala Ala Glu Leu Val Met Thr Gln Ser Pro Ala Thr Leu Ser Leu Ser
1               5                   10                  15

Pro Gly Glu Thr Ala Thr Leu Ser Cys Arg Ala Ser Gln Ser Ile Gly
            20                  25                  30

Ser Asn Leu Ala Trp Tyr Gln Gln Lys Pro Gly Gln Ala Pro Lys Leu
        35                  40                  45

Leu Val His Ser Ala Asn Ile Arg Ala Thr Gly Ile Pro Asp Arg Phe
    50                  55                  60

Ile Gly Ser Gly Ser Arg Thr Asp Phe Thr Leu Thr Ile Ser Ser Leu
65                  70                  75                  80

Glu Pro Glu Asp Val Gly Val Tyr His Cys Gln Gln Tyr Asn Asp Phe
                85                  90                  95

Leu Pro Leu Thr Phe Gly Gly Gly Thr Lys Val Glu Ile Lys
            100                 105                 110

<210> SEQ ID NO 286
<211> LENGTH: 110
<212> TYPE: PRT
<213> ORGANISM: Homo sapiens

<400> SEQUENCE: 286

Ala Ala Glu Leu Thr Leu Thr Gln Ser Pro Ala Thr Leu Ser Leu Ser
1               5                   10                  15

```
Pro Gly Glu Thr Ala Thr Leu Ser Cys Arg Ala Ser Gln Ser Leu Gly
            20                  25                  30

Gly Arg Leu Ala Trp Tyr Gln Gln Lys Pro Gly Gln Ala Pro Arg Leu
        35                  40                  45

Leu Ile Tyr Gly Ala Ser Thr Arg Ala Thr Gly Ile Pro Asp Arg Phe
 50                  55                  60

Ser Gly Ser Gly Ser Arg Thr Glu Phe Thr Leu Thr Ile Ala Gly Leu
 65                  70                  75                  80

Glu Pro Glu Asp Val Gly Val Tyr His Cys Gln Gln Tyr Asn Asp Phe
                85                  90                  95

Leu Pro Leu Thr Phe Gly Gly Gly Thr Lys Val Glu Ile Lys
            100                 105                 110

<210> SEQ ID NO 287
<211> LENGTH: 108
<212> TYPE: PRT
<213> ORGANISM: Homo sapiens

<400> SEQUENCE: 287

Ala Ala Glu Leu Thr Gln Ser Pro Ala Ile Leu Ser Leu Ser Pro Gly
 1               5                  10                  15

Glu Thr Ala Thr Leu Ser Cys Arg Ala Ser Gln Ser Ile Gly Thr Ser
            20                  25                  30

Leu Ala Trp Tyr Gln Gln Lys Pro Gly Gln Ala Pro Lys Leu Leu Val
        35                  40                  45

His Ser Ala Tyr Tyr Arg Ala Thr Asp Ile Pro Glu Arg Phe Ser Gly
 50                  55                  60

Ser Gly Ser Arg Thr Asp Phe Thr Leu Thr Ile Ser Ser Leu Glu Pro
 65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 288
<211> LENGTH: 108
<212> TYPE: PRT
<213> ORGANISM: Homo sapiens

<400> SEQUENCE: 288

Ala Ala Glu Leu Thr Gln Ser Pro Ala Thr Leu Ser Leu Ala Pro Gly
 1               5                  10                  15

Glu Thr Ala Thr Leu Ser Cys Arg Ala Ser Gln Ser Ile Gly Thr Asn
            20                  25                  30

Leu Ala Trp Tyr His Gln Lys Pro Gly Gln Pro Pro Lys Leu Leu Val
        35                  40                  45

His Ser Ala Tyr Val Arg Ala Thr Gly Ile Pro Asn Arg Phe Ser Gly
 50                  55                  60

Ser Gly Ser Arg Thr Asp Phe Thr Leu Thr Ile Asn Ser Leu Gln Pro
 65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Ile Asp Ile Lys
            100                 105

<210> SEQ ID NO 289
<211> LENGTH: 108
```

<212> TYPE: PRT
<213> ORGANISM: Homo sapiens

<400> SEQUENCE: 289

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Leu Ala Trp Tyr Gln Gln Lys Pro Gly Gln Ala Pro Lys Leu Leu Val
        35                  40                  45

His Ser Ala Ser Val Arg Ala Thr Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Phe Phe Pro
                85                  90                  95

Leu Thr Phe Gly Gly Gly Thr Lys Val Glu Ile Lys
            100                 105

<210> SEQ ID NO 290
<211> LENGTH: 108
<212> TYPE: PRT
<213> ORGANISM: Homo sapiens

<400> SEQUENCE: 290

Ala Ala Glu Leu Thr Gln Ser Pro Ala Thr Leu Ser Val Ser Pro Gly
1               5                   10                  15

Glu Ala Ala Thr Leu Ser Cys Arg Ala Ser Gln Thr Val Gly Arg Asn
            20                  25                  30

Leu Ala Trp Tyr Gln Gln Lys Pro Gly Gln Ala Pro Lys Leu Leu Val
        35                  40                  45

His Ser Ala His Phe Arg Ala Thr Gly Ile Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Ala Gly Ile Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 291
<211> LENGTH: 108
<212> TYPE: PRT
<213> ORGANISM: Homo sapiens

<400> SEQUENCE: 291

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Leu Gly Ser Arg
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Asp Arg Phe Ser Gly
    50                  55                  60

Ser Gly Ser Arg Thr Asp Phe Thr Leu Thr Ile Ser Ser Leu Glu Pro
65                  70                  75                  80

Glu Asp Val Gly Val Tyr His Cys Gln Gln Tyr Asn Asp Phe Leu Pro

```
                        85                  90                  95

Leu Thr Phe Gly Gly Gly Thr Lys Val Glu Ile Lys
            100                 105

<210> SEQ ID NO 292
<211> LENGTH: 110
<212> TYPE: PRT
<213> ORGANISM: Homo sapiens

<400> SEQUENCE: 292

Ala Ala Glu Leu Thr Leu Thr Gln Ser Pro Ala Thr Leu Ser Leu Ser
1               5                   10                  15

Pro Gly Glu Thr Ala Thr Leu Ser Cys Arg Ala Ser Gln Ser Val Gly
            20                  25                  30

Ser Tyr Leu Ala Trp Tyr Gln Gln Lys Pro Gly Gln Ala Pro Lys Leu
        35                  40                  45

Leu Val His Ser Ala His Phe Arg Ala Thr Gly Ile Pro Asp Arg Phe
    50                  55                  60

Ser Gly Ser Gly Ser Arg Thr Asp Phe Thr Leu Thr Ile Ser Ser Leu
65                  70                  75                  80

Glu Pro Glu Asp Val Gly Val Tyr His Cys Gln Gln Tyr Asn Asp Leu
                85                  90                  95

Leu Pro Leu Thr Phe Gly Gly Gly Thr Lys Val Glu Ile Lys
            100                 105                 110

<210> SEQ ID NO 293
<211> LENGTH: 110
<212> TYPE: PRT
<213> ORGANISM: Homo sapiens

<400> SEQUENCE: 293

Ala Ala Glu Leu Val Met Thr Gln Ser Pro Ala Thr Leu Ser Leu Ser
1               5                   10                  15

Pro Gly Glu Thr Ala Thr Leu Ser Cys Arg Ala Ser Gln Ser Val Gly
            20                  25                  30

Ser Asn Leu Ala Trp Tyr Gln Gln Lys Pro Gly Gln Ala Pro Lys Leu
        35                  40                  45

Leu Val His Ser Ala Asn Phe Arg Ala Thr Gly Ile Ser Asp Arg Phe
    50                  55                  60

Ser Gly Ser Gly Ser Arg Thr Asp Phe Thr Leu Thr Ile Ser Ser Leu
65                  70                  75                  80

Glu Pro Glu Asp Val Gly Val Tyr His Cys Gln Gln Tyr Asn Asp Leu
                85                  90                  95

Leu Pro Leu Thr Phe Gly Gly Gly Thr Lys Val Glu Ile Lys
            100                 105                 110

<210> SEQ ID NO 294
<211> LENGTH: 108
<212> TYPE: PRT
<213> ORGANISM: Homo sapiens

<400> SEQUENCE: 294

Ala Ala Glu Leu Thr Gln Ser Pro Ala Thr Leu Ser Leu Ser Pro Gly
1               5                   10                  15

Glu Thr Ala Thr Leu Ser Cys Arg Ala Ser Gln Ser Val Gly Ser Asn
            20                  25                  30

Val Ala Trp Tyr Gln Gln Lys Pro Gly Gln Ala Pro Lys Leu Leu Val
        35                  40                  45
```

His Ser Ala Tyr Tyr Arg Ala Thr Gly Ile Pro Asp Arg Phe Ser Gly
        50                  55                  60

Ser Gly Ser Arg Thr Asp Phe Thr Leu Thr Ile Ser Ser Leu Glu Pro
 65                  70                  75                  80

Glu Asp Val Gly Val Tyr His Cys Gln Gln Tyr Asn Asp Leu Leu Pro
                85                  90                  95

Leu Thr Phe Gly Gly Gly Thr Lys Val Glu Ile Lys
            100                 105

<210> SEQ ID NO 295
<211> LENGTH: 366
<212> TYPE: DNA
<213> ORGANISM: Homo sapiens

<400> SEQUENCE: 295
gaggtgcagc tgctcgagtc gggcccagga ctggtgaagc cttcggagac cctgtccctc    60
acctgcgctg tctctggtga ctccatcagc agtggtttgg ctggagctg atccgccag    120 accccaggga aggggctgga gtggattgga tacatcggtg gtagtagggg caacaccaac    180
tacaacccct cgttcaagag tcgagtcacc atttcaaggg acacgtccaa gaaccagttc    240
tccctgaggc tgtcctctat gaccgccgcg gacacggccg tctattactg tgcgagaagg    300
gccccgtatt ggggttattc ctatcttgac tactggggcc agggagtcct ggtcaccgtc    360
tcctca                                                               366

<210> SEQ ID NO 296
<211> LENGTH: 327
<212> TYPE: DNA
<213> ORGANISM: Homo sapiens

<400> SEQUENCE: 296
gcggccgagc tcacgcagtc tccagccacc ctgtctttgt ctccagggga aacagccacc    60
ctctcctgca gggccagtca gagtattggc agctccttag cctggtacca gcagagacct    120
gggcaggctc ccaagctcct cgtccatagt gcatacttca gggccgctgg catcccagac    180
aggttcagcg gcagcgggtc taggacagac ttcactctca ccattagcag cctggagcct    240
gaagatgttg gagtttatca ctgtcagcag tataacgact tgcttccgct cactttcggc    300
ggagggacca aggtggaact caagcga                                        327

<210> SEQ ID NO 297
<211> LENGTH: 327
<212> TYPE: DNA
<213> ORGANISM: Homo sapiens

<400> SEQUENCE: 297
gcggccgagc tcacgcagtc tccagccacc ctgtctttgt ttccagggga aacagccacc    60
ctctcctgca gggccagtca gagtattggc agccacttag cctggtacca gcagaaacct    120
gggcaggctc ccaagctcct cgtccatagt gtatccttca gggccactgg catcccagac    180
aggttccgtg gcagcgggtc taggacagac ttcactctca ccattagcag cctggaacct    240
gaagatgttg gagtttatca ctgtcagcag tataacgact tacttccgct cactttcggc    300
ggagggacca aggtggagat caaacga                                        327

<210> SEQ ID NO 298
<211> LENGTH: 333
<212> TYPE: DNA

<213> ORGANISM: Homo sapiens

<400> SEQUENCE: 298

| gcggccgagc tcacactcac gcagtctcca gccaccctgt ctttgtctcc aggggaaaca | 60 |
| gccaccctct cgtgcagggc cagtcagagt gttggcagcc acttagcctg gtaccagcag | 120 |
| aaacctggac aggctcccaa gctcctcgtc catagtgcgt acttcagggc cactggcatc | 180 |
| ccagacaggt tcagtggcag cgggtctagg acagacttca ctctcaccat tagcagcctg | 240 |
| gagcctgaag atgttggagt ttatcactgt cagcagtata acgacttgct tccgctcact | 300 |
| ttcggcggag ggaccaaggt ggagatcaaa cga | 333 |

<210> SEQ ID NO 299
<211> LENGTH: 327
<212> TYPE: DNA
<213> ORGANISM: Homo sapiens

<400> SEQUENCE: 299

| gcggccgagc tcactcagtc tccagccacc ctgtctttgt ctccagggga acagccacc | 60 |
| ctctcctgca gggccagtca gagtgttggc agctccttag cctggtacca gcagaaacct | 120 |
| gggcaggctc ccaaactcct cgtccatagt atatccgtag ggccactgg catcccagac | 180 |
| aggttcagtg gcagcgggtc taggacagac ttcactctca ccatcaccag cctggagcct | 240 |
| gaagatgttg gagtttatca ctgtcaacaa tataacgact tctttccgct cactttcggc | 300 |
| ggagggacca aggtggagat caaacga | 327 |

<210> SEQ ID NO 300
<211> LENGTH: 333
<212> TYPE: DNA
<213> ORGANISM: Homo sapiens

<400> SEQUENCE: 300

| gcggccgagc tcgtgatgac gcagtctcca gccaccctgt ctttgtctcc aggggaaaca | 60 |
| gccaccctct cctgcagggc cagtcagagt gttggcagta acttagcctg gtaccagcag | 120 |
| aaacctgggc aggctcccaa gctcctcgtc catagtgcat acttcagggc cactggcatc | 180 |
| ccagacaggt tcagtggcag cgggtctagg acagacttca ctctcaccat tagcagcctg | 240 |
| gagcctgaag atgttggagt ttatcactgt cagcagtata acgacttgct tccgctcact | 300 |
| ttcggcggag ggaccaaggt ggagatcaat cga | 333 |

<210> SEQ ID NO 301
<211> LENGTH: 327
<212> TYPE: DNA
<213> ORGANISM: Homo sapiens

<400> SEQUENCE: 301

| gcggccgagc tcacgcagtc tccagccacc ctgtctttgt ctccagggga ggcagccacc | 60 |
| ctctcctgca gggccagtca gagtattggc acctccttag cctggtacca acagaaacct | 120 |
| ggacaggctc ccaggctcct cgtccatagt gcatacttca gggccactgg catcgcagac | 180 |
| aggttcagtg gcagcgggtc taggacagac ttcactctca ccattagcag cctggagcct | 240 |
| gaagatgttg gagtttatta ctgtcagcag tataacgact tgctcccgct cactttcggc | 300 |
| ggagggacca aggtggagat caaacga | 327 |

<210> SEQ ID NO 302
<211> LENGTH: 327

```
<212> TYPE: DNA
<213> ORGANISM: Homo sapiens

<400> SEQUENCE: 302
gcggccgagc tcacacagtc tccagccacc ctgtctttgt ctccagggga aagagccacc      60
ctctcctgca gggccagtca gagtgttggc agcaggttag cctggtacca gcagaaacct     120
gggcaggctc ccaggctcct catctatggt gcatccagca gggccactgg catcccagac     180
aggttcagtg gcagcgggtc taggacagac ttcactctca ccattagcag cctggagcct     240
gaagatgttg gagtttatca ctgtcagcag tataacgact tgcttccgct cactttcggc     300
ggagggacca aggtggagat caaacga                                         327

<210> SEQ ID NO 303
<211> LENGTH: 333
<212> TYPE: DNA
<213> ORGANISM: Homo sapiens

<400> SEQUENCE: 303
gcggccgagc tcacactcac gcagtctcca gccaccctgt ctttgtctcc agggaaaaca      60
gccaccctct cctgcagggc cagtcagagt cttggcagca ggttagcctg gtaccaacag     120
aaacctgggc agcctcccag gctcctcatc tatggtgcat ccaccagggc cactggcatc     180
ccagacaggt tcagtggcag cgggtctagg acagacttca ctctcaccat tagcagcctg     240
gagcctgaag atgttggagt ttatcactgt cagcagtata cgacttccc tccgctcact      300 ttcggcggag ggaccaaggt ggagatcaaa cga                                  333

<210> SEQ ID NO 304
<211> LENGTH: 327
<212> TYPE: DNA
<213> ORGANISM: Homo sapiens

<400> SEQUENCE: 304
gcggccgagc tcacgcagtc tccagccacc ctgtctttgg ctccagggga aacagccacc      60
ctctcctgca gggccagtca gagtattggc actaacttag cctggtatca ccagaaacct     120
gggcagcctc ccaagctcct cgtccatact gcatatgtca gggccactgg catcccaaac     180
aggttcagtg gcagcgggtc taggacagac ttcactctca ccattaacag cctgcagcct     240
gaagatgttg gcgtttatca ctgtcagcaa tacaacgact tgcttcctct cactttcggc     300
ggagggacca agatagacat caaacga                                         327

<210> SEQ ID NO 305
<211> LENGTH: 327
<212> TYPE: DNA
<213> ORGANISM: Homo sapiens

<400> SEQUENCE: 305
gcggccgagc tcacgcagtc tccagccacc ctgtctttgt ctccagggga aacagccacc      60
ctctcctgca gggccagtga gagtgttggc agctccttag cctggtacca ccagaagcct     120
gggcaggctc ccaggctcct cgtccatagt gcatccttca gggccactgg catcccagac     180
aggttcagtg gcagcgggtc taggacagag ttcactctca ccgttagcag cctggagcct     240
gaagatgttg gagtttatca ctgtcagcag tataacgact tgcttccgct cactttcggc     300
ggagggacca aggtggagat caaacga                                         327

<210> SEQ ID NO 306
```

```
<211> LENGTH: 327
<212> TYPE: DNA
<213> ORGANISM: Homo sapiens

<400> SEQUENCE: 306
gcggccgagc tcacgcagtc tccagccacc ctgtctgtgt ctccagggga agcagccacc      60
ctctcctgca gggccagtca gactgttggc agaaacttag cctggtacca gcagaagcct     120
gggcaggctc ccaagctcct cgtccatagt gcacacttca gggccactgg catcccggac     180
aggttcagtg gcagcgggtc tgggacagac ttcactctca ccattagcag cctggagcct     240
gaagacgctg gaatttatca ctgtcagcaa tataacgact tgcttccgct cactttcggc     300
ggagggacca aggtggagat caaacga                                         327

<210> SEQ ID NO 307
<211> LENGTH: 324
<212> TYPE: DNA
<213> ORGANISM: Homo sapiens

<400> SEQUENCE: 307
gcggccgagc tcacacagtc tccagccttt cggtctgtga ctctgaagga gaaagtcacc      60
atcacctgcc aggccagtca gagcattggt agtagcttac actggtacca gcagaaaccg     120
gatcagtctc caaaactcct catcaagttt gcttcccagt ccatttcagg ggtcccctca     180
aggttcagtg gcagtggata tgggacagat ttcaccctca ctatcaatag cctggaagct     240
gaagatgctg cgacgtatta ctgtcatcag agtagtagtt tcccgtggac gttcggccaa     300
gggaccaagg tggaaatcaa acga                                            324

<210> SEQ ID NO 308
<211> LENGTH: 324
<212> TYPE: DNA
<213> ORGANISM: Homo sapiens

<400> SEQUENCE: 308
gcggccgagc tcactcagtc tccagccttt cggtctgtga ctctaaagga gaaagtcacc      60
atcacctgcc aggccagtca gagcattggt agtagcttac actggtacca gcagaaaccg     120
gatcagtctc caaagctcct catcaagtat gcttcccagt ccatctcagg ggtcccctca     180
aggttcagtg gcagtggatc tgggacagat ttcaccctca ctatcaatag cctggaagct     240
gaagatgctg cgacgtatta ctgtcagcag agtagtagtt tcccattcac tttcggcccc     300
gggaccaaac tggatatcaa acga                                            324

<210> SEQ ID NO 309
<211> LENGTH: 333
<212> TYPE: DNA
<213> ORGANISM: Homo sapiens

<400> SEQUENCE: 309
gcggccgagc tcacactcac gcagtctcca gccaccctgt ctttgtctcc aggggaaaga      60
gccaccctct cctgcagggc cagtcagagt gtcagcagca ggttagcctg gtaccagcag     120
aaacctgggc aagctcccag gctcctcatc tatgatgcat ccagcagggt cactggtatc     180
ccagacaggt tcagtggcag cgggtctggg acagacttca ctctcaccat cagcagcctg     240
gagcctgaag atgttggagt ttatcactgt cagcagtata cgacttgctc cgctcact       300 ttcggcggag ggaccaaggt ggagatcaaa cga                                  333
```

```
<210> SEQ ID NO 310
<211> LENGTH: 327
<212> TYPE: DNA
<213> ORGANISM: Homo sapiens

<400> SEQUENCE: 310
gcggccgagc tcacgcagtc tccagccacc ctgtctttgt ctccagggga aacagccacc      60
ctctcctgca gggccagtca gagtgttggc agcaacttag cctggtacca gcagaaacct     120
gggcaggctc ccaagctcct cgtccatagt ggttccgtca gggccactgg catcccagac     180
aggttcagtg gcagcgggtc taggacagac ttcactctca tcattagcag cctggagcct     240
gaagatgttg gagtttatca ctgtcagcag tataacgact tgcttccgct cactttcggc     300
ggagggacca aggtggagat caaacga                                         327

<210> SEQ ID NO 311
<211> LENGTH: 333
<212> TYPE: DNA
<213> ORGANISM: Homo sapiens

<400> SEQUENCE: 311
gcggccgagc tcacactcac gcagtctcca gccaccctgt ctttggctcc aggggaaaca      60
gccaccctct cctgtagggc cagtcagagt attggcacta acttagcctg gtatcaccaa     120
aaacctgggc agtctcccaa gctcctcgtc catagtgcat atgtccgggc cactggcatc     180
ccagacaggt tcagtggcag cgggtctagg acagacttca ctctcaccat taacagcctg     240
cagcctgaag atgttggcgt ttatcactgt cagcagtata cgacttgct ccgctcact      300 ttcggcggag gaaccaaggt ggagatcaaa cga                                  333

<210> SEQ ID NO 312
<211> LENGTH: 333
<212> TYPE: DNA
<213> ORGANISM: Homo sapiens

<400> SEQUENCE: 312
gcggccgagc tcacactcac gcagtctcca gccaccctgt ctttgtctcc aggggaaaca      60
gccaccctct cctgcagggc cagtcagact gttggcagaa acttagcctg gtaccagcag     120
aggcctgggc aggctcccaa cctcctcgtc catagtgcat acttcagggc cactggcatc     180
ccggacaggt tcagtggcag cgggtctggg acagacttca ctctcaccat tagcagcctg     240
gagcctgaag atgctggagt ttatcactgt cagcaatata cgacttgct ccgctcact      300 ttcggcggag ggaccaaggt ggagatcaaa cga                                  333

<210> SEQ ID NO 313
<211> LENGTH: 327
<212> TYPE: DNA
<213> ORGANISM: Homo sapiens

<400> SEQUENCE: 313
gcggccgagc tcacgcagtc tccagccacc ctgtctttgg ctccagggga aacagccacc      60
ctctcctgca gggccagtca gagtgttggc actaacttag cctggtatca ccagaaacct     120
gggcagcctc ccaagctcct cgtccatagt gcatatgtca gggccactgg catcccagac     180
aggttcagtg gcagcgggtc taggacagac ttcactctca ccattaacag cctgcagcct     240
gaagatgttg gcgtttatca ctgtcagcag tataacgact tgcttccgct cactttcggc     300
ggagggacca agatagacat caaacga                                         327
```

<210> SEQ ID NO 314
<211> LENGTH: 324
<212> TYPE: DNA
<213> ORGANISM: Homo sapiens

<400> SEQUENCE: 314
gcggccgagc tcactcagtc tccagccttt cggtctgtga gtctgaagga gacagtcacc     60
ctcacctgcc aggccagtca gagcgttggt agtaacttac actggtacca gcagaaaccg    120
gctcagtctc caaaactcct catcaagtat gcttcccagt ccatctcagg ggtcccctca    180
aggttcagtg cactggatc tgggacagat tcacccctca ctatcaatag tctggaagct    240
gaagatgctg cgacatatta ctgtcagcag actaatactt tcccgtggac gttcggccaa    300
gggaccaggg tggaaatcaa gcga                                           324

<210> SEQ ID NO 315
<211> LENGTH: 327
<212> TYPE: DNA
<213> ORGANISM: Homo sapiens

<400> SEQUENCE: 315
gcggccgagc tcactcagtc tccagccacc ctgtctttgt ctccagggga aacagccacc     60
ctctcctgca gggccagtca gagtgttggc agcaacttag cctggtacca gcagaaacct    120
gggcaggctc ccaagctcct cgtccatagt gcatacttca gggccactgg catcccagac    180
aggttcagtg gcagcgggtc taggacagac ttcactctca ccattagcag cctggagcct    240
gaagatgttg gagtttatca ctgtcagcag tataacgact gcttccgct cactttcggc    300 ggagggacca aggtggagat caaacga                                        327

<210> SEQ ID NO 316
<211> LENGTH: 327
<212> TYPE: DNA
<213> ORGANISM: Homo sapiens

<400> SEQUENCE: 316
gcggccgagc tcacgcagtc tccagccacc ctgtctttgt ctccagggga aacagccacc     60
ctctcctgca gggccagtca gagtgttggc agctacttag cctggtacca gcagaaacct    120
gggcaggctc ccaagctcct cgtccatggt gcatacttca gggccgctgg catcccagac    180
aggttcactg gcagcgggtc tcggacagac ttcactctca ccattagcag cctggagcct    240
gaagatgttg gaatttatca ctgtcagcag tataacgact gcttccgct cactttcggc    300 ggagggacca aggtggagat caaacga                                        327

<210> SEQ ID NO 317
<211> LENGTH: 327
<212> TYPE: DNA
<213> ORGANISM: Homo sapiens

<400> SEQUENCE: 317
gcggccgagc tcacgcagtc tccagccacc ctgtctttgt ctccagggga aacagccacc     60
ctctcctgca gggccagtca gagtgttggc agctccttag cctggtacca gcagaaacct    120
gggcaggctc ccaagctcct cgtccatagt gcatacttca gggccactgg catcccagac    180
aggttcagtg gcagcgggtc taggacagac ttcactctca ccattagcag cctggagcct    240
gaagatgttg gagtttatca ctgtcaccag tataacgact gcttccgct cactttcggc    300 ggagggacca aggtggagat caaacga                                        327

```
<210> SEQ ID NO 318
<211> LENGTH: 327
<212> TYPE: DNA
<213> ORGANISM: Homo sapiens

<400> SEQUENCE: 318
gcggccgagc tcacgcagtc tccagccacc ctgtctttgt ctccagggga aacagccacc      60
ctctcctgca gggccagtca gagtgttggc agctccttag cctggtacca gcagaaacct     120
gggcaggctc ccaaactcct cgtccatagt gcatacttca gggccactgg catcccagac     180
aggttcagtg gcagcgggtc taggacagac ttcactctca ccattagcag cctggagcct     240
gaagatgttg gagtttatca ctgtcagcag tataacgact tgcttccgct cactttcggc     300
ggagggacca aggtggagat caaacga                                         327

<210> SEQ ID NO 319
<211> LENGTH: 333
<212> TYPE: DNA
<213> ORGANISM: Homo sapiens

<400> SEQUENCE: 319
gcggccgagc tcgtgatgac acagtctcca gccaccctgt ctttgtctcc aggggaaaca     60
gccacccttt cctgcagggc cagtcagagt attggcagca acttagcctg gtaccagcag    120
aaacctgggc aggctcccaa gctcctcgtc catagtgcaa acatcagggc cactggcatc    180
ccagacaggt tcattggcag cgggtctagg acagacttca ctctcaccat tagcagcctg    240
gagcctgaag atgttggagt ttatcactgt cagcagtata cgacttcct ccgctcact     300 ttcggcggag ggaccaaggt ggagatcaaa cga                                 333

<210> SEQ ID NO 320
<211> LENGTH: 333
<212> TYPE: DNA
<213> ORGANISM: Homo sapiens

<400> SEQUENCE: 320
gcggccgagc tcacactcac gcagtctcca gccaccctgt ctttgtctcc aggggaaaca     60
gccaccctct cctgcagggc cagtcagagt cttggcggca ggttagcctg gtaccagcag    120
aaacctgggc aggctcccag gctcctcatc tatggtgcat ccaccagggc cactggcatc    180
ccagacaggt tcagtggcag cgggtctagg acagagttca ctctcaccat tgccggcctg    240
gagcctgaag atgttggagt ttatcactgt cagcagtata cgacttcct ccgctcact     300 ttcggcggag ggaccaaggt ggagatcaaa cga                                 333

<210> SEQ ID NO 321
<211> LENGTH: 327
<212> TYPE: DNA
<213> ORGANISM: Homo sapiens

<400> SEQUENCE: 321
gcggccgagc tcacgcagtc tccagccatc ctgtctttgt ctccagggga aacagccacc      60
ctctcctgta gggccagtca gagtattggc acgtccttag cctggtacca gcagaaacct     120
gggcaggctc ccaagctcct cgtccatagt gcatactaca gggccactga catcccagag     180
aggttcagtg gcagcggatc taggacagac ttcactctca ccattagcag cctggagcct     240
gaagatgttg gagtttatca ctgtcagcag tataacgact tgcttccgct cactttcggc     300
```
ggagggacca aggtggagat caaacga                                              327

<210> SEQ ID NO 322
<211> LENGTH: 327
<212> TYPE: DNA
<213> ORGANISM: Homo sapiens

<400> SEQUENCE: 322
gcggccgagc tcacgcagtc tccagccacc ctgtctttgg ctccagggga aacagccacc    60
ctctcctgca gggccagtca gagtattggc actaacttag cctggtatca ccagaaacct   120
gggcagcctc ccaagctcct cgtccatagt gcatatgtca gggccactgg catcccaaac   180
aggttcagtg gcagcgggtc taggacagac ttcactctca ccattaacag cctgcagcct   240
gaagatgttg gcgtttatca ctgtcaacag tacaacgact tgcttcctct cactttcggc   300
ggagggacca agatagacat caaacga                                              327

<210> SEQ ID NO 323
<211> LENGTH: 327
<212> TYPE: DNA
<213> ORGANISM: Homo sapiens

<400> SEQUENCE: 323
gcggccgagc tcacacagtc tccagccacc ctgtctttgt ctccagggga aacagccacc    60
ctctcctgca gggccagtca gagtgttggc agcaacttag cctggtacca gcagaaacct   120
gggcaggctc ccaagctcct cgtccatagt gcatccgtca gggccactgg catcccagac   180
aggttcagtg gcagcgggtc taggacagac ttcactctca ccattagtag cctggagcct   240
gaagatgttg gagtttatca ctgtcagcag tataacgact tctttccgct cactttcggc   300
ggagggacca aggtggagat caaacga                                              327

<210> SEQ ID NO 324
<211> LENGTH: 327
<212> TYPE: DNA
<213> ORGANISM: Homo sapiens

<400> SEQUENCE: 324
gcggccgagc tcacgcagtc tccagccacc ctgtctgtgt ctccagggga agcagccacc    60
ctctcctgca gggccagtca gactgttggc agaaacttag cctggtacca gcagaagcct   120
gggcaggctc ccaagctcct cgtccatagt gcacacttca gggccactgg catcccggac   180
aggttcagtg gcagcgggtc tgggacagac ttcactctca ccattagcag cctggagcct   240
gaagatgctg gaatttatca ctgtcagcaa tataacgact tgcttccgct cactttcggc   300
ggagggacca aggtggagat caaacga                                              327

<210> SEQ ID NO 325
<211> LENGTH: 327
<212> TYPE: DNA
<213> ORGANISM: Homo sapiens

<400> SEQUENCE: 325
gcggccgagc tcacgcagtc tccagccacc ctgtctttgt ctccagggga aacagccacc    60
ctctcctgca gggccagtca gagtcttggc agcaggttag cctggtacca gcagaaacct   120 ggcaggctc ccaggctcct catctatggt gcatccacca gggccactgg catcccagac   180
aggttcagtg gcagcgggtc taggacagac ttcactctca ccattagcag cctggagcct   240
gaagatgttg gagtttatca ctgtcagcag tataacgact tccttccgct cacgttcggc   300

```
ggagggacca aggtggagat caaacga                                              327
```

<210> SEQ ID NO 326
<211> LENGTH: 333
<212> TYPE: DNA
<213> ORGANISM: Homo sapiens

<400> SEQUENCE: 326

```
gcggccgagc tcacactcac gcagtctcca gccaccctgt ctttgtctcc aggggaaaca    60
gccaccctct cctgcagggc cagtcagagt gttggcagct acttagcctg gtaccagcag   120
aaacctgggc aggctcccaa gctcctcgtc catagtgcac acttcagggc cactggcatc   180
ccagacaggt tcagtggcag cgggtctagg acagacttca ctctcaccat tagcagcctg   240
gagcctgaag atgttggagt ttatcactgt cagcagtata cgacttact tcccctcact    300
ttcggcggag ggaccaaggt ggagatcaaa cga                                 333
```

<210> SEQ ID NO 327
<211> LENGTH: 333
<212> TYPE: DNA
<213> ORGANISM: Homo sapiens

<400> SEQUENCE: 327

```
gcggccgagc tcgtgatgac gcagtctcca gccaccctgt ctttgtctcc aggggaaaca    60
gccaccctct cctgcagggc cagtcagagt gttggcagca acttagcctg gtaccagcag   120
aaacctgggc aggctcccaa gctcctcgtc catagtgcaa acttcagggc cactggcatc   180
tcagacaggt tcagtggcag cgggtctagg acagacttca ctctcaccat cagcagcctg   240
gagcctgaag atgttggagt ttatcactgt cagcagtata cgacttgct tccgctcact    300
ttcggcggag ggaccaaggt ggagatcaaa cga                                 333
```

<210> SEQ ID NO 328
<211> LENGTH: 327
<212> TYPE: DNA
<213> ORGANISM: Homo sapiens

<400> SEQUENCE: 328

```
gcggccgagc tcacacagtc tccagccacc ctgtctttgt ctccagggga aacagccacc    60
ctctcctgca gggccagtca gagtgttggc agtaatgtag cctggtacca gcagaaacct   120
gggcaggctc ccaagctcct cgtccatagt gcatactaca gggccactgg catcccagac   180
aggttcagtg gcagcgggtc taggacagac ttcactctca ccattagcag cctggagcct   240
gaggatgttg gagtttatca ctgtcagcag tataacgact tgcttccgct cactttcggc   300
ggagggacca aggtggagat caaacga                                        327
```

<210> SEQ ID NO 329
<211> LENGTH: 363
<212> TYPE: DNA
<213> ORGANISM: Homo sapiens

<400> SEQUENCE: 329

```
gaggtgcagc tgctcgagtc aggtccagga ctggtgaagc cttcagagac cctgtcgctc    60
acctgcgctg tctctggagg ctctctcagc ggtgggtatg actggagctg gatccgccag   120
tcctcaagaa aggggctgga gtggattggc tatatctatg atagtcgttg gaccaccaac   180
tacaacccgt ccctcaagaa gcgcgtcacc atttcaatag acacgtccaa gaaccagttc   240
```

```
tccctgaacc tcaagtctgt gaccgccgcg gacacggccg tgtattattg tgcgagacga    300
ggcggctacg gtgccagcta ctttgactta tggggccagg gagtcctggt caccgtctcc    360
tca                                                                  363
```

<210> SEQ ID NO 330
<211> LENGTH: 363
<212> TYPE: DNA
<213> ORGANISM: Homo sapiens

<400> SEQUENCE: 330

```
gaggtgcagc tgctcgagtc gggcccagga ctggtgaagc catcggagac cctgtccctc     60
acctgcgctg tctctggtta ctccctcagc agtgcttatg ctggaactg gatccgacag    120 tcccccggga aggggctgga gtggattggg tctatcggtg gtagtaggga taatgtcaac    180
tacaacccct ccctcaagag cgagtcacc atttcaaaag acacgtccac gaaccacttc    240
tccctgaggc tgagttctgt gacggccgcg gacacggccg tgtattattg tgtgagacgc    300
gcgacctacg gtaacagcta ctttgactcc tggggccagg gagtccaggt cacggtctct    360
tca                                                                  363
```

<210> SEQ ID NO 331
<211> LENGTH: 363
<212> TYPE: DNA
<213> ORGANISM: Homo sapiens

<400> SEQUENCE: 331

```
gaggtgcagc tgctcgagtc tggcccagga ctggtgaagc cttcggagac cctgtccctc     60
acctgcactg tctctggttc ctccctcagc agtgcttatg ggtggaactg gatccgccag    120
cccccaggga aggggctgga gtggattggg tctatcggtg gtagtaggga taacaccaac    180
tataatccct ccctcaagag gcgagtcacc atttcaaagg acacgtccaa gaaccagttc    240
tccctgaagc tgaagtctgt gaccgccgcg gacacggctg tctattactg tgcgcagagg    300
ggtgcttacg gttattccta ttttgactac tggggacagg gagtcctggt cgccgtctcc    360
tca                                                                  363
```

<210> SEQ ID NO 332
<211> LENGTH: 363
<212> TYPE: DNA
<213> ORGANISM: Homo sapiens

<400> SEQUENCE: 332

```
gaggtgcagc tgctcgagtc tggcccggga ctggtgaagc cttcggagac cctgtccctc     60
acctgcgctg tctctggtga ctccatcagc agcggctatg ctggcactg gatccgccag    120 gtcccaggga gggggctgga gtggattgga tctatcggtg gtagtagggg tacgaccaac    180
tacaatccct ccctcaagag tcgagtcacc atttcagaag acacgtccaa gaaccagttc    240
tccctgagtc tgaggtcagt gtccgccgcg gacacggccg tgtatttctg tgcgagagac    300
agcggatata gtttccgtta ctttgacttc tggggtcagg gagtcctggt caccgtctcc    360
tca                                                                  363
```

<210> SEQ ID NO 333
<211> LENGTH: 363
<212> TYPE: DNA
<213> ORGANISM: Homo sapiens

<400> SEQUENCE: 333

```
gaggtgcagc tgctcgagtc gggcccagga ctggtgaagc cttcggagac cctgtccctc    60
acctgcgctg tctctggtta ctccatcagc agtggttatg gctggaactg gatccgccag   120
cccccaggga aggggctgga gtggattggg tctatcggcg gtagtaggga taacaccaac   180
tacaacccct ccctcaaaag tcgagtcacc ctttcaaaag acacatccaa gaaccacttc   240
tccctgaggc tgcgctctgt gaccgccgcg gacacggctg tgtattactg cgagagat    300
ggtgggtacg gttcccgata catggactcc tggggccagg gagtcctggt cgccgtctcc   360
tct                                                                 363

<210> SEQ ID NO 334
<211> LENGTH: 363
<212> TYPE: DNA
<213> ORGANISM: Homo sapiens

<400> SEQUENCE: 334
gaggtgcagc tgctcgagtc gggcccagga ctggtgaggc cttcggagac cctgtccctc    60
acctgcgctg tctctggtta ctccatcagc agtggttatg gctggcactg gatccgccag   120
cccccaggga aggggctgga gtcgcttggc tatatcggtg gtagtagggg taacaccaac   180
tacaaccct ccctcaagag tcgagtcacc atttcaacag acacgtccaa gaaccagttc    240
tccctgaagc tgaggtctgt gaccgccgcg gacacggccg tgtattactg cgagagat    300
tccggataca acacaagata cttttgactac tggggccagg gagtcctggt caccgtctcc   360
tca                                                                 363

<210> SEQ ID NO 335
<211> LENGTH: 363
<212> TYPE: DNA
<213> ORGANISM: Homo sapiens

<400> SEQUENCE: 335
gaggtgcagc tgcagctgcc tgggccagga ctggtgaagc cttcggagac cctgtccctc    60
acctgcactg tctctggttc ctccctcagc agtgcttatg ggtggaactg gatccgccag   120
cccccaggga aggggctgga gtggattggg tctatcggtg gtagtaggga taacaccaac   180
tataatccct ccctcaagag gcgagtcacc atttcaaagg acacgtccaa gaaccagttc   240
tccctgaagc tgaagtctgt gaccgccgcg gacacggccg tctattactg cgcagagg    300
ggtgcttacg gttattccta ttttgactac tggggacagg gagtcctggt cgccgtctcc   360
tca                                                                 363

<210> SEQ ID NO 336
<211> LENGTH: 363
<212> TYPE: DNA
<213> ORGANISM: Homo sapiens

<400> SEQUENCE: 336
gaggtgcagc tgctcgagtc aggcccagga ctggtgaagc cttcagagac cctgtccctc    60
acctgcgctg tctctggagg ctctatcagc ggtggttatg actggagttg gatccgccag   120
tccccaggga aggggctgga gtggattggt tatatctatg atagtagggg gaccaccaac   180
tacaaccgt ccctcaggaa gcgggtcgcc atttcaatag acacgtccag gaaccagttt    240
tccctgaacc tgagatctct gaccgccgcg gacacggccg tctattactg cgagacga    300
gccggctacg gtagcgccta cttttgactac tggggccagg gagtcctggt caccgtctcc   360
```

```
tca                                                                    363

<210> SEQ ID NO 337
<211> LENGTH: 363
<212> TYPE: DNA
<213> ORGANISM: Homo sapiens

<400> SEQUENCE: 337
gaggtgcagc tgctcgagtc tggcccagga ctggtgaagc cttcggagac cctgtccctc      60
acctgcgctg tgtctggttc ctccctcagc agtgcttatg ggtggaactg gatccgtcag     120
gctccaggga agcgcctgga gtggattggg tttatcggtg gtagtcgtga taacaccaat     180
tacaacccct ccctcaggag tcgggtcacc atttcaaaag acacgtccaa gaaccacttc     240
tccctgaaac tgacttctgt gaccgccgcg gacacggccg tgtatttctg tgcgagaagg     300
ggggccttcg gtaactccta ctttgactac tggggccagg gagtcccggt caccgtctcc     360
tca                                                                    363

<210> SEQ ID NO 338
<211> LENGTH: 363
<212> TYPE: DNA
<213> ORGANISM: Homo sapiens

<400> SEQUENCE: 338
gaggtgcagc tgctcgagtc tggcccagga ctggtgaagc cttcagagac cctgtccctc      60
acctgcgctg tctctggagg ctctatcagc ggtggttatg actggagttg gatccgccag     120
tccccaggga agggactgga gtggattggt tatatctatg atagcagggg gaccaccaac     180
tacaacccgt ccctcaggaa cgggtcacc atttcaatag acacgtccag gaaccagttc      240
tccctgaagc tgagatctct gaccgccgcg gacacggccg tctattactg tgcgagacga     300
gccggctacg gtagcgccta ctttgactac tggggccagg gagtcctggt caccgtctcc     360
tca                                                                    363

<210> SEQ ID NO 339
<211> LENGTH: 363
<212> TYPE: DNA
<213> ORGANISM: Homo sapiens

<400> SEQUENCE: 339
gaggtgcagc tgctcgagtc gggcccagga ctggtgaagc cttcggagac cctgtccctc      60
acctgcgctg tctctggtta ctccatcagc agtggttatg gctggacctg gatccgccag     120
cccccaggga aggggctgga gtggattggc tatatcggtg gtagtagggg aaacgccaac     180
tacaacccct ccctcaagag tcgagtcacc atttcaaaag acacgtccaa gaaccagttc     240
tccctgaagc tgacctctgt gaccgccgcg gacacggccg tgtattactg tgcgagagat     300 ggggggatacg gagagagata cctcgaattc tggggccagg gcgccctggt caccgtctcc    360
tcc                                                                    363

<210> SEQ ID NO 340
<211> LENGTH: 363
<212> TYPE: DNA
<213> ORGANISM: Homo sapiens

<400> SEQUENCE: 340
gaggtgcagc tgctcgagtc aggcccagga ctggtgaggc cttcggagac cctgtccctc      60
acctgcactg tctctggtaa ctccatcagc agtggttatg gctggaactg gatccgccag     120
```

```
cccccaggga aggggctgga gttgattggg tatatcggtg aagtagaag taataccaac    180 tacaacccct ccctcaagag tcgagtcacc atttcaatag acacgtccaa gaaccagttc    240
tccctgaaac tgaggtctgt gactgccgcg gacacggctg tgtattactg tgcgagagat    300
tggggctacg gttacagata ccttgactac tggggccagg gagtcctggt caccgtctcc    360
tca                                                                  363
```

<210> SEQ ID NO 341
<211> LENGTH: 363
<212> TYPE: DNA
<213> ORGANISM: Homo sapiens

<400> SEQUENCE: 341

```
gaggtgcagc tgctcgagtc tggcccagga ctggtgaagc cttcagagac cctgtccctc    60
acctgcgctg tctctggagg ctctatcaac ggtggttatg actggacctg gatccgccag    120
tccccaggga aggggctgca gtggattggg tggatctatg gtagtagggg gaccaccaac    180
tacaacccgt ccctcaggaa tcgagtcacc atttcaatag acacgtccag gaaccagttc    240
tccctgagcc tgagctctct gaccgccgcg gacacggccg tctattactg tgcgaaacga    300
gtcggctacg gtaacagcta ctttgactcc tggggccagg gagtcctggt caccgtgtcc    360
tca                                                                  363
```

<210> SEQ ID NO 342
<211> LENGTH: 363
<212> TYPE: DNA
<213> ORGANISM: Homo sapiens

<400> SEQUENCE: 342

```
gaggtgcagc tgctcgagtc aggcccagga ctggtgaagc cttcagagac cctgtccctc    60
acctgcgctg tctctggagg ctctatcagc ggtggttatg actggagttg gatccgccag    120
tccccaggga agggactgga gtggattggt tatatctatg atagcagggg gaccaccaac    180
tacaacccgt ccctcaggaa acgggtcacc atttcaatag acacgtccag gaaccagttc    240
tccctgaagc tgagatctct gaccgccgcg gacacggccg tctattactg tgcgagacga    300
gccggctacg gtagcgccta ctttgactac tggggccagg gagtcctggt caccgtctcc    360
tca                                                                  363
```

<210> SEQ ID NO 343
<211> LENGTH: 366
<212> TYPE: DNA
<213> ORGANISM: Homo sapiens

<400> SEQUENCE: 343

```
gaggtgcagc tgctcgagtc gggcccagga ctggtgaagc cttcggagac cctgtccctc    60
acctgcgctg tctctggtga ctccatcagc agtggttatg gctggagctg gatccgccag    120
accccaggga aggggctgga gtggattgga tacatcggtg gtagtagggg caacaccaac    180
tacaacccct ccctcaagag tcgagtcacc atttcaaaag acacgtccaa gaaccagttc    240
tccctgaagc tgagctctgt gaccgccgcg gacacggccg tgtattactg tgcgagaagg    300
gccccgtact ggggttattc ctatcttgac tactggggcc agggagtcct ggtcaccgtc    360
tcctca                                                               366
```

<210> SEQ ID NO 344

<211> LENGTH: 363
<212> TYPE: DNA
<213> ORGANISM: Homo sapiens

<400> SEQUENCE: 344

```
gaggtgcagc tgctcgagtc tggcccagga ctggtgaagc cttcggagac cctgtccctc      60
acctgcactg tctctggttc ctccctcagc agtgcttatg ggtggaactg gatccgccag     120
cccccaggga aggggctgga gtggattggg tctatcggtg gtagtaggga taacaccaac     180
tataatccct ccctcaagag gcgagtcacc atttcaaagg acacgtccaa gaaccagttc     240
tccctgaagc tgaagtctgt gaccgccgcg gacacggccg tctattactg tgcgcagagg     300
ggtgcttacg gttattccta ttttgactac tggggacagg gagtcctggt cgccgtctcc     360
tca                                                                    363
```

<210> SEQ ID NO 345
<211> LENGTH: 363
<212> TYPE: DNA
<213> ORGANISM: Homo sapiens

<400> SEQUENCE: 345

```
gaggtgcagc tgctcgagtc gggcccagga ctggtgaagc cttcggagac cctgtccctc      60
acctgcactg tctctggtta ctccatcagc agtggttatg gctggggctg gatccgccag     120
tccccaggga aggggctgga gtggattggc tattttggtg gtagtagagg taacaccaac     180
tacaacccct ccctcaagag tcgagtcacc atttcacaag acacgtccaa gaatcagttc     240
tccctgaaac tgaagtctgt gaccgccgcg gacacgggca tttattactg cgcgcgagac     300
agcggttatt cccggcgttg ggttgactac tggggccagg gagtcctggt caccgtctcc     360
tca                                                                    363
```

<210> SEQ ID NO 346
<211> LENGTH: 363
<212> TYPE: DNA
<213> ORGANISM: Homo sapiens

<400> SEQUENCE: 346

```
gaggtgcagc tgctcgagtc gggcccagga ctggtgaagc ctttggagac cctgtccctc      60
acctgcgatg tctctggttt ctccattagt agtgattatg gctggagctg gatccgccag     120
cccccaggga aggggctgga gttgattggc tatatcggtg gtagtcgtgg taacaccaac     180
tataacccct ccctcaagag tcgagtcacc atttcaagag acacttccaa gaatcagttc     240
tccctgaagc tgacctctgt gaccgccgcg gacacggccg tctactactg tgcgagagat     300
tggggctacg gttataggta ctttgacttc tggggccagg gagtcctggt caccgtctcc     360
tca                                                                    363
```

<210> SEQ ID NO 347
<211> LENGTH: 363
<212> TYPE: DNA
<213> ORGANISM: Homo sapiens

<400> SEQUENCE: 347

```
gaggtgcagc tgctcgagtc gggcccagga ctggtgaggc cttcggagac cctgtccctc      60
acctgcgctg tctctggtta ctccatcagc agtggttatg gctggcactg gatccgccag     120
cccccaggga aggggctgga gtcgcttggc tatatcggtg gtagtagggg taacaccaac     180
tacaacccct ccctcaagag tcgagtcacc atttcaacag acacgtccaa gaaccagttc     240
```

```
tccctgaagc tgaggtctgt gaccgccgcg gacacggccg tgtattactg tgcgagagat      300
tccggataca acacaagata ctttgactac tggggccagg gagtcctggt caccgtctcc      360
tca                                                                    363
```

<210> SEQ ID NO 348
<211> LENGTH: 372
<212> TYPE: DNA
<213> ORGANISM: Homo sapiens

<400> SEQUENCE: 348

```
gaggtgcagc tggaggtgca gctgctcgag tctggcccag gactggtgaa gccttcggag       60
accctgtccc tcacctgcac tgtctctggt tcctccctca gcagtgctta tgggtggaac      120
tggatccgcc agcccccagg gaaggggctg gagtggattg gtctatcgg tggtagtagg       180 gataacacca actataatcc ctccctcaag aggcgagtca ccatttcaaa ggacacgtcc      240
aagaaccagt tctccctgaa gctgaagtct gtgaccgccg cggacacggc tgtctattac      300
tgtgcgcaga ggggtgctta cggttattcc tattttgact actggggaca gggagtcctg      360
gtcgccgtct cc                                                          372
```

<210> SEQ ID NO 349
<211> LENGTH: 363
<212> TYPE: DNA
<213> ORGANISM: Homo sapiens

<400> SEQUENCE: 349

```
gaggtgcagc tgctcgagtc gggcccagga ctggtgaagc cttcggagac cctgtccctc       60
acctgcactg tctctggttc ctccctcagc agtgcttatg ggtggaactg gatccgccag      120
ccccagggaa ggggctgga gtggattggg tctatcggtg gtagtaggga taacaccaac      180
tataatccct ccctcaagag gcgagtcacc atttcaaagg acacgtccaa gaaccagttc      240
tccctgaagc tgaagtctgt gaccgccgcg gacacggccg tctattactg tgcgcagagg      300
ggtgcttacg gttattccta ttttgactac tggggacagg gagtcctggt cgccgtctcc      360
tca                                                                    363
```

<210> SEQ ID NO 350
<211> LENGTH: 360
<212> TYPE: DNA
<213> ORGANISM: Homo sapiens

<400> SEQUENCE: 350

```
gaggtgcagc tgctcgagtc gggcccagga ctggtgaggc cttcggagac cctgtctgtc       60
acctgcgatg tctctggtgg ctcaatcagc agtgcttcct ggagctggat ccgccaggcc      120
ccagggaaga gactggagtg gattggggct atctctggta gtggtagtcc caccaacgtc      180
aacccctccc tcaagagtcg agtcaccctg tcagtagaca cgtccaagaa ccagctctcc      240
ctgaagttga ggtcaatgac cgccgcggac acggccgtat attactgtgc aagacgaggg      300
ggttacggta atagatactt tgactattgg ggccagggag tcgcggtcac cgtctcctca      360
```

<210> SEQ ID NO 351
<211> LENGTH: 363
<212> TYPE: DNA
<213> ORGANISM: Homo sapiens

<400> SEQUENCE: 351

```
gaggtgcagc tgctcgagtc gggcccagga ctggtgaagc cttcggagac cctgtccctc      60
acctgcactg tctctggttc ctccctcagc agtgcttatg ggtggaactg gatccgccag     120
cccccaggga aggggctgga gtggattggg tctatcggtg gtagtaggga taacaccaac     180
tataatccct ccctcaagag gcgagtcacc atttcaaagg acacgtccaa gaaccagttc     240
tccctgaagc tgaagtctgt gaccgccgcg gacacggccg tctattactg tgcgcagagg     300
ggtgcttacg gttattccta ttttgactac tggggacagg gagtcctggt caccgtctcc     360
tca                                                                   363

<210> SEQ ID NO 352
<211> LENGTH: 363
<212> TYPE: DNA
<213> ORGANISM: Homo sapiens

<400> SEQUENCE: 352
gaggtgcagc tgctcgagtc gggcccagga ctggtgaagc cttcggagac cctgtccctc      60
acctgcactg tctctggttc ctccctcagc agtgcttatg ggtggaactg gatccgccag     120
cccccaggga aggggctgga gtggattggg tctatcggtg gtagtaggga taacaccaac     180
tataatccct ccctcaagag gcgagtcacc atttcaaagg acacgtccaa gaaccagttc     240
tccctgaagc tgaagtctgt gaccgccgcg gacacggccg tctattactg tgcgcagagg     300
ggtgcttacg gttattccta ttttgactac tggggacagg gagtcctggt cgccgtctcc     360
tca                                                                   363

<210> SEQ ID NO 353
<211> LENGTH: 363
<212> TYPE: DNA
<213> ORGANISM: Homo sapiens

<400> SEQUENCE: 353
gaggtgcagc tgctcgagtc tgggccagga ctggtgaagc cttcggagac cctgtcgctc      60
acctgcgctg tctctagtct gtccctcagt agtggttttg cctggagctg gatccgccag     120
cccccaggag agggactgga gtggattggg tctatcggtg gtagtcgtga caacgtcaat     180
tataccccct ccctcaagag tcgagtcacc atttcgaaag acacgtccaa gaaccagttc     240
tccctgagcc tgcgttctgt gaccgccgcg gacacggccg tgtattactg tgtgaccatt     300
catggctacc gtaactggta tcttgaccac tggggccagg gagtcctggt caccgtctcc     360
aca                                                                   363

<210> SEQ ID NO 354
<211> LENGTH: 363
<212> TYPE: DNA
<213> ORGANISM: Homo sapiens

<400> SEQUENCE: 354
gaggtgcagc tgctcgagtc tggcccagga ctggtgaagc cttcggagac cctgtccctc      60
acctgcgctg tctctggtaa ctccatcagc agcgcctatg gctggcactg gatccgccag     120
gtcccaggga aggggctgga gtggattgga tctatcggtg gtagtagggg tacgaccaac     180
tacaatccct ccctcaagag tcgaggcacc atttcagaag acacgtccaa gaaccagttc     240
tccctgagcc tgaggtcagt gtccgccgcg gacacggccg tgtatttctg tgcgagagac     300
agcggatata gtttccgtta ctttgacttc tggggtcggg gagttctggt caccgtctcc     360
tca                                                                   363
```

<210> SEQ ID NO 355
<211> LENGTH: 363
<212> TYPE: DNA
<213> ORGANISM: Homo sapiens

<400> SEQUENCE: 355

```
gaggtgcagc tgctcgagtc gggcccagga ctggtgaggc cttcagagac cctgtcgctc    60
acctgcgctg tctctggagg ctctctcagc ggtggttatg actggagctg gatccgccag   120
tccccaagaa aggggctgga gtggattggc tatatctatg atagtcgtgg gaccaccaac   180
tacaacccgt ccctcaagag gcgagtcacc atttcaatag acacgtccaa gaaccagttc   240
tccctgaacc tcaagtctgt gaccgccgcg gacacggccg tgtattattg cgagacga    300 ggcggctacg gtgccagcta ctttgactta tggggccagg gagtcctggt caccgtctcc   360
tca                                                                  363
```

<210> SEQ ID NO 356
<211> LENGTH: 363
<212> TYPE: DNA
<213> ORGANISM: Homo sapiens

<400> SEQUENCE: 356

```
gaggtgcagc tgctcgagtc tggcccagga ctggtgaagc cttcggagac cctgtccctc    60
acctgcactg tctctggttc ctccctcagc agtgcttatg ggtggaactg gatccgccag   120
cccccaggga aggggctgga gtggattggg tctatcggtg taataggga taacaccaac   180 tataatccct ccctcaagag gcgagtcacc atttcaaagg acacgtccaa gaaccagttc   240
tccctgaagc tgaagtctgt gaccgccgcg gacacggccg tctattactg cgcagagg    300 ggtgcttacg gttattccta ttttgactac tggggacagg gagtcctggt cgccgtctcc   360
tca                                                                  363
```

<210> SEQ ID NO 357
<211> LENGTH: 363
<212> TYPE: DNA
<213> ORGANISM: Homo sapiens

<400> SEQUENCE: 357

```
gaggtgcagc tgctcgagtc tggcccagga ctggtgaagc cttcggagac cctgtccctc    60
acctgcactg tctctggttc ctccctcagc agtgcttatg ggtggaactg gatccgccag   120
cccccaggga aggggctgga gtggattggg tctatcggtg gtagtaggga taacaccaac   180
tataatccct ccctcaagag gcgagtcacc atttcaaagg acacgtccaa gaaccagttc   240
tccctgaagc tgaagtctgt gaccgccgcg gacacggccg tctattactg cgcagagg    300 ggtgcttacg gttattccta ttttgactac tggggacagg gagtcctggt cgccgtctcc   360
tca                                                                  363
```

<210> SEQ ID NO 358
<211> LENGTH: 363
<212> TYPE: DNA
<213> ORGANISM: Homo sapiens

<400> SEQUENCE: 358

```
gaggtgcagc tgctcgagtg gggcccagga ctggtgaagc catcggagac cctgtccctc    60
acctgcgctg tctctggtta ctccctcagc agtgcttatg gctggaactg gatccgacag   120
```

```
tcccccggga agggctgga gtggattggg tctatcggtg gtagtaggga taatgtcaac    180
tacaacccct ccctcaagag gcgagtcacc atttcaaaag acacgtccac gaaccacttc    240
tccctgaggc tgagttctgt gacggccgcg gacacggccg tgtattattg tgtgagacgc    300
gcgacctacg gtaacagcta ctttgactcc tggggccagg gagtccaggt cacggtctct    360
tca                                                                   363

<210> SEQ ID NO 359
<211> LENGTH: 363
<212> TYPE: DNA
<213> ORGANISM: Homo sapiens

<400> SEQUENCE: 359
gaggtgcagc tgctcgagtc aggcccagga ctggtgaagc cctcagagac cctgtccctc    60
acctgcgcgg tctctggagg ctctctcagt ggtggttatg actggtactg gatccgccag    120
tccccaagaa agggcctgga gtatattggt tatatctatg atagtcgtgg gaccaccaac    180
tacaacccgt ccctcaagaa tcgagtcacc atttcaatag acacgtccaa gaaccacttc    240
tccctgaacc tcaagtctgt gaccgccgcg gacacggccg tgtattactg tgcgagacga    300
gtcgggtacg gtgccaccta ttttgactta tggggccagg gagtcctggt caccgtctcc    360
tca                                                                   363

<210> SEQ ID NO 360
<211> LENGTH: 363
<212> TYPE: DNA
<213> ORGANISM: Homo sapiens

<400> SEQUENCE: 360
gaggtgcagc tgctcgagtc tggcccagga ctggtgaagc cttcggagac cctgtccctc    60
acctgcgctg tgtctggtta ctccatcagc agtggttttg cctggaactg gatccgccag    120
accccaggga agggactgga gtggattggg tatatcggtg gtagtcgtga taacaccaac    180
tacaacccct ccctcaagag tcgagtcacc atttcaaaag acacgtccaa gaaccagttc    240
tcccttaagc tgacttctat gaccgccgcg gacacggcca tgtattactg tgcgagaagg    300
ggggcctacg gtaactccta ctttgacttc tggggccagg gagtcccggt caccgtctcc    360
tca                                                                   363

<210> SEQ ID NO 361
<211> LENGTH: 12
<212> TYPE: PRT
<213> ORGANISM: Homo sapiens

<400> SEQUENCE: 361

Leu Val Leu His Thr Val Trp Asn Gly Asn Gly Met
1               5                   10

<210> SEQ ID NO 362
<211> LENGTH: 12
<212> TYPE: PRT
<213> ORGANISM: Homo sapiens

<400> SEQUENCE: 362

Leu Val Leu Asp Thr Val Gly Ala Gly Asn Gly Met
1               5                   10

<210> SEQ ID NO 363
<211> LENGTH: 12
```

```
<212> TYPE: PRT
<213> ORGANISM: Mus musculus

<400> SEQUENCE: 363

Gln Ile Val Thr Glu Pro Lys Ser Ser Asp Leu Trp
1               5                   10

<210> SEQ ID NO 364
<211> LENGTH: 12
<212> TYPE: PRT
<213> ORGANISM: Macaca mulatta

<400> SEQUENCE: 364

Met Ala Leu Arg Val Phe Trp Ala Ser Ser Asn Met
1               5                   10

<210> SEQ ID NO 365
<211> LENGTH: 5
<212> TYPE: PRT
<213> ORGANISM: Homo sapiens

<400> SEQUENCE: 365

His Thr Val Trp Asn
1               5

<210> SEQ ID NO 366
<211> LENGTH: 417
<212> TYPE: PRT
<213> ORGANISM: Homo sapiens

<400> SEQUENCE: 366

Met Ser Ser Lys Tyr Pro Arg Ser Val Arg Arg Cys Leu Pro Leu Trp
1               5                   10                  15

Ala Leu Thr Leu Glu Ala Ala Leu Ile Leu Leu Phe Tyr Phe Phe Thr
                20                  25                  30

His Tyr Asp Ala Ser Leu Glu Asp Gln Lys Gly Leu Val Ala Ser Tyr
            35                  40                  45

Gln Val Gly Gln Asp Leu Thr Val Met Ala Ala Leu Gly Leu Gly Phe
        50                  55                  60

Leu Thr Ser Asn Phe Arg Arg His Ser Trp Ser Ser Val Ala Phe Asn
65                  70                  75                  80

Leu Phe Met Leu Ala Leu Gly Val Gln Trp Ala Ile Leu Leu Asp Gly
                85                  90                  95

Phe Leu Ser Gln Phe Pro Pro Gly Lys Val Val Ile Thr Leu Phe Ser
                100                 105                 110

Ile Arg Leu Ala Thr Met Ser Ala Met Ser Val Leu Ile Ser Ala Gly
            115                 120                 125

Ala Val Leu Gly Lys Val Asn Leu Ala Gln Leu Val Val Met Val Leu
        130                 135                 140

Val Glu Val Thr Ala Leu Gly Thr Leu Arg Met Val Ile Ser Asn Ile
145                 150                 155                 160

Phe Asn Thr Asp Tyr His Met Asn Leu Arg His Phe Tyr Val Phe Ala
                165                 170                 175

Ala Tyr Phe Gly Leu Thr Val Ala Trp Cys Leu Pro Lys Pro Leu Pro
            180                 185                 190

Lys Gly Thr Glu Asp Asn Asp Gln Arg Ala Thr Ile Pro Ser Leu Ser
        195                 200                 205

Ala Met Leu Gly Ala Leu Phe Leu Trp Met Phe Trp Pro Ser Val Asn
        210                 215                 220
```

```
Ser Pro Leu Leu Arg Ser Pro Ile Gln Arg Lys Asn Ala Met Phe Asn
225                 230                 235                 240

Thr Tyr Tyr Ala Leu Ala Val Ser Val Val Thr Ala Ile Ser Gly Ser
            245                 250                 255

Ser Leu Ala His Pro Gln Arg Lys Ile Ser Met Thr Tyr Val His Ser
            260                 265                 270

Ala Val Leu Ala Gly Gly Val Ala Val Gly Thr Ser Cys His Leu Ile
            275                 280                 285

Pro Ser Pro Trp Leu Ala Met Val Leu Gly Leu Val Ala Gly Leu Ile
            290                 295                 300

Ser Ile Gly Gly Ala Lys Cys Leu Pro Val Cys Cys Asn Arg Val Leu
305                 310                 315                 320

Gly Ile His His Ile Ser Val Met His Ser Ile Phe Ser Leu Leu Gly
                325                 330                 335

Leu Leu Gly Glu Ile Thr Tyr Ile Val Leu Leu Val Leu His Thr Val
            340                 345                 350

Trp Asn Gly Asn Gly Met Ile Gly Phe Gln Val Leu Leu Ser Ile Gly
            355                 360                 365

Glu Leu Ser Leu Ala Ile Val Ile Ala Leu Thr Ser Gly Leu Leu Thr
370                 375                 380

Gly Leu Leu Asn Leu Lys Ile Trp Lys Ala Pro His Val Ala Lys
385                 390                 395                 400

Tyr Phe Asp Asp Gln Val Phe Trp Lys Phe Pro His Leu Ala Val Gly
                405                 410                 415

Phe

<210> SEQ ID NO 367
<211> LENGTH: 911
<212> TYPE: PRT
<213> ORGANISM: Homo sapiens

<400> SEQUENCE: 367

Met Glu Glu Leu Gln Asp Asp Tyr Glu Asp Met Met Glu Glu Asn Leu
1               5                   10                  15

Glu Gln Glu Glu Tyr Glu Asp Pro Asp Ile Pro Glu Ser Gln Met Glu
                20                  25                  30

Glu Pro Ala Ala His Asp Thr Glu Ala Thr Ala Thr Asp Tyr His Thr
            35                  40                  45

Thr Ser His Pro Gly Thr His Lys Val Tyr Val Glu Leu Gln Glu Leu
    50                  55                  60

Val Met Asp Glu Lys Asn Gln Glu Leu Arg Trp Met Glu Ala Ala Arg
65                  70                  75                  80

Trp Val Gln Leu Glu Glu Asn Leu Gly Glu Asn Gly Ala Trp Gly Arg
                85                  90                  95

Pro His Leu Ser His Leu Thr Phe Trp Ser Leu Leu Glu Leu Arg Arg
            100                 105                 110

Val Phe Thr Lys Gly Thr Val Leu Leu Asp Leu Gln Glu Thr Ser Leu
        115                 120                 125

Ala Gly Val Ala Asn Gln Leu Leu Asp Arg Phe Ile Phe Glu Asp Gln
    130                 135                 140

Ile Arg Pro Gln Asp Arg Glu Glu Leu Leu Arg Ala Leu Leu Leu Lys
145                 150                 155                 160

His Ser His Ala Gly Glu Leu Glu Ala Leu Gly Gly Val Lys Pro Ala
                165                 170                 175
```

```
Val Leu Thr Arg Ser Gly Asp Pro Ser Gln Pro Leu Leu Pro Gln His
                180                 185                 190

Ser Ser Leu Glu Thr Gln Leu Phe Cys Glu Gln Gly Asp Gly Gly Thr
            195                 200                 205

Glu Gly His Ser Pro Ser Gly Ile Leu Glu Lys Ile Pro Pro Asp Ser
        210                 215                 220

Glu Ala Thr Leu Val Leu Val Gly Arg Ala Asp Phe Leu Glu Gln Pro
225                 230                 235                 240

Val Leu Gly Phe Val Arg Leu Gln Glu Ala Glu Leu Glu Ala Val
                245                 250                 255

Glu Leu Pro Val Pro Ile Arg Phe Leu Phe Val Leu Leu Gly Pro Glu
                260                 265                 270

Ala Pro His Ile Asp Tyr Thr Gln Leu Gly Arg Ala Ala Ala Thr Leu
                275                 280                 285

Met Ser Glu Arg Val Phe Arg Ile Asp Ala Tyr Met Ala Gln Ser Arg
            290                 295                 300

Gly Glu Leu Leu His Ser Leu Glu Gly Phe Leu Asp Cys Ser Leu Val
305                 310                 315                 320

Leu Pro Pro Thr Asp Ala Pro Ser Glu Gln Ala Leu Leu Ser Leu Val
                325                 330                 335

Pro Val Gln Arg Glu Leu Leu Arg Arg Arg Tyr Gln Ser Ser Pro Ala
                340                 345                 350

Lys Pro Asp Ser Ser Phe Tyr Lys Gly Leu Asp Leu Asn Gly Gly Pro
            355                 360                 365

Asp Asp Pro Leu Gln Gln Thr Gly Gln Leu Phe Gly Gly Leu Val Arg
            370                 375                 380

Asp Ile Arg Arg Arg Tyr Pro Tyr Tyr Leu Ser Asp Ile Thr Asp Ala
385                 390                 395                 400

Phe Ser Pro Gln Val Leu Ala Ala Val Ile Phe Ile Tyr Phe Ala Ala
                405                 410                 415

Leu Ser Pro Ala Ile Thr Phe Gly Gly Leu Leu Gly Glu Lys Thr Arg
                420                 425                 430

Asn Gln Met Gly Val Ser Glu Leu Leu Ile Ser Thr Ala Val Gln Gly
            435                 440                 445

Ile Leu Phe Ala Leu Leu Gly Ala Gln Pro Leu Leu Val Val Gly Phe
        450                 455                 460

Ser Gly Pro Leu Leu Val Phe Glu Glu Ala Phe Phe Ser Phe Cys Glu
465                 470                 475                 480

Thr Asn Gly Leu Glu Tyr Ile Val Gly Arg Val Trp Ile Gly Phe Trp
                485                 490                 495

Leu Ile Leu Leu Val Val Leu Val Ala Phe Glu Gly Ser Phe Leu
                500                 505                 510

Val Arg Phe Ile Ser Arg Tyr Thr Gln Glu Ile Phe Ser Phe Leu Ile
                515                 520                 525

Ser Leu Ile Phe Ile Tyr Glu Thr Phe Ser Lys Leu Ile Lys Ile Phe
            530                 535                 540

Gln Asp His Pro Leu Gln Lys Thr Tyr Asn Tyr Asn Val Leu Met Val
545                 550                 555                 560

Pro Lys Pro Gln Gly Pro Leu Pro Asn Thr Ala Leu Leu Ser Leu Val
                565                 570                 575

Leu Met Ala Gly Thr Phe Phe Phe Ala Met Met Leu Arg Lys Phe Lys
                580                 585                 590
```

-continued

```
Asn Ser Ser Tyr Phe Pro Gly Lys Leu Arg Arg Val Ile Gly Asp Phe
        595                 600                 605

Gly Val Pro Ile Ser Ile Leu Ile Met Val Leu Val Asp Phe Phe Ile
    610                 615                 620

Gln Asp Thr Tyr Thr Gln Lys Leu Ser Val Pro Asp Gly Phe Lys Val
625                 630                 635                 640

Ser Asn Ser Ser Ala Arg Gly Trp Val Ile His Pro Leu Gly Leu Arg
            645                 650                 655

Ser Glu Phe Pro Ile Trp Met Met Phe Ala Ser Ala Leu Pro Ala Leu
            660                 665                 670

Leu Val Phe Ile Leu Ile Phe Leu Glu Ser Gln Ile Thr Thr Leu Ile
        675                 680                 685

Val Ser Lys Pro Glu Arg Lys Met Val Lys Gly Ser Gly Phe His Leu
    690                 695                 700

Asp Leu Leu Leu Val Val Gly Met Gly Gly Val Ala Ala Leu Phe Gly
705                 710                 715                 720

Met Pro Trp Leu Ser Ala Thr Thr Val Arg Ser Val Thr His Ala Asn
            725                 730                 735

Ala Leu Thr Val Met Gly Lys Ala Ser Thr Pro Gly Ala Ala Ala Gln
            740                 745                 750

Ile Gln Glu Val Lys Glu Gln Arg Ile Ser Gly Leu Leu Val Ala Val
            755                 760                 765

Leu Val Gly Leu Ser Ile Leu Met Glu Pro Ile Leu Ser Arg Ile Pro
    770                 775                 780

Leu Ala Val Leu Phe Gly Ile Phe Leu Tyr Met Gly Val Thr Ser Leu
785                 790                 795                 800

Ser Gly Ile Gln Leu Phe Asp Arg Ile Leu Leu Leu Phe Lys Pro Pro
            805                 810                 815

Lys Tyr His Pro Asp Val Pro Tyr Val Lys Arg Val Lys Thr Trp Arg
            820                 825                 830

Met His Leu Phe Thr Gly Ile Gln Ile Ile Cys Leu Ala Val Leu Trp
        835                 840                 845

Val Val Lys Ser Thr Pro Ala Ser Leu Ala Leu Pro Phe Val Leu Ile
    850                 855                 860

Leu Thr Val Pro Leu Arg Arg Val Leu Leu Pro Leu Ile Phe Arg Asn
865                 870                 875                 880

Val Glu Leu Gln Cys Leu Asp Ala Asp Asp Ala Lys Ala Thr Phe Asp
            885                 890                 895

Glu Glu Glu Gly Arg Asp Glu Tyr Asp Glu Val Ala Met Pro Val
            900                 905                 910
```

FUSION PROTEINS AND ANTIBODIES TARGETING HUMAN RED BLOOD CELL ANTIGENS

CROSS-REFERENCE TO RELATED APPLICATIONS

This application is a national stage of International Patent Application No. PCT/US2018/064089, filed Dec. 5, 2018, which claims the benefit of the priority of U.S. Provisional Patent Application No. 62/594,909, filed Dec. 5, 2017, which applications are incorporated herein by reference.

INCORPORATION-BY-REFERENCE OF MATERIAL SUBMITTED IN ELECTRONIC FORM

Applicant hereby incorporates by reference the Sequence Listing material filed in electronic form herewith. This file is labeled "17-8117PCT_Seq_Listing_ST25.txt".

STATEMENT OF GOVERNMENT INTEREST

This invention was made with government support under HL121134 awarded by the National Institutes of Health. The government has certain rights in the invention.

BACKGROUND OF THE INVENTION

Drug delivery by red blood cells (RBCs) was envisioned many decades ago[1-3] and the field has recently seen substantial growth [4-6], spurred by advances in drug loading within cells [7, 8] and coupling to the cell surface[9, 10], new technologies for genetic manipulation[11], and clinical successes in cellular therapeutics overall[12]. Furthermore, recent reports that carriage of drugs by RBCs can modulate immunogenicity, even inducing tolerance, expand the potential applications of RBC delivery[13-15]. Delivery by carrier RBCs enhances the pharmacokinetics and, in some cases, the pharmacodynamics of the loaded agents. RBC-encapsulated agents, including dexamethasone and L-asparaginase, have entered clinical trials.

Surface-coupling may offer some advantages with respect to clinical translatability, manufacturing, and bio-compatibility[16]. Animal studies demonstrated highly desirable features of surface-coupled anti-thrombotic and anti-inflammatory agents[10, 17-20]. For example, coupling of thrombomodulin (TM) to murine RBCs improves its efficacy in thrombotic[20], inflammatory, and ischemia-reperfusion injuries[21].

Previous reports have generally used fusion proteins, antibodies, and peptides to couple therapeutics to the surface of murine and porcine, but not human, RBCs. Fusion to murine RBCs is typically accomplished by derivatives of Ter119, an antibody to an epitope associated with glycophorin A (GPA)[22], or with ERY1 peptide, whose putative target is also GPA[13]. While no overt adverse effects on RBCs have been noted when using these ligands, the effects of their binding to murine RBCs have not been characterized extensively [23].

The translational aspects of RBC delivery are challenging, as the considerable polymorphism of RBC antigenic determinants among species hinders any generalization of the effects of extracellular ligands to human RBCs. While we expect that surface-coupling is comparatively less-damaging than encapsulation methods (for example, hypotonic opening of membrane pores), careful and rigorous examination of affinity-coupling of bio-therapeutics to the surface of human red blood cells, assessment of their perturbation of red cell physiology, and subsequent demonstration of efficacy in humanized models, have not been reported.

It is known that RBC ligands, even monovalent, specifically targeted to GPA and Band 3, have the potential to cause undesirable alterations of RBC, including changes in deformability[24-28], exposure of phosphatidylserine (PS) [29], and generation of reactive oxygen species (ROS)[30]. These effects have been shown to vary even among epitopes within the same target protein. It is critical to examine these effects to identify the optimal RBC target for each therapeutic ligand, which should be erythroid specific, present in sufficient copy number for its therapeutic intent, be widely distributed among human populations, be non-immunogenic, and for most applications, not compromise RBC biocompatibility. Importantly, expression of three blood group systems is largely confined to erythropoiesis, GPA (MNS system), Band 3 (Diego system), and Rhesus family members (RhCE and RhD, Rh system)[34].

Therefore, antibodies and fusion proteins useful for targeting RBCs for drug delivery in subjects are needed.

SUMMARY OF THE INVENTION

The compositions and methods described herein relate to antibodies, fragments, fusion proteins and conjugates which specifically bind red blood cells, specifically via anti-RHCE or anti-Band 3. In one aspect, an antibody or fragment thereof comprising at least a VH or VL sequence as shown in Table 2 or Table 5 is provided, wherein said antibody or fragment thereof specifically binds an erythrocyte. In one embodiment, the antibody or fragment comprises a VH and a VL sequence as shown in Table 2 or Table 5. In one embodiment, the antibody is an scFv.

In another aspect, compositions are provided in which any pharmacological, therapeutic, prophylactic, imaging or diagnostic agent which is coupled to, bound, fused, associated with or conjugated to an anti-RHCE or anti-Band 3 antibody described herein. In one embodiment, the cargo is a liposome.

In another aspect, a method for delivering an agent using red blood cells is provided. The method includes administering any of the compositions described herein to a subject in need thereof. In another embodiment, a method of prolonging circulation of an agent in the body is provided. The method includes administering any of the compositions described herein to a subject in need thereof. In another aspect, a method for preventing or reducing coagulation is provided. The method includes administering any of the compositions described herein to a subject in need thereof. In yet another aspect, a method of treating or preventing thrombosis, tissue ischemia, acute myocardial infarction (AMI), non-segmented elevated AMI, deep vein thrombosis, ischemic stroke, hyperoxic injury, transient ischemic attack (TIA), cerebrovascular disease, disseminated intravascular coagulation (DIC), pulmonary embolism, ischemic peripheral vascular disease, inflammation, pulmonary edema, sepsis, malaria, SDC, PNH, hemolytic anemia, acute lung injury (ALI), acute respiratory distress syndrome (ARDS), a bleeding disorder such as hemophilia, or aseptic systemic inflammation is provided. The method includes administering any of the compositions described herein to a subject in need thereof."

BRIEF DESCRIPTION OF THE DRAWINGS

FIG. 1A-FIG. 1G provide characterization of aRh17 and aWrb ligands and their binding to human RBCs. Representative size exclusion HPLC analysis of (FIG. 1A) hTM-scFv fusions and (FIG. 1B) scFvs alone directed to Band3/GPA (aWrb, solid blue lines) and RhCE (aRh17, dashed red lines) demonstrates high purity of recombinant proteins and elution times consistent with theoretical molecular weights. Direct binding assays with radiolabeled proteins demonstrates high affinity and Bmax (Table 7) consistent with reported copy number of the surface targets for both the (FIG. 1C) hTM-scFv fusions and the (FIG. 1D) scFv antibodies. No significant non-specific binding to control murine RBCs was seen. Representative data of 3 independent experiments are shown. Ligand dissociation studies demonstrated slow dissociation kinetics (>50% bound at 3 hours) for both the (FIG. 1E) TM-scFv fusions and (FIG. 1F) scFv antibodies. (FIG. 1G) Binding assay by hemagglutination techniques demonstrated that when anti-hTM IgG antibody (100 nM) was added to RBC pre-bound with the indicated concentration of hTM-scFv fusions, agglutination was observed when 1000 copies of hTM would be expected on the surface. Representative data of 3 independent experiments are shown. No agglutination was seen with RBCs treated with either scFv or hTM-scFv alone or with mouse, rat, or pig RBCs treated with scFv or hTM-scFv followed by anti-hTM.

(FIG. 2A) RBCs treated with 500 nM aWrb scFv (blue) showed a left shift in the osmotic lysis curve compared to naïve (black) or aRh17 scFv treated RBCs (red). (FIG. 2B) RBCs treated with aWrb but not aRh17 showed a significant change in the concentration required for 50% hemolysis (128 vs 120 mOsm, n=3, *p<0.05 one-way ANOVA with Holm-Sidak correction for multiple comparisons) (FIG. 2C) aWrb scFv treated RBCs (blue) show a dose-dependent decrease in hemolysis in response to osmotic stress at 128 mOsm (EC50 for naïve RBCs) and (FIG. 2D) a dose-dependent increase in hemolysis in response to mechanical stress. aRh17 scFv treated RBCs (red) do not demonstrate any significant change in response to (FIG. 2E) osmotic stress or (FIG. 2F) mechanical stress. In all experiments means±SD are shown, n=3 for each condition. (*p<0.05 compared to naive, one-way ANOVA with Holm-Sidak correction for multiple comparisons).

(FIG. 3A) aWrb hTM-scFv shows a dose-dependent decrease in hemolysis in response to osmotic stress and (FIG. 3B) a dose-dependent increase in hemolysis in response to mechanical stress. aRh17 hTM-scFv does not demonstrate any significant change in response to (FIG. 3C) osmotic stress or (FIG. 3D) mechanical stress. In all experiments means±SD are shown, n=3 for each condition. (*p<0.05 compared to naive, one-way ANOVA with Holm-Sidak correction for multiple comparisons)

(FIG. 4A) hTM-scFv fusions and (FIG. 4C) scFv antibodies targeted to Band3/GPA (aWrb blue dotted lines) demonstrated a rightward shift in the ektacytometry curves compared to naïve (solid line) while aRh17 fusions and scFv (red dashed lines) showed no change from naïve (scFvs and fusion proteins added at 1000 nM) (FIG. 4B and FIG. 4D) The shift in deformability was quantified as the SS1/2, which showed dose-dependent increases in response to Band3/GPA targeted ligands and not RhCE ligands. In (FIG. 4B) and (FIG. 4D), mean±SD is shown, n=3-5 per condition. (*p<0.05 compared to naive, one-way ANOVA with Holm-Sidak correction for multiple comparisons)

FIG. 5A-FIG. 5F show that IgG antibodies against Band3 and GPA rigidify RBCs, while IgGs against RhCE and RhD do not. Representative ektacytometric curves (at least 3 separate donors studied per antibody) of RBCs treated with antibodies targeting (FIG. 5A) RhD or RhCE, (FIG. 5B) Band 3 or Wrb, or (FIG. 5C) GPA. A 5% suspension of RhD+ human RBCs in PBS was treated with 100 nM of the indicated antibody clones (~100,000 IgG/RBC). After incubation for 1 hour at 37° C., the red cell suspensions were read on an ektacytometer in 5.5% PVP. Legends indicate antibody clones. (FIG. 5D) Ektacytometric dose-response of anti-RhCE versus anti-Wrb IgG antibodies. Selected antibody clones against RhCE (BRIC69, red) and Wrb (BRIC14, blue) were added at 100 nM to varying hematocrit RBC suspensions (2.5, 5, 10, and 20%, 6 donors tested) to result in ligand ratios of 25,000-100,000 IgG/RBC. aWrb demonstrated a significant increase in SS1/2 at all ligand loading ratios, while no significant difference was seen for aRhCE antibodies. Mean±SD is shown, n=3-6 for each condition. (FIG. 5E) Flow cytometry on aRhCE (BRIC69, red) and aWrb (BRIC14, blue) IgG treated RBCs stained with AlexaFluor488 labeled anti-mouse secondary antibodies shows no significant difference in bound IgGs (based on median fluorescence) at the indicated loading ratios. (FIG. 5F) Representative histogram demonstrating similar antibody loading for RBCs treated with aRhCE (BRIC69, red) and aWrb (BRIC14, blue) antibodies.

Soluble hTM (shTM) treated RBCs are shown as a non-binding control (open squares) (FIG. 6B) Comparison of APC generative capacity of sTM versus hTM-scFv fusions (added at 50 nM) in a high hematocrit (20%) RBC suspension. Mean±SD is shown, n=3 for each condition. (*p<0.05 vs sTM, one-way ANOVA with Holm-Sidak correction for multiple comparisons) A slight reduction in activity was seen for hTM-aBand3 but not hTM-aRhCE. (FIG. 6C) Fibrin generation on TNF-alpha activated, endothelialized microfluidic channels perfused with human whole blood preincubated with either PBS control (open squares), shTM control (crosses), hTM-Wrb (blue circles), or hTM-aRh17 (red triangles). Both fusion proteins (and shTM positive control) significantly reduced fibrin generation. (*p<0.05 vs untreated, one-way ANOVA with Holm-Sidak correction for multiple comparisons) as compared to the control channel. An increase in fibrin generation was noted toward the end of the observation period for the hTM-aWrb treated channels. (FIG. 6D) hTM-aRh17 treatment (red triangles) more effectively reduced platelet and leukocyte adhesion (quantified with calcein AM fluorescence) than hTM-aWrb (blue circles) versus untreated control (open squares). hTM-Rh17 treatment was similar to shTM positive control (crosses). For (FIG. 6C) and (FIG. 6D) mean±SEM for 2 independent channels is shown. (FIG. 6E) Representative composite images of whole blood (fibrin in red, platelets and leukocytes in green, brightfield image in gray) flowing through endothelialized channels at the end of the observation period (t=20 min). Fibrin is decreased in both fusion treated channels. An increase in platelet adhesion with associated fibrin (yellow, arrowhead) is seen in the hTM-aWrb treated channels compared to hTM-aRh17. Videos of the full time-course are not provided.

FIG. 9A-FIG. 9C show that dissociation and exchange of scFv from pre-treated RBCs onto naïve RBCs under constant mixing at 37° C. A fraction of washed, isolated human RBCs was treated with saturating concentrations of anti-Wrb or anti-Rh17 scFv labeled with Alexa Flour 647 or Alexa Flour 488, respectively. The labeled RBCs were then added to fresh donor human whole blood (collected in citrate) at 0.5-1% of the total RBC population. This mixture was then incubated at 37° C. under constant mixing by inversion. We observed (FIG. 9A) a gradual decrease in fluorescence intensity in the targeted RBCs, with >65% of fluorescence signal retained on the targeted RBCs at two hours. We quantified both the (FIG. 9B) dissociation of the scFvs and their (FIG. 9C) gradual rebinding to the naive population.

FIG. 10 shows Wright-Giemsa stained blood smears of hTM-scFv treated RBCs. Whole blood was treated with 1 μM hTM-scFv and incubated for 1 hour prior to preparation of smears. At a normal hematocrit, this ratio is ~105 fusions/RBC. Slides were dried and stained with a commercial Wright-Giemsa stain (Sigma Aldrich) per package insert.

(FIG. 14D) SS1/2 derived from ektacytometric curves demonstrates a significant, dose-dependent increase in SS1/2 with Ter119-TM treatment of murine RBCs. Mean±SD is shown, n=5-8 for each condition. (*p<0.05 vs naïve RBCs, one-way ANOVA with Holm-Sidak correction for multiple comparisons).

(FIG. 15A) No significant ROS generation was observed for cells treated with aWrb, aRh17, or aGPA ligands. Human RBCs were preincubated with 5 µM dihydrorhodamine 123 (Thermo Fisher Scientific) at 1% hematocrit for 30 min at 37 C, washed, then treated with either t-butyl hydrogenperoxide (10 µM) as a positive control or 100 nM of the indicated ligands for 1 hr at 37 C. ROS generation was measured as median FL1 fluorescence and the mean±SD are shown (n=4). (FIG. 15B) No significant PS exposure was observed for cells treated with aWrb, aRh17, or aGPA ligands. Human RBCs were treated with 200 nM of the indicated ligands at 5% hematocrit (~2×105 ligands/RBC). Ter119-mTM was used as a non-binding negative control, and 2 mM t-butyl hydrogenperoxide was used as a positive control. Cells were treated at 37° C. for 1 hour, washed, and resuspended in annexin V-Alexa Fluor 488 in annexin assay buffer (Thermo Fisher Scientific) per manufacturer protocol. Mean±SD, n=3 is shown for each condition. (*p<0.05 vs non-binding control, one-way ANOVA with Holm-Sidak correction for multiple comparisons)

FIG. 19A-FIG. 19C demonstrate that RBC-targeted liposomes are maintained in circulation significantly longer than conventional 'stealth' liposomes. (FIG. 19A) Whole animal biodistribution of Ter119-liposomes (100-200 scFv:liposome) loaded onto RBCs in vivo by direct injection into the blood stream (blue) or unconjugated PEGylated liposomes (red). For in vivo loading liposomes were injected at a ratio of approximately 50 liposomes per RBC. (FIG. 19B) Blood PK curves demonstrate that the large majority of both in vivo loaded Ter119-liposomes (blue) are maintained in circulation at 3 hours and gradually drop off over 24 hours. Compared to traditional "stealth" liposomes (red), there is approximately a 2-fold increase in area under the curve (p<0.05) (FIG. 19C) Ter-119 liposomes are found mostly (>80%) in the RBC pellet of collected blood and gradually clear this compartment while free liposomes are largely in the plasma fraction.

(FIG. 20A) Schema for ex vivo loading of RBCs with liposomes, 15 min of incubation typically resulted in >65% of liposomes bound (FIG. 20B) 30 min biodistribution of 51-Cr labeled RBCs loaded with either 200 or 20,000 liposomes per RBC demonstrates that while high loading leads to rapid clearance, low loading maintains near normal circulation of RBCs. For liposomes loaded ex vivo at a 200:1 ratio, PK data (up to 3 hours) were nearly identical to in vivo loading approaches.

(FIG. 21A) High ratios of liposome loading on RBCs leads to agglutination in vitro, while lesser ratios (<200: RBC) do not induce macroscopically detectable agglutination, as measured in a round-bottom well agglutination assay. Human RBCs shown as negative control. (FIG. 21B) Ektacytometry demonstrates that RBCs maintain normal membrane deformability at ratios up to 200 liposomes per RBC, above which dose-dependent rigidification of the membrane was observed FIG. 22 demonstrates that Ter119IgG-liposomes are less stably retained on circulating RBCs and produce greater RBC rigidification than Ter119scFv-liposomes. (left panel) Mice were injected with radiolabeled liposomes conjugates with similar numbers (100-200/lipo) of either Ter119 IgG or Ter119 scFv. A higher percentage of Ter119-scFv liposomes remained in the RBC pellet, while Ter119-IgG was more rapidly cleared. (Middle and right panels) Ter119-IgG liposomes produced a higher degree of RBC membrane rigidification, as measured by ektacytometry (curves in middle panel, quantification in right panel, *p<0.05)

(FIG. 24A) Representative image of endothelialized channels subjected to flow with either (top) aWrb scFv treated whole blood or (bottom) aRh17 scFv treated whole blood. Blood was collected in citrate with corn trypsin inhibitor, incubated with scFv (500 nM) for 15 minutes, recalcified, and flowed over channels for 15 min after which images were captured across the channels. Prior to flow, platelets and leukocytes were stained by addition of calcein AM dye. (FIG. 24B) Quantification of the experiments in panel A (mean fluorescence intensity) demonstrate a significant increase in calcein AM signal in the aWrb scFv treated blood but not aRh17 scFv (n=4, *p<0.05, one-way ANOVA).

DETAILED DESCRIPTION OF THE INVENTION

Figure 1D:
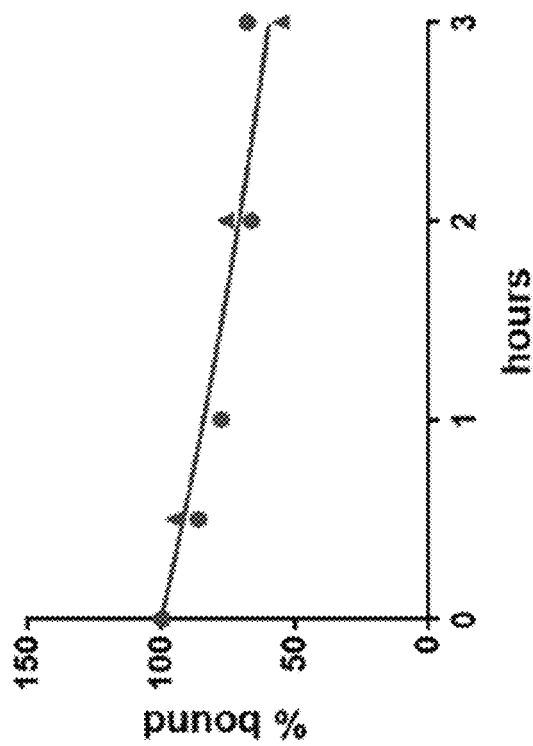

Carriage of drugs by red blood cells (RBCs) enhances pharmacokinetics and pharmacodynamics, modulates immune responses, and is approaching clinical translation. The effects of attaching therapeutics to human RBCs have not been well defined and optimal RBC surface determinants have not been identified. As described herein, non-human-primate single chain antibodies (scFv) directed to human RBCs were engineered and fused with human thrombomodulin (hTM) as a representative therapeutic cargo (hTM-scFv). Binding these fusions to RBC determinants Band3 (Wrb) and RHCE (Rh17) endowed RBC with hTM activity, but differed in their effect on RBC physiology and specific activity. scFv and hTM-scFv targeted to Band3 increased membrane rigidity, sensitized RBCs to hemolysis induced by mechanical stress, and decreased hypo-osmotic hemolysis. Similar trends were seen for monovalent ligands bound to glycophorin A (GPA) on human and murine RBCs. In contrast, binding of scFv and hTM-scFv to RHCE did not alter RBC deformability or sensitivity to mechanical and osmotic stress at similar copy numbers per RBC. Although RBC-bound hTM-scFv fusions all generated APC in the presence of thrombin, RHCE-bound TM demonstrated superior specific activity. Both fusion proteins were efficacious in endothelialized microfluidic models of inflammatory thrombosis in human whole blood wherein they significantly decreased fibrin deposition in response to TNF-alpha activation, but RHCE-bound hTM-scFv more effectively reduced platelet and leukocyte adhesion.

As used herein, the term "subject" means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

The term "immunoglobulin" or "antibody" is used herein to include antibodies, including functional fragments thereof. As used herein, the term antibody includes scFvs. As used herein, the term antibody also includes FABs, single domain antibodies, heavy chain antibodies (camelids), DARTs, F(ab')2, BITEs, and immunoadhesins. These antibody fragments or artificial constructs may include a single chain antibody, a Fab fragment, a univalent antibody, a bivalent of multivalent antibody, or an immunoadhesin. An scFv is a fusion protein of the variable regions of the heavy (VH) and light chains (VL) of immunoglobulins, connected with a short linker peptide of ten to about 25 amino acids. The antibody may also be a monoclonal antibody, a "humanized" antibody, a multivalent antibody, or another suitable construct. An "immunoglobulin molecule" is a protein containing the immunologically-active portions of an immunoglobulin heavy chain and immunoglobulin light chain covalently coupled together and capable of specifically combining with an antigen. Immunoglobulin molecules are of any type (e.g., IgG, IgE, IgM, IgD, IgA and IgY), class (e.g., IgG1, IgG2, IgG3, IgG4, IgA1 and IgA2) or subclass. The terms "antibody" and "immunoglobulin" may be used interchangeably herein. An "immunoglobulin heavy chain" is a polypeptide that contains at least a portion of the antigen binding domain of an immunoglobulin and at least a portion of a variable region of an immunoglobulin heavy chain. Thus, the immunoglobulin derived heavy chain has significant regions of amino acid sequence homology with a member of the immunoglobulin gene superfamily. For example, the heavy chain in a Fab fragment is an immunoglobulin-derived heavy chain. An "immunoglobulin light chain" is a polypeptide that contains at least a portion of the antigen binding domain of an immunoglobulin and at least a portion of the variable region. Thus, the immunoglobulin-derived light chain has significant regions of amino acid homology with a member of the immunoglobulin gene superfamily. An "immunoadhesin" is a chimeric, antibody-like molecule that combines the functional domain of a binding protein, usually a receptor, ligand, cell-adhesion molecule, or 1-2 immunoglobulin variable domains with immunoglobulin constant domains, usually including the hinge or GS linker and Fc regions. A "fragment antigen-binding" (Fab) fragment" is a region on an antibody that binds to antigens. It is composed of one constant and one variable domain of each of the heavy and the light chain. With respect to immunoglobulins or antibodies as described herein, each fragment of an immunoglobulin coding sequence may be derived from one or more sources, or synthesized. Suitable fragments may include the coding region for one or more of, e.g., a heavy chain, a light chain, and/or fragments thereof such as the constant or variable region of a heavy chain (CH1, CH2 and/or CH3) and/or or the constant or variable region of a light chain. Alternatively, variable regions of a heavy chain or light chain may be utilized. Where appropriate, these sequences may be modified from the "native" sequences from which they are derived, as described herein.

Antibodies may exist in a variety of forms including, for example, polyclonal antibodies, monoclonal antibodies, camelid heavy chain only (VHH) antibodies, intracellular antibodies ("intrabodies"), recombinant antibodies, multispecific antibody, antibody fragments, such as, Fv, Fab, $F(ab)_2$, $F(ab)_3$, Fab', Fab'-SH, F(ab')2, single chain variable fragment antibodies (scFv), tandem/bis-scFv, Fc, pFc', scFvFc (or scFv-Fc), disulfide Fv (dsfv), bispecific antibodies (bc-scFv) such as BiTE antibodies; humanized camelid antibodies, resurfaced antibodies, humanized antibodies, shark antibodies, fully human antibodies, single-domain antibody (sdAb, also known as NANOBODY®), chimeric antibodies, chimeric antibodies comprising at least one human constant region, and the like. "Antibody fragment" refers to at least a portion of the variable region of the immunoglobulin that binds to its target, e.g., the RHCE protein. In one embodiment, the antibody referred to herein is an scFv.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. With regard to the antibodies described herein, in one embodiment the constant regions of the heavy and/or light chain are from a different source (e.g., different clone) than the variable regions of the heavy and/or light chain. Thus, with reference to each other, said constant and variable regions are heterologous, or said heavy and light chains are heterologous. The different sources may be from the same species or different species.

As used herein, a "vector" or "plasmid" refers to a nucleic acid molecule which comprises an immunoglobulin coding sequence (e.g., an immunoglobulin VH or VL or another fragment of an immunoglobulin construct, or combinations thereof), promoter, and may include other regulatory sequences therefor, which plasmid or vector may be delivered to a host cell, wherein said coding sequence is expressed recombinantly.

In one embodiment, the "linker" refers to any moiety used to attach or associate the antibody to the cargo. Thus, in one embodiment, the linker is a covalent bond. In another embodiment, the linker is a non-covalent bond. In another embodiment the linker is composed of at least one to about 25 atoms. Thus, in various embodiments, the linker is formed of at least 2, 3, 4, 5, 6, 7, 8, 9, 10, 11, 12, 13, 14, 15, 16, 17, 18, 19, 20, 21, 22, 23, 24 or 25 atoms. In still another embodiment, the linker is at least one to about 60 nucleic acids. Thus in various embodiments, the linker is formed of a sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, up to 60 nucleic acids. In yet another embodiment, the linker refers to at least one to about 30 amino acids. Thus in various embodiments, the linker is formed of a sequence of at least 2, 3, 4, 5, 6, 7, 8, 9, 10, 11, 12, 13, 14, 15, 16, 17, 18, 19, 20, 21, 22, 23, 24, 25, 26, 27, 28, 29, up to about 30 amino acids. In still other embodiments, the linker can be a larger compound or two or more compounds that associate covalently or non-covalently. In still other embodiment, the linker can be a combination of the linkers defined herein. The linkers used in the constructs of the compositions and methods are in one embodiment cleavable. The linkers used in the constructs of the compositions and methods are in one embodiment non-cleavable. Without limitation, in one embodiment, the linker is a disulfide bond. In the examples below, the exemplified linker comprises a complex of biotin bound to the construct oligonucleotide sequence by a disulfide bond, with streptavidin fused to the ligand. In another embodiment, the biotin is bound to the ligand and the streptavidin is fused to the construct oligonucleotide sequence.

Antibodies

As described herein, antibodies and antibody fragments which specifically bind erythrocytes are provided. Antibodies and single chain antibody fragments (scFv) against epitopes on Band 3 protein (we) and RHCE protein (Rh17/Hr$_0$) on human erythrocytes are described herein. These antibodies and fragments were generated using phage display libraries prepared from immunized cynamolgous macaques (*Macaca fascicularis*). Both antigens are present on RBCs from nearly 100% of the human population and are considered relatively erythroid specific[31, 32].

RHCE

The Rh blood group system is the second most clinically significant of the blood groups, second only to ABO. It is also the most polymorphic of the blood groups, with variations due to deletions, gene conversions, and missense mutations. The Rh blood group includes this gene which encodes both the RhC and RhE antigens on a single polypeptide (RHCE) and a second gene which encodes the RhD protein. The classification of Rh-positive and Rh-negative individuals is determined by the presence or absence of the highly immunogenic RhD protein on the surface of erythrocytes. A mutation in this gene results in amorph-type Rh-null disease. Alternative splicing of this gene results in multiple transcript variants encoding several different isoforms.

As used herein, "RHCE" refers to the above-described polypeptide, including all isoforms thereof (UniProtKB-P18577). The "canonical" sequence can be found under Uniprot Identifier: P18577-1, also called isoform 1 or RHI, and is shown below and as SEQ ID NO: 366.

```
         10         20         30         40
 MSSKYPRSVR RCLPLWALTL EAALILLFYF FTHYDASLED 50         60         70         80
 QKGLVASYQV GQDLTVMAAL GLGFLTSNFR RHSWSSVAFN 90        100        110        120
 LFMLALGVQW AILLDGFLSQ FPPGKVVITL FSIRLATMSA 130        140        150        160
 MSVLISAGAV LGKVNLAQLV VMVLVEVTAL GTLRMVISNI 170        180        190        200
 FNTDYHMNLR HFYVFAAYFG LTVAWCLPKP LPKGTEDNDQ 210        220        230        240
 RATIPSLSAM LGALFLWMFW PSVNSPLLRS PIQRKNAMFN 250        260        270        280
 TYYALAVSVV TAISGSSLAH PQRKISMTYV HSAVLAGGVA 290        300        310        320
 VGTSCHLIPS PWLAMVLGLV AGLISIGGAK CLPVCCNRVL 330        340        350        260
 GIHHISVMHS IFSLLGLLGE ITYIVLLNLH TVWNGNGMIG 270        380        290        400
 FQVLLSIGEL SLAIVIALTS GLLTGLLLNL KIWKAPHVAK

410
 YFDDQVFWKF PHLAVGF
```

Figure 25:
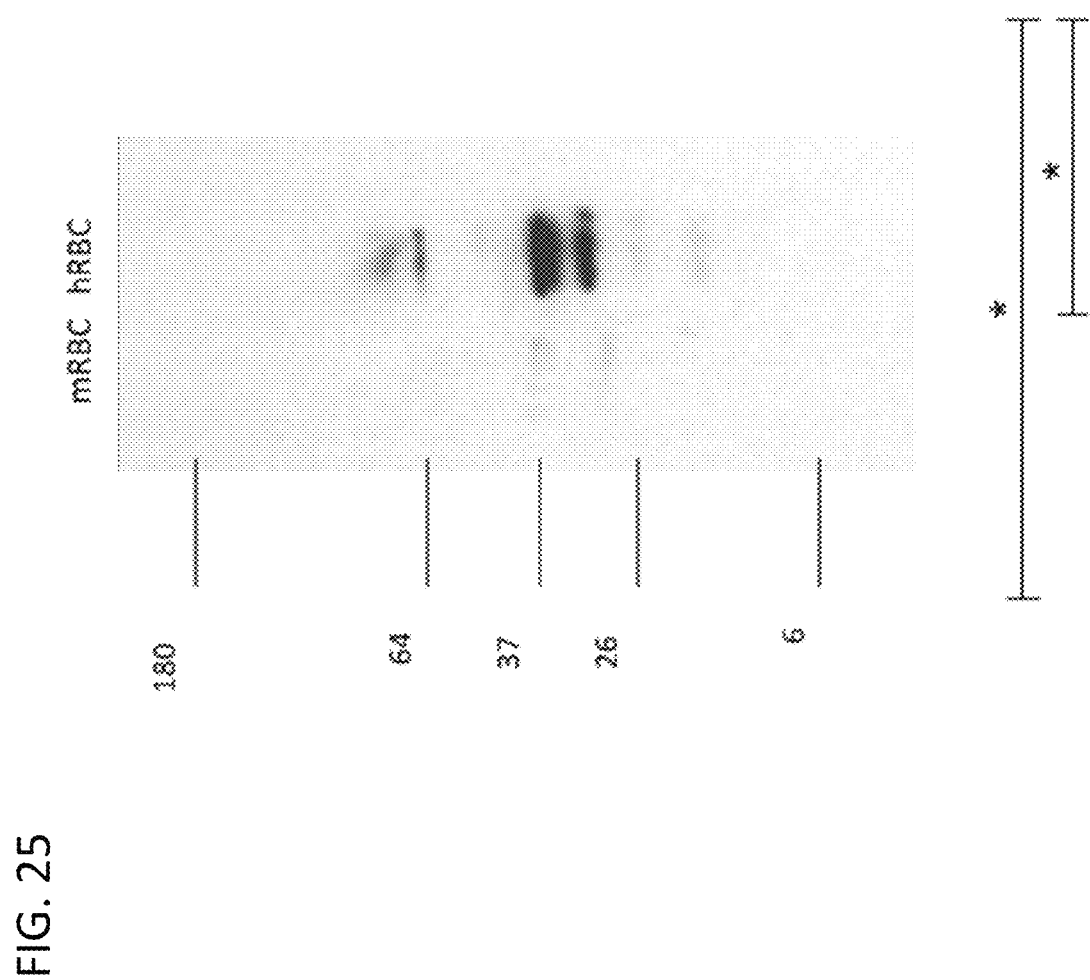
FIG. 25 is a Western blot that demonstrates that anti-Rh17 recognizes a linear epitope in human RhCE. A Western blot was performed to assess the binding of KP3-17 (anti-Rh17) to proteins extracted from mouse and human erythrocyte ghosts. Because proteins were denatured in reducing SDS-PAGE buffer prior to gel electrophoresis, the presence of binding is due to interaction with linear, and not conformational, epitopes. This is in contrast to anti-RhCE mAbs described by other groups, which recognize conformational epitopes.
Figure 27:
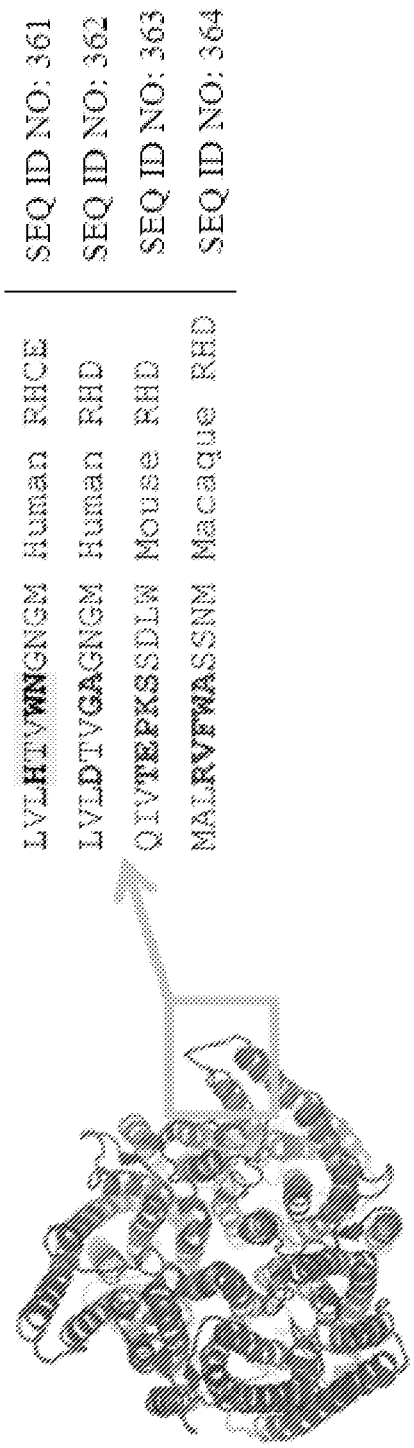
FIG. 27 is a 3D model of human RHCE (looking top down onto a membrane), with $6^{th}$ extracellular loop boxed.

Provided herein are antibodies which bind to one or more antigens on the RHCE polypeptide. Specifically, the antibodies are reactive against Rh17 (Hr$_0$). RH17 is an antigen present on all red blood cells having the common Rh phenotypes, except D- and Rh null RBCs. Because RBC lacking the rh17 antigen are extremely rare, antibodies against rh17 specifically bind to virtually all erythrocytes. Anti-rh17 antibodies are believed to bind to extracellular loops present in RHCE but not RHD. As is shown herein, the antibody termed KP3-17 (anti-Rh17) recognizes a linear epitope on human, but not mouse RBC (FIG. 25). A model showing the 6$^{th}$ extracellular loop can be seen in FIG. 27. It is believed the anti-rh17 antibodies described herein bind to all or a portion comprising at least 5 consecutive amino acids of SEQ ID NO: 361. In one embodiment, the epitope is HTVWN (SEQ ID NO: 365). In one embodiment, at least 100,000 copies of the epitope to which the subject antibody binds, are present on the erythrocyte.

In another embodiment, an antibody is provided which competes for the binding site of the anti-rh17 antibody.

In one embodiment, the antibodies described herein comprise one or more anti-rh17 antibody CDR sequence. Suitable CDR sequences are shown below in Table 1. In one embodiment, the CDRs from a single clone are used to produce an antibody or antibody fragment, e.g., CDR1, CDR2 and CDR3 from KP3-11, KP3-14 or KP3-17. In another embodiment, the CDRs from one or more clone are used to produce an antibody. As a non-limiting illustrative example, CDR1 from clone KP3-11 and CDR2 and 3 from clone KP3-14 are used in conjunction to produce an antibody. In another embodiment, the VH CDRs from one clone are use with the VL CDRs from another clone. In another embodiment, the CDRs described herein are utilized with heterologous antibody sequences to produce a chimeric antibody. In one embodiment, the antibody comprises 1 CDR sequence selected from SEQ ID Nos 1-18. In another embodiment, the antibody comprises two CDR sequences selected from SEQ ID Nos 1-18. In another embodiment, the antibody comprises three CDR sequences selected from SEQ ID Nos 1-18. In another embodiment, the antibody comprises four CDR sequences selected from SEQ ID Nos 1-18. In another embodiment, the antibody comprises five CDR sequences selected from SEQ ID Nos 1-18. In another embodiment, the antibody comprises six CDR sequences selected from SEQ ID Nos 1-18.

In one embodiment, the antibodies described herein comprise one or more anti-rh17 antibody light (VL) or heavy (VH) variable chain sequence. Suitable VH and VL sequences are shown below in Table 2. In one embodiment, the VH and VL from a single clone are used to produce an antibody or antibody fragment, e.g., VH and VL from KP3-11, KP3-14 or KP3-17. In another embodiment, the VH from one clone is used in conjunction with a VL from another clone. In one embodiment, only a VH sequence is used. In another embodiment, only a VL sequence is used. In another embodiment, the variable chain sequences described herein are utilized with heterologous antibody sequences to produce a chimeric antibody. In one embodiment, the antibody comprises a VH sequence selected from SEQ ID NO: 19, 21, and 23. In another embodiment, the antibody comprises a VL sequence selected from SEQ ID NO: 20, 22 and 24. In one embodiment, the antibody comprises SEQ DI Nos: 19 and 20. In one embodiment, the antibody comprises SEQ ID Nos: 21 and 22. In another embodiment, the antibody comprises SEQ ID Nos: 23 and 24.

Also provided are nucleic acid sequence encoding the antibodies described herein. Such sequences include those shown in Table 3, SEQ ID Nos: 25-30. Also contemplated are nucleic acid sequences encoding the described antibodies. Such sequences include those which share at least about 60% identity with any of the sequence of SEQ ID Nos: 25-30. In another embodiment, the coding sequences share at least about 65% identity with any of the sequence of SEQ ID Nos: 25-30. In another embodiment, the coding sequences share at least about 70% identity with any of the sequence of SEQ ID Nos: 25-30. In another embodiment, the coding sequences share at least about 75% identity with any of the sequence of SEQ ID Nos: 25-30. In another embodiment, the coding sequences share at least about 80% identity with any of the sequence of SEQ ID Nos: 25-30. In another embodiment, the coding sequences share at least about 85% identity with any of the sequence of SEQ ID Nos: 25-30. In another embodiment, the coding sequences share at least about 90% identity with any of the sequence of SEQ ID Nos: 25-30. In another embodiment, the coding sequences share at least about 95% identity with any of the sequence of SEQ ID Nos: 25-30.

It is also contemplated that one or more of the antibody sequences useful herein encompasses variants of the antibody sequences described herein where modifications and/or substitutions have been made. In one embodiment, the antibody comprises one or more sequences sharing at least 80% identity with any of SEQ ID NOS: 1-24. In another embodiment, the antibody comprises one or more sequences sharing at least 85% identity with any of SEQ ID NOS: 1-24. In another embodiment, the antibody comprises one or more sequences sharing at least 90% identity with any of SEQ ID NOS: 1-24. In another embodiment, the antibody comprises one or more sequences sharing at least 91% identity with any of SEQ ID NOS: 1-24. In another embodiment, the antibody comprises one or more sequences sharing at least 92% identity with any of SEQ ID NOS: 1-24. In another embodiment, the antibody comprises one or more sequences sharing at least 93% identity with any of SEQ ID NOS: 1-24. In another embodiment, the antibody comprises one or more sequences sharing at least 94% identity with any of SEQ ID NOS: 1-24. In another embodiment, the antibody comprises one or more sequences sharing at least 95% identity with any of SEQ ID NOS: 1-24. In another embodiment, the antibody comprises one or more sequences sharing at least 96% identity with any of SEQ ID NOS: 1-24. In another embodiment, the antibody comprises one or more sequences sharing at least 97% identity with any of SEQ ID NOS: 1-24. In another embodiment, the antibody comprises one or more sequences sharing at least 98% identity with any of SEQ ID NOS: 1-24. In another embodiment, the antibody comprises one or more sequences sharing at least 99% identity with any of SEQ ID NOS: 1-24.

In one embodiment, the antibody described herein does not significantly adversely alter the membrane deformability of the erythrocyte to which it is bound. As used herein, the term "does not significantly adversely alter the membrane deformability" means less than a 10% change in membrane rigidity as compared to a naïve erythrocyte. Membrane deformability can be measured by the person of skill in the art using known techniques and those described herein, e.g., in Example 4. For example, ektacytometry can be used to test whether alterations in membrane deformability are observed. In this technique, a decrease in the maximal elongation index (EImax) or an increase in the shear stress to reach half-maximal deformation (SS1/2) reflects an increase in RBC rigidity. See, e.g., Bessis M., Mohandas N., and Feo C., "Automated ektacytometry: A new method of measuring red cell deformability and red cell indices," Blood Cells 6(3), 315-327 (1979) and Chien S., "Principles and techniques for assessing erythrocyte deformability," in Red Cell Rheology, edited by Bessis M., Shohet S., and Mohandas N. (Springer; Berlin Heidelberg, 1978), pp. 71-99, which are incorporated herein by reference.

In another embodiment, the antibody described herein does not significantly alter the resistance to stress of the erythrocyte to which it is bound. As used herein, the term "does not significantly alter resistance to stress" means less than a 10% change to physical, chemical, mechanical and/or other stresses, or combinations of thereof. In one embodiment, the term does not significantly alter resistance to stress" means less than a 10% change in osmotic hemolysis or hemolysis induced by mechanical stress as compared to a naïve erythrocyte. Stress to the erythrocyte can be measured by the person of skill in the art using known techniques and those described herein, e.g., in Example 4. For example, osmotic stress can be measured using an osmotic fragility test. See, Godal et al. The normal range of osmotic fragility of red blood cells, Scand J Haematol. 1980 August; 25(2):107-12, which is incorporated herein by reference. Mechanical stress can be measured using, e.g., the mechanical stress assay (Pan D, Vargas-Morales O, Zern B, et al. The Effect of Polymeric Nanoparticles on Biocompatibility of Carrier Red Blood Cells. PLoS One. 2016; 11(3):e0152074, which is incorporated herein by reference) does not directly represent a pathophysiologic scenario, it is intended to reflect overall integrity of the RBC membrane architecture.

Band 3

Band 3, the human RBC anion exchange protein (AE1), is the most abundant integral membrane protein found in erythrocytes and a well-characterized transporter and is encoded by the SLC4a1 gene. There are two blood group antigens, the low-incidence Wr(a) and the high-incidence Wr(b), that are considered to be antithetical and are produced as allelic forms of the same structural gene defined in the Band 3 protein. The Wr(b) antigen requires glycophorin A for surface presentation. See, Huang et al, Blood, Vol 87, No 9 (May I), 1996: pp 3942-3947, which is incorporated herein by reference.

As used herein, "Band 3" refers to the above-described polypeptide, including all isoforms thereof (UniProtKB-P02730). The "canonical" sequence can be found under Uniprot Identifier: P02730-1, also called isoform 1 or eAE1, and is shown below and in SEQ ID NO: 367. The molecular basis of the Wr(a)/Wr(b) blood group antigens is a single variation in position 658; Lys-658 corresponds to Wr(a) and Glu-658 to Wr(b).

```
         10         20         30         40
    MEELQDDYED MMEENLEQEE YEDPDIPESQ MEEPAAHDTE 50         60         70         80
    ATATDYHTTS HPGTHKVYVE LQELVMDEKN QELRWMEAAR 90        100        110        120
    WVQLEENLGE NGAWGRPHLS HLTFWSLLEL RRVFTKGTVL 130        140        150        160
    LDLQETSLAG VANQLLDRFI FEDQIRPQDR EELLRALLLK 170        180        190        200
    HSHAGELEAL GGVKPAVLTR SGDPSQPLLP QHSSLETQLF 210        220        230        240
    CEQGDGGTEG HSPSGILEKI PPDSEATLVL VGRADFLEQP 250        260        270        280
    VLGFVRLQEA AELEAVELPV PIRFLFVLLG PEAPHIDYTQ 290        300        310        320
    LGRAAATLMS ERVFRIDAYM AQSRGELLHS LEGFLDCSLV 330        340        350        360
    LPPTDAPSEQ ALLSLVPVQR ELLRRRYQSS PAKPDSSFYK 370        380        390        400
    GLDLNGGPDD PLQQTGQLFG GLVRDIRRRY PYYLSDITDA 410        420        430        440
    FSPQVLAAVI FIYFAALSPA ITFGGLLGEK TRNQMGVSEL 450        460        470        480
    LISTAVQGIL FALLGAQPLL VVGFSGPLLV FEEAFFSFCE 490        500        510        520
    TNGLEYIVGR VWIGFWLILL VVLVVAFEGS FLVRFISRYT 530        540        550        560
    QEIFSFLISL IFIYETFSKL IKIFQDHPLQ KTYNYNVLMV 570        580        590        600
    PKPQGPLPNT ALLSLVLMAG TFFFAMMLRK FKNSSYFPGK 610        620        630        640
    LRRVIGDFGV PISILIMVLV DFFIQDTYTQ KLSVPDGFKV
```

```
        650        660        670        680
    SNSSARGWVI HPLGLRSEFP IWMMFASALP ALLVFILIFL 690        700        710        720
    ESQITTLIVS KPERKMVKGS GFHLDLLLVV GMGGVAALFG 730        740        750        760
    MPWLSATTVR SVTHANALTV MGKASTPGAA AQIQEVKEQR 770        780        790        800
    ISGLLVAVLV GLSILMEPIL SRIPLAVLFG IFLYMGVTSL 810        820        830        840
    SGIQLFDRIL LLFKPPKYHP DVPYVKRVKT WRMHLFTGIQ 850        860        870        880
    IICLAVLWVV KSTPASLALP FVLILTVPLR RVLLPLIFRN 890        900        910
    VELQCLDADD AKATFDEEEG RDEYDEVAMP V
```

Provided herein are antibodies which bind to one or more antigens on the Band 3 polypeptide. Specifically, the antibodies are reactive against Wr(b) ("Wrb" also called DI4). See, Pool J., The Diego blood group system—an update, Immunohematology, 15(4), 1999, which is incorporated herein by reference.

In one embodiment, the antibodies described herein comprise one or more anti-Wrb antibody CDR sequence. Suitable CDR sequences are shown below in Table 4. In one embodiment, the CDRs from a single clone are used to produce an antibody or antibody fragment, e.g., CDR1, CDR2 and CDR3 from KP2-01, KP2-02 or KP2-04, KP2-06, KP2-07, KP2-08, KP2-09, KP2-11, KP2-13, KP2-14, KP2-15, KP2-17, KP2-18, KP2-19, KP2-20, KP2-22, KP2-23, KP2-24, KP3-01, KP3-02, KP3-03, KP3-05, KP3-06, KP3-07, KP3-08, KP3-09, KP3-12, KP3-13, KP3-15, KP3-16, KP3-18, KP3-19, or KP3-20. In another embodiment, the CDRs from one or more clone are used to produce an antibody. As a non-limiting illustrative example, CDR1 from clone KP2-01 and CDR2 and 3 from clone KP2-02 are used in conjunction to produce an antibody. In another embodiment, the VH CRDs from one clone are use with the VL CDRs from another clone. In another embodiment, the CDRs described herein are utilized with heterologous antibody sequences to produce a chimeric antibody. In one embodiment, the antibody comprises 1 CDR sequence selected from SEQ ID Nos 31-228. In another embodiment, the antibody comprises two CDR sequences selected from SEQ ID Nos 31-228. In another embodiment, the antibody comprises three CDR sequences selected from SEQ ID Nos 31-228. In another embodiment, the antibody comprises four CDR sequences selected from SEQ ID Nos 31-228. In another embodiment, the antibody comprises five CDR sequences selected from SEQ ID Nos 31-228. In another embodiment, the antibody comprises six CDR sequences selected from SEQ ID Nos 31-228.

In one embodiment, the antibodies described herein comprise one or more anti-Wrb antibody light (VL) or heavy (VH) variable chain sequence. Suitable VH and VL sequences are shown below in Table 5. In one embodiment, the VH and VL from a single clone are used to produce an antibody or antibody fragment, e.g., VH and VL from from KP2-01, KP2-02 or KP2-04, KP2-06, KP2-07, KP2-08, KP2-09, KP2-11, KP2-13, KP2-14, KP2-15, KP2-17, KP2-18, KP2-19, KP2-20, KP2-22, KP2-23, KP2-24, KP3-01, KP3-02, KP3-03, KP3-05, KP3-06, KP3-07, KP3-08, KP3-09, KP3-12, KP3-13, KP3-15, KP3-16, KP3-18, KP3-19, or KP3-20. In another embodiment, the VH from one clone is used in conjunction with a VL from another clone. In one embodiment, only a VH sequence is used. In another embodiment, only a VL sequence is used. In another embodiment, the variable chain sequences described herein are utilized with heterologous antibody sequences to produce a chimeric antibody. In one embodiment, the antibody comprises a VH sequence selected from SEQ ID NO: 229-261. In another embodiment, the antibody comprises a VL sequence selected from SEQ ID NO: 262-294. In one embodiment, the antibody comprises SEQ ID Nos. 229 and 262. In another embodiment, the antibody comprises SEQ ID Nos: 230 and 263. In another embodiment, the antibody comprises SEQ ID Nos: 231 and 264. In another embodiment, the antibody comprises SEQ ID Nos: 232 and 265. In another embodiment, the antibody comprises SEQ ID Nos: 233 and 266. In another embodiment, the antibody comprises SEQ ID Nos: 234 and 267. In another embodiment, the antibody comprises SEQ ID Nos: 235 and 268. In another embodiment, the antibody comprises SEQ ID Nos: 236 and 269. In another embodiment, the antibody comprises SEQ ID Nos: 237 and 270. In another embodiment, the antibody comprises SEQ ID Nos: 238 and 271. In another embodiment, the antibody comprises SEQ ID Nos: 239 and 272. In another embodiment, the antibody comprises SEQ ID Nos: 240 and 273. In another embodiment, the antibody comprises SEQ ID Nos: 241 and 274. In another embodiment, the antibody comprises SEQ ID Nos: 242 and 275. In another embodiment, the antibody comprises SEQ ID Nos: 243 and 276. In another embodiment, the antibody comprises SEQ ID Nos: 244 and 277. In another embodiment, the antibody comprises SEQ ID Nos: 245 and 278. In another embodiment, the antibody comprises SEQ ID Nos: 246 and 279. In another embodiment, the antibody comprises SEQ ID Nos: 247 and 280. In another embodiment, the antibody comprises SEQ ID Nos: 248 and 281. In another embodiment, the antibody comprises SEQ ID Nos: 249 and 282. In another embodiment, the antibody comprises SEQ ID Nos: 250 and 283. In another embodiment, the antibody comprises SEQ ID Nos: 251 and 284. In another embodiment, the antibody comprises SEQ ID Nos: 252 and 285. In another embodiment, the antibody comprises SEQ ID Nos: 253 and 286. In another embodiment, the antibody comprises SEQ ID Nos: 254 and 287. In another embodiment, the antibody comprises SEQ ID Nos: 255 and 288. In another embodiment, the antibody comprises SEQ ID Nos: 256 and 289. In another embodiment, the antibody comprises SEQ ID Nos: 257 and 290. In another embodiment, the antibody comprises SEQ ID Nos: 258 and 291. In another embodiment, the antibody comprises SEQ ID Nos: 259 and 292. In another embodiment, the antibody comprises SEQ ID Nos: 260 and 293. In another embodiment, the antibody comprises SEQ ID Nos: 261 and 294.

Also provided are nucleic acid sequence encoding the antibodies described herein. Such sequences include those shown in Table 6, SEQ ID Nos: 295-360. Also contemplated are nucleic acid sequences encoding the described antibodies. Such sequences include those which share at least about 60% identity with any of the sequence of SEQ ID Nos: 295-360. In another embodiment, the coding sequences share at least about 65% identity with any of the sequence of SEQ ID Nos: 295-360. In another embodiment, the coding sequences share at least about 70% identity with any of the sequence of SEQ ID Nos: 295-360. In another embodiment, the coding sequences share at least about 75% identity with any of the sequence of SEQ ID Nos: 295-360. In another embodiment, the coding sequences share at least about 80% identity with any of the sequence of SEQ ID Nos: 295-360. In another embodiment, the coding sequences share at least about 85% identity with any of the sequence of SEQ ID Nos: 295-360. In another embodiment, the coding sequences share at least about 90% identity with any of the sequence of SEQ ID Nos: 295-360. In another embodiment, the coding sequences share at least about 95% identity with any of the sequence of SEQ ID Nos: 295-360.

It is also contemplated that one or more of the antibody sequences useful herein encompasses variants of the antibody sequences described herein where modifications and/or substitutions have been made. In one embodiment, the antibody comprises one or more sequences sharing at least 80% identity with any of SEQ ID NOS: 229-294. In another embodiment, the antibody comprises one or more sequences sharing at least 85% identity with any of SEQ ID NOS: 229-294. In another embodiment, the antibody comprises one or more sequences sharing at least 90% identity with any of SEQ ID NOS: 229-294. In another embodiment, the antibody comprises one or more sequences sharing at least 91% identity with any of SEQ ID NOS: 229-294. In another embodiment, the antibody comprises one or more sequences sharing at least 92% identity with any of SEQ ID NOS: 229-294. In another embodiment, the antibody comprises one or more sequences sharing at least 93% identity with any of SEQ ID NOS: 229-294. In another embodiment, the antibody comprises one or more sequences sharing at least 94% identity with any of SEQ ID NOS: 229-294. In another embodiment, the antibody comprises one or more sequences sharing at least 95% identity with any of SEQ ID NOS: 229-294. In another embodiment, the antibody comprises one or more sequences sharing at least 96% identity with any of SEQ ID NOS: 229-294. In another embodiment, the antibody comprises one or more sequences sharing at least 97% identity with any of SEQ ID NOS: 229-294. In another embodiment, the antibody comprises one or more sequences sharing at least 98% identity with any of SEQ ID NOS: 229-294. In another embodiment, the antibody comprises one or more sequences sharing at least 99% identity with any of SEQ ID NOS: 229-294.

The antibody sequences herein were produced by immunizing a non-human primate with human erythrocytes. Thus, it may be desirable to make certain changes to the described sequences to make the antibodies more effective in human subjects. For example, in one embodiment, changes are made to one or more of the described sequences to make the antibody more human like. See, Gao S H, Huang K, Tu H, Adler A S. Monoclonal antibody humanness score and its applications. BMC Biotechnol. 2013; 13:55, which is incorporated herein by reference.

Such modifications and/or substitutions can be made at the nucleic acid or amino acid level. In one embodiment, the coding sequence of one or more immunoglobulin chain or region is codon optimized.

Once the target and immunoglobulin are selected, the coding sequences for the selected immunoglobulin (e.g., heavy and/or light chain(s)) may be obtained and/or synthesized. Methods for sequencing a protein, peptide, or polypeptide (e.g., as an immunoglobulin) are known to those of skill in the art. Once the sequence of a protein is known, there are web-based and commercially available computer programs, as well as service-based companies which back translate the amino acids sequences to nucleic acid coding sequences. See, e.g., backtranseq by EMBOSS, http://www.ebi.ac.uk/Tools/st/; Gene Infinity (http://www.geneinfinity.org/sms/sms_backtranslation.html); ExPasy (http:// www.expasy.org/tools/). In one embodiment, the RNA and/or cDNA coding sequences are designed for optimal expression in human cells.

Codon-optimized coding regions can be designed by various methods. This optimization may be performed using methods which are available on-line (e.g., GeneArt), published methods, or a company which provides codon optimizing services, e.g., DNA2.0 (Menlo Park, Calif.). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered (e.g., heavy constant, light constant, heavy variable, light variable chains). By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In one embodiment, such variants include sequences in which amino acid substitutions have been made to the known anti-RHCE or anti-Band3 variable chain sequences or heterologous backbone sequences described herein. Substitutions may also be written as (amino acid identified by single letter code)-position #-(amino acid identified by single letter code) whereby the first amino acid is the substituted amino acid and the second amino acid is the substituting amino acid at the specified position. The terms "substitution" and "substitution of an amino acid" and "amino acid substitution" as used herein refer to a replacement of an amino acid in an amino acid sequence with another one, wherein the latter is different from the replaced amino acid. Methods for replacing an amino acid are well known to the person skilled in the art and include, but are not limited to, mutations of the nucleotide sequence encoding the amino acid sequence. Methods of making amino acid substitutions in IgG are described, e.g., for WO 2013/046704, which is incorporated by reference for its discussion of amino acid modification techniques.

The term "amino acid substitution" and its synonyms described above are intended to encompass modification of an amino acid sequence by replacement of an amino acid with another, substituting amino acid. The substitution may be a conservative or non-conservative substitution. The term conservative, in referring to two amino acids, is intended to mean that the amino acids share a common property recognized by one of skill in the art. The term non-conservative, in referring to two amino acids, is intended to mean that the amino acids which have differences in at least one property recognized by one of skill in the art. For example, such properties may include amino acids having hydrophobic nonacidic side chains, amino acids having hydrophobic side chains (which may be further differentiated as acidic or nonacidic), amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Thus, a conservative amino acid substitution may involve changing a first amino acid having a hydrophobic side chain with a different amino acid having a hydrophobic side chain; whereas a non-conservative amino acid substitution may involve changing a first amino acid with an acidic hydrophobic side chain with a different amino acid having a different side chain, e.g., a basic hydrophobic side chain or a hydrophilic side chain. Still other conservative or non-conservative changes change be determined by one of skill in the art.

In still other embodiments, the substitution at a given position will be to an amino acid, or one of a group of amino acids, that will be apparent to one of skill in the art in order to accomplish an objective identified herein.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., any one of the modified ORFs provided herein when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). As another example, polynucleotide sequences can be compared using Fasta, a program in GCG Version 6.1. Fasta provides alignments and percent sequence identity of the regions of the best overlap between the query and search sequences. For instance, percent sequence identity between nucleic acid sequences can be determined using Fasta with its default parameters (a word size of 6 and the NOPAM factor for the scoring matrix) as provided in GCG Version 6.1, herein incorporated by reference. Generally, these programs are used at default settings, although one skilled in the art can alter these settings as needed. Alternatively, one of skill in the art can utilize another algorithm or computer program that provides at least the level of identity or alignment as that provided by the referenced algorithms and programs. This definition also refers to, or can be applied to, the compliment of a sequence. The definition also includes sequences that have deletions and/or additions, as well as those that have substitutions. As described below, the preferred algorithms can account for gaps and the like. Preferably, identity exists over a region that is at least about 25, 50, 75, 100, 150, 200 amino acids or nucleotides in length, and oftentimes over a region that is 225, 250, 300, 350, 400, 450, 500 amino acids or nucleotides in length or over the full-length of an amino acid or nucleic acid sequences.

Typically, when an alignment is prepared based upon an amino acid sequence, the alignment contains insertions and deletions which are so identified with respect to a reference AAV sequence and the numbering of the amino acid residues is based upon a reference scale provided for the alignment. However, any given AAV sequence may have fewer amino acid residues than the reference scale. In the present invention, when discussing the parental sequence, the term "the same position" or the "corresponding position" refers to the amino acid located at the same residue number in each of the sequences, with respect to the reference scale for the aligned sequences. However, when taken out of the alignment, each of the proteins may have these amino acids located at different residue numbers. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCK-MAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, *Nucl. Acids. Res*., "A comprehensive comparison of multiple sequence alignments", 27(13):2682-2690 (1999).

Cargoes

For several decades, researchers have used erythrocytes for drug delivery of a wide variety of therapeutics to improve their pharmacokinetics, biodistribution, controlled release and pharmacodynamics. Provided herein are compositions in which both therapeutic and non-therapeutic cargoes are coupled to the surface of the red blood cell using the antibodies described herein.

As used herein, the term "cargo" or "agent" refers to any pharmacological, therapeutic, prophylactic, imaging or diagnostic agent which is coupled to, bound, fused, associated with or conjugated to an anti-RHCE or anti-Band 3 antibody described herein. In one embodiment, the term cargo or agent refers to more than one cargo or agent described herein, e.g., liposomes loaded with other drugs. Drugs whose delivery may be improved by coupling to RBCs include antigens and cytokines to stimulate the immune response, antibodies for vascular targeting of RBC-loaded cargoes, antibodies and other ligands to capture circulating pathological mediators such toxins and pathogens themselves, therapeutic enzymes and other biomolecules whose targets are localized within the bloodstream, and complement inhibitors to protect RBCs against pathological hemolysis. See, Villa et al, Delivery of drugs bound to erythrocytes: new avenues for an old intravascular carrier, Therapeutic Delivery, 6(7), 2015, which is incorporated herein by reference.

In one embodiment, the cargo is a liposome. Liposomes are small artificial vesicles of spherical shape that can be created from cholesterol and natural non-toxic phospholipids. See, Akbarzakeh et al, Nanoscale Res Lett. 2013; 8(1): 102, which is incorporated herein by reference. Liposomes consist of an aqueous core surrounded by a lipid bilayer, much like a membrane, separating the inner aqueous core from the bulk outside. Liposomes have been used to improve the therapeutic index of new or established drugs by modifying drug absorption, reducing metabolism, prolonging biological half-life or reducing toxicity. Drug distribution is then controlled primarily by properties of the carrier and no longer by physico-chemical characteristics of the drug substance only.

Lipids forming liposomes may be natural or synthetic, and liposome constituents are not exclusive of lipids, new generation liposomes can also be formed from polymers (sometimes referred to as polymersomes). Whether composed of natural or synthetic lipids or polymers, liposomes are biocompatible and biodegradable which make them suitable for biomedical research. The unique feature of liposomes is their ability to compartmentalize and solubilize both hydrophilic and hydrophobic materials by nature. Hydrophobic drugs place themselves inside the bilayer of the liposome and hydrophilic drugs are entrapped within the aqueous core or at the bilayer interface. Liposomal formulations enhance the therapeutic efficiency of drugs in preclinical models and in humans compared to conventional formulations due to the alteration of biodistribution. Liposome binding drugs, into or onto their membranes, are expected to be transported without rapid degradation and minimum side effects to the recipient because generally liposomes are composed of biodegradable, biologically inert and non-immunogenic lipids. Moreover, they produce no pyrogenic or antigenic reactions and possess limited toxicity. Consequently, all these properties as well as the ease of surface modification to bear the targetable properties make liposomes attractive candidates for use as drug-delivery. Additional cargoes may be loaded into the liposomes and coupled to the described antibodies. Such additional cargoes are selected from any useful agent, including those described herein.

In one embodiment, the cargo may be any anti-thrombotic agent (molecule), anti-inflammatory agent, or pro-drug thereof for which targeting to a red blood cell is desired for purposes of systemic delivery, or alternatively, for delivery to the site of a pathological condition including conditions characterized by the production or presence of an enzyme that can cleave the anti-thrombotic agent, anti-inflammatory agent, or the pro-drug, from the fusion protein.

As used herein, the term "pro-drug" or "prodrug" encompasses any polypeptide encoding an anti-thrombotic or anti-inflammatory agent and a cleavage site for activation of the agent. The pro-drug is inactive (or significantly less active) upon administration, and is metabolized in vivo into an active form. In further embodiments, the pro-drug is a pro-drug of an anti-thrombotic or anti-inflammatory agent.

In one embodiment, the anti-thrombotic agent is one that is capable of producing its therapeutic effect when attached to the RBC, i.e., an active anti-thrombotic agent. In another embodiment, the anti-thrombotic agent is a pro-drug which contains a native or synthetic cleavage site and which produces an active anti-thrombotic effect only upon cleavage from its pro-drug state.

Among such anti-thrombotic agents include without limitation, plasminogen activators. In still a further embodiment, the plasminogen activator is tPA, urokinase, tenectase, retavase, streptokinase, staphylokinase, or a plasminogen activator from venoms and saliva of bats, insects, and other animals. In another embodiment, the plasminogen activator is anistreplase, pro-urokinase (pUK), or a hybrid plasminogen activator (e.g., as described in U.S. Pat. No. 4,916,071). In one embodiment, the cargo is thrombomodulin, as shown in the examples herein.

In a further embodiment the anti-thrombotic agent is the low molecular weight single chain urokinase-like plasminogen activator described in the examples below (also termed uPA (as the exemplary plasminogen activator), lUK, lmwUK, and lmw scuPA within the examples). Also included are mutants or variants thereof, which retain plasminogen activator activity, such as variants which have been chemically modified or in which one or more amino acids have been added, deleted or substituted or in which one or more functional domains have been added, deleted or altered such as by combining the active site of one plasminogen activator or fibrin binding domain of another plasminogen activator or fibrin binding molecule. In a further embodiment, the anti-thrombotic agent contains a moiety presented by a protease domain of a plasminogen activator. Naturally-occurring pro-drugs of these agents may be employed. Synthetically designed prodrugs based on these agents may also be employed. Prodrugs containing modified cleavage sites may also be employed.

In one embodiment, the cargo is a therapeutic protein or pro-drug of an anti-inflammatory agent. In one embodiment, the anti-inflammatory agent is an antibody against a cytokine or other pro-inflammatory mediator. In a further embodiment, the anti-inflammatory agent may comprise a moiety presented by thrombomodulin or a domain thereof. Among other anti-inflammatory agents for use in the fusion proteins described herein are, without limitation, somatostatin, adiponectin, cortistatin, corticotrophin releasing factor, sauvagine, nocifensins, as well as the anti-inflammatory cytokines, IL-1 receptor antagonist (IL-lra), IL-4, IL-6, IL-10, and IL-13 and the soluble receptors sTNFRI, sTN-FRp55, sTNFRII, sTNFRp75, sIL-1RII, mIL-1RII, and IL-18BP, among others. Anti-inflammatory proteins may be native or mutated proteins. Similarly, native, mutated or synthetic anti-inflammatory peptides, including without limitation, peptides described in U.S. Pat. Nos. 5,480,869; 7,816,449 and 5,229,367, among other known peptides may also form part of the fusion proteins described herein. One of skill in the art may select or design an appropriate anti-inflammatory agent or prodrug depending on the pathological condition being treated.

In still another embodiment, the therapeutic molecule is a molecule which binds a pro-inflammatory mediator. In one embodiment, the pro-inflammatory mediator is the HMGB1 cytokine. In one embodiment, signaling by HMGB1 is disrupted by binding of the lectin-like domain of thrombomodulin (abbreviated herewith as TM). In other embodiments, the pro-inflammatory cytokine is IL-1-α, IL-1-β, IL-6, TNF-α, TGF-β, LIF, IFN-γ, OSM, CNTF, GM-CSF, IL-8, IL-11, IL-12, IL-17, and IL-18.

In one embodiment, a fusion protein may contain a therapeutically-active site, domain or moiety of any of the anti-thrombotic agents, anti-inflammatory agents, or pro-drugs listed herein or known to the art to be suitable for direct targeted administration to the site of a thrombus. Other useful pro-drugs known to one of skill in the art may be used herein.

In still other embodiments, mutations in protein sequence of the anti-thrombotic agent or anti-inflammatory agent, therapeutically-active site, domain, or moiety thereof allows its conversion into a pro-drug activated and/or released locally at a desired pathological site (e.g., pathological nascent intravascular thrombi) using specific activity of pathological factors that exist only in these pathological sites, such as protease thrombin. Such mutations in the amino acid sequences or nucleotide sequences encoding the therapeutic protein can be employed to insert a desired cleavage, enzymatic or activation site into the therapeutic molecule, or into or adjacent the linker between the antibody and the cargo. Alternatively, such mutations can change a native cleavage site to another desired cleavage site, or to insert a cleavage site where none naturally existed into or adjacent to a cargo.

In one embodiment, the therapeutic pro-drug molecule is activated or the mature drug molecule released from the fusion protein by an enzyme, which level is locally elevated under pathological conditions. In a further embodiment, the enzyme is a protease. In still further embodiments, the protease is a leukocyte protease (e.g., cathepsin), an activated protease in the coagulation cascade (e.g., activated Factor Xa), or an activated protease in the complement cascade. In other embodiments, the protease's activity is elevated locally in tissue. In still other embodiments, the protease is a metalloproteinase, elastase, or collagenase.

In still other embodiments of fusion proteins containing therapeutic pro-drug molecules, the enzyme is a pathological mediator. In further embodiments, the pathological mediator is involved in coagulation or fibrinolysis. In another embodiment, the pathological mediator is thrombin or plasmin. In a further embodiment, the pathological mediator is thrombin. Thus, for example, in one embodiment, the therapeutic pro-drug molecule is the thrombin activatable low molecular weight single chain urokinase-like plasmin activator, described in the examples below. In another embodiment, the therapeutic pro-drug molecule is thrombin-activatable thrombomodulin, or thrombin-activatable tPA (or its mouse analog, mRNK-T).

Other cargoes useful include blood factors including those involved in blood clotting. Such blood factors include factor VIII and factor IX. Further cargoes include small molecule drugs. Other cargoes useful herein include anti-malarial drugs, such as chloroquine, quinine sulfate, hydroxychloroquine, mefloquine, atovaquone and proguanil. Other useful cargoes include anti-hemolytic agents. In one embodiment, such drugs are loaded into liposomes, polymeric particles, lipid nanoparticles, natural or artificial biomolecules or assemblies. See, e.g., Giri et al, Anticancer Agents Med Chem. 2016; 16(7):816-31; WO 2017/023358; Jo et al, Colloids Surf B Biointerfaces. 2014 Nov. 1; 123:345-63. doi: 10.1016/j.colsurfb.2014.09.029. Epub 2014 Sep. 22, each of which is incorporated herein by reference.

Fusion Proteins and Conjugates

The cargoes and antibodies described herein are coupled in one of various appropriate methods. Such methods include fusion proteins, chemical conjugation, chemical crosslinking, use of a linker, click chemistry and the like. Such methods are known in the art. As used herein, terms such as and including "coupled to", "bound", "fused, "associated with" or "conjugated to" are used interchangeably. Where one embodiment is provided utilizing the antibody and cargo as e.g., a fusion protein, another embodiment is contemplated in which the antibody and cargo are coupled via another method, e.g., using click chemistry or the like.

In one embodiment, the antibody and the cargo are expressed as a fusion protein. Fusion proteins are created through the joining of two or more genes that originally coded for separate proteins. In one embodiment, the fusion protein comprises an scFv and a heterologous expression product. Such expression products include certain of the cargoes described herein. In one embodiment, the fusion proteins contain a targeting single chain antigen-binding domain (scFv) that binds to a determinant expressed on the surface of a red blood cell, e.g., RHCE (rh17) or Band3 (Wrb). Use of an scFv (monovalent) avoids cross-linking of binding sites or determinants, thereby avoiding potentially harmful cell membrane modification and cell aggregation.

ScFvs may be generated conventionally, e.g., by the method of Spitzer, et al. (Mol. Immunol. 2003, 40:911-919), or by the methods described herein. Total RNA of a hybridoma cell line is isolated (e.g., by RNeasy, Qiagen, Velencia, Calif.), followed by reverse transcription, e.g., using the SMART™ technology (Clontech, Palo Alto, Calif.) employing known primers (e.g., those of Dübel, et al. (J. Immunol. Methods 1994, 175:89-95)). The resulting heavy (VH) and light (VL) chain variable cDNA fragments are then subcloned into a suitable plasmid, e.g., pCR®2.1-TOPO® (Invitrogen, Carlsbad, Calif.). The materials utilized are not a limitation of these embodiments. The VH and VL chains generated are combined with a suitable linker, resulting in the desired scFv (see, e.g., Example 1). In one embodiment, the scFV comprises anti-RHCD sequences. In one embodiment, the scFv comprises SEQ ID Nos. 19 and 20. In another embodiment, the scFv comprises SEQ ID Nos: 21 and 22. In another embodiment, the scFv comprises SEQ ID Nos: 23 and 24. In one embodiment, the scFV comprises anti-Band3 sequences. In one embodiment, the scFv comprises SEQ ID Nos. 229 and 262. In another embodiment, the scFv comprises SEQ ID Nos: 230 and 263. In another embodiment, the scFv comprises SEQ ID Nos: 231 and 264. In another embodiment, the scFv comprises SEQ ID Nos: 232 and 265. In another embodiment, the scFv comprises SEQ ID Nos: 233 and 266. In another embodiment, the scFv comprises SEQ ID Nos: 234 and 267. In another embodiment, the scFv comprises SEQ ID Nos: 235 and 268. In another embodiment, the scFv comprises SEQ ID Nos: 236 and 269. In another embodiment, the scFv comprises SEQ ID Nos: 237 and 270. In another embodiment, the scFv comprises SEQ ID Nos: 238 and 271. In another embodiment, the scFv comprises SEQ ID Nos: 239 and 272. In another embodiment, the scFv comprises SEQ ID Nos: 240 and 273. In another embodiment, the scFv comprises SEQ ID Nos: 241 and 274. In another embodiment, the scFv comprises SEQ ID Nos: 242 and 275. In another embodiment, the scFv comprises SEQ ID Nos: 243 and 276. In another embodiment, the scFv comprises SEQ ID Nos: 244 and 277. In another embodiment, the scFv comprises SEQ ID Nos: 245 and 278. In another embodiment, the scFv comprises SEQ ID Nos: 246 and 279. In another embodiment, the scFv comprises SEQ ID Nos: 247 and 280. In another embodiment, the scFv comprises SEQ ID Nos: 248 and 281. In another embodiment, the scFv comprises SEQ ID Nos: 248 and 281. In another embodiment, the scFv comprises SEQ ID Nos: 249 and 282. In another embodiment, the scFv comprises SEQ ID Nos: 250 and 283. In another embodiment, the scFv comprises SEQ ID Nos: 251 and 284. In another embodiment, the scFv comprises SEQ ID Nos: 252 and 285. In another embodiment, the scFv comprises SEQ ID Nos: 253 and 286. In another embodiment, the scFv comprises SEQ ID Nos: 254 and 287. In another embodiment, the scFv comprises SEQ ID Nos: 255 and 288. In another embodiment, the scFv comprises SEQ ID Nos: 256 and 289. In another embodiment, the scFv comprises SEQ ID Nos: 257 and 290. In another embodiment, the scFv comprises SEQ ID Nos: 258 and 291. In another embodiment, the scFv comprises SEQ ID Nos: 259 and 292. In another embodiment, the scFv comprises SEQ ID Nos: 260 and 293. In another embodiment, the scFv comprises SEQ ID Nos: 261 and 294.

In one aspect, nucleic acid sequences are provided which encode the scFv. In one embodiment, the coding sequences include one of the sequences of Table 3 or Table 6. A cartoon of an exemplary RHCE scFv-human thrombomodulin fusion protein plasmid is provided in FIG. 18.

In another embodiment, the antibodies are chemically conjugated to their cargoes using molecular cross-linkers, spacers, and bridges. By cross-linkers, spacer and bridges are meant any moiety used to attach or associate the antibody to the cargo. In one embodiment, the cross-linker is a covalent bond. In another embodiment, the linker is a non-covalent bond. In still other embodiments, the linker can be a larger compound or two or more compounds that associate covalently or non-covalently. In still other embodiment, the linker can be a combination of the linkers, e.g., chemical compounds, nucleotides, amino acids, proteins, etc. In one embodiment, the cross-linker is biotin-streptavidin. In this embodiment, interconnecting molecule(s) such as streptavidin can be coupled to RBC either directly via chemical modification, or via biotin derivatives conjugated to the functional groups on RBC, inserted into RBC phospholipids or coupled to other appropriate RBC components such as sugars, with or without additional spacers between the active group anchoring biotin derivative to RBC. In turn, cargo molecules are coupled to streptavidin either via chemical conjugation or via using biotin derivatives as described above. In one embodiment a spacer is positioned between biotin and a reactive group, such as succinimide ester group. Various methods of bioconjugation are known in the art. See, e.g., Kalia and Raines, Curr Org Chem. 2010 January; 14(2): 138-147, which is incorporated herein by reference.

In one embodiment, a fusion protein as described herein is prepared by linking (fusing) the above-described scFv to a described cargo, (e.g., a above-described anti-thrombotic agent, anti-inflammatory agent, or pro-drug molecule). Moreover, genetic engineering allows the design and synthesis of targeted pro-drugs which can be cleaved by pathophysiologically relevant enzymes that are generated at the size of disease that cannot be attained using chemical conjugation.

Linkers may also be utilized to join variable heavy and variable light chain fragments. A linker as used herein refers to a chain of as short as about 1 amino acid to as long as about 100 amino acids, or longer. In a further embodiment, the linker is 3, 4, 5, 6, 7, 8, 9, 10, 11, 12, 13, 14, 15, 16, 17, 18, 19, or 20 amino acids in length. In one embodiment, the linker is 13 amino acids in length.

Further, a cleavage sequence, such as the thrombin-sensitive cleavage sequence or other enzyme cleavage sequence, can be inserted in the linker to provide for release of the drug when the RBC to which it is targeted encounters the appropriate cleaving enzyme at the site of the pathological condition, e.g., upon active thrombosis. This cleavage sequence may be located within a linker or at a terminus thereof. In one embodiment, a thrombin cleavage site -Met-Tyr-Pro-Arg-Gly-Asn- may be inserted in, or appended to, the linker between the scFv and the therapeutic molecule or pro-drug. In another embodiment, the thrombin cleavage site is Pro-Arg. In still a further embodiment, lack of the native Phe-Lys plasmin cleavage site prevents single chain (sc) uPA activation (into fully active two-chain plasminogen activator (tcuPA)) via plasmin.

In another embodiment, antibody-derived scFv with a thrombin releasing site can be cloned by an upstream primer, which anneals to the carboxy terminus and introduces the sequence including a short peptide linker with the thrombin cleavage site. In still another embodiment, the cleavage site is internal to the pro-drug itself.

In one embodiment, the antibody and cargo are conjugated using click chemistry. In one embodiment, the conjugation is done using copper-independent click chemistry. Briefly, the antibody (e.g., scFV) is chemically modified to site-specifically incorporate a strained alkyne for 'click' coupling. The cargo (e.g., liposome) is functionalized with a complementary group, such as DBCO and azide. Other examples of click chemistry reactions, include, without limitation: cycloaddition reactions, such as the 1,3-dipolar family, and hetero Diels-Alder reactions; nucleophilic ring-opening reactions (e.g., epoxides, aziridines, cyclic sulfates, and so forth); carbonyl chemistry, such as the formation of oxime ethers, hydrazones, and aromatic heterocycles; in addition to carbon-carbon multiple bonds, such as epoxidation and dihydroxylation and azide-phosphine coupling (Staudinger ligation). See, Nwe and Brechbiel, Cancer Biother Radiopharm. 2009 June; 24(3): 289-302, which is incorporated herein by reference.

Methods of Preparation

The sequences, antibodies, fragments, fusion proteins and conjugates described herein may be produced by any suitable means, including recombinant production, chemical synthesis, or other synthetic means. Suitable production techniques are well known to those of skill in the art. See, e.g., Sambrook et al, Molecular Cloning: A Laboratory Manual, Cold Spring Harbor Press (Cold Spring Harbor, N.Y.). Alternatively, peptides can also be synthesized by the well-known solid phase peptide synthesis methods (Merrifield, J. Am. Chem. Soc., 85:2149 (1962); Stewart and Young, Solid Phase Peptide Synthesis (Freeman, San Francisco, 1969) pp. 27-62). Polymerase chain reaction (PCR) and related techniques are described in Derbyshire, et al. (Immunochemistry 1: A practical approach. M. Turner, A. Johnston eds., Oxford University Press 1997, e.g., at pp. 239-273). Plasmids useful herein have been described in Derbyshire, et al. (cited above), as well as Gottstein, et al. (Biotechniques 30: 190-200, 2001). Cloning techniques are also described in these and other suitable production methods are within the knowledge of those of skill in the art and are not a limitation of the compositions and methods described herein. Generation of recombinant proteins provides flexibility in design, rapid production, large-scale production and uniform composition.

In one aspect, a construct is provided which encodes the fusion proteins or antibodies described herein. Such a construct is, in on aspect, delivered to a subject in need thereof via an appropriate viral vector or the like. Suitable viral vectors include, without limitation, retrovirus, adenovirus, adeno-associated virus (AAV), herpes simplex virus, lentivirus, and chimeric viral vectors. These vectors may be designed and employed by the person of skill in the art using the sequences and teachings herein.

As an example, reference is made to the use of an AAV as a viral vector for gene therapy. However, similar vectors can be constructed using other types of viral vectors. Typically, an expression cassette for an AAV vector comprises an AAV 5' inverted terminal repeat (ITR), the immunoglobulin/antibody coding sequences and any regulatory sequences, and an AAV 3' ITR. However, other configurations of these elements may be suitable. In one embodiment, the expression cassette encodes a fusion protein, e.g., the scFv coding sequences in combination with the coding sequence for a cargo. Such a construct is shown in FIG. 18.

Figure 18:
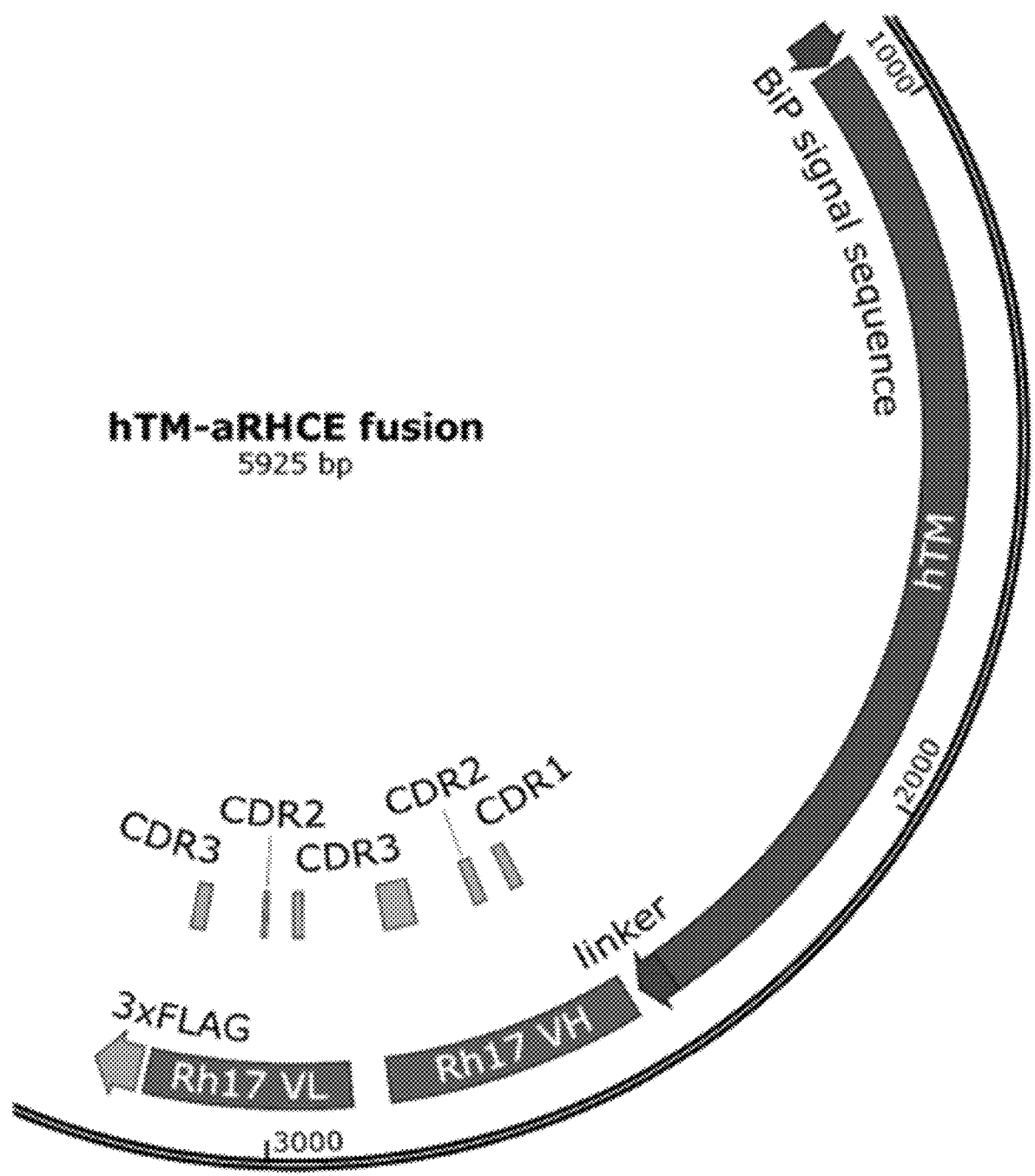
FIG. 18 is a schematic of the hTM-aRHCE vector which includes a human thrombomodulin domain (hTM), and Rh17 VH and VL chains.

The expression cassette may contain at least one internal ribosome binding site, i.e., an IRES, located between the coding regions of the heavy and light chains, or located between the coding regions of the scFv and the cargo (e.g., thrombomodulin as in FIG. 18). Alternatively, the heavy and light chain or scFv and the cargo coding sequences may be separated by a furin-2a self-cleaving peptide linker (see, e.g., Radcliffe and Mitrophanous, Gene Therapy (2004), 11, 1673-1674, which is incorporated herein by reference). The use of AAV for delivering antibody sequences is known. See, e.g., WO 2017/106326, which is incorporated by reference herein.

In one embodiment, the antibody genes described herein are engineered into a genetic element (e.g., a plasmid) useful for generating viral vectors which transfer the immunoglobulin construct sequences carried thereon. The selected vector may be delivered to a packaging cell by any suitable method, including transfection, electroporation, liposome delivery, membrane fusion techniques, high velocity DNA-coated pellets, viral infection and protoplast fusion. Stable packaging cells can also be made. The methods used to make such constructs are known to those with skill in nucleic acid manipulation and include genetic engineering, recombinant engineering, and synthetic techniques. See, e.g., Molecular Cloning: A Laboratory Manual, ed. Green and Sambrook, Cold Spring Harbor Press, Cold Spring Harbor, N.Y. (2012).

Pharmaceutical Compositions and Methods of Treatment

Pharmaceutical compositions containing antibodies, fragments, fusion proteins and/or conjugates described herein and a pharmaceutically acceptable carrier or vehicle as described herein are useful for the treatment of a variety of diseases and disorders, depending upon the selection and identity of the cargo. In one embodiment, a composition comprises a pharmaceutically acceptable vehicle for intravenous administration. In another embodiment, a composition comprises a pharmaceutically acceptable vehicle for administration via other vascular routes, including but not limited to, intra-arterial and intra-ventricular administration, as well as routes providing slower delivery of drugs to the bloodstream such as intramuscular administration to an animal in need thereof. As used herein, the terms "subject" and "patient" include any mammal. In a further embodiment, the terms "subject" and "patient" refer to a human.

Pharmaceutically acceptable vehicles/carriers include any of those conventionally used in the art, e.g., saline, phosphate buffered saline (PBS), or other liquid sterile vehicles accepted for intravenous injections in clinical practice. Pharmaceutical compositions may also include buffers, pH adjusting agents, and other additives conventionally used in medicine. Other exemplary carriers include sterile saline, lactose, sucrose, maltose, and water. Optionally, the compositions of the invention may contain excipient, diluent and/or adjuvant, other conventional pharmaceutical ingredients, such as preservatives, or chemical stabilizers. In one embodiment, compositions described herein are administered systemically as a bolus intravenous injection of a single therapeutic dose of the fusion protein. In a further embodiment, the dose is 0.1-5.0 mg/kg. In another embodiment, the dose is 0.01-0.5 mg/kg.

In one embodiment, methods of treatment are provided comprising delivering antibodies, fragments, fusion proteins and/or conjugates described herein, or a pharmaceutical composition described herein, to a mammalian subject, particularly a human. In other embodiments, methods of treatment are provided comprising delivering antibodies, fragments, fusion proteins and/or conjugates described herein, or a pharmaceutical composition described herein, to a blood vessel. In one embodiment, antibodies, fragments, fusion proteins and/or conjugates described herein are administered via a systemic intravascular route, e.g., a vascular catheter. In some embodiments, rapid targeting of an organ or system may be accomplished by delivery via coronary artery (e.g., for prophylaxis of acute myocardial infarction (AMI)) or the cerebral artery (e.g., for prophylaxis of stroke and other cerebrovascular thrombotic events). Further, the antibodies, fragments, fusion proteins and/or conjugates described herein may be administered prophylactically, i.e., in patients predisposed to thrombosis. In a further embodiment, the antibodies, fragments, fusion proteins and/or conjugates described herein may be administered to an organ donor, utilized with an isolated organ transplant (e.g., via perfusion), or used with vascular stents.

Thus, in one embodiment, methods of treating or preventing a cardiovascular disorder, such as thrombosis, tissue ischemia, AMI, ischemic stroke, pulmonary embolism, sepsis, acute lung injury (ALI) or other type of vascular inflammation, or ischemic peripheral vascular disease, involves administering antibodies, fragments, fusion proteins and/or conjugates described herein, or a pharmaceutical composition as described herein, to a blood vessel in a mammal in need thereof. In such disorders, the anti-thrombotic or anti-inflammatory agent and its dosage in delivery (i.e., the amount fused to an individual RBC may be selected and adjusted by an attending physician with regard to the nature of the disorder, the physical condition of the patient, and other such factors). The selection of the cleavage site, where included, may also be selected to match the disorder, e.g., a thrombin cleavage site suitable for most cardiovascular disorders. Loading red blood cells (RBC) in vivo with anti-thrombotic agents (ATAs) constitutes a new approach to thromboprophylaxis that holds promise for improving the management of patients at high risk of thrombosis for a defined period of time in whom anticoagulation poses an unacceptable risk. Delivery of plasminogen activators (PAs) and thrombomodulin (TM) via RBCs markedly prolongs intravascular lifespan and restricts vascular and tissue damage.

In one embodiment, the compositions described herein are effective in the treatment or prevention of cerebrovascular thrombi. In a further embodiment, the compositions described herein are effective in the treatment or prevention of cerebrovascular disease, such as transient ischemic attack and stroke. In yet another embodiment, the antibodies, fragments, fusion proteins and/or conjugates described herein, or a pharmaceutical composition as described herein are effective in prolonging the circulation of a cargo in a subject in need thereof.

Similarly, in another embodiment, methods of treating or preventing disseminated intravascular coagulation (DIC), sepsis, acute lung injury (ALI/ARDS), aseptic systemic inflammation, and other inflammatory conditions are provided by administering the appropriately designed fusion proteins and/or conjugate described herein, according to the teachings of this specification.

Also provided is the use of antibodies, fragments, fusion proteins and/or conjugates described herein or a pharmaceutical composition as described herein as a medicament. The use of antibodies, fragments, fusion proteins and/or conjugates described herein or a pharmaceutical composition as described herein is provided to treat any of the above conditions.

Provided herein is a method of treating or preventing thrombosis, tissue ischemia, acute myocardial infarction (AMI), non-segmented elevated AMI, deep vein thrombosis, ischemic stroke, hyperoxic injury, transient ischemic attack (TIA), cerebrovascular disease, disseminated intravascular coagulation (DIC), pulmonary embolism, ischemic peripheral vascular disease, inflammation, pulmonary edema, sepsis, acute lung injury (ALI), acute respiratory distress syndrome (ARDS), aseptic systemic inflammation, malaria, SCD, hemolytic anemia, or a bleeding disorder such as hemophilia. The method includes administering an antibody-cargo conjugate composition as described herein to a subject in need thereof.

The dosages, administrations and regimens may be determined by the attending physician given the teachings of this specification. In one embodiment, the composition is administered in a single dosage. In another embodiment, the composition is administered as a split dosage. Split administration may imply a time gap of administration from intervals of minutes, hours, days, weeks or months. In another embodiment, a second administration of a composition as described herein is performed at a later time point. Such time point may be weeks, months or years following the first administration. In one embodiment, the second administration is 1, 2, 3, 4, 5, 6, 7, 8, 9, 10 years or more after the first administration.

In still other embodiments, the compositions described herein may be delivered in a single composition or multiple compositions. Optionally, two or more different antibody conjugates, fusion proteins, or AAV may be delivered, or multiple viruses [see, e.g., WO 2011/126808 and WO 2013/049493]. In another embodiment, multiple viruses may contain different replication-defective viruses (e.g., AAV and adenovirus or lentivirus).

The compositions described herein have been shown to have little effect on RBC cell physiology. Previously used constructs, directed to Ter119, have been shown to induce rigidity in RBC. While targeting Wrb might be expected to induce rigidity[28], ligands to RHCE determinants were not previously characterized on human RBCs with respect to effects on cell physiology. These antibodies were then fused to the extracellular domain of human thrombomodulin (hTM-scFv) to produce an exemplary multi-faceted thromboprophylactic agent[20]. The binding of the scFv and hTM-scFv was characterized and examination of how both affected several clinically relevant aspects of human RBC physiology including osmotic resistance, mechanical strength, deformability under flow, and exposure of phosphatidylserine was performed. The efficacy of these human RBC-coupled TMs was compared using a whole-blood, microfluidic model of inflammatory microthrombosis recently described [33], as shown in the examples below.

In one aspect, a method of loading red blood cells is provided. In one embodiment, the red blood cells are loaded ex vivo. In said method, red blood cells are collected from a subject. The RBCs are isolated and contacted with an antibody-cargo construct of the invention. The loaded RBCs are then infused into a subject. In one embodiment, the subject is the same subject from which the RBCs were harvested. In another embodiment, the subject or a different subject from which the RBCs were harvested.

As described above, the term "about" when used to modify a numerical value means a variation of ±10%, unless otherwise specified. As used throughout this specification and the claims, the terms "comprise" and "contain" and its variants including, "comprises", "comprising", "contains" and "containing", among other variants, is inclusive of other components, elements, integers, steps and the like. The term "consists of" or "consisting of" are exclusive of other components, elements, integers, steps and the like.

The following examples are illustrative only and are not a limitation on the invention described herein. It is demonstrated herein, that a human antibody was murinized and administered to a mouse to effectively lower cholesterol levels in a model of familial hypercholesterolemia.

Example 1—Materials and Methods

Cell Lines

Human umbilical vein endothelial cells (HUVECs) were purchased and maintained in complete EGM (Lonza, Walkersville, Md.). Stably transfected Drosophila S2 cells were maintained in Schneider's complete medium (Thermo Fisher Scientific, Philadelphia, Pa.) with 25 µg/mL blasticidin (Thermo Fisher Scientific, Carlsbad, Calif.) and transitioned to serum free Insect-Xpress (Lonza, Walkersville, Md.) supplemented with Glutamax and 0.8 mM CuSO4 (Sigma Aldrich, St. Louis, Mo.) for recombinant protein expression. Chemically competent One Shot Top10 E. coli were used for subcloning as well as for production of scFvs using the pBAD/gIII periplasmic production system (Thermo Fisher Scientific, Carlsbad, Calif.).

Reagents

Human α-thrombin, human protein C, corn trypsin inhibitor (CTI), and blood collection tubes containing citrate and CTI were all purchased from Haematologic Technologies (Essex Junction, VT). Recombinant human TNF-α was purchased from Corning (Corning, N.Y.). Anti-human CD141 (thrombomodulin) antibody (clone Phx-01) was purchased from BioLegend (San Diego, Calif.). Calcein AM and flourescent labeling reagents AlexaFlour 647-NHS Ester and AlexaFlour 488-TFP Ester were purchased from Thermo Fisher Scientific (Carlsbad, Calif.). Anti-human fibrin (clone 59D8) was purified from hybridoma supernatant using protein G and fluorescently labeled with AlexaFluor 568-NHS Ester (Thermo Fisher Scientific). Monoclonal antibodies BRIC256 (anti-GPA), BRAD2 (anti-RHD), BRAD3 (anti-RHD), FOG-1 (anti-RHD), BRIC14 (anti-Band3/Wrb), BIRMA84b (anti-Band3/Wrb), and BRIC200 (anti-Band3) were purchased from the International Blood Group Reference Laboratory (Bristol, England, UK). Antibody BRIC69 (anti-RHCE) was purchased from Thermo Fisher Scientific (Carlsbad, Calif.).

Red Blood Cells

Human whole blood was obtained from healthy volunteer donors. All studies involving human subjects were approved by the Institutional Review Board of the University of Pennsylvania. Written informed consent was obtained and phlebotomy was performed via the antecubital veins using a 21-gauge butterfly needle. Specimens were drawn into 3.2% sodium citrate vacuum tubes (BD, Franklin Lakes, N.J.). To obtain red blood cells, whole blood was spun at 1000×g for 10 min and the plasma and buffy coat were discarded. A portion of the packed red cells was then suspended in phosphate buffered saline (PBS) with 2% normal human AB serum (Sigma Aldrich, St. Louis, Mo.) at the indicated hematocrit for each subsequent assay. To measure osmotic resistance and mechanical resistance, human RBCs were isolated from the retained segments of non-expired O positive, leukoreduced, irradiated RBCs from our hospital blood bank and prepared similarly. Similar results were seen using either fresh RBCs or donor units.

Derivation and Production of Antibodies and Fusion Proteins

An IgG Fab/phage display library was prepared from the peripheral blood lymphocytes of a hyperimmunized macaque using homologous human V-region oligonucleotides (Siegel D L, R. M., Lee H, Blancher A., Production of large repertoires of macaque mAbs to human RBCs using phage display. Transfusion, 1999. 39(S10): p. 92S, which is incorporated herein by reference). Fab/phage specific for human RBCs were isolated by panning on intact human RBCs. Monoclonal Fab/phage were grown to produce antibodies for immunoassays and their corresponding DNA was extracted for sequencing. To identify target epitopes, antibodies were screened against RBCs of known serologic phenotypes, including rare cells lacking highly conserved antigens, using standard immunohematologic techniques (Roback, J. D., Technical Manual. 2014: American Association of Blood Banks (AABB), which is incorporated herein by reference.)

After identification of the target epitopes, clones reactive against Wrb and Rh17 present at the highest titers were chosen to produce scFv derivatives of the encoded antibodies. Sequences of the antibody clones examined herein are available in the supporting information. For each VH and VL region, restriction enzyme sites were introduced for cloning into expression vectors and fusion to the extracellular domain of human TM (Glu22-Ser515). VH and VL were also ligated into a pBAD/gIII expression system (Thermo Fisher Scientific, Carlsbad, Calif.) to produce scFv alone in E. coli. Sequences were modified by custom synthesis of double-stranded gene fragments (gBlock, IDT, Coralville, Iowa).

Recombinant Protein Expression and Purification pMT/hTM-aBand3, pMT/hTM-aRh17, and pMT/shTM were each co-transfected with pCoBLAST in Drosophila S2 cells and selected with blasticidin to generate stable cell lines. Expression and purification were performed as described previously (Ding, B. S., et al., Anchoring fusion thrombomodulin to the endothelial lumen protects against injury-induced lung thrombosis and inflammation. Am J Respir Crit Care Med, 2009. 180(3): p. 247-56, which is incorporated herein by reference), using a copper-induced promoter for secreted expression. Proteins harvested from culture supernatants were purified using an anti-FLAG (M2, Sigma, St Louis, Mo.) affinity resin. Purified proteins were assessed by SDS-PAGE and HPLC (Waters) using a size-exclusion column (Yarra, Phenomenex, Torrance, Calif.). HPLC was used to removed dimers from purified products when present. scFvs were produced using a pBAD/gIII vector production system (Thermo Fisher Scientific, Carlsbad, Calif.) for periplasmic secretion. Cultures of transformed *E. Coli* were induced with 0.02% arabinose and grown for at least 6 hours at room temperature. The periplasmic fraction was isolated by osmotic shock and the resulting shock fluid was purified on an L5 anti-FLAG column (Biolegend, San Diego, Calif.).

Binding Assays

Recombinant proteins were radiolabeled with $Na^{125}I$ (Perkin Elmer, Exton, Pa.) using pre-formulated iodination reagent (Pierce Iodination Reagent, Thermo Fisher Scientific, Carlsbad, Calif.) per the manufacturer's protocol. Radiochemical purity was verified by instant thin layer chromatography on silica and was typically >95%. Radiolabeled proteins were added to human RBCs at 0.02% hematocrit in PBS with 2% human AB serum. Binding was allowed to reach equilibrium over 4 hours at 37 degrees C. After binding, cell suspensions were rapidly washed at least four times with cold PBS. The resulting cell pellet was counted using a Perkin Elmer Wizard2 gamma counting system. Dissociation of the fusion proteins was assessed using RBCs saturated with radiolabeled proteins, washing unbound ligands, and placing in dilute suspensions prior to measurement of bound ligand at specified time points. Similar binding experiments were performed with fluorescently-labeled recombinant proteins and cells were analyzed by flow cytometry (Accuri C6, BD Biosciences, San Jose, Calif.). Fluorescently labeled proteins were produced by reaction with amine-reactive derivatives of fluorescent dyes AlexaFlour488 and AlexaFlour647 (typically 10- to 20-fold excess at pH 8) and purified using 10,000 MWCO centrifugal filter devices (EMD Milipore, Billerica, Mass.).

Activated Protein C Assay

Generation of activated protein C by TM proteins or TMs coupled to RBCs was measured as described previously (Carnemolla, R., et al., Quantitative analysis of thrombomodulin-mediated conversion of protein C to APC: translation from in vitro to in vivo. J Immunol Methods, 2012. 384(1-2): p. 21-4). In brief, a given concentration of recombinant protein (1-20 nM) or fusion-loaded RBCs was suspended with 300 nM human protein C and 1 nM human alpha thrombin for 1 hour at 37 degrees C. A portion of the reaction supernatant was then added to an excess of hirudin and 500 µM S-2366 chromogenic substrate. The absorbance was read kinetically at 405 nm with the slope of the linear portion of the resulting curve reflecting APC concentration.

Microfluidic Assay

Microfluidic experiments were performed on a Bioflux 1000 (Fluxion Biosciences, San Francisco, Calif.) multi-well microfluidic system. Microchannels were endothelialized with HUVECs as described previously (Colin F. Greineder, I. H. J., Carlos H. Villa, Douglas B. Cines, Mortimer Poncz, and Vladimir R. Muzykantov, Microfluidic Modeling of Human Disseminated Intravascular Coagulation Reveals Efficacy and Mechanism of Targeted Thrombomodulin. Submitted, 2017) which typically resulted in complete coverage of the micro-channels. Channels were treated with TNF-alpha (10 ng/mL) under flow (at shear stress of 5 dyne/cm2) for 6 hours to flow condition and induce activation prior to exposure to whole blood. Whole blood was obtained from healthy volunteer donors and collected into citrate collection tubes containing corn trypsin inhibitor (CTI, Essex Junction, CT). The indicated concentrations of recombinant proteins were added to the whole blood for hour at prior to perfusion through the microchannels. Flourescently labeled anti-fibrin antibodies and calcein AM were also added to blood 15 minutes before microfluidic assay to image fibrin deposition and leukocyte and platelet adhesion, respectively. Blood was flowed through the channels under conditions mimicking post capillary venules (5 dyne/cm2) for 20 minutes while images were continuously acquired. Controls and experimental conditions were compared on simultaneously run channels using a motorized stage for real-time acquisition. Images were analyzed using ImageJ for quantification of mean fluorescence intensity.

Osmotic and Mechanical Resistance Assays

Osmotic and mechanical resistance was measured as previously described (Pan, D., et al., The Effect of Polymeric Nanoparticles on Biocompatibility of Carrier Red Blood Cells. PLoS One, 2016. 11(3): p. e0152074). In brief, human RBCs obtained from retained segments of donor RBCs were suspended in PBS at 5% hematocrit prior to incubation with various concentrations of antibodies or fusion proteins. The RBCs were then washed and exposed to osmotic or mechanical stress. Osmotic stress was induced by incubation in 64 mM NaCl solution, conditions that give approximately 50% hemolysis of normal RBCs. The suspensions were then centrifuged at 13,400 g and the resulting supernatants were assayed for hemoglobin content by measuring absorbance at 540 nm. Hemolysis of equivalent concentrations of RBCs in water was taken as 100% hemolysis. To measure mechanical stress, RBCs were similarly treated with antibodies and fusion proteins, resuspended at 1% hematocrit, and rotated in the presence of 8×4 mm glass beads (Corning Pyrex, Corning, N.Y.) for 1 hour at 37 C. The RBC suspension supernatants were then similarly analyzed spectrophotometrically for hemolysis.

Ekacytometry

Ektacytometry was performed using a RheoScan AnD system (Rheo Meditech, Seoul, Republic of Korea). In a typical experiment, 50 µL of 5% RBC or 5 µL of whole blood was suspended in 700 µL of a 5.5% (w/v) solution of 360 kDa poly-vinylpyrrolidine (Sigma Aldrich, St. Louis, Mo.) in PBS. A 500 µL sample within each microfluidic chamber was then analyzed per the manufacturer's protocol. The elongation indices at the corresponding shear stresses were then input into statistical software (Prism, GraphPad, San Diego, Calif.) and the data were fit using non-linear regression and a Streekstra-Bronkhost model (Baskurt, O. K. and H. J. Meiselman, Data reduction methods for ektacytometry in clinical hemorheology. Clin Hemorheol Microcirc, 2013. 54(1): p. 99-107) to derive the maximal elongation indices (EImax) and shear stress at half-maximal deformation (SS1/2).

Example 2: Synthesis of Targeting Ligands

Figure 1E:
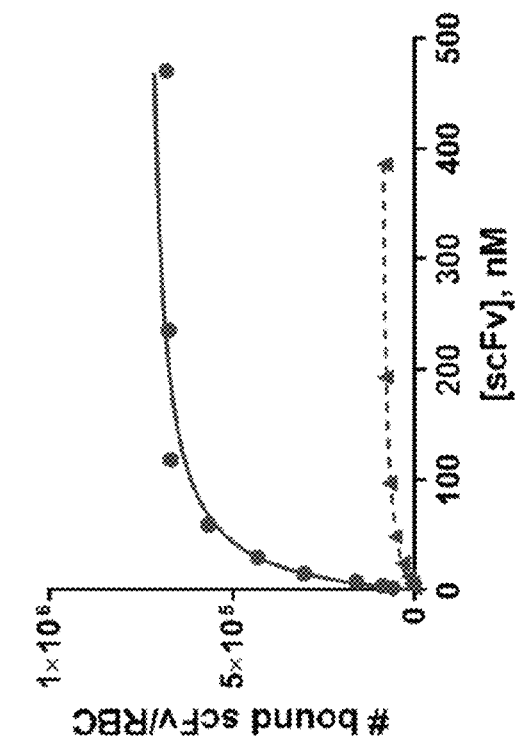
Figure 1F:
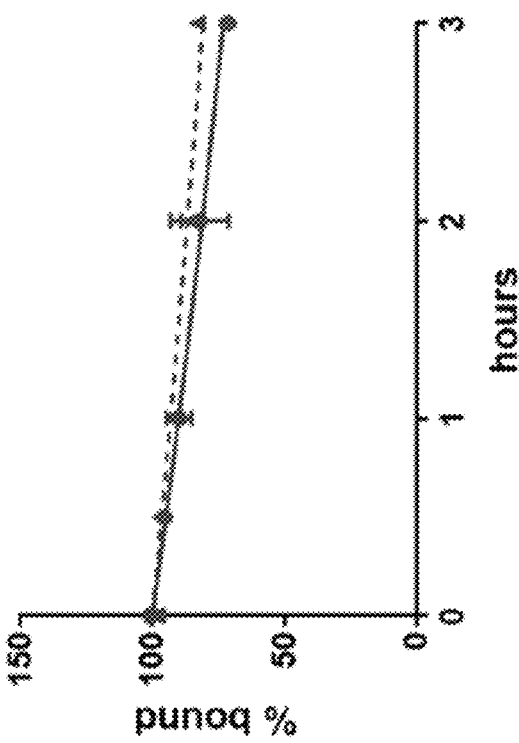
Figure 1G:
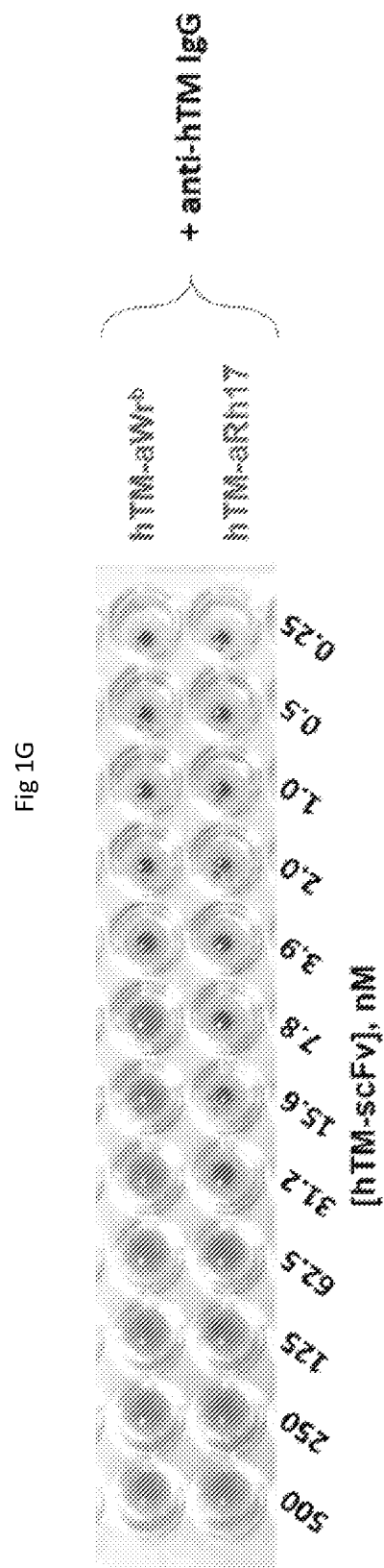

Using antibody phage display, we identified non-human-primate Fab antibody fragments to antigenic determinants on human RBCs. By panning phage libraries on human RBCs, we produced a Fab/phage preparation with $>10^7$ RBC-specific clones capable of agglutinating human RBCs. By performing binding assays against rare RBC types lacking highly conserved antigens and epitopes, we identified the target antigens of >30 of these clones. At least 34 clones bound the Wright b (Wrb) epitope formed by a Band 3/GPA interaction, present on the RBCs of essentially 100% of the human population. The Wrb epitope, determined by the protein sequence of Band 3, is a site of association between Band 3 with GPA, and GPA expression is simultaneously required for its presence on the membrane (Huang C H, Reid M E, Xie S S, Blumenfeld 00. Human red blood cell Wright antigens: a genetic and evolutionary perspective on glycophorin A-band 3 interaction. Blood. 1996; 87(9):3942-3947). At least 3 other clones bound to a highly-conserved epitope Rh17(Hr0) on human RhCE protein, also present on essentially 100% of the human population. Both these targets are specific for erythroid lineage (Rojewski M T, Schrezenmeier H, Flegel W A. Tissue distribution of blood group membrane proteins beyond red cells: evidence from cDNA libraries. Transfus Apher Sci. 2006; 35(1):71-82; Huang C H, Reid M E, Xie S S, Blumenfeld O O. Human red blood cell Wright antigens: a genetic and evolutionary perspective on glycophorin A-band 3 interaction. Blood. 1996; 87(9):3942-3947; and Chou S T, Westhoff C M. The Rh and RhAG blood group systems. Immunohematology. 2010; 26(4):178-186). We assessed the extent of humanness of the variable chains using T20 scores44; scores of 79.8 for VH and 93.5 for VL framework regions were calculated for the anti-Rh17(aRh17), and 86.0 for VH and 85.4 for VL framework regions were calculated for anti-Wrb (aWrb). These scores are comparable with 'humanized' antibodies (Gao S H, Huang K, Tu H, Adler A S. Monoclonal antibody humanness score and its applications. BMC Biotechnol. 2013; 13:55) and therefore are encouraging with respect to potential lack of immunogenicity of derivatives of these ligands.

produced with high purity as characterized by SDS gel electrophoresis and size-exclusion HPLC, with peaks consistent with the expected molecular weights (FIG. 1A and FIG. 1B). We then performed direct binding assays with radio-labeled and fluorescently-labeled scFv antibody fragments and fusion proteins (see Example 1). The aRh17 and aWrb scFvs and their corresponding TM fusions demonstrated similar binding affinities (KD 21-53 nM, FIG. 1C and FIG. 1D, and Table 7), as did both radio-iodinated and fluorescently-labeled proteins (FIG. 7A-FIG. 7D). The scFvs and fusion proteins bound to conserved epitopes on human, but not mouse, rat, or pig RBCs (FIG. 7A-FIG. 7D), and binding parameters (Kd, Bmax) were consistent between multiple donors. Binding saturated at the expected level of target expression (Bmax of 100,000 to 160,000 copies/RBC for aRh17 and 750,000 to 900,000 copies/RBC for aWrb) (Lomas-Francis C, Olsson M L. The blood group antigen factsbook: Elsevier/Academic Press; 2012). The dissociation rates were similar for both scFvs alone and their corresponding fusions, with >50% of the ligands remaining bound after 4 hours at 37 degrees (FIG. 1E and FIG. 1F, Table 7). We also examined effects of shear stress on scFv binding and the potential for ligand exchange onto unbound RBCs in whole blood under constant mixing (FIG. 8A-FIG. 8E and FIG. 9A-FIG. 9C). These experiments demonstrated that short periods of low (5 dyne/cm$^2$) and high (200 dyne/cm$^2$) shear in whole blood did not alter scFv binding and that similar dissociation kinetics were seen in the presence of whole blood containing mostly unbound RBCs (with gradual exchange onto the unbound RBC population). Hemagglutination by an anti-TM secondary antibody was seen when hTM-scFv fusions were added at concentrations estimated to generate 1000 copies of TM per RBC based on the calculated affinities (FIG. 1G). The fusion proteins alone did not induce aggregation or agglutination of RBCs in the absence of secondary anti-TM. Morphology of fusion protein loaded RBCs was confirmed on Wright-Giemsa stained peripheral blood smears and no morphologic abnormalities in the RBCs were noted (FIG. 10).

TABLE 7

Anti-Band3 and anti-RHCE antibody clones from phage library. scFv produced as H$_2$N-VH-(GGGGS)3-VL-FLAGx3-COOH.

| Clone# | Specificity | VH gene family | Vk gene family | VH sequence | VL sequence |
|---|---|---|---|---|---|
| KP3-17 | Rh17 | 4 | 1 | EVQLLESGPGLLKPSETLSLTCAVSGAPISNYW WSWIRQSPGKGLEWIGEIDGSIYTTYYNPSLKS RVAISKDTSKNRLSLKLTSVTAADTAVYYCAREG QNPLVPTYGSTGFGLDFWGHGLAVTVSS | AAELTQSPSSLSASVGDRVTITCQASQGISS WLAWYQQKPGKAPKLLIYKASSLQSGVPS RFSGSGSGTDFTLTISSLQSEDFATYYCQQY SSSPRTFGQGTKVEIK |
| KP2-23 | Wr$^b$ | 4 | 3 | EVQLLESGPGLVKPSETLSLTCTVSGSSLSSAYG WNWIRQPPGKGLEWIGSIGGSRDNTNYNPSL KRRVTISKDTSKNQFSLKLKSVTAADTAVYYCA QRGAYGYSYFDYWGQGVLVAVSS | AAELTLTQSPATLSLSPGETATLSCRASQTV GRNLAWYQQRPGQAPNLVHSAYFRATG IPDRFSGSGSGTDFTLTISSLEPEDAGVYHC QQYNDLLPLTFGGGTKVEIK |

Example 3: Binding of Ligands and Cargoes to RBCs

The sequences of the variable fragment genes (amino acid sequences shown in Tables 2 and 5, nucleic acid sequences shown in Tables 3 and 6) were cloned into plasmids to produce single chain variants (scFv) of the parent Fab, as well as fusions of the scFv antibodies with human thrombomodulin (hTM-scFv). These scFvs and hTM-scFvs were

TABLE 8

Binding parameters for radiolabeled anti-RBC ligands. A slight decrease in affinity and increase in k$_{off}$ are seen for fusions in comparison to scFv alone.

| Protein | K$_D$ (95% CI), nM | Bmax (95% CI), copies/RBC × 10$^3$ | k$_{off}$ (95% CI), s$^{-1}$ |
|---|---|---|---|
| aRh17 scFv (anti-RhCE) | 41.4 (34.1, 50.2) | 99 (93, 105) | 2.0 × 10$^{-5}$ (1.6, 2.4) |
| aWr$^b$ scFv (anti-Band3/GPA) | 21.3 (17.0, 26.5) | 746 (704, 790) | 2.9 × 10$^{-5}$ (2.0, 3.8) |

TABLE 8-continued

Binding parameters for radiolabeled anti-RBC ligands. A slight decrease in affinity and increase in $k_{off}$ are seen for fusions in comparison to scFv alone.

| Protein | $K_D$ (95% CI), nM | Bmax (95% CI), copies/RBC × $10^3$ | $k_{off}$ (95% CI), $s^{-1}$ |
|---|---|---|---|
| hTM-aRh17 (anti-RhCE) | 45.6 (34.8, 56.5) | 184 (173, 195) | 4.7 × $10^{-5}$ (3.2, 6.5) |
| hTM-aWr$^b$ (anti-Band3/GPA) | 52.6 (40.1, 65.1) | 904 (848, 961) | 4.8 × $10^{-5}$ (2.9, 7.0) |

Example 4: Effect of Ligands and Cargoes on RBC Function

Having characterized the binding of the antibody fragments and fusion proteins to human RBCs, we then investigated how the binding of these ligands may affect several parameters of RBC integrity including osmotic fragility, mechanical resistance, membrane deformability, exposure of phosphatidylserine, and generation of reactive oxygen species. These experiments were conducted at 5% hematocrit and with ligand:RBC ratios calculated to yield 10,000 and 100,000 copies/RBC for both ligands based on their affinity and the known concentration of RBC targets. These copy numbers are below saturation for both Wrb and Rh17.

Figure 2A:
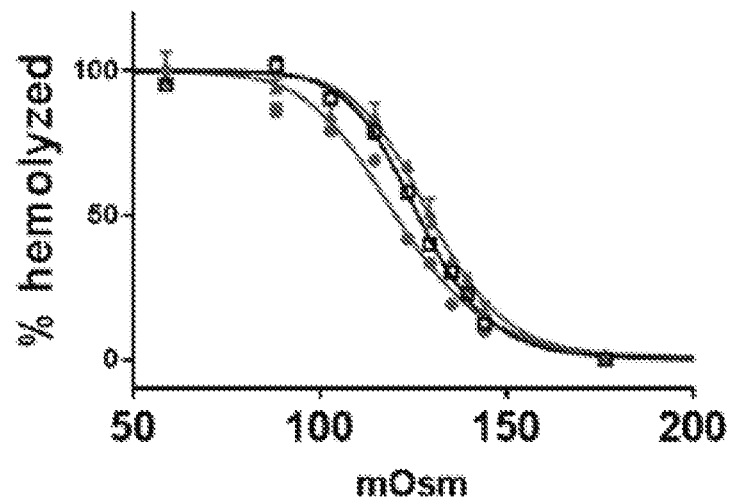
FIG. 2A-FIG. 2F show that aRh17 and aWrb antibodies demonstrate differential effects on RBC resistance to osmotic and mechanical stress. Osmotic stress was induced by incubation in buffered (10 mM sodium phosphate) saline at a range of osmolalities (0-308 mOsm). Mechanical stress was induced by rotation in the presence of glass beads at 1% Hct. Antibodies were added at 10 nM and 100 nM to 5% Hct RBC suspension, which produces a ratio of approximately 104 and 105 ligands per RBC and is below saturation for both target antigens.
Figure 2B:
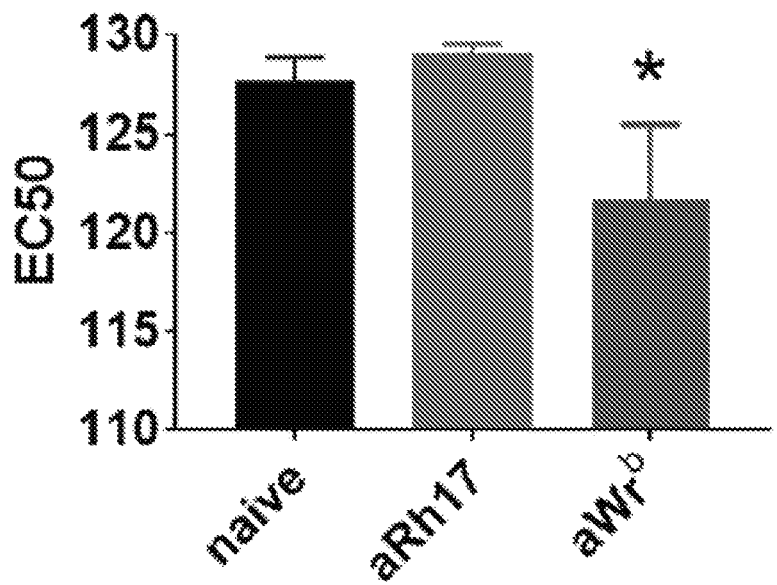
Figure 2C:
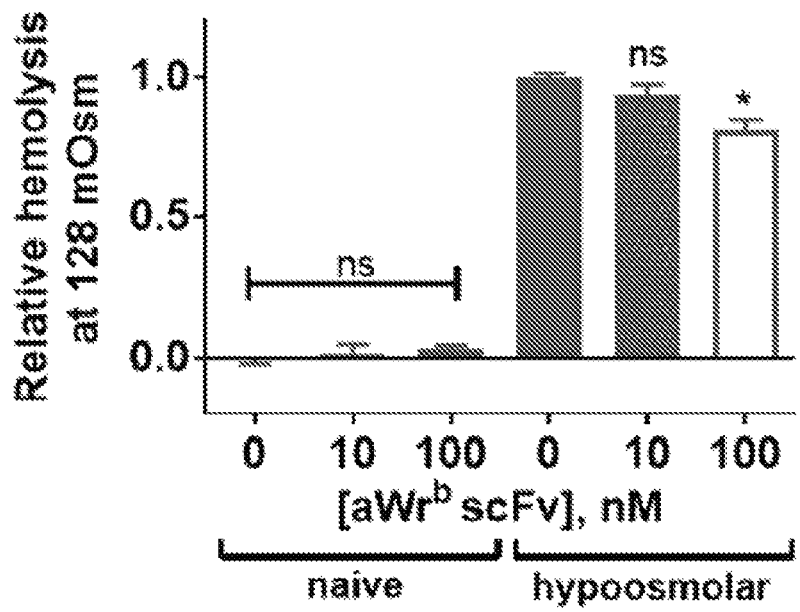
Figure 2D:
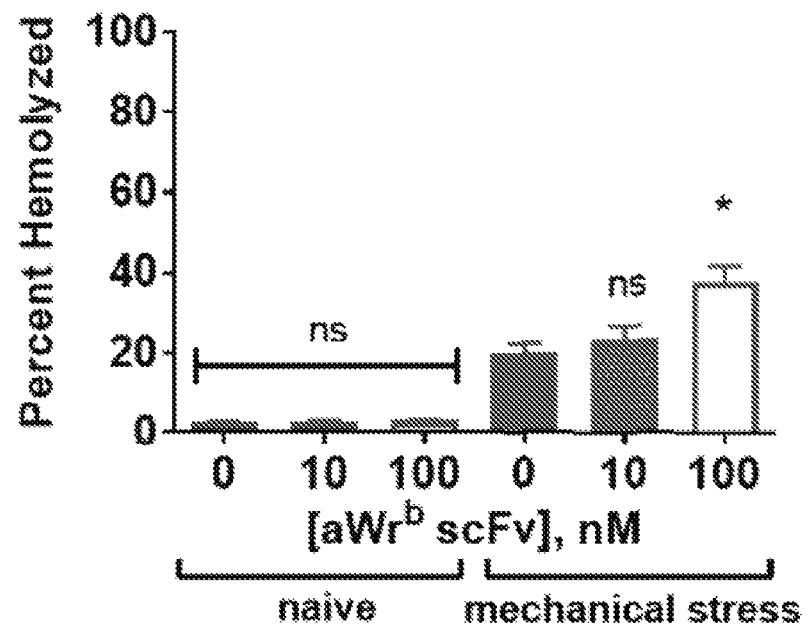
Figure 2E:
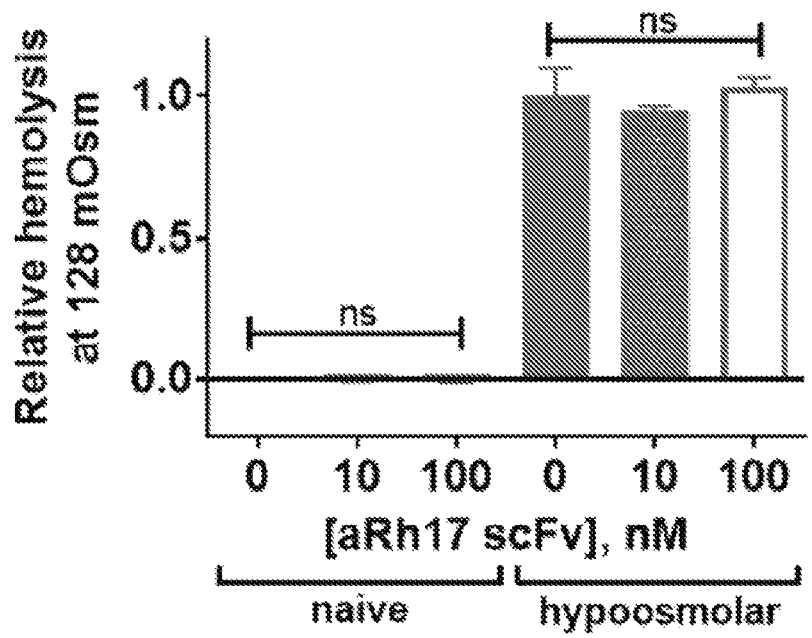
Figure 2F:
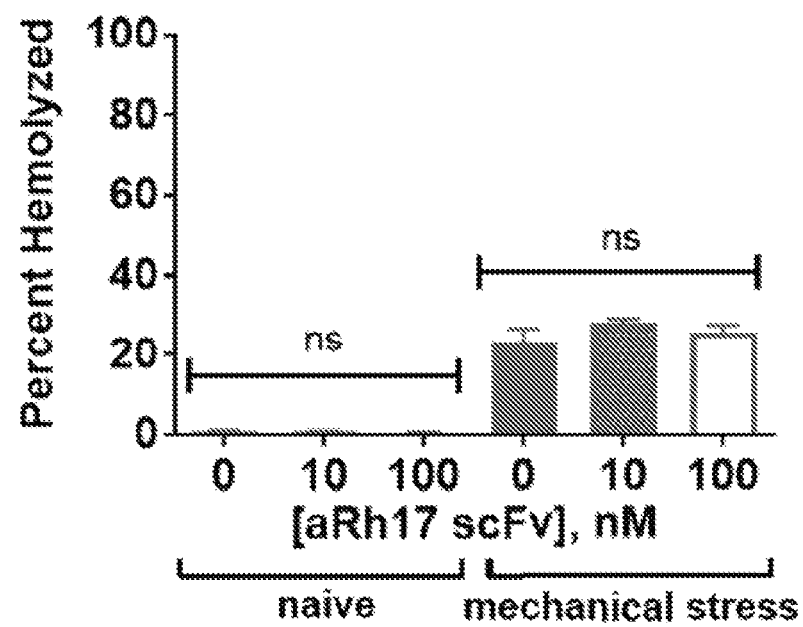
Figure 3A:
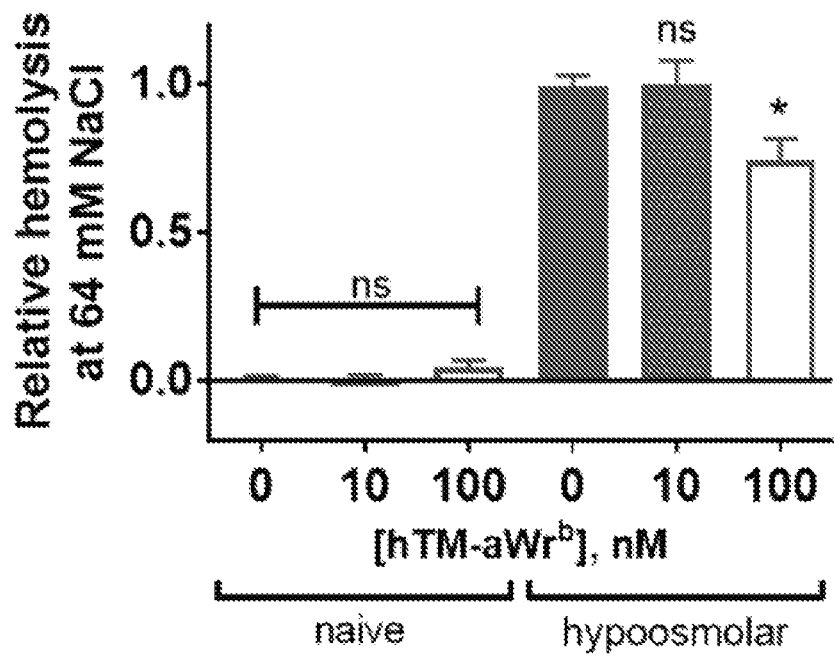
FIG. 3A-FIG. 3D show that aRh17 and aWrb hTM-scFv fusion proteins demonstrate similar patterns of changes in RBC resistance to osmotic and mechanical stress as the parent scFv. Fusion proteins were added at 10 nM and 100 nM to 5% Hct RBC suspension, which produces a ratio of approximately 104 and 105 fusion proteins per RBC and is below saturation for both target antigens.
Figure 3B:
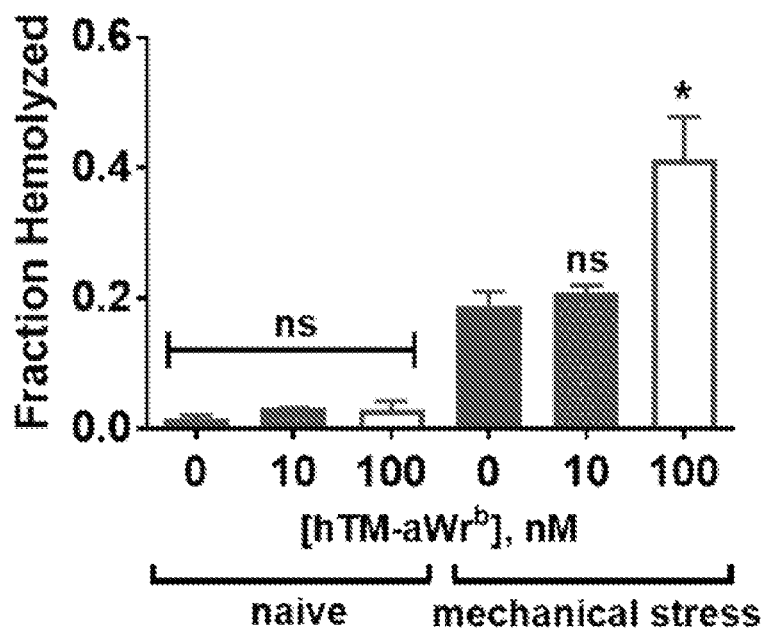
Figure 3C:
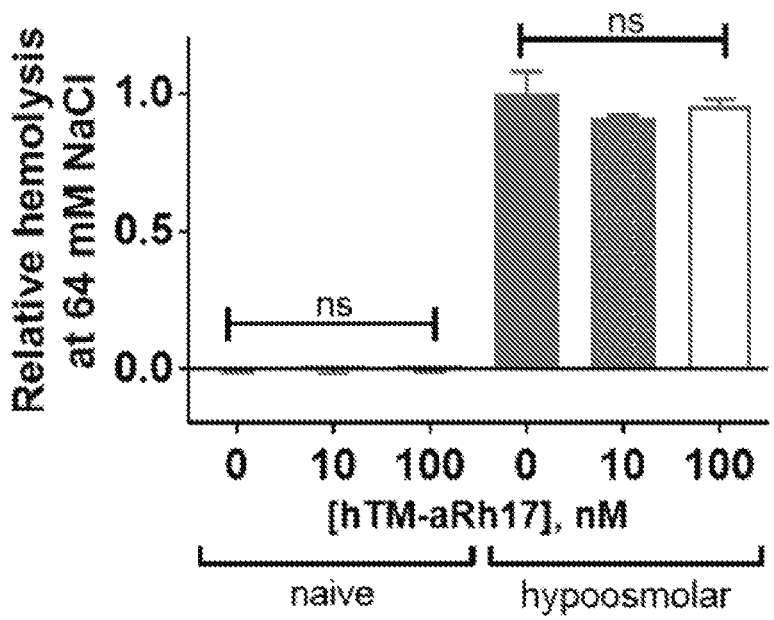
Figure 3D:
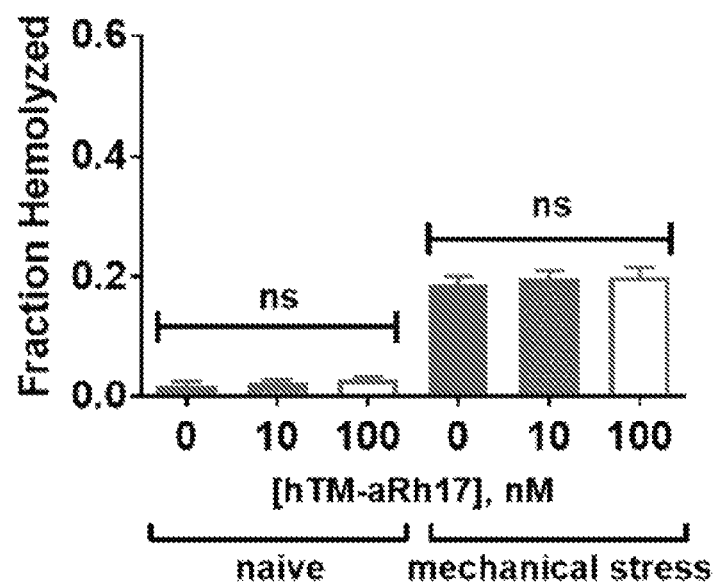

We found that the two scFvs (and their corresponding thrombomodulin fusions) had significantly different effects on target RBCs. Targeting of Wrb, but not Rh17, by the antibody fragments induced a left-shift in osmotic fragility curves (EC50 122 vs 128 mOsm, p<0.05) with a pattern suggesting a whole population change rather than just a subset (FIG. 2A and FIG. 2B). We tested the dose-dependence of the observed changes in osmotic resistance using the EC50 of naïve RBCs (128 mOsm) (FIG. 2C and FIG. 2E) and again found that aRh17 did not produce changes in osmotic hemolysis at this osmolarity, while aWrb again decreased hemolysis. The changes in osmotic resistance were paralleled by an increase in hemolysis following mechanical stress for aWrb (FIG. 2D), but similarly, no change was seen after treatment with aRh17 (FIG. 2F). While the mechanical stress assay (Pan D, Vargas-Morales O, Zern B, et al. The Effect of Polymeric Nanoparticles on Biocompatibility of Carrier Red Blood Cells. PLoS One. 2016; 11(3):e0152074) does not directly represent a pathophysiologic scenario, it is intended to reflect overall integrity of the RBC membrane architecture. Nearly identical effects were observed after treatment with the scFvs alone or with their corresponding TM fusions (FIG. 3A and FIG. 3B).

Figure 4A:
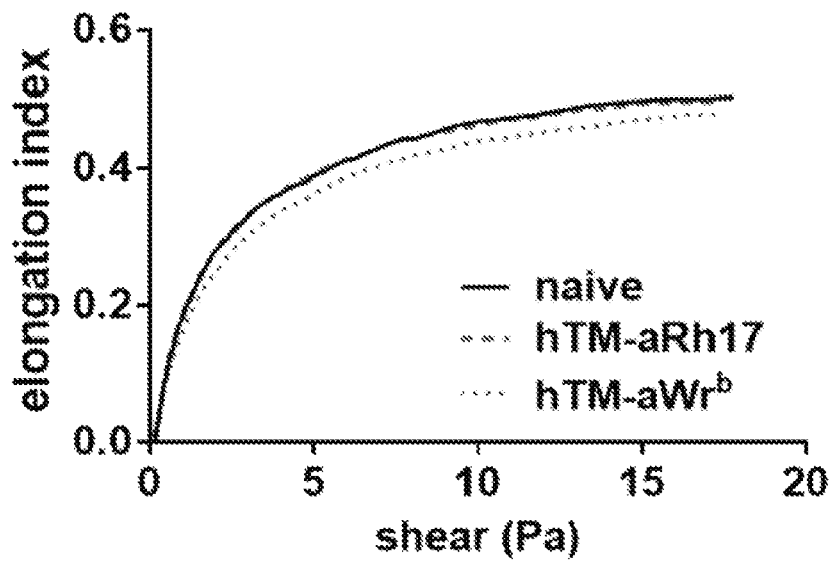
FIG. 4A-FIG. 4D show that aWrb scFv and hTM-scFv increase RBC rigidity, while aRh17 scFv and hTM-scFv show no changes compared to naïve RBC. Ektacytometry was performed on 5% Hct RBC suspensions incubated with scFv or hTM-scFv at the indicated concentrations. Elongation index (as calculated automatically by the instrument) was read as a function of shear stress and non-linear regression was used to calculate the shear stress required for half-maximal deformation and the maximum elongation index. Representative curves of at least 3 independent experiments with different donors.
Figure 4B:
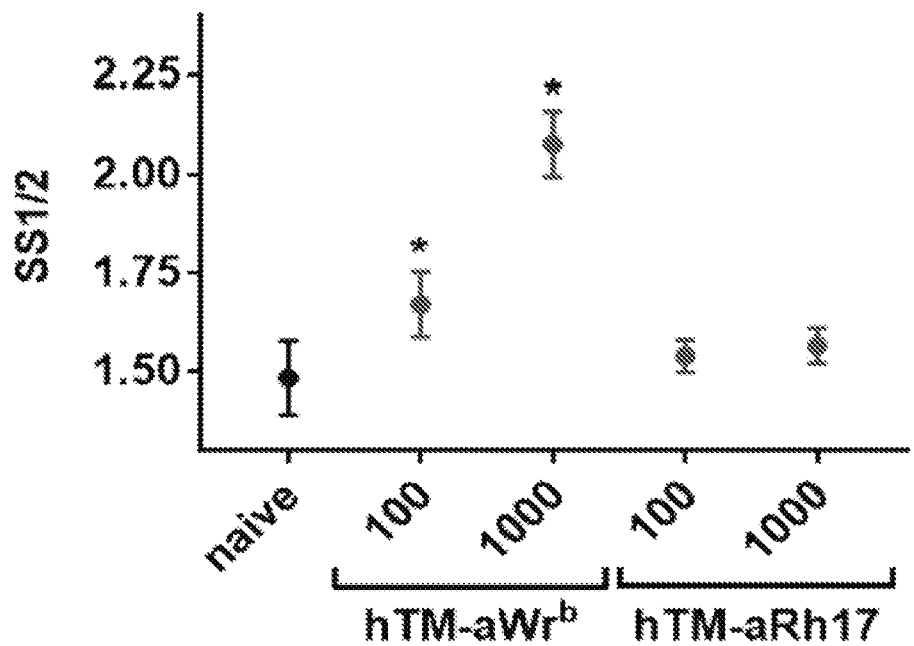
Figure 4C:
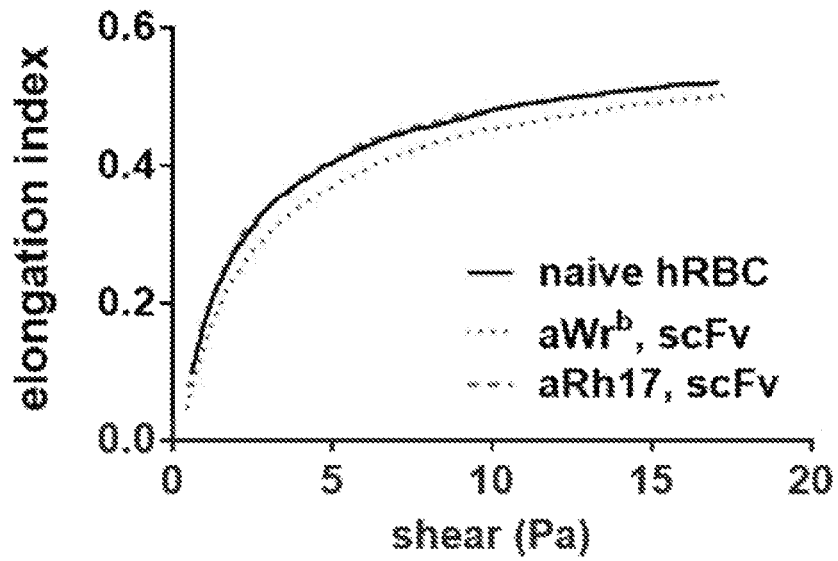
Figure 4D:
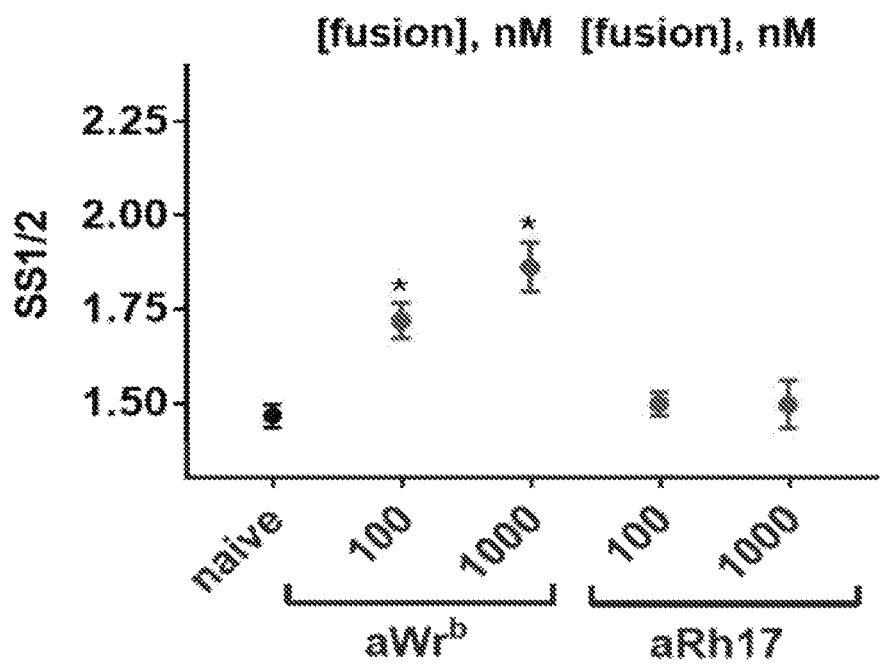
Figure 11:
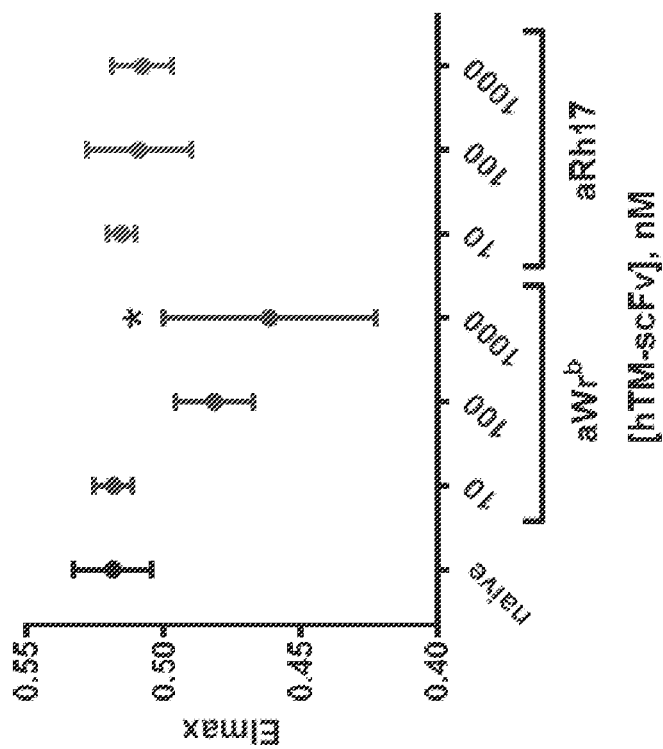
FIG. 11 provides maximum elongation index (EImax) of human RBCs treated with hTM-aWrb and hTM-aRh17 fusion proteins. Donor RBCs at 5% Hct were treated with the indicated concentration of fusion protein and measured in the ektacytometer. EImax calculated using non-linear regression. Mean±SD is shown (n=3-5 for each condition). (*p<0.05 vs naïve RBC, one-way ANOVA with Holm-Sidak correction for multiple comparisons)
Figure 13A:
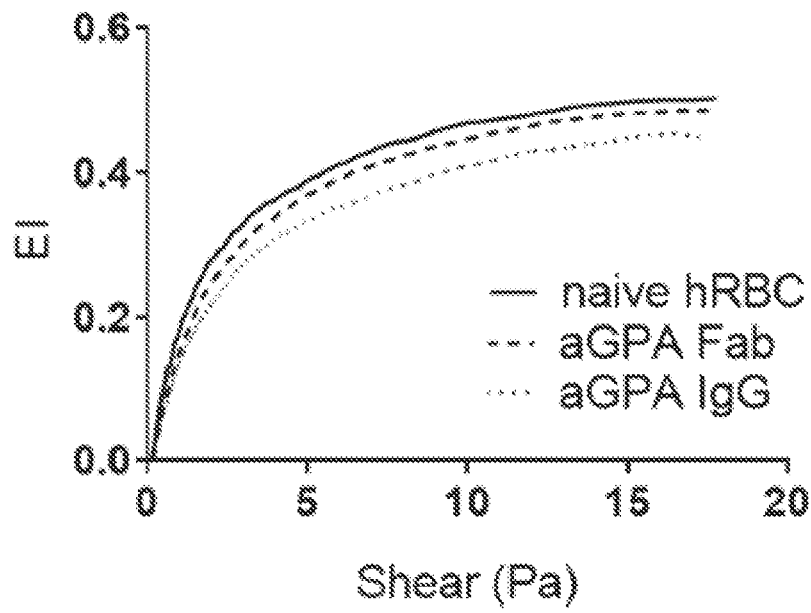
(FIG. 13A) Representative ektacytometric curves of at least 3 studies of human RBCs treated with anti-GPA Fab and IgG, derived from antibody clone YTH89.1 demonstrate a rightward shift after antibody treatment (FIG. 13B) At high ligand loading, anti-GPA Fab induced a significant increase in SS1/2 while anti-GPA IgG (100 nM) more potently induced rigidification. Mean±SD is shown, n=3 for each condition. (*p<0.05, one-way ANOVA with Holm-Sidak correction for multiple comparions) (FIG. 13C) Anti-GPA Fab induced increased hemolysis in response to hypo-osmolar stress and (FIG. 13D) slightly increased hemolysis in response to mechanical stress. Mean±SD, n=3 is shown, representative of 2 independent experiments. (*p<0.05 vs naïve RBCs, one-way ANOVA with Holm-Sidak correction for multiple comparisons)
Figure 13B:
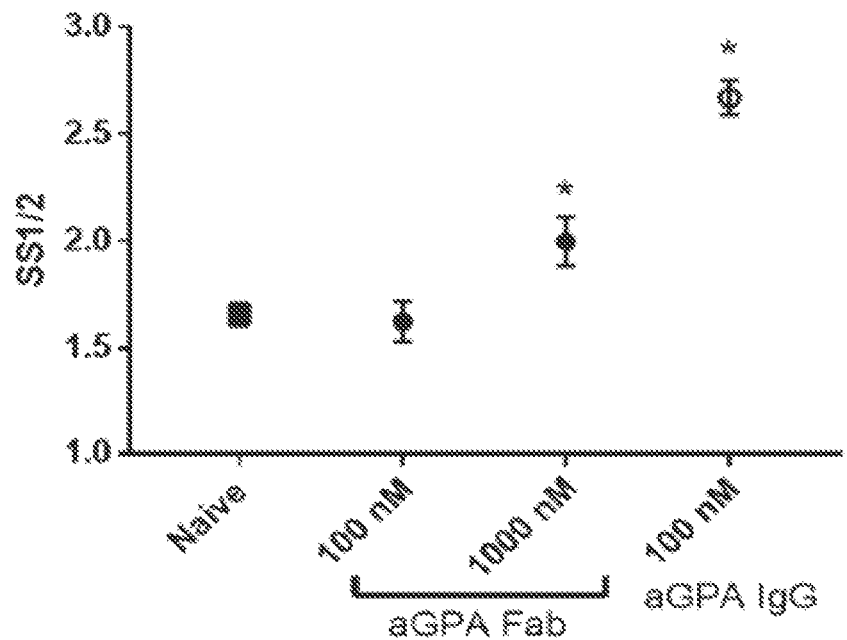
FIG. 13 shows RBCs bound by ligands to human GPA also demonstrate slight increases in rigidity and changes in mechanical and osmotic resistance.
Figure 13C:
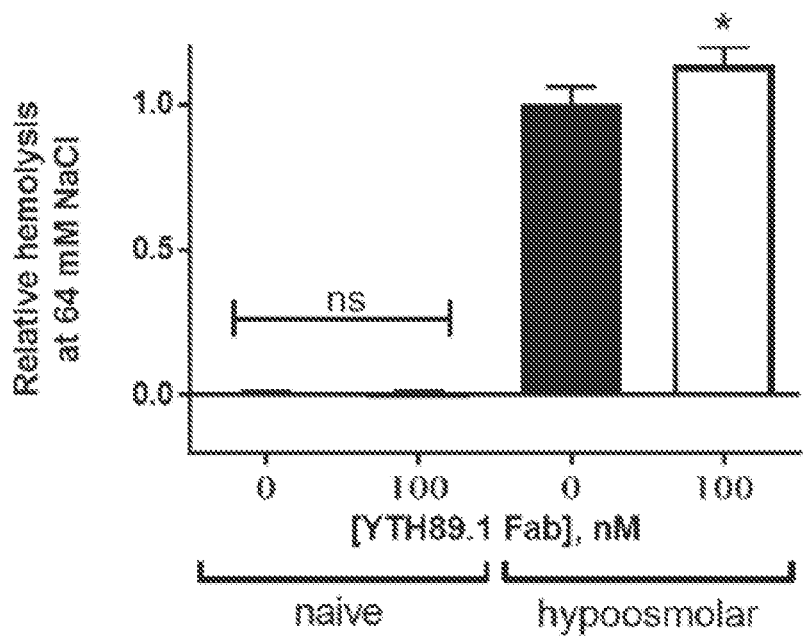
Figure 13D:
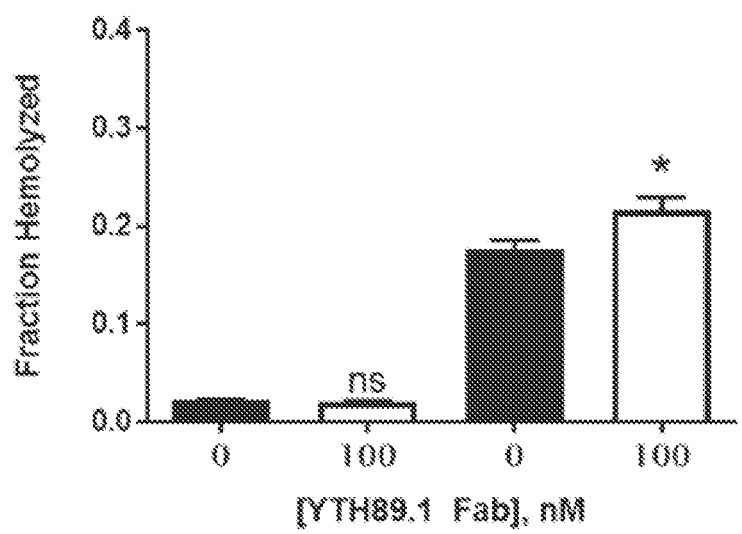
Figure 14A:
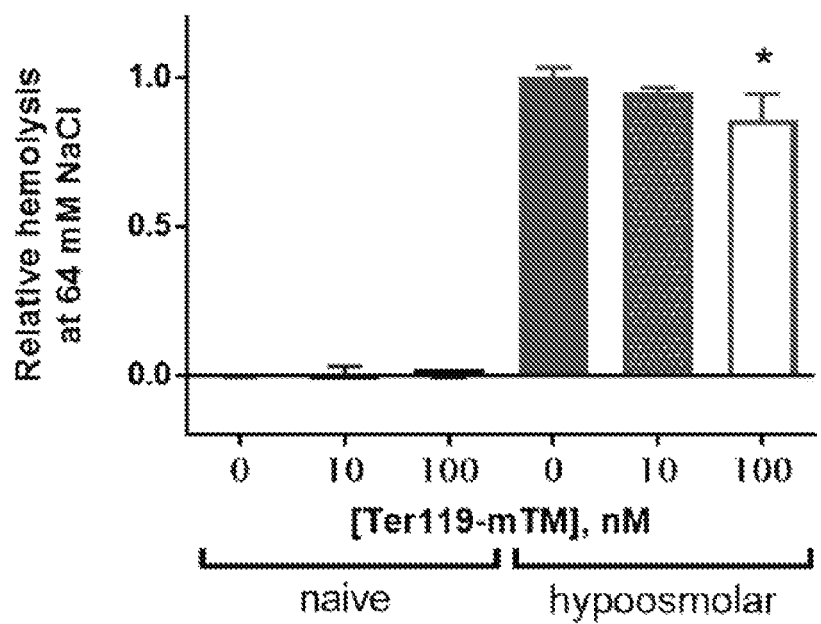
FIG. 14A-FIG. 14D show Ter119 ligands induce changes in murine RBCs similar to human RBCs treated with Wrb ligands. Ter119-TM fusion proteins induce changes to (FIG. 14A) osmotic resistance and (FIG. 14B) mechanical resistance similar to aWrb fusions in human RBCs. Mean±SD is sown, n=3 for each condition. (*p<0.05 vs naïve RBCs, one-way ANOVA with Holm-Sidak correction for multiple comparisons) (FIG. 14C) Representative ektacytometric curves of at least 3 independent experiments showing that Ter119-TM (1000 induced a slight rightward shift in ektacytometric curves, indicating increased RBC rigidity. The parent Ter119 IgG induced marked ektacytometric changes.
Figure 14B:
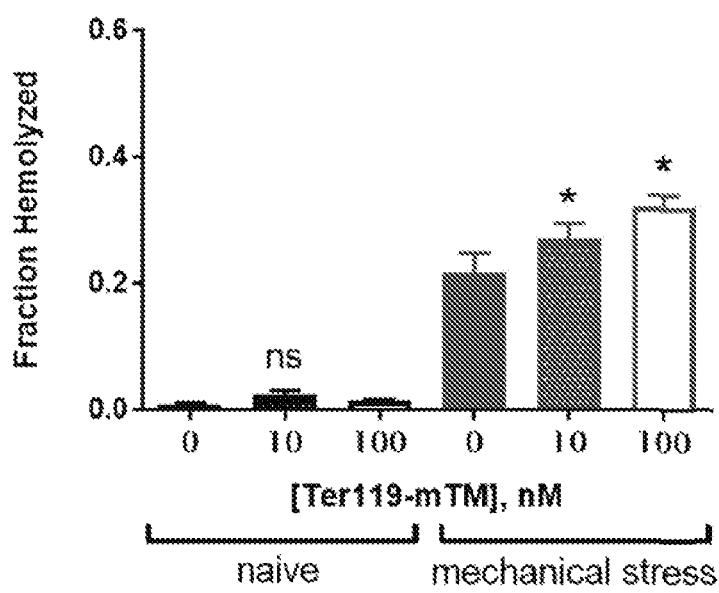
Figure 14C:
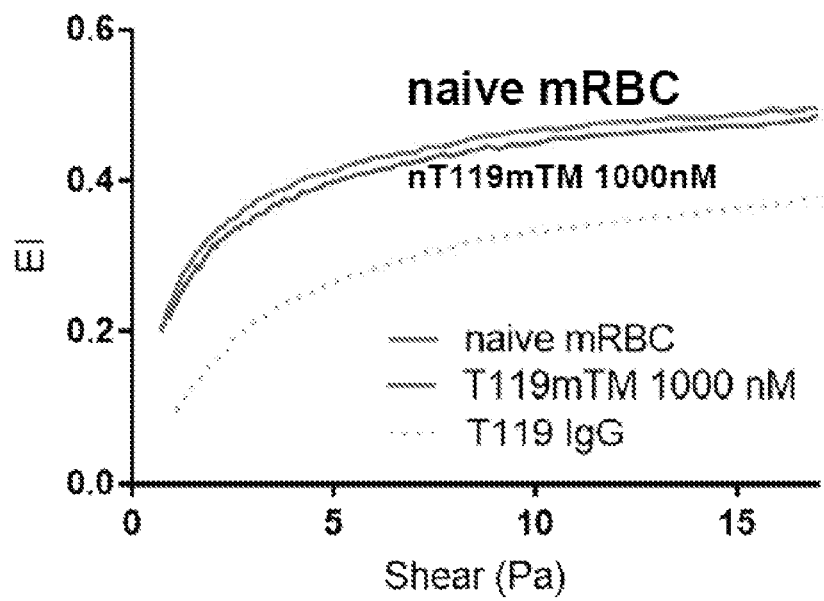
Figure 14D:
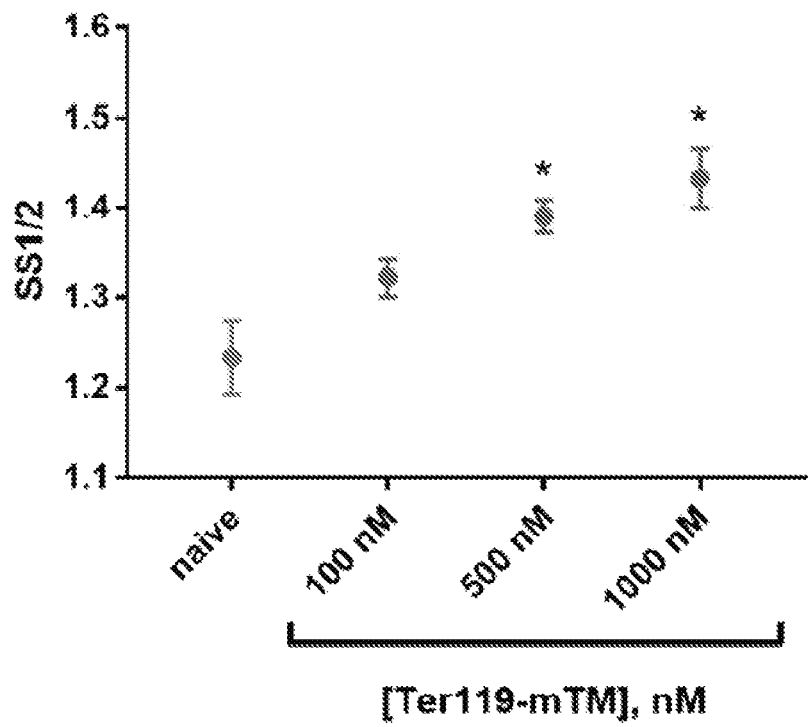

We then used ektacytometry to test whether effects on osmotic and mechanical fragility were mirrored by alterations in membrane deformability. In this technique, a decrease in the maximal elongation index (EImax) or an increase in the shear stress to reach half-maximal deformation (SS1/2) reflects an increase in RBC rigidity. As we expected, when ligands were bound to Wrb, there was a dose-dependent increase in RBC rigidity (FIG. 4), reflected in both increased SS1/2 (FIG. 4B and FIG. 4D) or decreased EImax (FIG. 11). This rigidifying effect was identical for TM-scFv fusions and scFvs alone, again demonstrating that the ligand, and not the TM cargo, induced these changes. Consistent with the mechanical and osmotic stress assays, binding of fusions or scFvs to RhCE did not change ektacytometric curves or indices (FIG. 4) and the behavior of aRh17 treated RBCs was consistently identical to naïve donor RBCs.

Figure 12:
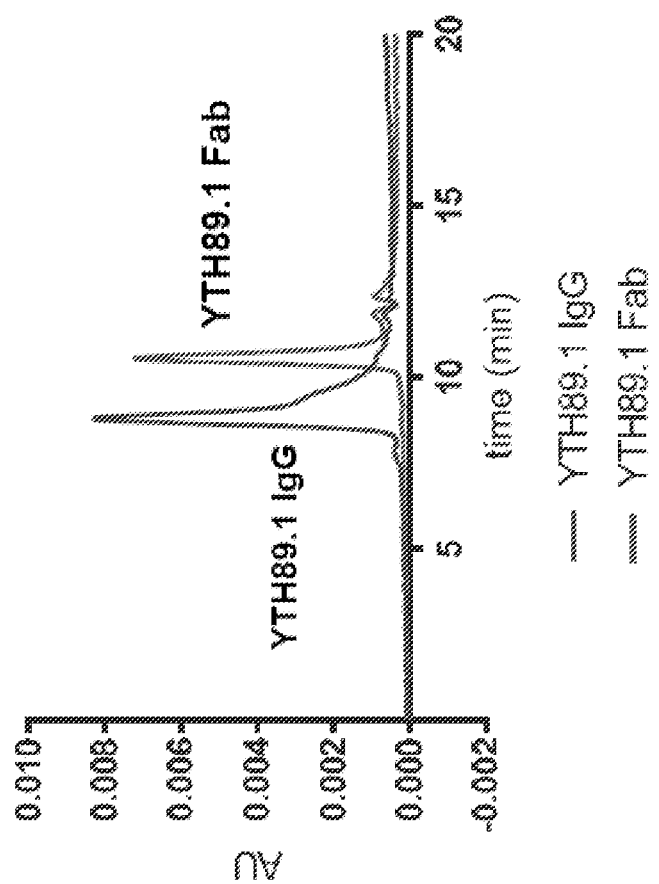
FIG. 12 shows size-exclusion HPLC of IgG and Fab antibodies against GPA. Antibodies prepared from hybridoma clone YTH89.1 which targets human glycophorin A. Full IgG was prepared from hybridoma supernatant using standard techniques and purified using protein G. Fab was prepared by enzymatic digestion of IgG with papain solution (Immucor) followed by treatment with protein A-sepharose (Thermo Fisher Scientific) for removal of Fc fragments and preparative size-exclusion HPLC for removal of residual papain enzyme. Representative HPLC from two independent antibody production runs.

The target-dependent effect of these ligands on membrane deformability raised the question of how targeting other RBC epitopes (particularly on GPA, given its ubiquity as an erythroid specific target) might affect RBC physiology. To probe this question, we produced anti-GPA antibodies and Fab fragments from a commercially available hybridoma, YTH89.146 (FIG. 12). After incubating human RBCs with the anti-GPA IgG antibodies or their monovalent Fabs, we observed similar rigidifying effects to those seen with aWrb ligands. Monovalent Fab induced a slight dose-dependent change in ektacytometric indices, while the parent antibody induced more marked changes in red cell rigidity (FIG. 13A-FIG. 13D). The Fab also induced a slight increase in hemolysis under mechanical stress, while also inducing a slight increase in hemolysis under hypo-osmolar conditions. Because prior studies loading drugs onto murine RBCs have largely relied on Ter119 or other GPA-associated ligands as the targeting agent, we also examined the effects of a scFv-TM fusion of this antibody on mouse RBCs (Zaitsev S, Kowalska M A, Neyman M, et al. Targeting recombinant thrombomodulin fusion protein to red blood cells provides multifaceted thromboprophylaxis. Blood. 2012; 119(20): 4779-4785). As with targeting of human Wrb or glycophorin A, Ter119-TM fusions decreased deformability of murine RBCs (increased SS1/2, decreased EImax) as a monovalent fusion protein (Ter119-mTM), and markedly so as the parent IgG antibody (FIG. 14A-FIG. 14D). As with the human ligands, these changes in deformability were accompanied by changes in susceptibility to osmotic and mechanical stress.

Figure 5A:
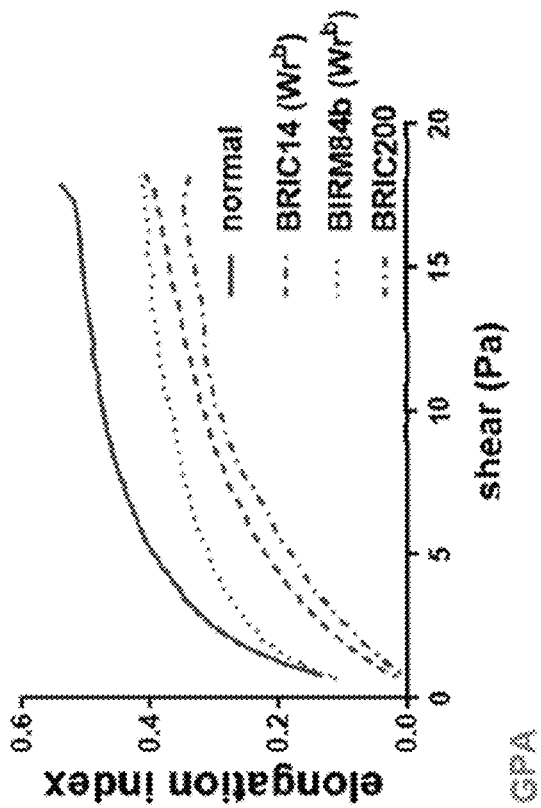
Figure 5B:
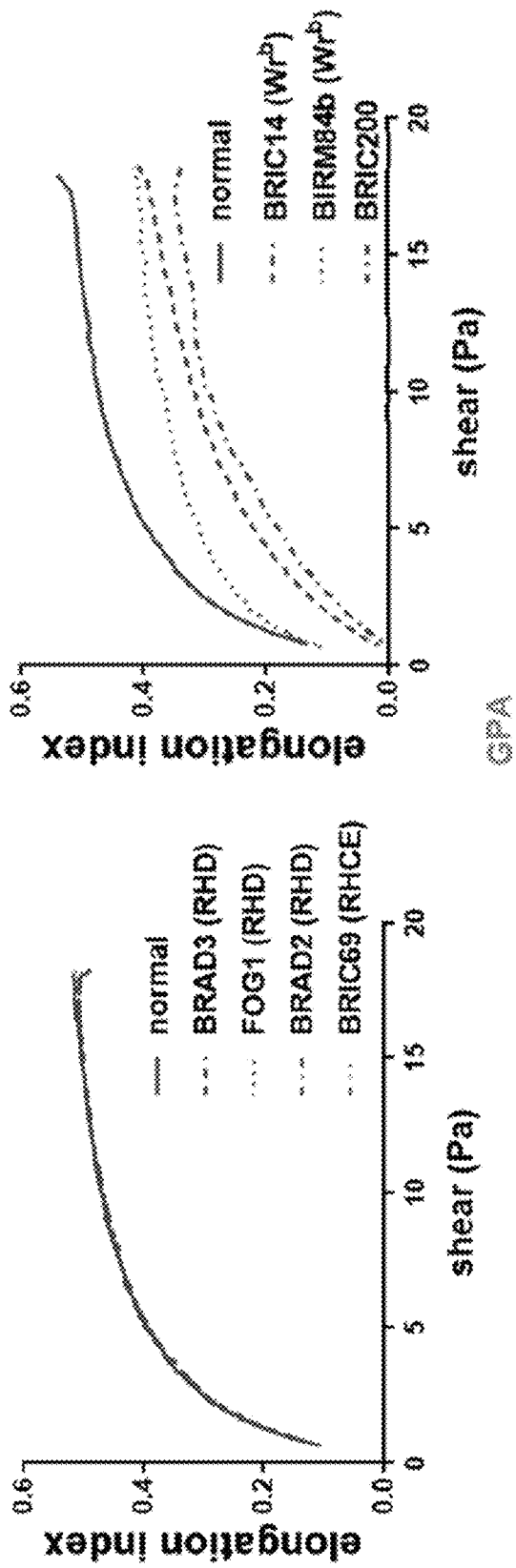
Figure 5C:
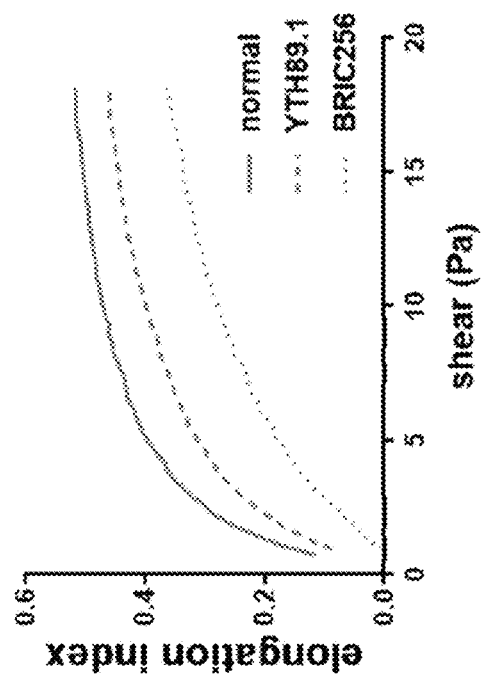
Figure 5E:
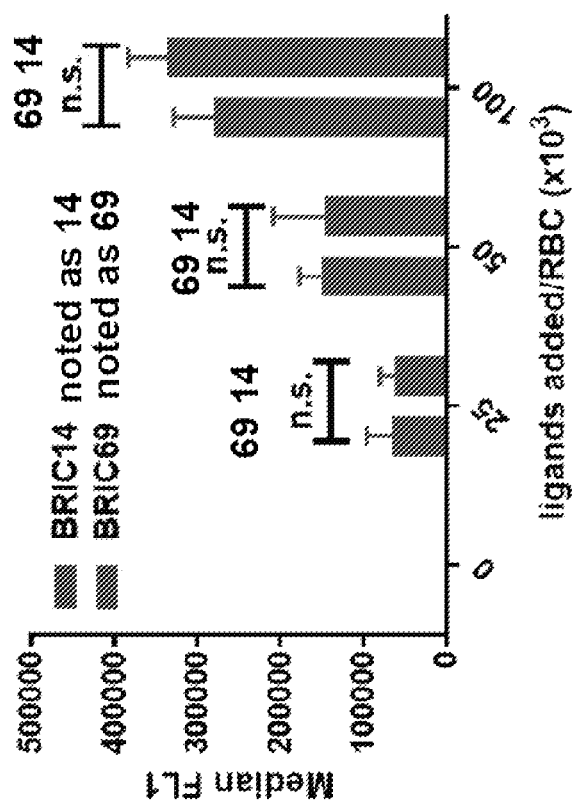
Figure 5D:
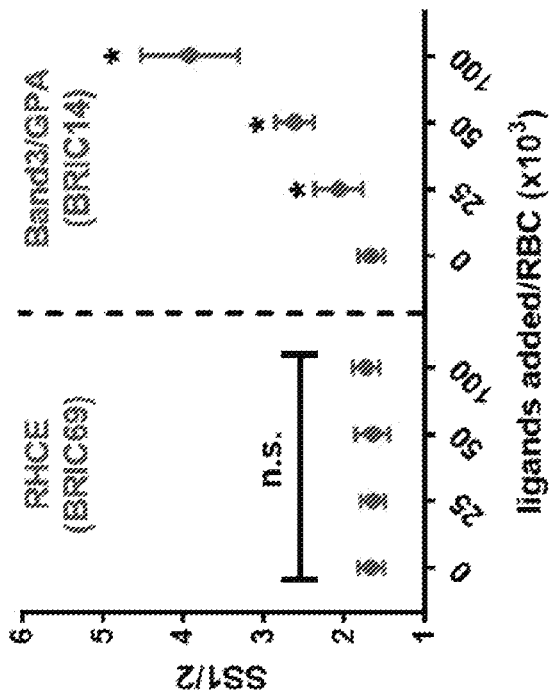

To address the generalizability of the observed deformability effects of the Band 3, GPA, and RhCE ligands, we also compared the ektacytometric effects of a range of full-length IgG antibodies covering different epitopes on these membrane targets. For this purpose, we used BRIC69 (anti-RHCE, mouse IgG1), BRAD2 (anti-D, human IgG1), BRAD3 (anti-D, human IgG3), FOG1 (anti-D, human IgG1), BIRMA84b (anti-Wrb, mouse IgG3), BRIC14 (anti-Wrb, mouse IgG2a), YTH89.1 (anti-GPA, rat IgG2b), BRIC256 (anti-GPA, mouse IgG1), and BRIC200 (anti-Band3, mouse IgG1). In agreement with prior studies[26-28, 31], we found that all IgGs tested against epitopes on GPA and Band3 induced decreases in deformability, while antibodies to RhCE and RhD (on serologically confirmed RHD positive RBC donors) showed minimal change from naïve RBCs (FIG. 5A-FIG. 5C). Although all IgGs were added at a ratio of approximately 104 mAbs per RBC (10 nM mAb in a 5% RBC suspension), the differences in affinities of these clones would likely result in different numbers of bound copies and, therefore, the relative degrees of rigidification as a function of bound copy numbers remained uncertain. To address this, we selected representative anti-RhCE (BRIC69) and anti-Wrb (BRIC14) IgG antibodies and performed additional dose-titration experiments to show that when the anti-RhCE antibodies were added at ratios below saturation and which resulted in similar total numbers of bound IgG as anti-Wrb antibodies (FIG. 5D-FIG. 5F), no change in SS1/2 was seen for anti-RhCE while anti-Wrb showed significant, dose-dependent rigidification.

Figure 15A:
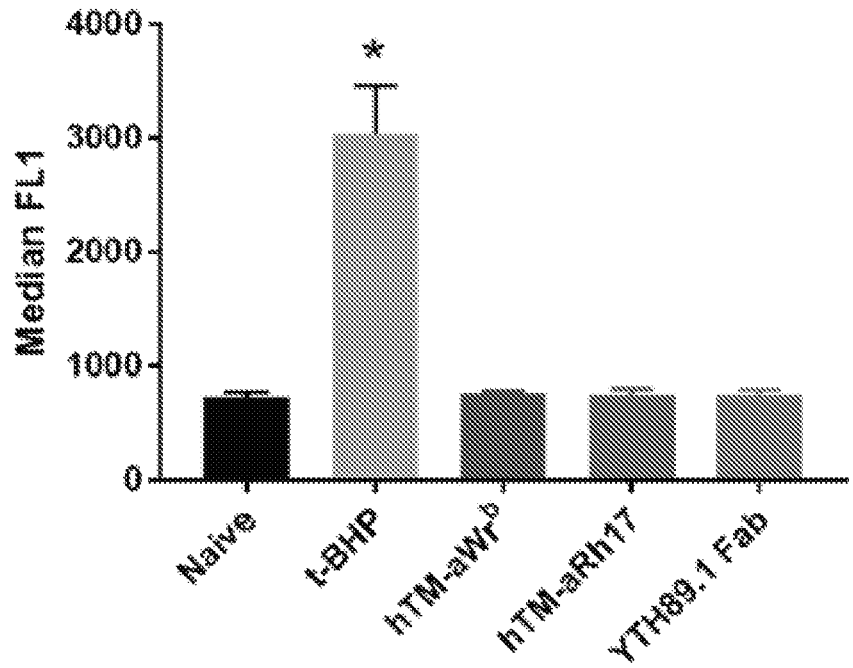
FIG. 15A-FIG. 15B show human RBC ligands do not induce significant ROS generation or PS exposure.
Figure 15B:
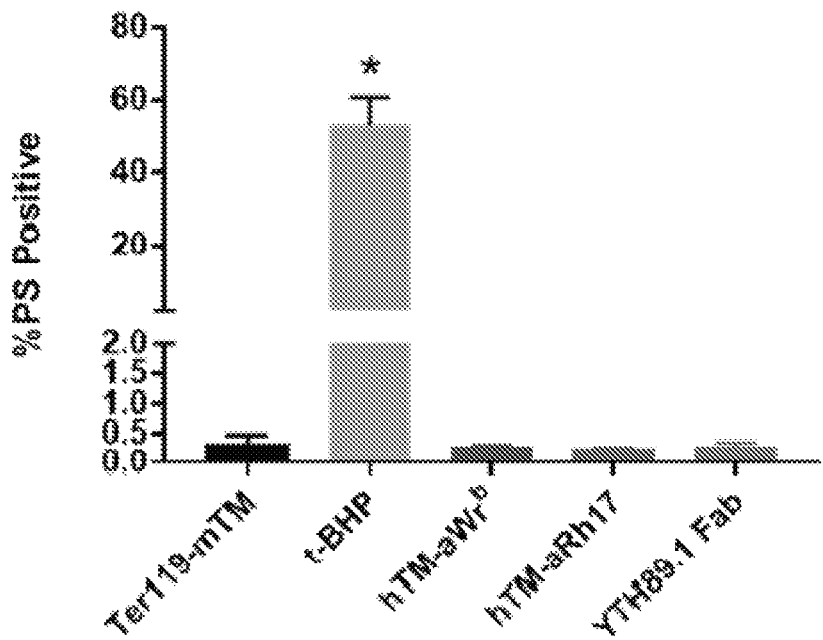

Additional characterization of the effects of the scFvs and fusions on RBCs included assays of PS surface exposure, as measured by annexin V binding, and ROS generation. Binding of both scFvs and hTM-scFv fusions did not lead to detectable increase in PS exposure (FIG. 15A). None of the scFv ligands examined demonstrated detectable induction of ROS generation by a dihydrorhodamine-based assay (FIG. 15B).

Example 5: Therapeutic Effectiveness of RBC Cargoes

Figure 6A:
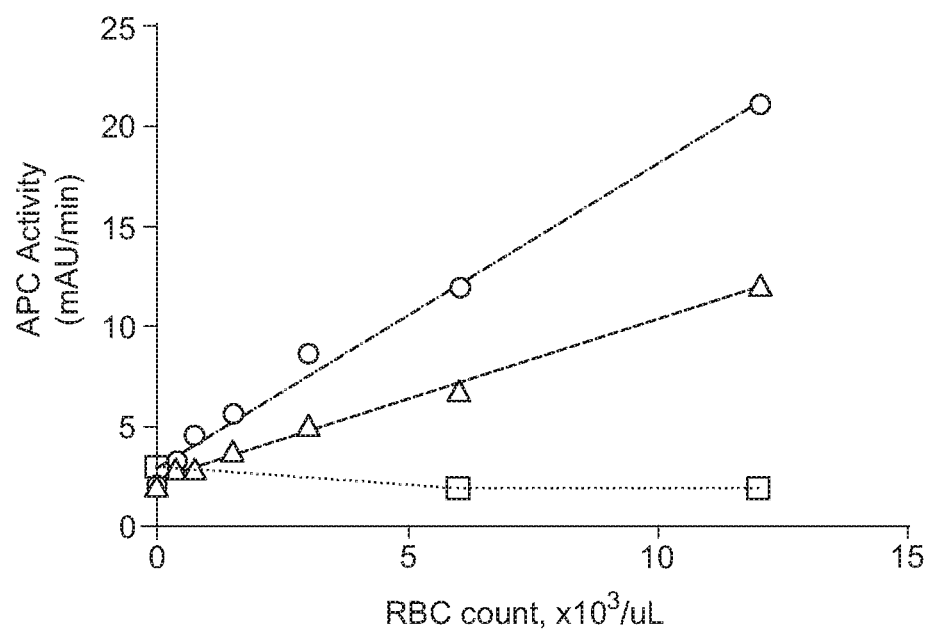
FIG. 6A-FIG. 6E provide characterization of the activity of RBCs bound by hTM-scFv fusions and their therapeutic efficacy in a microfluidic model of inflammatory thrombosis (FIG. 6A) APC generation by RBCs loaded with hTM-scFv demonstrates a dose- and copy-number dependent response in APC generation as measured by chromogenic assay. hTM-aBand3 (circles) showed about 2-fold higher APC generation per RBC compared to hTM-aRhCE (triangles), although copy numbers are expected to 5- to 10-fold higher.
Figure 6B:
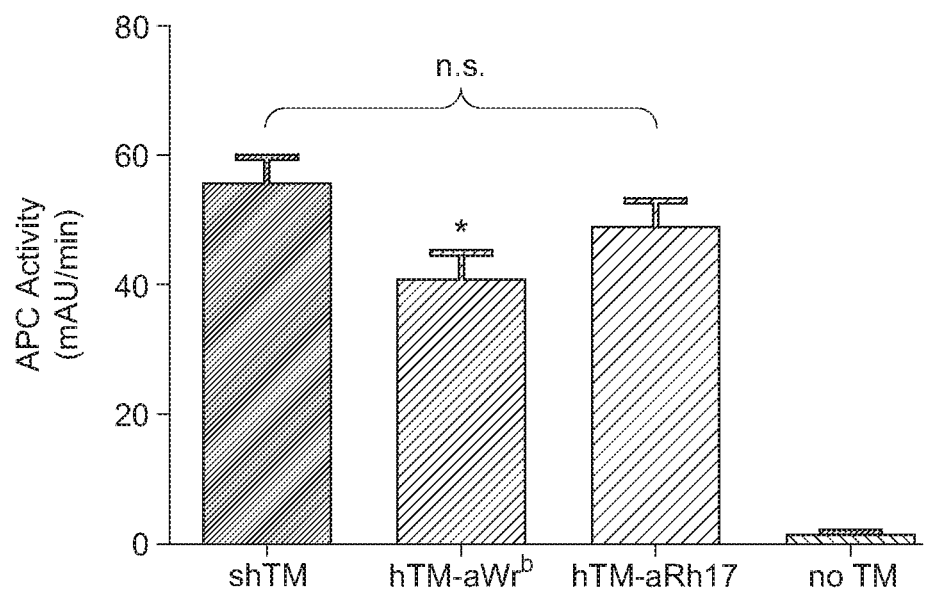
Figure 16:
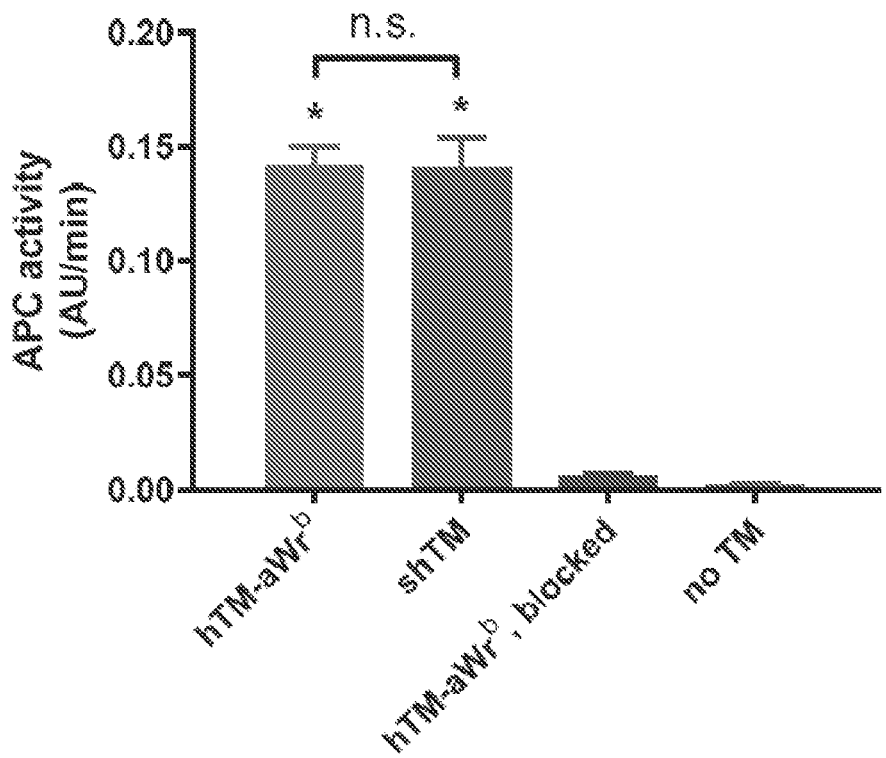
FIG. 16 shows APC generation by fusion proteins (hTM-scFv). APC generation by fusion proteins in soluble phase (green) is similar to shTM alone (red). shTM or hTM-aBand3 (20 nM) were assayed by chromogenic methods. No significant APC generation was seen in the presence of excess anti-TM blocking antibody (Phx-01, blue) or without TM added (purple). Mean±SD is shown (n=3). (*p<0.05 vs no TM, one-way ANOVA)
Figure 17:
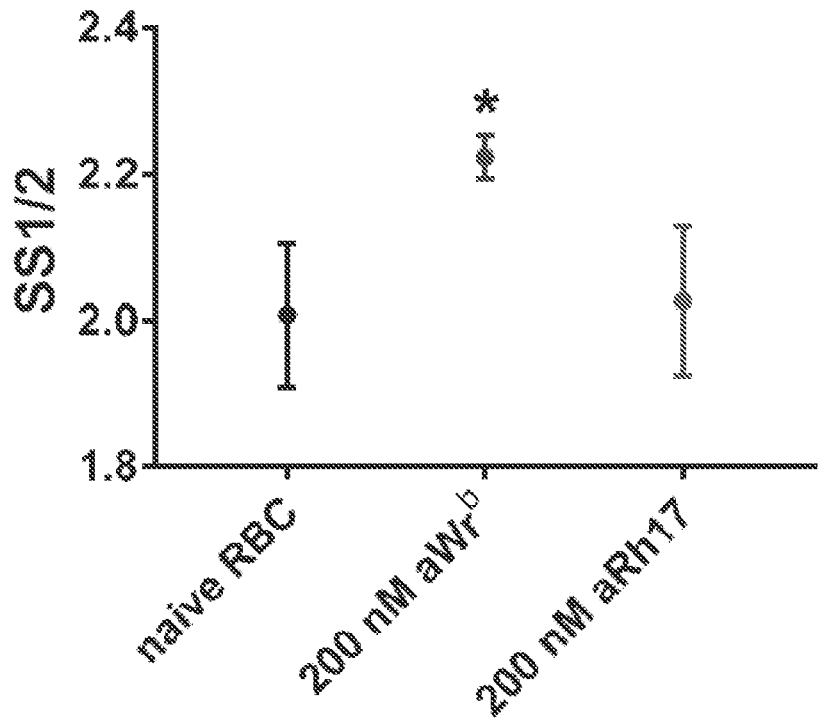
FIG. 17 shows aWrb scFvs rigidify human RBCs in whole blood at 200 nM. Whole blood treated with 200 nM aWrb scFv shows significant rigidification (increased SS1/2) while treatment with 200 nM aRh17 scFv shows no change compared to naïve whole blood. Blood was treated at 37 C for 1 hour prior to ektacytometry in 5.5% PVP solution. These ratios produce approximately 25,000 ligands per RBC. Mean±SD is shown, n=5-6, three donors tested. (*p<0.05 vs naïve RBC, one-way ANOVA with Holm-Sidak correction for multiple comparisons).

Having examined the effects on aWrb and aRh17 scFvs and their respective TM fusion proteins on human RBC physiology, we next compared the enzymatic activity and therapeutic efficacy of these fusions. In solution, fusion proteins demonstrated APC generative capacity identical to soluble TM in the presence of human protein C and thrombin (FIG. 16). Fusion proteins were then pre-bound to human RBCs at saturating concentrations and their capacity to generate APC was measured as a function of RBC concentration. The fusions generated a RBC-dose dependent increase in APC generation by carrier RBCs (FIG. 6A). Using a standard curve generated with soluble TM, the Wrb-coupled RBC-TM generated roughly 100,000 soluble TM 'equivalents' per loaded RBC at saturation while the RhCE-coupled RBC-TM generated 50,000. Therefore, although Wrb-coupled TM would be predicted to carry 5- to 10-fold more copies of the fusion per RBC at saturation, the APC generating capacity was only 2-fold higher. We then reversed these conditions such that RBCs and target epitopes were at excess (50 nM fusion in 20% Hct, approximately 10,000 copies/RBC), which would drive fusions to be essentially completely RBC-bound. At these high concentrations of RBCs, comparable to the circulatory environment, APC generation was similar for both fusion proteins and comparable to that seen for soluble TM, although a slight reduction was seen for hTM-aBand3/GPA and not hTM-aRhCE (FIG. 6B). These results confirm that the fusions maintain their enzymatic activity when coupled to RBCs, and suggest that RhCE-coupled TM may better conserve specific activity.

Figure 6C:
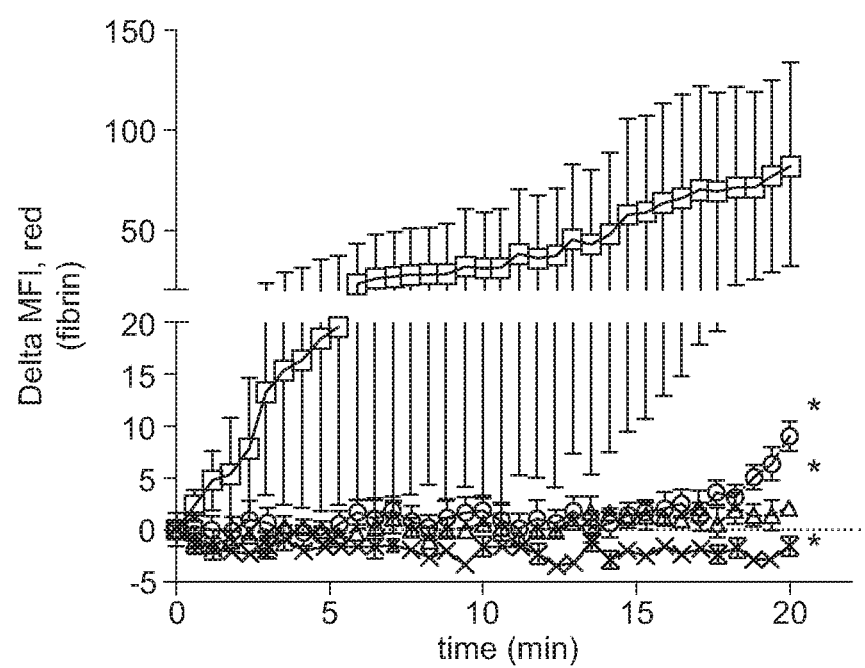
Figure 6D:
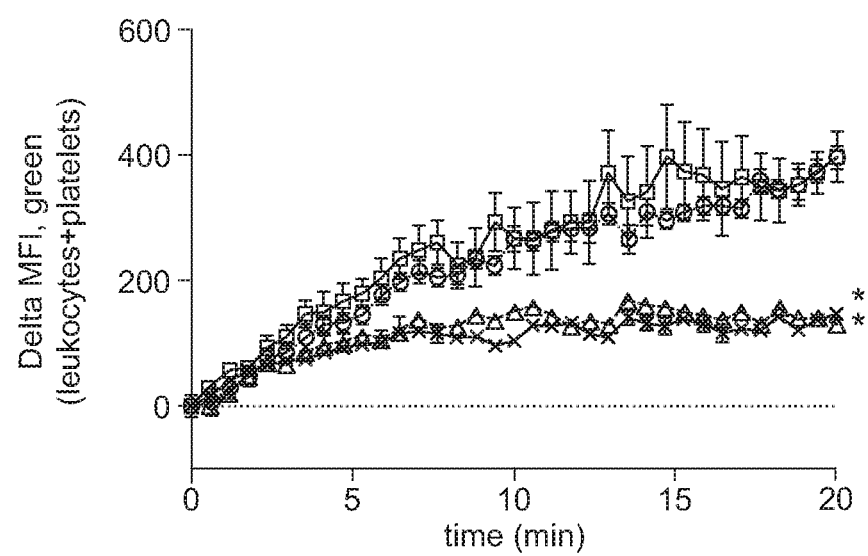
Figure 6E:
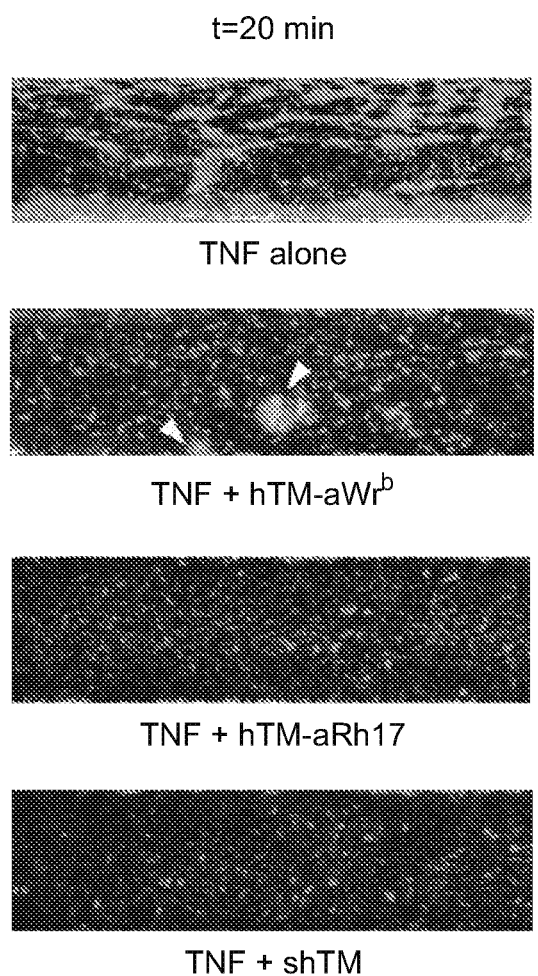
Figure 7A:
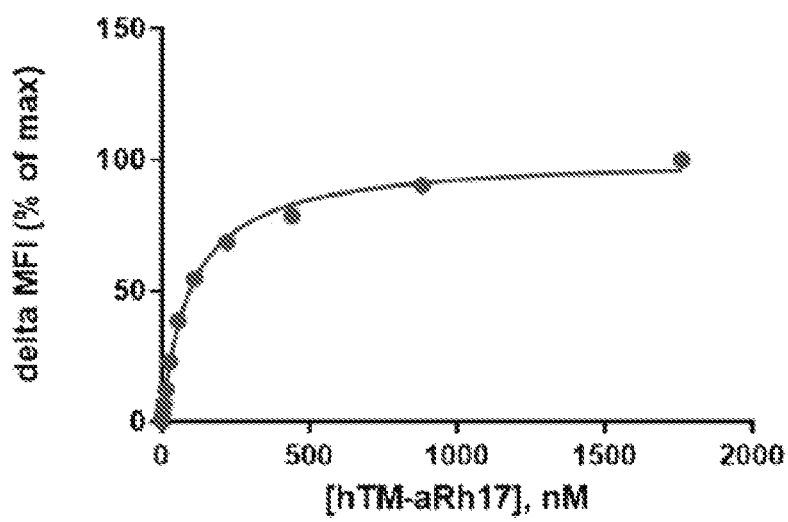
FIG. 7A-FIG. 7D show that binding of fluorescent fusion proteins to RBCs measured by flow cytometry. Representative binding curves for fluorescently labeled (FIG. 7A) hTM-aRh17 and (FIG. 7B) hTM-aWrb fusions demonstrate similar binding parameters as radiolabeled fusions (representative of at least 3 repeated studies). Histograms for mouse (red), pig (blue), rat (black) and human (green) RBCs bound by fluorescently labeled fusion proteins demonstrate that both (FIG. 7C) hTM-Rh17 and (FIG. 7D) hTM-Wrb bind to human and not mouse, rat, or pig RBCs.
Figure 7B:
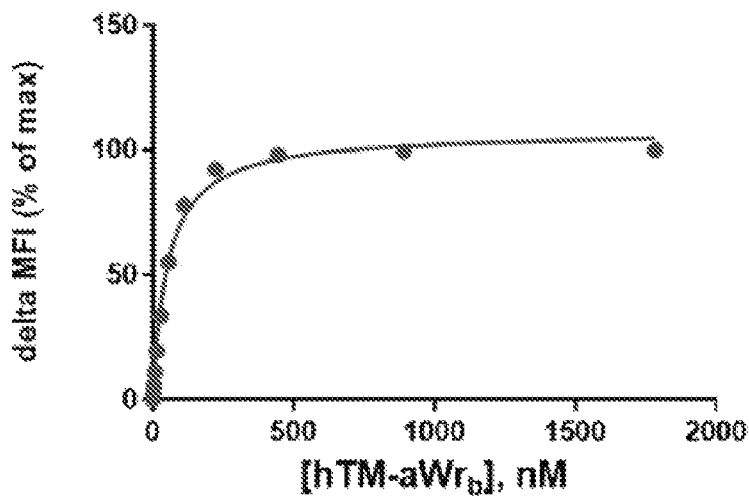
Figure 7C:
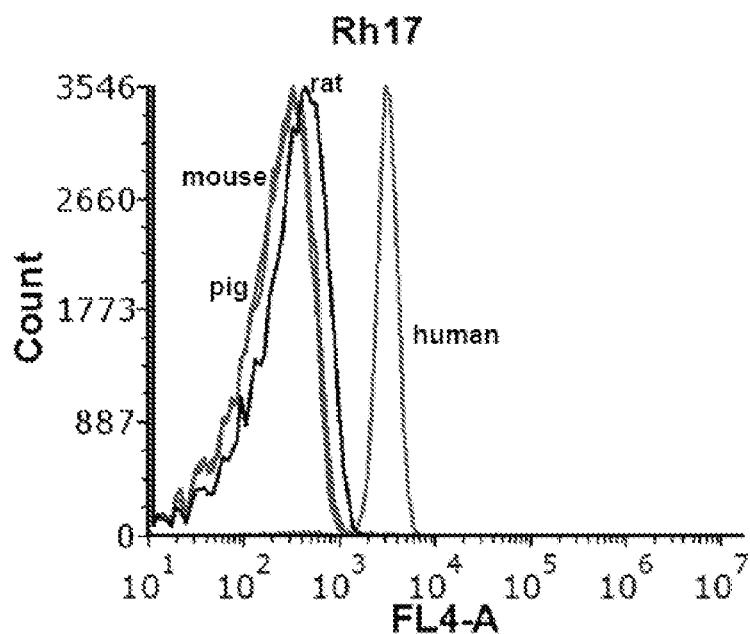
Figure 7D:
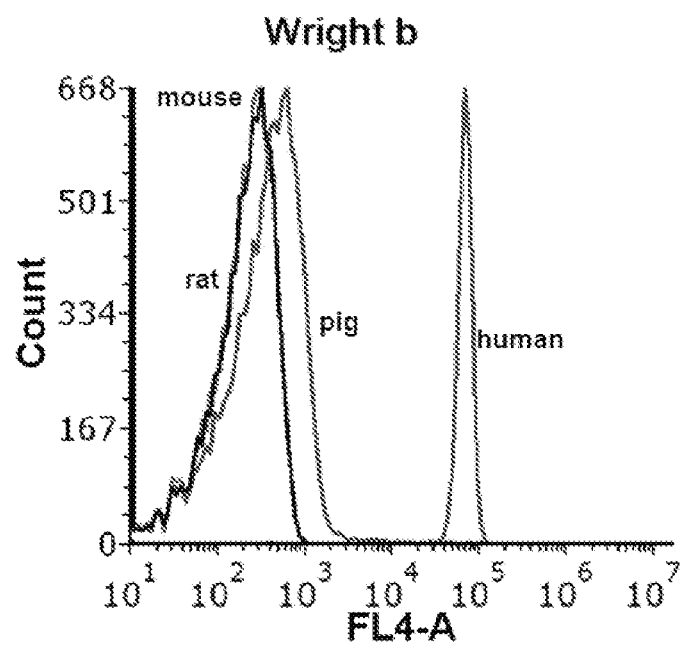
Figure 8A:
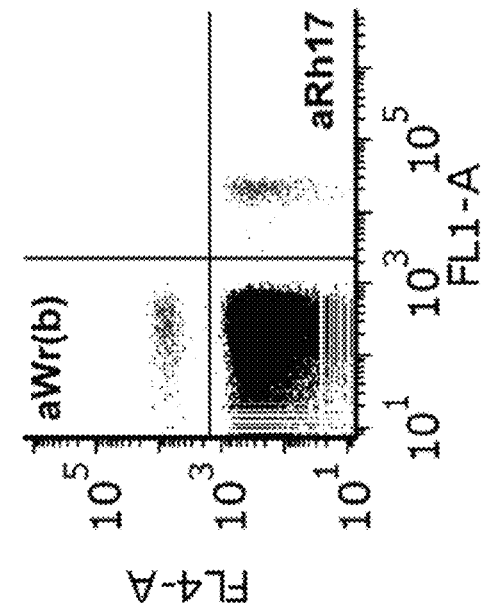
FIG. 8A-FIG. 8E shows that binding of scFvs to RBCs is maintained after exposure to low (5 dyne/cm2) and high (200 dyne/cm2) shear stress flow. A fraction of washed, isolated human RBCs was treated with saturating concentrations of anti-Wrb or anti-Rh17 scFv labeled with Alexa Flour 647 or Alexa Flour 488, respectively. The labeled RBCs were then added to fresh donor human whole blood (collected in citrate) at 0.5% of the total RBC population. The resulting blood was flowed through the Bioflux microfluidic device at either 5 dyne/cm2 or 200 dyne/c2 and the (FIG. 8A) inlet and (FIG. 8B and FIG. 8C) outlet blood was analyzed by flow cytometry. The results demonstrate that (FIG. 8D) the labeled RBCs maintained the same fluorescence intensity as the inlet populations and (FIG. 8E) were present in equal proportion to the unlabeled RBCs.
Figure 8B:
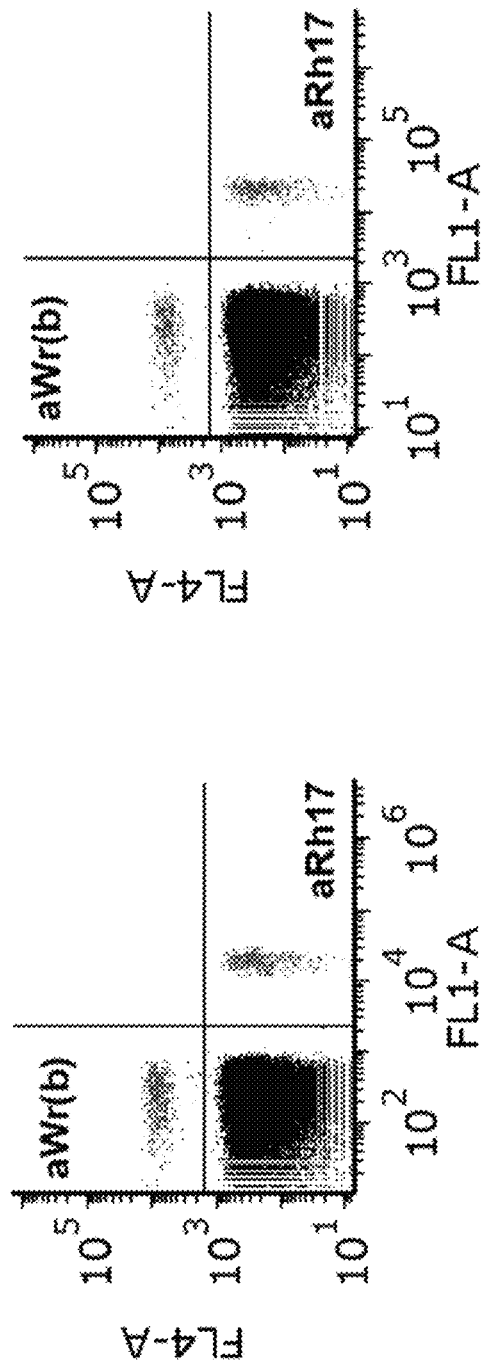
Figure 8C:
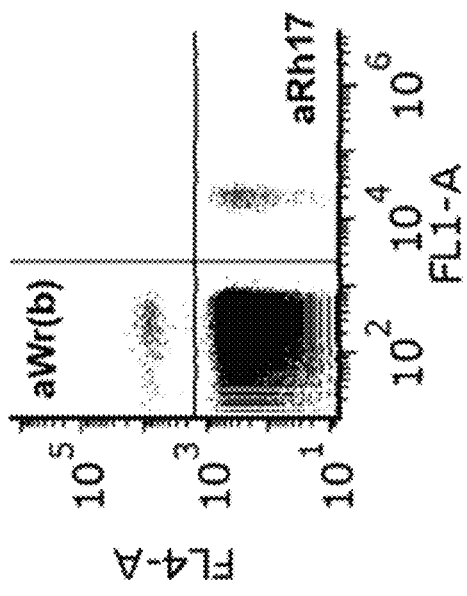
Figure 8E:
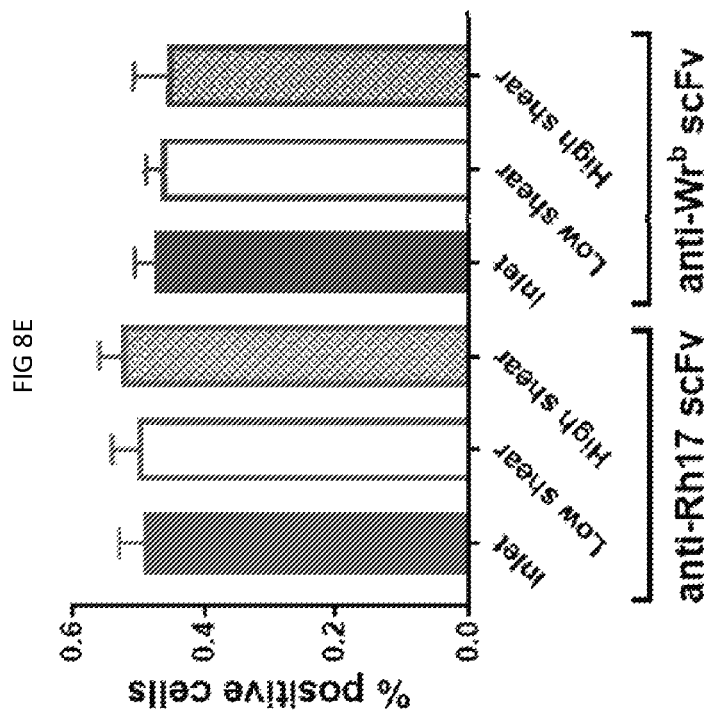
Figure 8D:
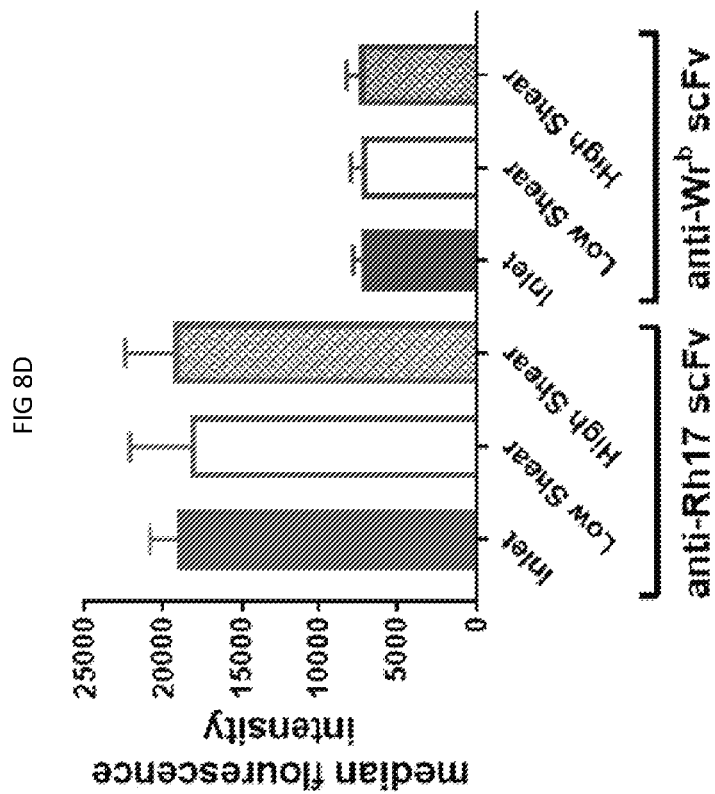
Figure 9A:
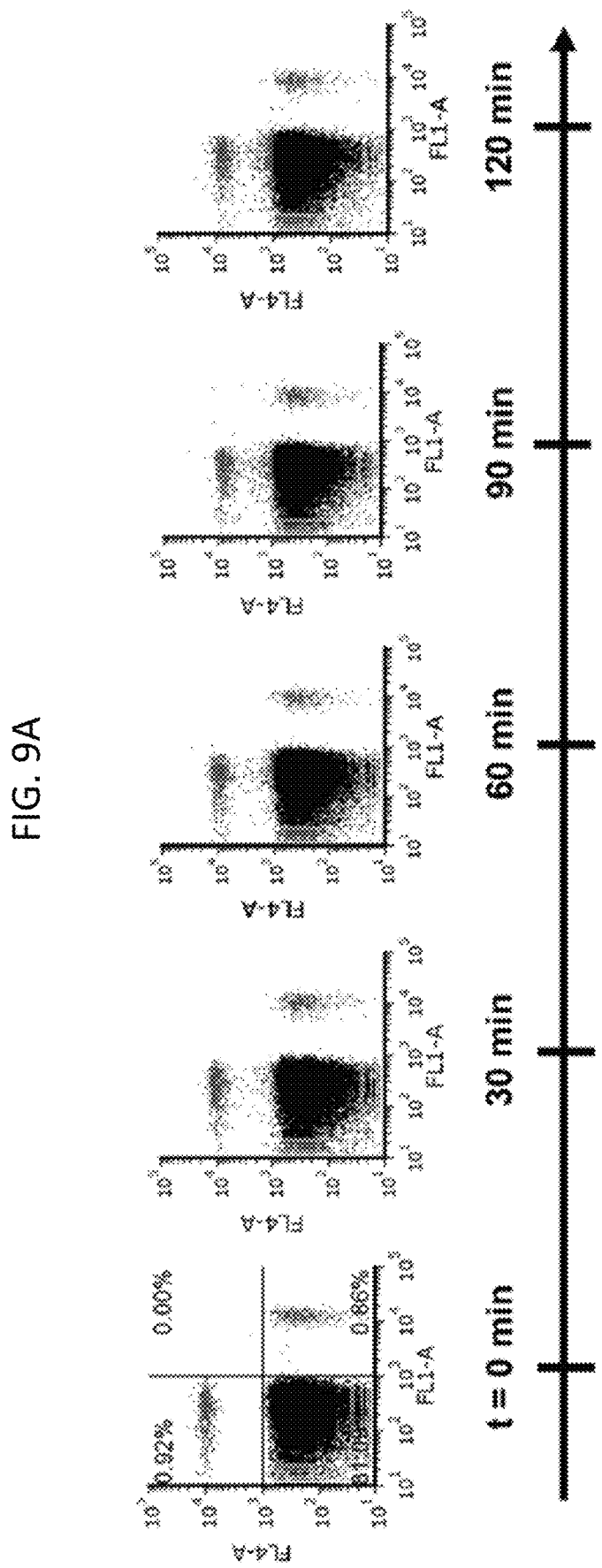

We then tested the therapeutic activity of hTM/scFv fusions bound to human RBC in a microfluidic model of microvascular inflammatory thrombosis that permits assessment of human-targeted therapeutics in whole blood in a system simulating human vessels[37]. In this model, fully endothelialized micro-channels are activated with an inflammatory mediator (e.g. TNF-α), inducing leukocyte and platelet adhesion and widespread fibrin generation when the channels are exposed to flowing human whole blood. We hypothesized that if the fusions maintain their activity in whole blood, they would significantly reduce fibrin and platelet deposition in response to inflamed endothelium. To do so, we added 200 nM of each fusion protein (and soluble TM as a control) to whole blood (a ratio of approximately 25,000 copies of TM per RBC at normal RBC counts). Both fusions significantly reduced fibrin deposition (measured by red fluorescence) in response to TNF-α activation (FIG. 6C). Channels exposed to Wrb-targeted fusions, as compared to RhCE-targeted, showed a slight increase in mostly platelet-associated fibrin deposition at the end of the perfusion period (20 minutes), but both remained significantly reduced compared to untreated controls and similar to soluble TM (data not shown). Additional analysis of fluorescence from calcein AM labeling (leukocytes and platelets) demonstrated that RhCE targeted hTM-scFv was more effective than the Wrb targeted fusion at reducing platelet and leukocyte adhesion (FIG. 6D), with efficacy of hTM-aRhCE again similar to soluble TM. Hypothesizing that the increase in calcein signal and late fibrin generation in hTM-aWrb compared to hTM-aRhCE was a result of rigidifying effects of the aWrb, we performed additional experiments in this model using the aWrb and aRHCE scFvs alone (not fused to TM), and demonstrated that after 15 minutes of flow, activated channels exposed to aWrb treated blood showed greater platelet and leukocyte accumulation compared to that treated with aRh17 (FIG. 6E), suggesting the difference in efficacy of hTM-aRHCE and hTM-aWrb is due to aWrb promotion of leukocyte and platelet adhesion rather than a loss of efficacy of the appended TM. We also confirmed that RBC rigidification was seen at this ratio of scFv to RBC in whole blood (FIG. 15A-FIG. 15B).

Example 6

As a critical step in the translation of RBC-targeted therapeutic fusion proteins to clinical practice, we designed human RBC-specific fusion proteins based on scFvs derived from non-human-primate antibody phage-display libraries. Using this technique, we generated antibodies against highly conserved, erythroid-specific epitopes on Band3/GPA (Wrb) and RhCE (Rh17) proteins. Both epitopes are on multi-pass transmembrane proteins and exist predominantly within discrete multiprotein complexes. While Wrb is more widely distributed between Band3/ankrin complexes, junctional complexes, and free forms, Rh17 (as part of RhCE) exists largely within Band/ankrin complexes[47]. Wrb has been localized to a juxtamembrane site of interaction between GPA and Band3, but the precise epitope for Rh17, which is defined serologically, is unknown. Both antibody fragments and their respective TM fusions showed affinities sufficient to drive rapid, complete binding in whole blood, where concentrations of their targets are >1 μM. While only a slight increase in off-rate was noted for TM fusion proteins, interaction with TM binding partners (thrombin, PF4, protein C) may promote dissociation in whole blood under flow, which was not directly assessed this in the present study. The primate origin of these ligands is expected to confer less immunogenicity than non-engineered murine monoclonal antibodies or foreign peptides, but further data would be required to support this.

Targeting of Band3/GPA (Wrb) led to changes in RBC membrane deformability, mechanical resistance, and osmotic resistance, while RhCE-targeted fusions and antibody fragments did not perturb any of the physiologic parameters assessed in this study. Membrane effects were shared, to varying extents, by other GPA and Band 3 ligands against human and murine RBCs, including Ter119, particularly for bivalent IgG ligands. In contrast, antibodies against RhD and RhCE failed to demonstrate significant rigidification of human RBCs. Antibodies against GPA and RhD also produce markedly different effects on different subsets of phagocytic cells[32], and while the authors hypothesized that copy number was critical, the current findings suggest that altered deformability may have also been contributory. The precise function of RhCE has been difficult to define[48] and a large diversity of polymorphisms have been described[43]. Individuals expressing RhD but not RhCE (rare D-phenotype) show modest alteration of membranes without overt RBC or clinical phenotypes[49]. While homologous proteins participate in ammonia/ammonium transport and acid/base balance, RhCE and RhD do not[50,51]. Band 3 and GPA are highly expressed membrane proteins important for structural membrane complexes and ion exchange, and carriage of sialoglycoproteins, respectively. In this context, the apparent "unresponsiveness" of RBCs bound by RhD/RhCE-targeted ligands is consistent with a lack of recognized function in mature RBCs.

As a representative therapeutic, we coupled TM to both scFvs. TM shows promise in the treatment of sepsis[52] and RBC-coupled TM has demonstrated superiority to soluble TM in mouse models[20,21]. Coupling TM to either epitope resulted in efficacious RBC drug carriers as measured by enzymatic activity and in a humanized microfluidic model of inflammatory thrombosis. However, RhCE-coupled TM showed higher specific activity in vitro and improved efficacy in our microfluidic model. The reasons for the difference in enzymatic activity may reflect spatial localization, as the Wrb epitope is immediately adjacent to the RBC membrane which may limit substrate accessibility, while the precise Rh17 epitope localization is unknown. The difference in efficacy in our humanized microfluidic model was unexpected, but because cellular rigidity has significant effects on margination of red cells, white cells, and platelets within the vascular lumen, and decreased RBC deformability can drive increased platelet adhesion[53,54], we speculate that the difference in efficacy reflects the observed difference in membrane effects. Our observation of higher platelet adhesion after treatment with Wrb-targeted scFv is consistent with this phenomenon. The potential for drug or antibody loading of RBCs to affect their intravascular distribution and margination of cellular components, and how this distribution affects their therapeutic efficacy, warrants further investigation.

RBCs can respond to their environment in diverse ways including dynamic changes in linkage of membrane protein complexes[55], phosphorylation of membrane and cytoskeletal components[56-59], calcium influx[60,61], PS exposure[29,62], and oxidative stress responses[30]. In targeting RBCs for delivery of therapeutics, the present findings suggest that dose and target dependent changes in membrane physiology, and ultimately, circulatory behavior should be carefully considered[24-29,63]. As increases in RBC rigidity can result in an override of the CD47/SIRPA interaction[64], these factors may also play a role in RBC interactions with host defenses and immune response. This is especially important because RBC drug carriers are drawing increased attention for their apparent ability to modulate immune responses and even induce immune tolerance[13-15]. However, while ligands to murine RBCs have been explored (e.g. Ter119, ERY1) in this approach, application to human RBCs has not been well-developed.

Based on the current findings, RhCE (on Rh17) may be a particularly attractive target for surface-loading of RBCs given its erythroid specificity, high copy number, apparent lack of adverse impact on RBC physiology, and presence on the RBCs of essentially 100% of the human population. The therapeutic efficacy of hTM targeted to human RBCs on either epitope was comparable to soluble TM, and was optimal when coupled to RhCE. The ligands described in the present study offer a new set of biochemical tools for optimizing the delivery of therapeutics by human RBCs.

Example 7: Red Blood Cell Targeting of Liposomes Provides Markedly Enhanced Circulation Liposomes and other nanoparciles are limited by rapid reticuloendothelial system uptake and poor circulation. Red blood cells are natural long-circulating (~120 days in humans) carriers. Targeting liposomes to red blood cells may offer the ability to prolong their circulation. Red blood cell targeting must be carefully controlled with respect to target epitopes, binding affinities and loading ratios to maximize biocompatibility.

RBC-targetable liposomes were synthesized to include site-specifically modified RBC-targeting antibody fragments (scFv). Copper-independent click chemistry coupling allowed for precise control of ligand loading. Targeting via scFv and IgG was compared. Radiolabeled liposomes were loaded onto mouse RBCs bod in vivo by direct intravenous injection and ex vivo onto isolated RBCs before transfusion. Biocompatibility was assessed by agglutination assays and ektacytometry to determine membrane disruptive effects.

Figure 19A:
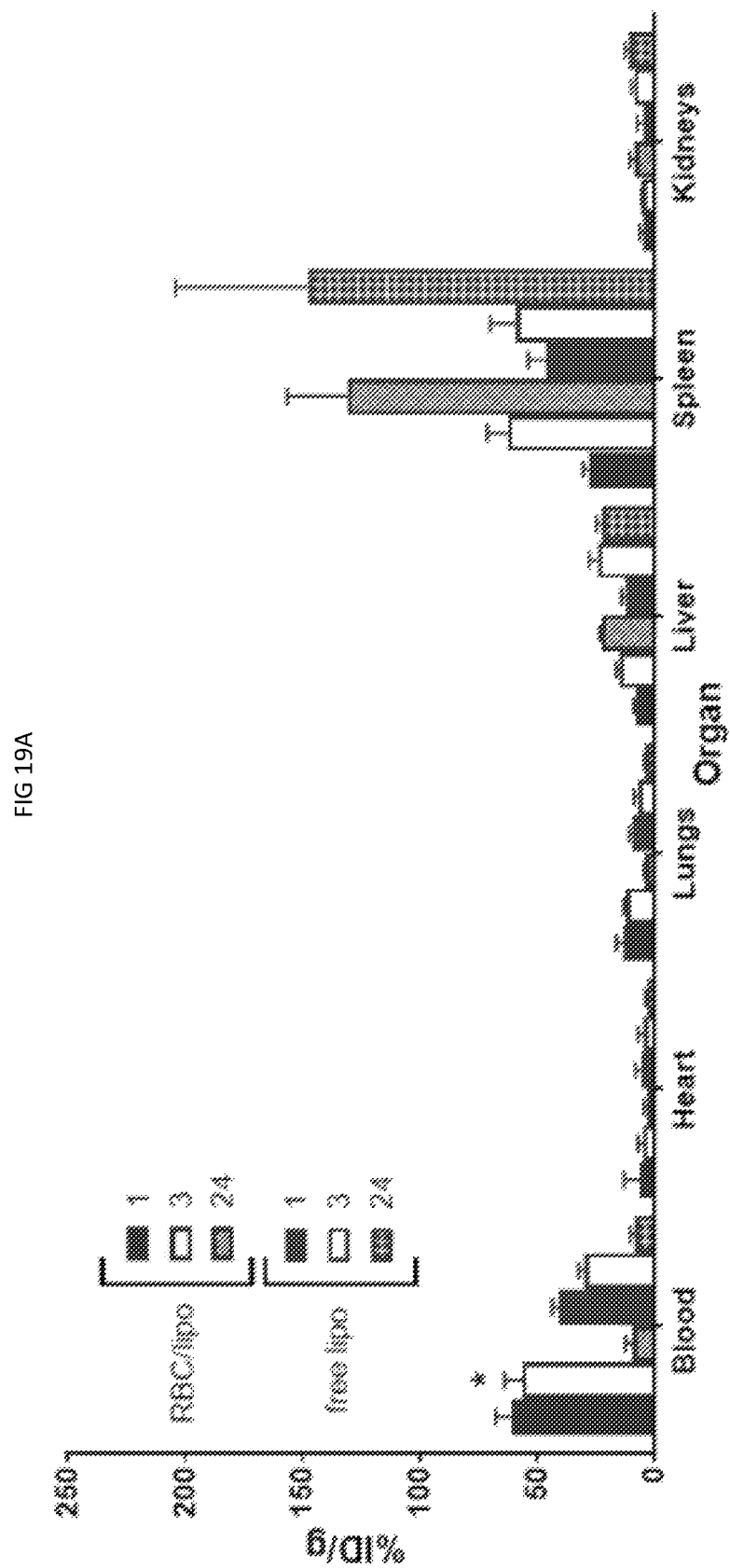

RBC-targeted liposomes are maintained in circulation significantly longer than conventional 'stealth' liposomes. Whole animal biodistribution of Ter119-liposomes (100-200 scFv:liposome) loaded onto RBCs in vivo by direct injection into the blood stream (blue) or unconjugated PEGylated liposomes (red) (FIG. 19A). For in vivo loading liposomes were injected at a ratio of approximately 50 liposomes per RBC. Blood PK curves demonstrate that the large majority of both in vivo loaded Ter119-liposomes (blue) are maintained in circulation at 3 hours and gradually drop off over 24 hours (FIG. 19B). Compared to traditional "stealth" liposomes (red), there is approximately a 2-fold increase in area under the curve (p<0.05). Ter-119 liposomes are found mostly (>80%) in the RBC pellet of collected blood and gradually clear this compartment while free liposomes are largely in the plasma fraction (FIG. 19C).

Figure 20A:
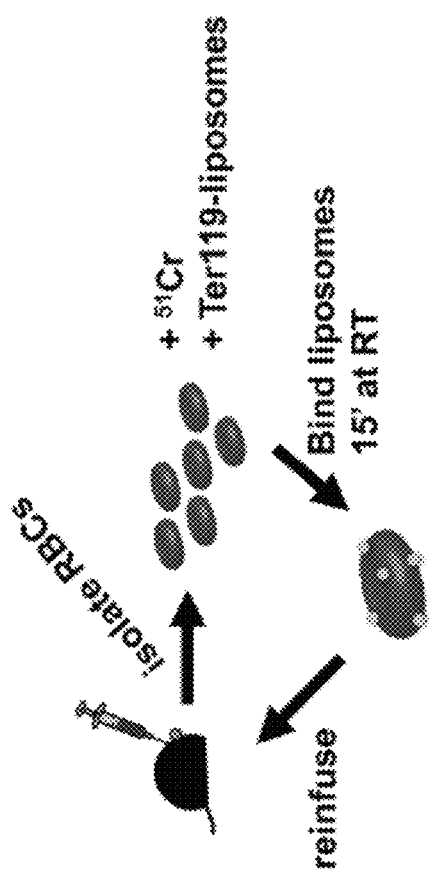
FIG. 20A-FIG. 20B demonstrate circulation of ex vivo liposome loaded RBCs is dependent on the number of loaded nanocarriers.
Figure 20B:
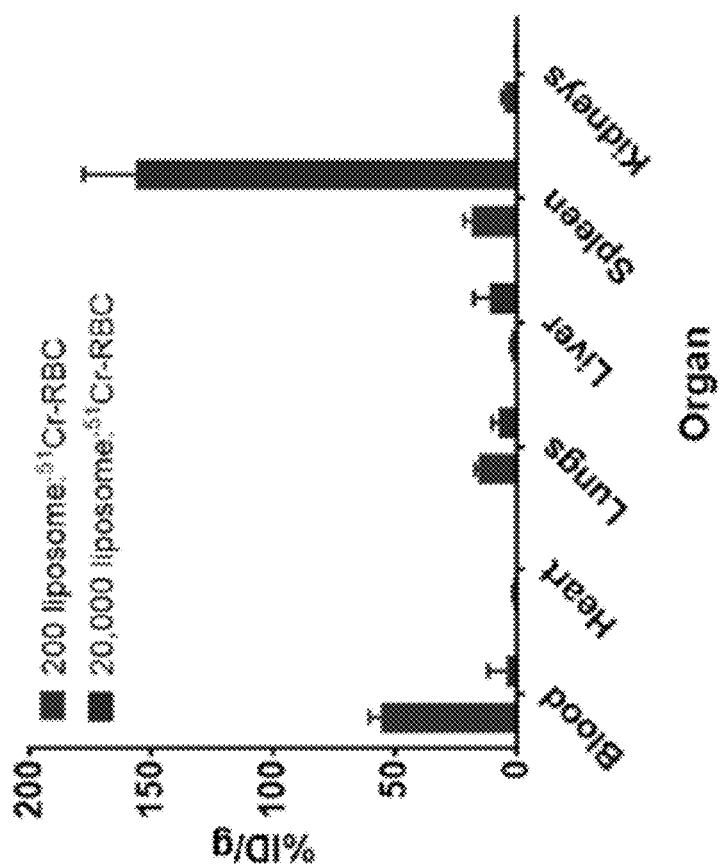
Figure 21B:
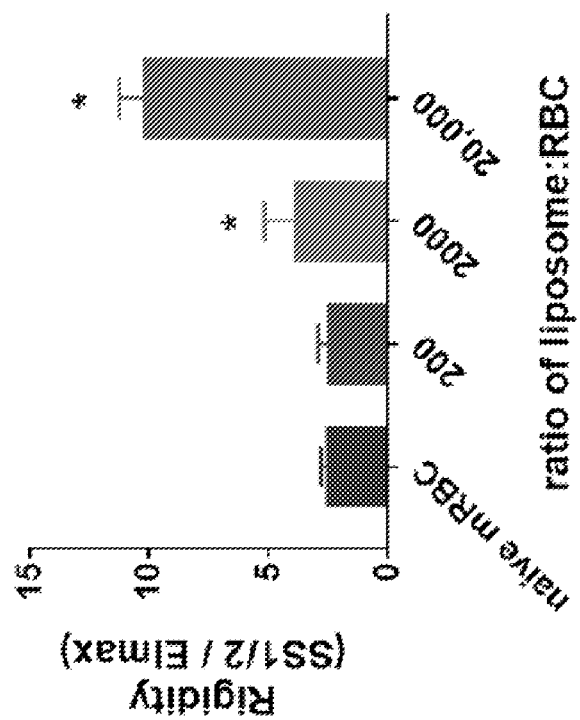
FIG. 21A-FIG. 21B demonstrate effects of liposome binding on RBC agglutination and RBC membrane deformability.
Figure 21A:
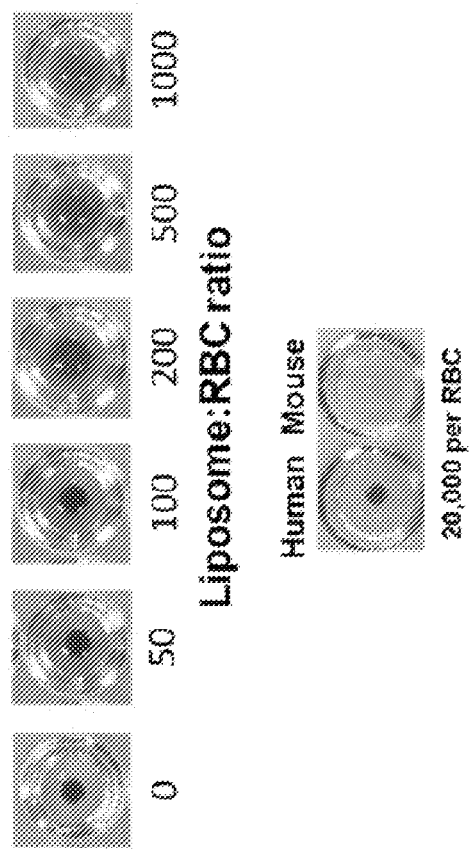
Figure 22:
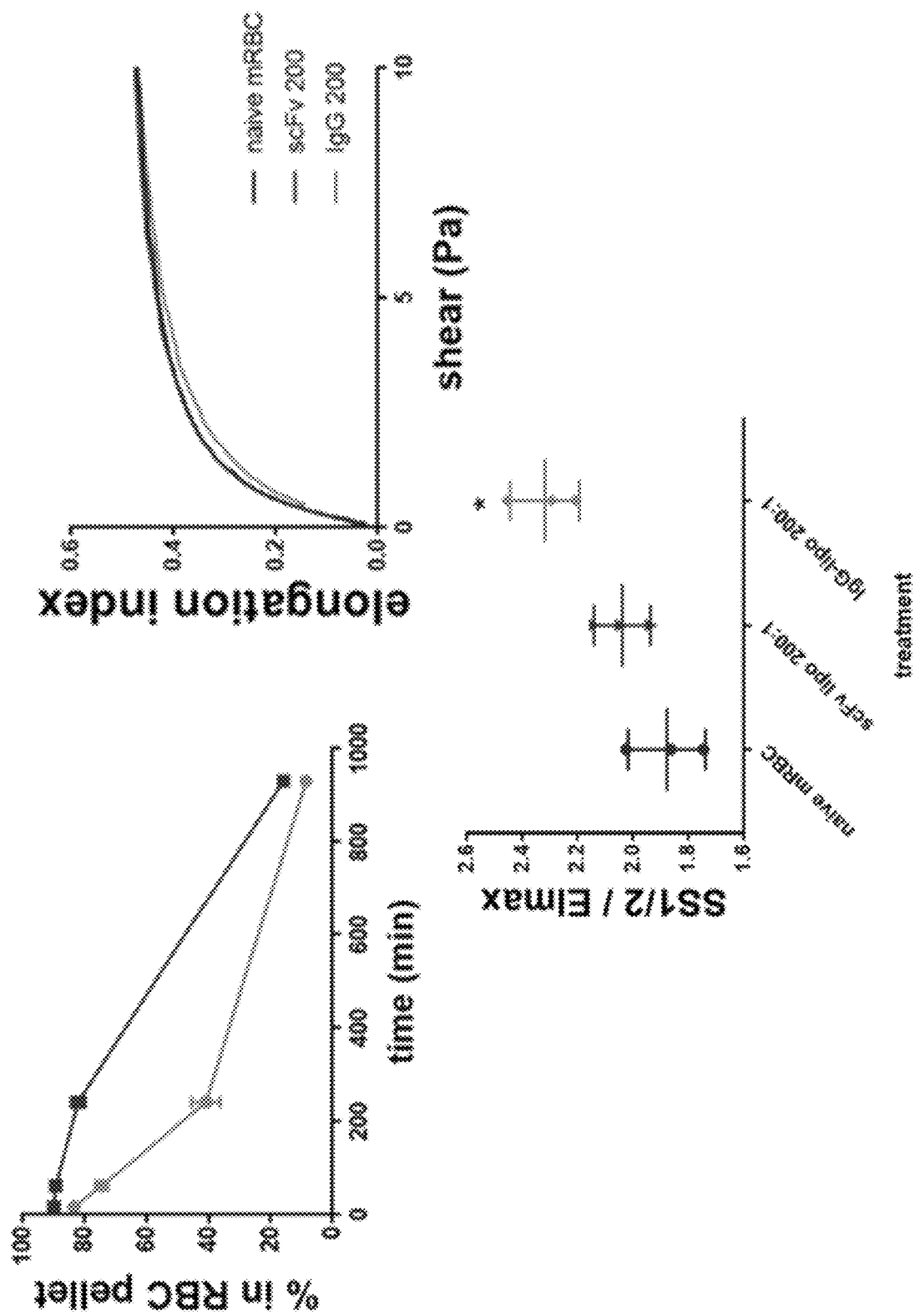
Figure 23:
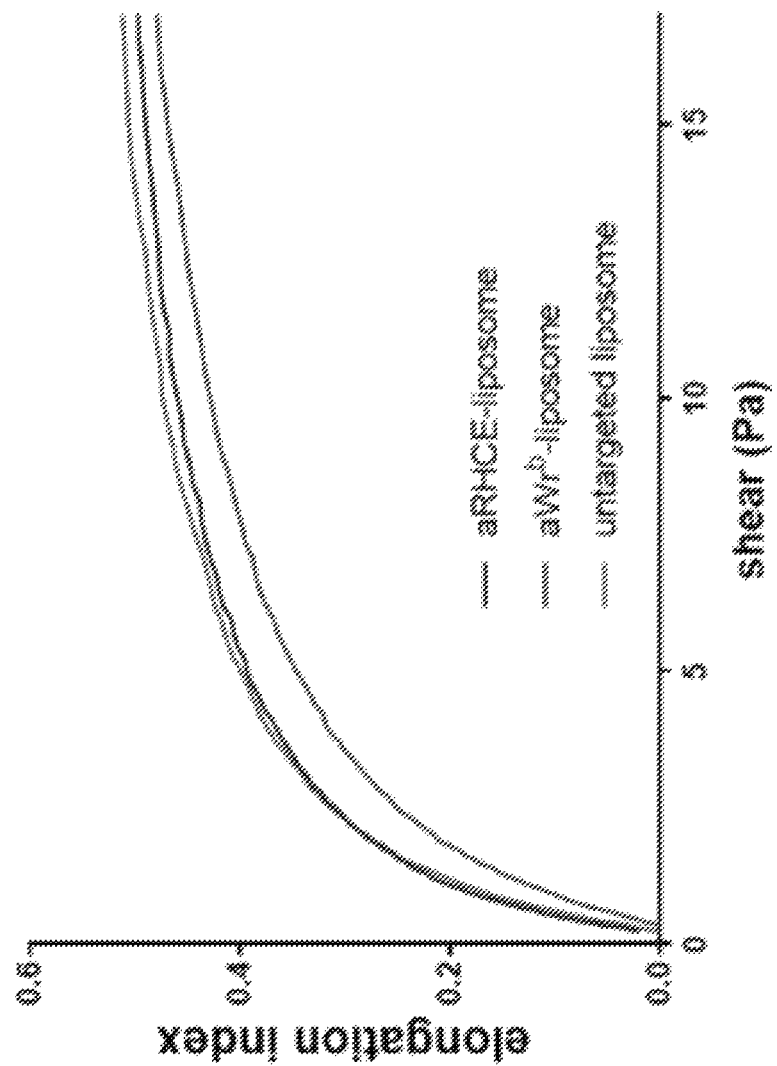
FIG. 23 shows that rigidification of RBC membranes by loaded liposomes is target dependent. Ektacytometry on human RBCs loaded with liposomes targeted to Wright(b) antigen (red) or RHCE (blue), compared to human RBCs mixed with untargeted liposomes (green). Liposomes loaded onto Wright(b) demonstrate significant rigidification while RHCE targeted liposomes preserve normal RBC deformability. Liposomes were targeted with IgGs to human RHCE (BRIC69) or Wright(b) (BRIC14).
Figure 24A:
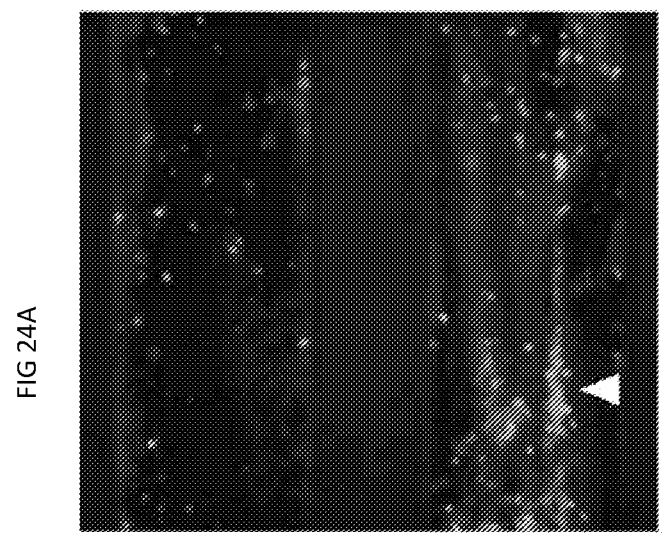
FIG. 24A-FIG. 24B show that whole blood treated with aWrb scFv shows increased platelet adhesion in response to flow over TNF-α activated endothelium compared to blood treated with aRh17.
Figure 24B:
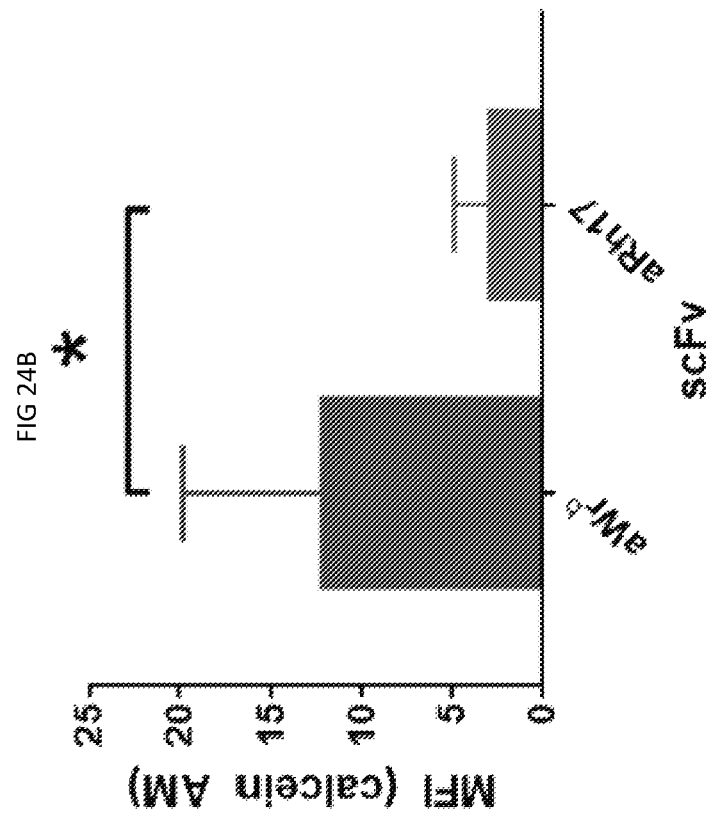

These data demonstrate that RBC-targeted liposomes markedly prolonged the circulation of liposomes compared to traditional "stealth" technology (FIG. 19A-FIG. 19C). Circulation of ex vivo liposome loaded RBCs is dependent on the number of loaded nanocarriers. (FIG. 20A and FIG. 20B). RBC-bound liposomes circulate predominantly on the RBC surface over the initial 12 hours after which they are gradually cleared. Mechanisms of clearance remain uncertain. High loading induces RBC agglutination (FIG. 21A and FIG. 21B). Circulation is dependent on low loading ratios. scFv-liposomes provide superior circulation (FIG. 22) and better preserve normal RBC membrane physiology compared to IgG-liposomes (FIG. 23). Normal membrane deformability is both loading-ratio and target dependent.

Example 8: Rh17 Recognizes a Linear Epitope in Human RhCE

A Western blot was performed to assess the binding of Rh17 to proteins extracted from mouse and human erythrocyte ghosts (FIG. 25). Because proteins were denatured in reducing SDS-PAGE buffer prior to gel electrophoresis, the presence of binding is due to interaction with linear, and not conformational, epitopes. This is in contrast to anti-RhCE mAbs described by other groups, which recognize conformational epitopes.

Figure 26:
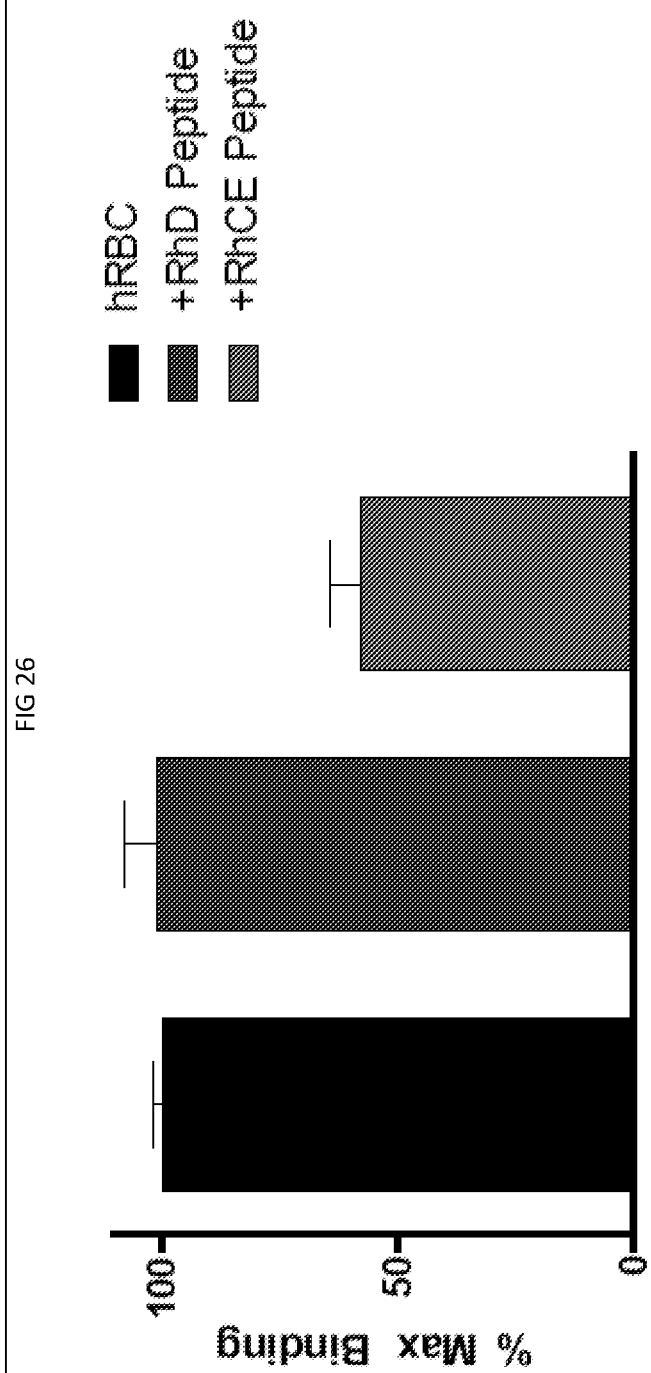
FIG. 26 is a bar graph which demonstrates that KP3-17 (anti-Rh17) recognizes an epitope present in the 6th extracellular loop of human RhCE. Flow cytometry was used to assess the binding of anti-Rh17 to human erythrocytes in the presence and absence of linear peptides corresponding to the amino acid sequence 6th extracellular loop of human RhD (negative control) and human RhCE. A decrease in binding signal only in the presence of the RhCE-derived peptide demonstrates that the 6th extracellular loop of RhCE is involved in the binding of Rh17 to human erythrocytes. (* denotes p<0.05 by 1-way ANOVA with Tukey's post-hoc test).

Rh17 recognizes an epitope present in the 6th extracellular loop of human RhCE. Flow cytometry was used to assess the binding of Rh17 to human erythrocytes in the presence and absence of linear peptides corresponding to the amino acid sequence 6th extracellular loop of human RhD (negative control) and human RhCE (FIG. 26). A decrease in binding signal only in the presence of the RhCE-derived peptide demonstrates that the 6th extracellular loop of RhCE is involved in the binding of Rh17 to human erythrocytes.

REFERENCES

1. Ihler G M, Glew R H, Schnure F W. Enzyme loading of erythrocytes. Proc Natl Acad Sci USA. 1973; 70(9):2663-2666.
2. Ihler G, Lantzy A, Purpura J, Glew R H. Enzymatic degradation of uric acid by uricase-loaded human erythrocytes. J Clin Invest. 1975; 56(3):595-602.
3. Wakamiya R T, Lightfoot E N, Updike S J. Asparaginase entrapped in red blood cells: action and survival. Science (New York, N.Y. 1976; 193(4254).

4. Bourgeaux V, Lanao J M, Bax B E, Godfrin Y. Drug-loaded erythrocytes: on the road toward marketing approval. Drug Des Devel Ther. 2016; 10:665-676.
5. Villa C H, Cines D B, Siegel D L, Muzykantov V. Erythrocytes as Carriers for Drug Delivery in Blood Transfusion and Beyond. Transfus Med Rev. 2017; 31(1): 26-35.
6. Magnani M. Erythrocytes as carriers for drugs: the transition from the laboratory to the clinic is approaching. Expert Opin Biol Ther. 2012; 12(2):137-138.
7. Leuzzi V, Micheli R, D'Agnano D, et al. Positive effect of erythrocyte-delivered dexamethasone in ataxia-telangiectasia. Neurol Neuroimmunol Neuroinflamm. 2015; 2(3): e98.
8. Hunault-Berger M, Leguay T, Huguet F, et al. A Phase 2 study of L-asparaginase encapsulated in erythrocytes in elderly patients with Philadelphia chromosome negative acute lymphoblastic leukemia: The GRASPALL/GRAALL-SA2-2008 study. Am J Hematol. 2015; 90(9): 811-818.
9. Kontos S, Hubbell J A. Improving protein pharmacokinetics by engineering erythrocyte affinity. Mol Pharm. 2010; 7(6):2141-2147.
10. Zaitsev S, Spitzer D, Murciano J C, et al. Sustained thromboprophylaxis mediated by an RBC-targeted pro-urokinase zymogen activated at the site of clot formation. Blood. 2010; 115(25):5241-5248.
11. Shi J, Kundrat L, Pishesha N, et al. Engineered red blood cells as carriers for systemic delivery of a wide array of functional probes. Proc Natl Acad Sci USA. 2014; 111 (28):10131-10136.
12. Fesnak A D, June C H, Levine B L. Engineered T cells: the promise and challenges of cancer immunotherapy. Nat Rev Cancer. 2016; 16(9):566-581.
13. Kontos S, Kourtis I C, Dane K Y, Hubbell J A. Engineering antigens for in situ erythrocyte binding induces T-cell deletion. Proc Natl Acad Sci USA. 2013; 110(1): E60-68.
14. Grimm A J, Kontos S, Diaceri G, Quaglia-Thermes X, Hubbell J A. Memory of tolerance and induction of regulatory T cells by erythrocyte-targeted antigens. Sci Rep. 2015; 5:15907.
15. Lorentz K M, Kontos S, Diaceri G, Henry H, Hubbell J A. Engineered binding to erythrocytes induces immunological tolerance to E. coli asparaginase. Sci Adv. 2015; 1(6):e1500112.
16. Villa C H, Pan D C, Zaitsev S, Cines D B, Siegel D L, Muzykantov V R. Delivery of drugs bound to erythrocytes: new avenues for an old intravascular carrier. Ther Deliv. 2015; 6(7):795-826.
17. Murciano J C, Medinilla S, Eslin D, Atochina E, Cines D B, Muzykantov V R. Prophylactic fibrinolysis through selective dissolution of nascent clots by tPA-carrying erythrocytes. Nat Biotechnol. 2003; 21(8):891-896.
18. Ganguly K, Krasik T, Medinilla S, et al. Blood clearance and activity of erythrocyte-coupled fibrinolytics. J Pharmacol Exp Ther. 2005; 312(3):1106-1113.
19. Gersh K C, Zaitsev S, Cines D B, Muzykantov V, Weisel J W. Flow-dependent channel formation in clots by an erythrocyte-bound fibrinolytic agent. Blood. 2011; 117 (18):4964-4967.
20. Zaitsev S, Kowalska M A, Neyman M, et al. Targeting recombinant thrombomodulin fusion protein to red blood cells provides multifaceted thromboprophylaxis. Blood. 2012; 119(20):4779-4785.
21. Carnemolla R, Villa C H, Greineder C F, et al. Targeting thrombomodulin to circulating red blood cells augments its protective effects in models of endotoxemia and ischemia-reperfusion injury. FASEB J. 2017; 31(2):761-770.
22. Kina T, Ikuta K, Takayama E, et al. The monoclonal antibody TER-119 recognizes a molecule associated with glycophorin A and specifically marks the late stages of murine erythroid lineage. Br J Haematol. 2000; 109(2): 280-287.
23. Sahoo K, Koralege R S, Flynn N, et al. Nanoparticle Attachment to Erythrocyte Via the Glycophorin A Targeted ERY1 Ligand Enhances Binding without Impacting Cellular Function. Pharm Res. 2016; 33(5):1191-1203.
24. Knowles D W, Chasis J A, Evans E A, Mohandas N. Cooperative action between band 3 and glycophorin A in human erythrocytes: immobilization of band 3 induced by antibodies to glycophorin A. Biophys J. 1994; 66(5): 1726-1732.
25. Pasvol G, Chasis J A, Mohandas N, Anstee D J, Tanner M J, Merry A H. Inhibition of malarial parasite invasion by monoclonal antibodies against glycophorin A correlates with reduction in red cell membrane deformability. Blood. 1989; 74(5):1836-1843.
26. Chasis J A, Reid M E, Jensen R H, Mohandas N. Signal transduction by glycophorin A: role of extracellular and cytoplasmic domains in a modulatable process. J Cell Biol. 1988; 107(4):1351-1357.
27. Chasis J A, Mohandas N, Shohet S B. Erythrocyte membrane rigidity induced by glycophorin A-ligand interaction. Evidence for a ligand-induced association between glycophorin A and skeletal proteins. J Clin Invest. 1985; 75(6):1919-1926.
28. Paulitschke M, Nash G B, Anstee D J, Tanner M J, Gratzer W B. Perturbation of red blood cell membrane rigidity by extracellular ligands. Blood. 1995; 86(1):342-348.
29. Head D J, Lee Z E, Swallah M M, Avent N D. Ligation of CD47 mediates phosphatidylserine expression on erythrocytes and a concomitant loss of viability in vitro. Br J Haematol. 2005; 130(5):788-790.
30. Khoory J, Estanislau J, Elkhal A, et al. Ligation of Glycophorin A Generates Reactive Oxygen Species Leading to Decreased Red Blood Cell Function. PLoS One. 2016; 11(1):e0141206.
31. Ballas S K, Mohandas N, Clark M R, Shohet S B. Rheological properties of antibody-coated red cells. Transfusion. 1984; 24(2):124-129.
32. Lizcano A, Secundino I, Dohrmann S, et al. Erythrocyte sialoglycoproteins engage Siglec-9 on neutrophils to suppress activation. Blood. 2017; 129(23):3100-3110.
33. Schofield A E, Reardon D M, Tanner M J. Defective anion transport activity of the abnormal band 3 in hereditary ovalocytic red blood cells. Nature. 1992; 355(6363): 836-838.

34. Rojewski M T, Schrezenmeier H, Flegel W A. Tissue distribution of blood group membrane proteins beyond red cells: evidence from cDNA libraries. Transfus Apher Sci. 2006; 35(1):71-82.
35. Blancher A, Roubinet F, Reid M E, Socha W W, Bailly P, Benard P. Characterization of a macaque anti-Rh17-like monoclonal antibody. Vox Sang. 1998; 75(1):58-62.
36. Bruce L J, Ring S M, Anstee D J, Reid M E, Wilkinson S, Tanner M J. Changes in the blood group Wright antigens are associated with a mutation at amino acid 658 in human erythrocyte band 3: a site of interaction between band 3 and glycophorin A under certain conditions. Blood. 1995; 85(2):541-547.
37. Greineder C F, Johnston I H, Villa C H, et al. ICAM-1-targeted thrombomodulin mitigates tissue-factor driven inflammatory thrombosis in a human endothelialized microfluidic model. Blood Advances. 2017; 1(18):1452-1465.
38. Siegel D L R M, Lee H, Blancher A. Scientific Section. Transfusion. 1999; 39(S10):1S-123 S.
39. Roback J D. Technical Manual: American Association of Blood Banks (AABB); 2014.
40. Pan D, Vargas-Morales O, Zern B, et al. The Effect of Polymeric Nanoparticles on Biocompatibility of Carrier Red Blood Cells. PLoS One. 2016; 11(3):e0152074.
41. Baskurt O K, Meiselman H J. Data reduction methods for ektacytometry in clinical hemorheology. Clin Hemorheol Microcirc. 2013; 54(1):99-107.
42. Huang C H, Reid M E, Xie S S, Blumenfeld 00. Human red blood cell Wright antigens: a genetic and evolutionary perspective on glycophorin A-band 3 interaction. Blood. 1996; 87(9):3942-3947.
43. Chou S T, Westhoff C M. The Rh and RhAG blood group systems. Immunohematology. 2010; 26(4):178-186.
44. Gao S H, Huang K, Tu H, Adler A S. Monoclonal antibody humanness score and its applications. BMC Biotechnol. 2013; 13:55.
45. Lomas-Francis C, Olsson M L. The blood group antigen factsbook: Elsevier/Academic Press; 2012.
46. Jokiranta T S, Men S. Biotinylation of monoclonal antibodies prevents their ability to activate the classical pathway of complement. J Immunol. 1993; 151(4):2124-2131.
47. Burton N M, Bruce L J. Modelling the structure of the red cell membrane. Biochem Cell Biol. 2011; 89(2):200-215.
48. Westhoff C M. Deciphering the function of the Rh family of proteins. Transfusion. 2005; 45(2 Suppl):117S-121S.
49. Flatt J F, Musa R H, Ayob Y, et al. Study of the D-phenotype reveals erythrocyte membrane alterations in the absence of RHCE. British Journal of Haematology. 2012; 158(2):262-273.
50. Ripoche P, Bertrand O, Gane P, Birkenmeier C, Colin Y, Cartron J P. Human Rhesus-associated glycoprotein mediates facilitated transport of NH(3) into red blood cells. Proc Natl Acad Sci USA. 2004; 101(49):17222-17227.
51. Gruswitz F, Chaudhary S, Ho J D, et al. Function of human Rh based on structure of RhCG at 2.1 A. Proc Natl Acad Sci USA. 2010; 107(21):9638-9643.
52. Levi M. Recombinant soluble thrombomodulin: coagulation takes another chance to reduce sepsis mortality. J Thromb Haemost. 2015; 13(4):505-507.
53. Fay M E, Myers D R, Kumar A, et al. Cellular softening mediates leukocyte demargination and trafficking, thereby increasing clinical blood counts. Proc Natl Acad Sci USA. 2016; 113(8):1987-1992.
54. Watts T, Barigou M, Nash G B. Comparative rheology of the adhesion of platelets and leukocytes from flowing blood: why are platelets so small? Am J Physiol Heart Circ Physiol. 2013; 304(11):H1483-1494.
55. Chu H, McKenna M M, Krump N A, et al. Reversible binding of hemoglobin to band 3 constitutes the molecular switch that mediates 02 regulation of erythrocyte properties. Blood. 2016; 128(23):2708-2716.
56. Kalfa T A, Pushkaran S, Mohandas N, et al. Rac GTPases regulate the morphology and deformability of the erythrocyte cytoskeleton. Blood. 2006; 108(12):3637-3645.
57. Wautier M P, El Nemer W, Gane P, et al. Increased adhesion to endothelial cells of erythrocytes from patients with polycythemia vera is mediated by laminin alpha5 chain and Lu/BCAM. Blood. 2007; 110(3):894-901.
58. Glodek A M, Mirchev R, Golan D E, et al. Ligation of complement receptor 1 increases erythrocyte membrane deformability. Blood. 2010; 116(26):6063-6071.
59. Ferru E, Giger K, Pantaleo A, et al. Regulation of membrane-cytoskeletal interactions by tyrosine phosphorylation of erythrocyte band 3. Blood. 2011; 117(22): 5998-6006.
60. Brody J P, Han Y, Austin R H, Bitensky M. Deformation and flow of red blood cells in a synthetic lattice: evidence for an active cytoskeleton. Biophys J. 1995; 68(6):2224-2232.
61. Shields M, La Celle P, Waugh R E, Scholz M, Peters R, Passow H. Effects of intracellular Ca2+ and proteolytic digestion of the membrane skeleton on the mechanical properties of the red blood cell membrane. Biochim Biophys Acta. 1987; 905(1):181-194.
62. Nguyen D B, Wagner-Britz L, Maia S, et al. Regulation of phosphatidylserine exposure in red blood cells. Cellular physiology and biochemistry: international journal of experimental cellular physiology, biochemistry, and pharmacology. 2011; 28(5):847-856.
63. Head D J, Lee Z E, Poole J, Avent N D. Expression of phosphatidylserine (PS) on wild-type and Gerbich variant erythrocytes following glycophorin-C(GPC) ligation. Br J Haematol. 2005; 129(1):130-137.
64. Sosale N G, Rouhiparkouhi T, Bradshaw A M, Dimova R, Lipowsky R, Discher D E. Cell rigidity and shape override CD47's "self"-signaling in phagocytosis by hyperactivating myosin-II. Blood. 2015; 125(3):542-552.

All publications cited in this specification are incorporated herein by reference in their entireties as is U.S. Provisional patent Application No. 62/594,909, filed Dec. 5, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

TABLE 1

Anti-RHCE antibody CDRs

| Clone | VH CDR1 | SID NO. | CDR2 | SID NO. | CDR3 | SID NO. | VL CDR1 | SID NO. | CDR2 | SID NO. | CDR3 | SID NO. |
|---|---|---|---|---|---|---|---|---|---|---|---|---|
| KP3-11 | GASISNYW | 1 | IDGSTYST | 2 | AREGQDPLAPTLATSGSGLDS | 3 | ENVNNY | 4 | AAS | 5 | QHSYGTPLT | 6 |
| KP3-14 | GASISNYW | 7 | IDGSTYST | 8 | AREGQDPLAPTLATSGSGLDS | 9 | QDIYSN | 10 | GAS | 11 | QEVHRNPFT | 12 |
| KP3-17 | GAPISNYW | 13 | IDGSIYTT | 14 | AREGQNPLVPTYGSTGFGLDF | 15 | QGISSW | 16 | KAS | 17 | QQYSSSPRT | 18 |

TABLE 2

Anti-RHCE antibody heavy and light variable chain protein sequences

| Clone | VH | SID | VL | SID |
|---|---|---|---|---|
| KP3-11 | EVQLLESGPGLVKPSETLSLTCGVSGASISNYWWSWIRQSPGKGLEWIGEIDGSTYSTHYNPSLKGRVTISKDASKNQLSLRLTSVTAADTAVYYCAREGQDPLAPTLATSGSGLDSWGRGLVVSVSS | 19 | AAELQMTQSPSSLSASLGDRVTITCRASENVNNYLHWYQQKPGKAPKLLIYAASTLQSGVPSRFSGSGSGTDFTLTISSLQPEDVATYYCQHSYGTPLTFGGGTKVEIK | 20 |
| KP3-14 | EVQLLESGPGLGKPSETLSLTCGVSGASISNYWWSWIRQSPGKGLEWIGEIDGSTYSTHYNPSLKGRVTISKDASKNQLSLRLTSVTAADTAVYYCAREGQDPLAPTLATSGSGLDSWGRGLVVTVSS | 21 | AAELQMTQSPSALSASVGDRVTISCRASQDIYSNLAWYQQKPGKAPKLLIYGASRLQSGIPSRFSASGAGTEFTLTISGLQPEDSAVYYCQEVHRNPFTFGPGTKLDIK | 22 |
| KP3-17 | EVQLLESGPGLLKPSETLSLTCAVSGAPISNYWWSWIRQSPGKGLEWIGEIDGSIYTTYYNPSLKSRVAISKDTSKNRLSLKLTSVTAADTAVYYCAREGQNPLVPTYGSTGFGLDFWGHGLAVTVSS | 23 | AAELTQSPSSLSASVGDRVTITCQASQGISSWLAWYQQKPGKAPKLLIYKASSLQSGVPSRFSGSGSGTDFTLTISSLQSEDFATYYCQQYSSSPRTFGQGTKVEIK | 24 |

TABLE 3

Anti-RHCE antibody heavy and light variable chain coding sequences

| Clone | VH | SID | VL | SID |
|---|---|---|---|---|
| KP3-11 | GAGGTGCAGCTGCTCGAGTCAGGACTGGTGAAGCCTTCGG AGACCCTGTCCCCTCACCTGCGGTGTCTCTGGTGCCTCCATCAGTAATT ACTGGTGGAGTTGGGAGATCGATGGATGTATTAGCACCCACTACAACCC CTCCCCAAGGGTCGAGTCGAGCTGCCCCAAGGACGCGTCACACACCC AGTTCCCTGAGGCTGACCTCTGTGACCGCTGACACGGCCGT GTATTATTGTGCGAGAGGGACAGGATCCTTTAGCGCCTACCCTT GCCACGTCGGGTTCGGGGTTGAATTCCTGGGGCCGAGGCTCGTCG TCTCCGTCTCCTCC | 25 | GCGGCCGAGCTCCAGATGACCCAGTCTCCATCCTCCTATCTGCATC GCTGGGAGACAGAGTCACCATCACTTGCAGGCAAGTGAGAACGTT AACAACTATTTACATTGGTATCAGCAGAAACCAGGGAAAGCCCCTA AGCTCCTGATCTATGCTGCATCCACTTGCAAAGTGGGGTCCATCA AGTTCAGCGGCAGTGGATCTGGGACAGATTTCACTCTCACCATCA GCAGCCTGCAGCCTGAAGATGTGCAACTTATTACTGTCAGCATAGT TATGGTACCCCCTCACTTTCGGCCGAGGGACCAAGGTGGAGATCA AACGA | 26 |
| KP3-14 | GAGGTGCAGCTGCTCGAGTCAGGCCCAGGACTGGGAGAGCCTTCG GAGACCCTGTCCCTCACCTGCGGTGTCTCTGGTGCCTCCATCAGCAA TTACTGGTGGAGTGGATCCGCAGCCTCCAGGGAAGGACTGGA GTGGATTGGGAGAATCGATGGTAGTATTAGCACCTACAAC CCCTCCCTCAAGGGTCGAGTCACCATTTCAAAGACGCTCCAAGAA TCAGTTGTCCCTGAGGCTGAGAGAGGAGCCACAGGACAGGATCCTTTAGCGCCTACCC TGCCACGTCGGGTTCGGGGTTCCTGGGGCCGAGGCTCGT CGTCACCGTCTCCTCC | 27 | GCGGCCGAGCTCCAGATGACCCAGTCTCCATCTGCCTTGTCTGCATC TGTAGGAGACAGAGTCACCATCTCTTGCCGGGCAAGTCAGGACATT TATAGTAATTTAGCGTGGTATCAACAGAAACCAGGGAAAGCCCCTA AGCTCCTGATCTATGCGCATCCAGATTGCAATGTGGGATTCCTCT CGGTTCAGTGCGTAGCGAGCTGGGACAGAATTCACTCTCACCATCA GCGGCCTGCAACCTGAAGATTCTGAGTATTATTACTGTCAAGAGTT CATCGTAACCCATTCACTTTCGGCCCCGGACCAACTGGATATCAA ACGA | 28 |
| KP3-17 | GAGGTGCAGCTGCTCGAGTCGGGCCCAGGACTGCTGAAGCCATCG GAGACCCTGTCCCTCACCTGCGCTGTCTGTGCCCCCATCAGTAA CTACTGGTGGAGTTGGATCGTCAGTCCCAGGGAAGGACTGGAG TGGATTGGGAGGAGATCGATGGTAGTATTAGTACCTACTACAACCC CTCCCTCAAGAGTCGAGTCACCCTCTGAAACTCCAAGACCTACCC GGCTGTCCGATGTCGACCTCTGTGAACTGGCCCCGCCGGACACGT CTATTATTGTGCGAGAGGGCCAGAACCCTTGACTGGCTACATATG GTTCGACGGGATTCGGATTTCTGGGGCCAAGGGACTCTGCGCCGT CACCGTCTCGTCA | 29 | GCGGCCGAGCTCACCCAGTCTCCACCAGTCTCCATCTTCCTTGTCTGCATCGTAGG AGACAGAGTCACCATCACTTGCCAAGCCAGTCAGGTATTAGCAGC TGGTTAGCCTGGTATCAGCAGAAACCAGGGAAAGCCCTAAGCTCC TGATCTATAAGGCATCCAGTTTGCAAAGTGGGGGTCCCATCAAGGTTC AGCGGCAGTGGATCTGGACAGATTTCACTCTCACCATCAGCAGCCT GAGTCTGAAGACGTTTGCAACTTATTACTGTCAACGTATAGCAGTA GCCCTCGGACGTTCGGCCAAGGGACCAAGGTGGAAATCAAACGA | 30 |

TABLE 4

Anti-BAND 3 antibody CDRs

| Clone | VH CDR1 | SID | CDR2 | SID | CDR3 | SID | VL CDR1 | SID | CDR | SID | CDR3 | SID |
|---|---|---|---|---|---|---|---|---|---|---|---|---|
| KP2-01 | GDSISSGLG | 31 | IGGSRGNT | 64 | ARRAPYWGYSYLDY | 97 | QSIGSS | 130 | SAY | 163 | QQYNDLLPLT | 196 |
| KP2-02 | GGSLSGGYD | 32 | IYDSRWT | 65 | ARRGGYGASYFDL | 98 | QSIGSH | 131 | SVS | 164 | QQYNDLLPLT | 197 |
| KP2-04 | GYSLSSAY | 33 | IGGSRDNV | 66 | VRRATYGNSYFDS | 99 | QSVGSH | 132 | SAY | 165 | QQYNDLLPLT | 198 |
| KP2-06 | GSSLSSAYG | 34 | IGGSRDNT | 67 | AQRGAYGYSYFDY | 100 | QSVGSS | 133 | SIS | 166 | QQYNDFFPLT | 199 |
| KP2-07 | GDSISSGYG | 35 | IGGSRGTT | 68 | ARDSGYSFRYFDF | 101 | QSVGSN | 134 | SAY | 167 | QQYNDLLPLT | 200 |
| KP2-08 | GYSISSGYG | 36 | IGGSRDNT | 69 | ARDGGYGSRYIVIDS | 102 | QSIGTS | 135 | SAY | 168 | QQYNDLLPLT | 201 |
| KP2-09 | GYSISSGY | 37 | IGGSRGNT | 70 | ARDSGYNTRYFDY | 103 | QSVGSR | 136 | GAS | 169 | QQYNDLLPLT | 202 |
| KP2-11 | GSSLSSAYG | 38 | IGGSRDNT | 71 | AQRGAYGYSYFDY | 104 | QSLGSR | 137 | GAS | 170 | QQYNDFPPLT | 203 |
| KP2-13 | GGSISGGYD | 39 | IYDSRGTT | 72 | ARRAGYGSAYFDY | 105 | QSIGTN | 138 | TAY | 171 | QQYNDLLPLT | 204 |
| KP2-14 | GSSLSSAYG | 40 | IGGSRDNT | 73 | ARRGAFGNSYFDY | 106 | ESVGSS | 139 | SAS | 172 | QQYNDLLPLT | 205 |
| KP2-15 | GGSISGGYD | 41 | IYDSRGTT | 74 | ARRAGYGSAYFDY | 107 | QTVGRN | 140 | SAH | 173 | CQQYNDLLPLTF | 206 |
| KP2-17 | GYSISSGYG | 42 | IGGSRGNA | 75 | ARDGGYGERYLEF | 108 | QSIGSS | 141 | FAS | 174 | HQSSSFPWT | 207 |
| KP2-18 | GNSISSGYG | 43 | IGGSRSNT | 76 | ARDWGYGYRYLDY | 109 | QSIGSS | 142 | YAS | 175 | QQSSSFPFT | 208 |
| KP2-19 | GGSINGGYD | 44 | IYGSRGTT | 77 | AKRVGYGNSYFDS | 110 | QSVSSR | 143 | DAS | 176 | CQQYNDLLPLTF | 209 |
| KP2-20 | GGSISGGYD | 45 | IYDSRGTT | 78 | ARRAGYGSAYFDY | 111 | QSVGSN | 144 | SGS | 177 | QQYNDLLPLT | 210 |
| KP2-22 | GDSISSGYG | 46 | IGGSRGNT | 79 | ARRAPYWGYSYLDY | 112 | QSIGTN | 145 | SAY | 178 | QQYNDLLPLT | 211 |
| KP2-23 | GSSLSSAYG | 47 | IGGSRDNT | 80 | AQRGAYGYSYFDY | 113 | QTVGRN | 146 | SAY | 179 | QQYNDLLPLT | 212 |
| KP2-24 | GYSISSGYG | 48 | FGGSRGNT | 81 | ARDSGYSRRWVDY | 114 | QSVGTN | 14 | SAY7 | 180 | QQYNDLLPLT | 213 |
| KP3-01 | GFSISSDYG | 49 | IGGSRGNT | 82 | ARDWGYGYRYFDF | 115 | QSVGSN | 148 | YAS | 181 | QQTNTFPWT | 214 |
| KP3-02 | YSISSGYG | 50 | IGGSRGNT | 83 | ARDSGYNTRYFDY | 116 | QSVGSN | 14 | SAY9 | 182 | QQYNDLLPLT | 215 |
| KP3-03 | GSSLSSAYG | 51 | IGGSRDNT | 84 | AQRGAYGYSYFDY | 117 | QSVGSY | 150 | GAY | 183 | QQYNDLLPLT | 216 |
| KP3-05 | GSSLSSAYG | 52 | IGGSRDNT | 85 | AQRGAYGYSYFDY | 118 | QSVGSS | 151 | SAY | 184 | HQYNDLLPLT | 217 |
| KP3-06 | GGSISSAS | 53 | ISGSGSPT | 86 | ARRGGYGNRYFDY | 119 | QSVGSS | 152 | SAY | 185 | QQYNDLLPLT | 218 |
| KP3-07 | GSSLSSAYG | 54 | IGGSRDNT | 87 | AQRGAYGYSYFDY | 120 | QSIGSN | 153 | SAN | 186 | QQYNDFLPLT | 219 |
| KP3-08 | GSSLSSAYG | 55 | IGGSRDNT | 88 | AQRGAYGYSYFDY | 121 | QSLGGR | 154 | GAS | 187 | QQYNDFLPLT | 220 |

TABLE 4-continued

Anti-BAND 3 antibody CDRs

| Clone | VH CDR1 | SID | CDR2 | SID | CDR3 | SID | VL CDR1 | SID | CDR | SID | CDR3 | SID |
|---|---|---|---|---|---|---|---|---|---|---|---|---|
| KP3-09 | SLSLSSGFA | 56 | IGGSRDNV | 89 | VTIHGYRNWYLDH | 122 | QSIGTS | 155 | SAY | 188 | QQYNDLLPLT | 221 |
| KP3-12 | GNSISSAYG | 57 | IGGSRGTT | 90 | ARDSGYSFRYFDF | 123 | QSIGTN | 156 | SAY | 189 | QQYNDLLPLT | 222 |
| KP3-13 | GGSLSGGYD | 58 | IYDSRGTT | 91 | ARRGGYGASYFDL | 124 | QSVGSN | 157 | SAS | 190 | QQYNDFFPLT | 223 |
| KP3-15 | GSSLSSAYG | 59 | IGGNRDNT | 92 | AQRGAYGYSYFDY | 125 | QTVGRN | 158 | SAH | 191 | QQYNDLLPLT | 224 |
| KP3-16 | GSSLSSAYG | 60 | IGGSRDNT | 93 | AQRGAYGYSYFDY | 126 | QSLGSR | 159 | GAS | 192 | QQYNDFLPLT | 225 |
| KP3-18 | GYSLSSAYG | 61 | IGGSRDNV | 94 | VRRATYGNSYFDS | 127 | QSVGSY | 160 | SAH | 193 | QQYNDLLPLT | 226 |
| KP3-19 | GGSLSGGYD | 62 | IYDSRGTT | 95 | ARRVGYGATYFDL | 128 | QSVGSN | 161 | SAN | 194 | QQYNDLLPLT | 227 |
| KP3-20 | GYSISSGFA | 63 | IGGSRDNT | 96 | ARRGAYGNSYFDF | 129 | QSVGSN | 162 | SAY | 195 | QQYNDLLPLT | 228 |

TABLE 5

Anti-Band 3 antibody heavy and light variable chain protein sequences

| Clone | VH | SID | VL | SID |
|---|---|---|---|---|
| KP2-01 | EVQLLESGPGLVKPSETLSLTCAVSGDSISSGLGWSWIRQTPGKGLEW IGYIGGSRGNTNYNPSFKSRVTISRDTSKNQFSLRLSSMTAADTAVYYC ARRAPYWGYSYLDYWGQGVLVTVSS | 229 | AAELTQSPATLSLSPGETATLSCRASQSIGSSLAWYQQRPGQA PKLLVHSAYFRAAGIPDRFSGSGSRTDFTLTISSLEPEDVGVYH CQQYNDLLPLTFGGGTKVEIK | 262 |
| KP2-02 | EVQLLESGPGLVKPSETLSLTCAVSGGSSLSGGYDWSWIRQSSRKGLE WIGYIYDSRVVTTNYNPSLKKRVTISIDTSKNQFSLNLKSVTAADTAVYYC ARRGGYGASYFDLWGQGVLTVSS | 230 | AAELTQSPATLSLFPGETATLSCRASQSIGSHLAWYQQKPGQA PKLLVHSVSFRATGIPDRFRGSGSRTDFTLTISSLEPEDVGVYH CQQYNDLLPLTFGGGTKVEIK | 263 |
| KP2-04 | EVQLLESGPGLVKPSETLSLTCAVSGYSLSSAYGWNWIRQSPGKGLE WIGSIGGSRDNVNYNPSLKRRVTISKDTSTNHFSLRLSSVTAADTAVYY CVRRATYGNSYFDSWGQGVQVTVSS | 231 | AAELTLTQSPATLSLSPGETATLSCRASQSVGSHLAWYQQKPG QAPKLLVHSAYFRATGIPDRFSGSGSRTDFTLTISSLEPEDVGV YHCQQYNDLLPLTFGGGTKVEIK | 264 |
| KP2-06 | EVQLLESGPGLVKPSETLSLTCTVSGSSLSSAYGWNWIRQPPGKGLE WIGSIGGSRDNTNYNPSLKRRVTISKDTSKNQFSLKLKSVTAADTAVYY CAQRGAYGYSYFDYWGQGVLVAVSS | 232 | AAELTQSPATLSLSPGETATLSCRASQSVGSSLAWYQQKPGQ APKLLVHSLSVRATGIPDRFSGSGSRTDFTLTITSSLEPEDVGVYH CQQYNDFFPLTFGGGTKVEIK | 265 |
| KP2-07 | EVQLLESGPGLVKPSETLSLTCAVSGYSISSGYGWHWIRQVPGRGLE WIGSIGGSRGTTNYNPSLKSRVTISEDTSKNQFSLRLRSVTAADTAVYF CARDSGYSFRYFDFWGQGVLVAVSS | 233 | AAELVMTQSPATLSLSPGETATLSCRASEVGSNLAWYQQKP GQAPKLLVHSAYFRATGIADRFSGSGSRTDFTLTISSLEPEDVG VYHCQQYNDLLPLTFGGGTKVEIN | 266 |
| KP2-08 | EVQLLESGPGLVKPSETLSLTCAVSGYSISSGYGWHWIRQPPGKGLE WIGSIGGSRDNTNYNPSLKSRVTISTDTSKNQFSLKLRSVTAADTAVYYC ARDGGYGSRYMDSWGQGVLVTVSS | 234 | AAELTQSPATLSLSPGERATLSCRASQSVGSRLAWYQQKPG APRLLIYGASSRATGIPDRFSGSGSRTDFTLTISSLEPEDVGVY HCQQYNDLLPLTFGGGTKVEIK | 267 |
| KP2-09 | EVQLLESGPGLVKPSETLSLTCAVSGYSISSGYGWHWIRQPPGKGLES LGYIGGSRGTTNYNPSLKRRVTISKDSSKNQFSLKLKSVTAADTAVYYC ARDSGYNTRYFDYWGQGVLVTVSS | 235 | AAELTQSPATLSLSPGERATLSCRASQSLGSRLAWYQQKPG QPPPLLIYGASTRATGIPDRFSGSGSRTDFTLTISSLEPEDVGV YHCQQYNDPPLTFGGGTKVEIK | 268 |
| KP2-11 | EVQLQLPGLVKPSETLSLTCTVSGSSLSSAYGWNWIRQPPGKGLE WIGSIGGSRDNTNYNPSLKRKVAISIDTSRNQFSLNLRSLTAADTAVYYC CAQRGAYGYSYFDYWGQGVLTVSS | 236 | AAELTQSPATLSLAPGETATLSCRASQSIGTNLAWYHQKPGQP PKLLVHTAVFRATGIPNRFSGSGSRTDFTLTINSLQPEDVGVYH CQQYNDLLPLTFGGGTKIDIK | 269 |
| KP2-13 | EVQLLESGPGLVKPSETLSLTCAVSGGSSLSSAYGWNWIRQAPGKRLE WIGFGGSRDNTNYNPSLRSRVTISKDTSKNHFSLKLTSVTAADTAVYF CARRGAFGNSYFDYWGQGVPVTVSS | 237 | AAELTQSPATLSLSPGETATLSCRASESVGSSLAWYHQKPGQA PRLLVHSASFRATGIPDRFSGSGSRTEFTLTVSSLEPEDVGVYH CQQYNDLLPLTFGGGTKVEIK | 270 |
| KP2-14 | EVQLLESGPGLVKPSETLSLTCAVSGGSIGGSIGGYDWSWIRQSPGRLE WIGYIYDSRGTTNYNPSLRKRVTISKDTSRNQFSLKLRSLTAADTAVYYC ARRAGYGSAYFDYWGQGVLTVSS | 238 | AAELTQSPATLSVSPGEAATLSCRASQTVGRNLAWYQQKPGQ APKLLVHSAHFRATGIPDRFSGSGGTDFTLTISSLEPEDAGIYH CQQYNDLLPLTFGGGTKVEIK | 271 |
| KP2-15 | EVQLLESGPGLVKPSETLSLTCAVSGGSIGGSIGGYDWSWIRQSPGKGLE WIGYIYDSRGTTNYNPSLKKRVTISKDTSKNQFSLKLRSLTAADTAVYYC ARRAGYGSAYFDYWGQGVLTVSS | 239 | AAELTQSPATLSVSPGEAATLSCRASQTVGRNLAWYQQKPGQ APKLLVHSAHFRATGIPDRFSGSGGTDFTLTISSLEPEDAGIYH CQQYNDLLPLTFGGGTKVEIK | 272 |
| KP2-17 | EVQLLESGPGLVKPSETLSLTCAVSGYSISKDTSKNQFSLKLTSVTAADTAVYYC ARDGGYGERYLEFWGQGALVTVSS | 240 | AAELTQSPAFRSVTLKEKVTITCQASQSLHWYQQKPDQS PKLLIKFASQSISGVPSRFSGSGYTDFTLTINSLEABDAATYYC HQSSSFPVVTFGQGTKVEIK | 273 |

TABLE 5-continued

Anti-Band 3 antibody heavy and light variable chain protein sequences

| Clone | VH | SID | VL | SID |
|---|---|---|---|---|
| KP2-18 | EVQLLESGPGLVRPSETLSLTCTVSGNSISSGYGWNWIRQPPGKGLELI GYIGGSRSNTNYNPSLKSRVTISIDTSKNQFSLKLRSVTAADTAVYYCA RDWGYGYRLDYWGQGVLVTVSS | 241 | AAELTQSPAFRSVLKEKVTITCQASQSLHWYQQKPDQS PKLLIKYASQSISGVPSRFSGSGSTDFTLTINSLEAEDAATYYC QQSSSFPFTFGPGTKLDIK | 274 |
| KP2-19 | EVQLLESGPGLVKPSETLSLTCAVSGGSINGGYDWTWIRQSPGKGLQ WIGWTYGSRGTTNYNPSLRNRVTISDTSKNQFSLRLSSLLTAADTAVYY CAKRVGYGNSYFDSWGQGVLVTVSS | 242 | AAELTLTQSPATLSLSPGERATLSCRASQSVSSRLAWYQQKPG QAPRLLIYDASSRVTGIPDRFSGSGSGTDFTLTISSLEPEDVGV YHCQQYNDLLPLTFGGGTKVEIK | 275 |
| KP2-20 | EVQLLESGPGLVKPSETLSLTCAVSGGSISGGYDWSWIRQSPGKLE WIGYIYDSRGTTNNPSLRKRVTISIDTSKNQFSLKLRSLTAADTAVYYC ARRAGYGSAVFDYWGQGVLVTVSS | 243 | AAELTQSPATLSLSPGETATLSCRASQSVGSNLAWYQQKPG APKLLVHSGGVRATGIPDRFSGSGSRTDFTLITSSLEPEDVGVY HCQQYNDLLPLTFGGGTKVEIK | 276 |
| KP2-22 | EVQLLESGPGLVKPSETLSLTCAVSGDSISSGYGWSWIRQTPGKLEW IGYIGGSRGNTNYNPSLKSRVTISKDTSKNQFSLKLSSVTAADTAVYYC ARRAPWGYSYLDYWGQGVLVTVSS | 244 | AAELTLTQSPATLSLAPGETATLSCRASQSIGTNLAWYHQKPG QSPKLLVHSAYVRATGIPDRFSGSGSRTDFTLTINSLQPEDVGV YHCQQYNDLLPLTFGGGTKVEIK | 277 |
| KP2-23 | EVQLLESGPGLVKPSETLSLTCTVSGSSLSSAYGWNWIRQPPGKGLEWIG SIGGSRDNTNYNPSLKRRVTISKDTSKNQFSLKLKSVTAADTAVYHC GAYGYSYFDYWGQGVLVTVSS | 245 | AAELTLTQSPATLSLAPGETATLSCRASQSVGTNLAWYHQKPG APNLLVHSAYFRATGIPDRFSGSGSGTDFTLTISSLEPEDAGVYHC QQYNDLLPLTFGGGTKVEIK | 278 |
| KP2-24 | EVQLLESGPGLVKPSETLSLTCTVSGYSISSGYGWGWIRQSPGKGLEW IGYFGGSRGNTNYNPSLKRRVTISKDTSKNQFSLKLKSVTAADTIYYC ARDSGYSRRWVDYWGQGVLVTVSS | 246 | AAELTQSPATLSLAPGETATLSCRASQSVGTNLAWYHQKPG QPKLLVHSAYVRATGIPDRFSGSGSRTDFTLTINSLQPEDVGV YHCQQYNDLLPLTFGGGTKVEIK | 279 |
| KP3-01 | EVQLLESGPGLVKPETLSLTCDVSGFSISSDYGWSWIRQPPGKGLELI GYIGGSRGNTNYNPSLKSRVTISRDTSKNQFSLKLTSVTAADTAVXYCA RDWGYGYRLDYWGQGVLVTVSS | 247 | AAELTQSPAFRSVLKETVTLTCQASQSVGSNLHWYQQKPAQ SPKLLIKYASQSIGVPSRFSGTGSGTDFTLTINSLEAEDAATYY CQQTNTFPVVTFGGQTKVEIK | 280 |
| KP3-02 | EVQLLESGPGLVRPSETLSLTCAVSGYSISSGYGWHHWIRQPPGKGLESLG YIGGSRGNTNYNPSLRVTISDTSKNQFSLKLRSVTAADTAVYYCARDS GYNTRYFDYWGQGVLVTVSS | 248 | AAELTQSPATLSLPGETATLSCRASQSVGSNLAWYQQKPGQA PKLLVHSAYFRATGIPDRFSGSGSRTDFTLTISSLEPEDVGVYHCQ QYNDLLPLTFGGGTKVEIK | 281 |
| KP3-03 | EVQLLESGPGLVKPSETLSLTCTVSGSSLSSAYGWNWIRQPPGKGLE WIGSIGGSRDNTNYNPSLKRRVTISKDTSKNQFSLKLKSVTAADTAVYY CAQRGAYGYSYFDYWGQGVLVAVSS | 249 | AAELTQSPATLSLSPGETATLSCRASQSVGSYLAWYQQKPGQ APKLLVHGAYFRAAGIPDRFTGSGSRTDFTLTISSLEPEDVGIYH CQQYNDLLPLTFGGGTKVEIK | 282 |
| KP3-05 | EVQLLESGPGLVKPSETLSLTCTVSGSSLSSAYGWNWIRQPPGKGLE WIGSIGGSRDNTNYNPSLKRRVTISKDTSKNQFSLKLKSVTAADTAVYY CAQRGAYGYSYFDYWGQGVLVTVSS | 250 | AAELTQSPATLSLSPGETATLSCRASQSVGSSLAWYQQKPG QAPKLLVHSAYFRATGIPDRFSGSGSRTDFTLTISSLEPEDVGVY HCHQYNDLLPLTFGGGTKVEIK | 283 |
| KP3-06 | EVQLLESGPGLVRPSETLSLTCVDVSGGSISSASWSWIRQAPGKRLEWI GAISGGSGSPTNVRVTLSVDTSKNQLSLKLRSMTAADTAVYYCA RRGGAYGNRYFDYWGQGVAVTVSS | 251 | AAELTQSPATLSLSPGETATLSCRASQSVGSSLAWYQQKPG APKLLVHSAYFRATGIPDRFSGSGSRTDFTLTISSLEPEDVGVY HCQQYNDLLPLTFGGGTKVEIK | 284 |
| KP3-07 | EVQLLESGPGLVKPSETLSLTCTVSGSSLSSAYGWNWIRQPPGKGLE WIGSIGGSRDNTNYNPSLKRRVTISKDTSKNQFSLKLKSVTAADTAVYY CAQRGAYGYSYFDYWGQGVLVTVSS | 252 | AAELVMTQSPATLSLSPGETATLSCRASQSIGSNLAWYQQKPG QAPKLLVHSANIRATGIPDRFIGSGSRTDFTLTISSLEPEDVGVY HCQQYNDFLPLTFGGGTKVEIK | 285 |

TABLE 5-continued

Anti-Band 3 antibody heavy and light variable chain protein sequences

| Clone | VH | SID | VL | SID |
|---|---|---|---|---|
| KP3-08 | EVQLLESGPGLVKPSETLSLTCTVSGSSLSSAYGWNWIRQPPGKGLEWIGSIGGSRDNTNYNPSLKRVTISKDTSKNQFSLKLKSVTAADTAVYYCAQRGAYGYSYFDYWGQGVLVAVSS | 253 | AAELTLTQSPATLSLSPGETATLSCRASQSLGGRLAWYQQKPGQAPRLLIYGASTRATGIPDRFSGSGSRTEFTLTIAGLEPEDVGVYHCQQYNDFLPLTFGGGTKVEIK | 286 |
| KP3-09 | EVQLLESGPGLVKPSETLSLTCAVSSLSLSSGFAWSWIRQPPGEGLEWIGSIGGSRDNVNYNPSLKDTSKNQFSLRLRSVTAADTAVYYCVTIHGYRNWYLDHWGQGVLVTVST | 254 | AAELTQSPAILSLSPGETATLSCRASQSIGTSLAWYQQKPGQAPKLLVHSAYYRATDIPERRSGSGSRTDFTLTISSLEPEDVGVYHCQQYNDLLPLTFGGGTKVEIK | 287 |
| KP3-12 | EVQLLESGPGLVKPSETLSLTCAVSGNSISSAYGWHWIRQVPGKGLEWIGSIGGSRGTISEDTSKNQFSLRLRSVSAADTAVYFCARDSGYSFRYFDFWGRGVLVTVSS | 255 | AAELTQSPATLSLAPGETATLSCRASQSIGTNLAWYHQKPGQPPKLLVHSAVVRATGIPNRFSGSGSRTDFTLTINSLQPEDVGVYHCQQYNDLLPLTFGGGTKIDIK | 288 |
| KP3-13 | EVQLLESGPGLVRPSETLSLTCAVSGGSLSGGYDWSWIRQSPRKGLEWIGYIYDSRGTTNYNPSLKNFSLNLKSVTAADTAVYYCARRGGYGASYFDLWGQGVLVTVSS | 256 | AAELTQSPATLSLSPGETATLSCRASQSVGSNLAWYQQKPGQAPKLLVHSASVRATGIPDRFSGSGSRTDFTLTISSLEPEDVGVYHCQQYNDFFPLTFGGGTKVEIK | 289 |
| KP3-15 | EVQLLESGPGLVKPSETLSLTCTVSGSSLSSAYGWNWIRQPPGKGLEWIGSIGGSRDNTNYNPSLKRVTISKDTSKNQFSLKLKSVTAADTAVYYCAQRGAYGYSYFDYWGQGVLVAVSS | 257 | AAELTQSPATLSVSPGEAATLSCRASQTVGRNLAWYQQKPGQAPKLLVHSAHFRATGIPDRFSGSGSRTDFTLTISSLEPEDAGIYHCQQYNDLLPLTFGGGTKVEIK | 290 |
| KP3-16 | EVQLLESGPGLVKPSETLSLTCTVSGSSLSSAYGWNWIRQPPGKGLEWIGSIGGSRDNTNYNPSLKRVTISKDTSKNQFSLKLKSVTAADTAVYYCAQRGAYGYSYFDYWGQGVLVAVSS | 258 | AAELTQSPATLSLSPGETATLSCRASQSLGSRLAWYQQKPGQAPRLLIYGASTRATGIPDRFSGSGSRTDFTLTISSLEPEDVGVYHCQQYNDLLPLTFGGGTKVEIK | 291 |
| KP3-18 | EVQLLEWGPGLVKPSETLSLTCAVSGYSLSSAYGWNWIRQSPGKGLEWIGSIGGSRDVNTNYNPSLKRVTISKDTSTNHFSLRLSSVTAADTAVYYCVRRATGNSYFDSWGQGVQTVSS | 259 | AAELTLTQSPATLSLSPGETATLSCRASQSVGSYLAWYQQKPGQAPKLLVHSAHFRATGIPDRFSGSGSRTDFTLTISSLEPEDVGVYHCQQYNDLLPLTFGGGTKVEIK | 292 |
| KP3-19 | EVQLLESGPGLVKPSETLSLTCAVSGGGSLSGGYDWYWIRQSPRKGLEYIGYIYDSRGTTNYNPSLKNRVTISIDTSKNHFSLNLKSVTAADTAVYYCARRVGYGATYFDLWGQGVLVTVSS | 260 | AAELVMTQSPATLSLSPGETATLSCRASQSNLAWYQQKPGQAPKLLVHSANFRATGISDRFSGSGSRTDFTLTISSLEPEDVGVYHCQQYNDLPLTFGGTKVEIK | 293 |
| KP3-20 | EVQLLESGPGLVKPSETLSLTCAVSGYSISSGFAWNWIRQTPGKGLEWIGYIGGSRDNTNYNPSLKSRVTIISKDTSKNQFSLKLTSMTAADTAMYYCARRGAYGNSYFDWGQGVPVTVSS | 261 | AAELTQSPATLSLSPGETATLSCRASQSVGSNVAWYQQKPGQAPKLLVHSAYYRATGIPDRFSGSGSRTDFTLTISSLEPEDVGVYHCQQYNDLLPLTFGGGTKVEIK | 294 |

TABLE 6

Anti-Band 3 antibody heavy and light variable chain coding sequences

| Clone | VH | SID | VL | SID |
|---|---|---|---|---|
| KP2-01 | GAGGTGCAGCTGCTCGAGTGCTGGGCCCAGGACTGGTGAAGC CTTCGGAGACCCTGTCCCTCACCTGCGCTGCTTCTGGTGACT CCATCAGCAGTGGTTTGGGCTGGATCCGCCAGACC CCAGGGAAGGGGCTGGAGTGGATTGGATACATCGGTGGTAG TAGGGCAACACCAACTACAACCCCTCGTTCAAGAGTCGAGT CACCATTTCAAGGACACGTCCAAGAACCAGTTCTCCCTGAAG GCTGTCCTCTATGACACCGCCGGACACGGCCGTCTATTACT GTGCCAGAAGGGCCCCGTATTGGGTTATTCCTATCTTGACT ACTGGGGCCAGGGAGTCCTGGTCACCGTCCCTCA | 295 | GCGGCCGAGCTCACGCAGTCTCCAGCCACCCTGTCTTGTCTCCA GGGGAAACAGCCACCCTCTCGTGCAGGCCAGTCAGTATTGGC AGTCCTTAGCCTGGTACCAGCAGAGACTTGGGCAGGCTCCCAAG CTCCTGTCCATAGTGCATATTCAGGGCCCTGGCATCCCAGAC AGGTTCAGCGGCAGCGGGTCTAGGACACAGACTTCACTCTCACCATT AGCAGCCTGCAGCCTGAAGATGTTGGAGTTTATCACTGTCAGCAG TATAACGACTTGCTTCCGCTCACTTTCGGCGGAGGGACCAAGGTG GAACTCAAGCGA | 296 |
| KP2-02 | GAGGTGCAGCTGCTCGAGTCTCAGGTCAGGTGGTGAAGCC TTCAGAGACCCTGTCGCTCACCTGCGCTGCTTCTGGTGAGTCC TCTCAGCGGTGGGTATGACTGGAGCTGGATCCGCCAGTCCT CAAGAAAGGGCTGGAGTGGATTGGCTATATCTATGATAGTC GTTGGACCACCAACTACAACCCGTCCCTCAAGAGCGTCA CCATTTCAATAGACACGTCCAAGAACCAGTTCTCCCTGAACC TCAAGTCTGTGACCGCCGCGGACACGGCCGTGTATTATTGTG CGAGACGAGGCGGCTACGGTGCCAGTGACTTTGACTTACTGG GGCCAGGGAGTCCTGGTCACCGTCCCTCA | 329 | GCGGCCGAGCTCACGCAGTCTCCAGCCACCCTGTCTTTGTTTCCA GGGGAAACAGCCACCCTCTCCTGCAGGGCCAGTCAGTAGTATTGGC AGCCACTTAGCCTGGTACCAGCAGAAACCTGGGCAGGCTCCCAAG CTCCTGTCCATAGTGCTATATCTTCAGGGCCAGCACTGGCATCCCAGACA GGTTCCGTGGCAGCGGGTCTAGGACAGACTTCACTCTCACCATTA GCAGCCTGGAACCTGAAGATGTTGAGTTTATCACTGTCAGCAGTA TAACGACTTACTTCCGCTCACTTTCGGCGGAGGGACCAAGGTGGA GATCAAACGA | 297 |
| KP2-04 | GAGGTGCAGCTGCTCGAGTCTGGGCCCAGGACTGGTGAAGC CATCGGAGACCCTGTCCCTCACCTGCGCTGCTTGGTTACT CCCTCAGCAGTGCTTATGGCTGGAGCTGGATCCGACAGTCC CCCGGGAAGGGCTGGAGTGGATTGGGTCTATCGGTGGTAG TAGGGATAATGTCAACTACAACCCCTCGCTCCAAGAGGCGAGT CACCATTTCAAAGACACGTCCAAGAACCACTTCTCCCTGAAG GCTGAGTCTGTGACGGCCGCGGACACGGCCGTGTATTATT GTGTCGAGACCGCGACCTACGGTAACACAGCTACTTTGACTCCT GGGGCCAGGGAGTCCTCAGGTCACGGTCTCTTCA | 330 | GCGGCCGAGCTCACACTCACCCAGTCTCCAGCTCCAGGACACCCTGTCTTTG TCTCCAGGGGAAACAGCCACCCTTCCTGTGCAGGCCAGTCAGAGT GTTGGCAGCCACTTAGCCTGGTACCAGCAGAAACCTGGACAGGCT CCCAAGCTCCTCATAGTGCTACTTCAGGGCCACTGGCATC CCAGACAGGTTCAGTGGCAGCGGGTCTAGGACAGATTCACTCTC ACCATTAGCAGCCTGGAGCCTGAAGATGTTGGAGTTTATCACTGTC AGCAGTATAACGACTTGCTTCCGCTCACTTTCGGCGGAGGGACCA AGGTGGAGATCAAACGA | 298 |
| KP2-06 | GAGGTGCAGCTGCTCGAGTCTGGCCCAGGACTGGTGAAGCC TTCGGAGACCCTGTCCCTCACCTGCACTGTCTCTGGTTCCTC CCTCAGCAGTGCTTATGGGTGGAATCTGGATCCGCCAGCCC CAGGGAAGGGCCTGGAGTGGATTGGGTCTATCGGTGGTAGT AGGGATAACACCAACTATAATCCCCTCCAAGAGGCGAGTC ACCATTTCAAAGACACGTCCAAGAACCAGTTCTCCCTGAAG CTGAGTCTGTGACCGCCGCGGACACGGCCGTGTATTACTGT GCGCAGAGGGTGCTTACGGTTATTCCTATTTGACTACTGG GGCACGGGAGTCCTGGTCGCCGTCCCTCA | 331 | GCGGCCGAGCTCACTCCAGTCTCCAGCCACCCTGTCTTGTCTCCA GGGGAAACAGCCACCCTCTCCTGCAGGGCCAGTCAGAGTGTTGG CAGCTCCTTAGCCTGGTACCAGCAGAAACCTGGCCAGGCTCCCAA ACTCCTCGTCCATAGTATATCGTCAGGGCCACTGGCATCCCAGAC CAGGTTCAGTGGCAGTGGATCAGGACTTCACTCTCACCAT CACCAGCCTGGAGCCTGAAGATGTTGGAGATGTTGCCAGTAGTAATACTGTCAACAA TATAACGACTTCTTTCCGCTCACTTTCGGCGGAGGGACCAAGGTG GAGATCAAACGA | 299 |

TABLE 6-continued

Anti-Band 3 antibody heavy and light variable chain coding sequences

| Clone | VH | SID | VL | SID |
|---|---|---|---|---|
| KP2-07 | GAGGTGCAGCTGCTCGAGTCTGGCCCGGGACTGTGAAGCC<br>TTCGGAGACACCCTGTCCCTCACCTGCGCTGTCTCTGTGACTC<br>CATCAGCAGCGGCTATGGCTGGAGTGGGATTGGTGGTAGT<br>CAGGGAGGGGGCTGGAGTGGGATTGGTGGTAGT<br>AGGGGTACGAACTACAATACATCCCCTCAAGAGTCGAGTC<br>ACCATTTCAAGAGACACGTCAGAACCAGTTCTCCCTGAGT<br>CTGAGGTCAGTGTCCGCGGACACAGTGTTCCGTTATTCTG<br>TGCCAGAGACCAGCGGATATGTTCCGTTACTTTGACTTCTG<br>GGGTCAGGGAGTCCTGGTCACCGTCCTCA | 332 | GCGGCCGAGCTCGTGATGACCCAGTCTCCAGCCACCCTGTCTTTG<br>TCTCCAGGGGAAACAGCCACCCTCTCTGCAGGCCAGTCAGAGT<br>GTTGGCAGTAACTTAGCCTGGTACCAGCAGAAACCTGGCCAGGCT<br>CCCAAGCTCCTCGTCCATAGTGCATACTTCAGGGCCACTGGCATC<br>CCAGACAGGTTCAGTGGCAGCGGGTCTAGGACAGACTTCACTCTC<br>ACCATTAGCAGCCTGGAGCCTGAAGATGTTGGAGTTTATCACTGTC<br>AGCAGTATAACGACTTGCTTCCGCTCACTTTCGGCGGAGGGACCA<br>AGGTCGAGATCAATCGA | 300 |
| KP2-08 | GAGGTGCAGCTGCTCGAGTCGGGCCCAGGACTGGTGAAGC<br>CTTCGGAGACCCTGTCCCTCACCTGCGCTGTCTCTGGTTACT<br>CCATCAGCAGTGGTTATGGCTGGAACTGGATCCGCCAGCC<br>CCAGGGAAGGGACTGGAGTGGATTGGGTCTATCGGCGGTAGT<br>TAGGGATAACAACCAACTACAACCCCTCCCTCAAAAGTCGAGT<br>CACCCTTTCAAAGGACACATCCAAGAACCACTTCTCCCTGAG<br>GCTGCGCTCTGTGACCGCCGGGACACGGCTGTGTATTACT<br>GTGCGAGAGATGGTGGGTACGGTTCCGATACATGGACTCC<br>TGGGGCCAGGGAGTCCTGGTCGCCGTCTCCTCT | 333 | GCGGCCGAGCTCACGCAGTCTCCAGCCACCCTGTCTTTGTCTCCA<br>GGGGAGGCAGCCACCCTCTCCTGCAGGGCCAGTCAGAGTATTGG<br>CACTTCCTTAGCCTGGTACCAACAGAAACCTGGCCAGGCTCCCAG<br>GCTCCTCGTCCATAGTGCATATTCAGGGCCACTGGCATCGCAGA<br>CAGGTTCAGTGGCAGCGGGTCTAGGACAGACTTCACTCTCACCAT<br>TAGCAGCCTGGAGCCTGAAAGATGTTGGAGTTTATTACTGTCAGCAG<br>TATAAACGACTTGCTCCCGTCACTTTCGGCGGAGGGACCAAGGTG<br>GAGATCAAACGA | 301 |
| KP2-09 | GAGGTGCAGCTGCTCGAGTCGGGCCCAGGACTGGTGAAGC<br>CTTCGGAGACCCTGTCCCTGCGCTGCTCTCTGGTTACT<br>CCATCAGCAGTGGTTATGGCTGGAGTCGCTTGGCAGCCAGCC<br>CCAGGGAAGGGGCTGGAGTGGATTGGCTCTATCGTGGTAG<br>TAGGGTAACAACCAACTACAACCCCTCCCTCAAAGTCGAGT<br>CACCATTTCAACAGACACGTCCAAGAACCAGTTCTCCCTGAA<br>GCTGAGGTCTGTGACCGCCGCGGACACGGCTGTGTATTACT<br>GTGCCGAGAGAGATTCCGGATACAACACAAGATACTTTGACTACT<br>GGGGCCAGGGAGTCCTGGTCACCGTCTCCTCA | 334 | GCGGCCGAGCTCACACTCAGCCAGTCTCCAGCCACCCTGTCTTTGTCTCCA<br>GGGGAAAGAGCCACCCTCTCCTGCAGGGCCAGTCAGAGTGTTGG<br>CAGCAGTTAGCCTGGTACCAGCAGAAACCTGGCCAGGCTCCCAG<br>GCTCCTCATCTATGGTGCATCCAGCAGGGCCACTGGCATCTCCACCAT<br>CAGGTTCAGTGGCAGCGGGTCTGAAGATGTTGGAGTTTATCACTGTCAGCA<br>TAGCAGCCTGGAGCCTGAAGATTGCTTCCGCTCACTTCGGCCGAGGGACCAAGGT<br>GTATAACGACTTGCTTCCGCTCACTTTCGGCGGAGGGACCAAGGT<br>GGAGATCAAACGA | 302 |
| KP2-11 | GAGGTGCAGCTGCAGCTGCCTGGGCTGCCTGGGCCAGGACTGGTGAAGC<br>CTTCGGAGACCCTGTCCCTCACTTGCACTGTCTCTGGTTCCT<br>CCCTCAGCAGTGCTTATGGTGGAACTGACTGGATCCGCCAGCC<br>CCAGGGAAGGGGACTGGAGTGGATTGGGTATCGGTGGTAG<br>TAGGGATAACAACAACTATATCTCCCCTCAAGAGGCGAGT<br>CACCATTTCAAAGGACACGTCCAAGAACCAGTTCTCCCTGAA<br>GCTGAGTCTGTGACCGCCGCGGACACGGCCGTTATTACTGT<br>GCCAGAGGGGGTCTTACGGTTATTCCTATTTTTGACTACT<br>GGGGCCAGGGAGTCCTGGTCGCCGTCTCCTCA | 335 | GCGGCCGAGCTCACGCAGTCTCCAGCCACCCTGTCTTTG<br>TCTCCAGGGGAAACAGCCACCCTCTCTGCAGGGCCAGTCAGAGT<br>CTTGGCAGCAGGTTAGCTGGTACCAACAGAAACCTGGCCAGGCT<br>CCCAGGCTCCTCATCTATGGTCATCCACCAGGGCCACTGGCATC<br>CCAGACAGGTTCAGTGGCAGCGGGTCTAGGACAGACTTCACTCTC<br>ACCATTAGCAGCCTGGAGCCTGAAGATGTTGGAGTTTATCACTGTC<br>AGCAGTATAACGACTTCCCCGCTCACTTTCGGCGGAGGGACCA<br>AGGTCGAGATCAAACGA | 303 |
| KP2-13 | GAGGTGCAGCTGCTCGAGTCAGGCCCAGGACTGGTGAAGCC<br>TTCAGAGACCCTGTCCCTCACCTGCGCTGTCTCTGGAGGCTC<br>TATCAGCGGTGGTTATGACGTCTGAGTTGGATCCGCCAGTCCCC<br>AGGGAAGGGGCTGGAGTGGATTGGGATTGGTTATATCTATGATAGTAG | 336 | GCGGCCGAGCTCACGCAGTCTCCAGCCACCCTGTCTTTGGCTCCA<br>GGGGAAAACAGCCACCCTCTCCTGCAGGGCCAGTCAGAGTATTGGC<br>ACTAACTTAGCCTGGTATCACCAGAAACCTGGGCAGCCTCCCAAG<br>CTCCTCGTCCATATACTGCATATGTCAGGGCCACTGGCATCCCAAACA | 304 |

TABLE 6-continued

Anti-Band 3 antibody heavy and light variable chain coding sequences

| Clone | VH | SID | VL | SID |
|---|---|---|---|---|
| | GGGGACCACCAACTACAACCCGTCCCTCAAGGAAGCGGGTCG<br>CCATTTCAATAGAACACGTCCAGGAACCAGTTTCCCTGAACC<br>TGAGATCTCTGAAGACGCGGCCGCGACACGGCCCTACTACTG<br>GCGAGACGAGCCGCTACGTAGCCTACCTGGTCACCGTCCTCA<br>GGGCCCAGGGAGTCCTGGTCACCGTCTCCTCA | | GGTTCAGTGGCAGCGGGTCTAGGACAGACTTCACTCTCACCATTA<br>ACAGCCTGCTCCTGCCTGAAGATGTTGGCGTTTATCACTGTCAGCAATA<br>CAACGACTTGCTCCTCTCACTTTCGGCGGAGGACCAAGATAGA<br>CATCAAACGA | 305 |
| KP2-14 | GAGGTGCAGCTGCTCGAGTCTGGCCCAGGACTGGTGAAGCC<br>TTCGGAGACCCTGTCCCTCACCTGCGCTGTCTCTGGTTCCTC<br>CCTCAGCAGTGCTTATGGGTGGAATCTGGATCCGTCAGGGTC<br>CAGGGAAGGGCCTGGAGTGGATTGGGTATATCGGTTGGTAGT<br>CGTGATAATACAACCATTACAACCCTCCCTCAGGAGTCGGGTC<br>ACCATTTCAAAGACACGTCCAAGAACCACTTCCTGAAA<br>CTGACTTCTGTGACCGCCGCGGACACGGCCGTGTATTTCTGT<br>GCGAGAAGGGGGGCTTCGTAACTCCTACTTTGACTACTG<br>GGGCCAGGGAGTCCCGGTCACCGTCTCCTCA | 337 | GCGGCCGAGCTCACGGAGCTCCAGCCACCCTGTCTTCTGTCTCCA<br>GGGAAACAGCCACCCTCTCCTGCAGGGCCAGTGAGAGTGTTGG<br>CAGCCTTAGCCTGCTGTACCACCAGAAGCCTGGGCAGGCTCCCAG<br>GCTCCTCGTCATAGTGCATCTTCAGGGCCACTGGCATCCAGA<br>CAGGTTCAGTGCAGTGGGTCTAGGACAGAGTTCACTCTCACCGT<br>TAGCAGCCTGGAGCCTGCTTCCGCTCACTTTCGGCGGAGGACCAGCA<br>GTATAACGACTTGCTCTCCGCTCACTTTCGGCGGAGGACCAAGGT<br>GGAGATCAAACGA | 305 |
| KP2-15 | GAGGTGCAGCTGCTCGAGTCTGGCCCAGGACTGGTGAAGCC<br>TTCAGAGACCCTGTCCCTCACCTGCGCTGTCTCTGGAGGCTC<br>TATCAGCGGTGGTTATGACTGGAGTTGGATCCGCCAGTCCCC<br>AGGGAAGGGACTGGAGTGGATTGGTTATATCTATGATAGCAG<br>GGGGACCACCAACTACAACCCGTCCCTCAAGGACCAGTTCTCC<br>CCATTTCAATAGACACGTCCAAGAACCAGTTCCGCCTGAAGC<br>TGAGATCTCTGAAGACACGGCCGTGTACTACTGT<br>GCGAGCGAGCCGGTACGTAGCGCCTACTTTGACTACTG<br>GGGCCAGGGAGTCCTGGTCACCGTCTCCTCA | 338 | GCGGCCGAGCTCACGCAGTCTCCAGCCACCCTGTCTGTGTCTCCA<br>GGGGAAGACAGCCACCCTCTCCTGCAGGGCCAGTCAGACTGTTGG<br>CAGCTTCTGTACCACCGGTACCAGCCTGGCAGGCTCCCAA<br>GCTCCTCATAGTGCATCTTCAGGGCCACTGGCATCCGGA<br>CAGGTTCAGTGCAGCGGGTCTGAAGACGCTGGAATTTATACTGTCAGCA<br>GCATAACGACTTGCTTCCGCTCACTTTCGGCGGAGGGACCAAGGT<br>GGAGATCAAACGA | 306 |
| KP2-17 | GAGGTGCAGCTGCTCGAGTCTGGCCCAGGACTGGTGAAGCC<br>CTTCGGAGACCCTGTCCCTCACCTGCGCTGTCTCTGGTTACT<br>CCATCAGCAGTGGTTATGCCTGGACCTGGATCCGCCAGCCC<br>CCAGGGAAGGGCTGGAGTGGATTGGCTATATCGGTGGTAG<br>TAGGGAAACGCCAACTACAACCCCTCCCTCAAGAGTCGAGT<br>CACCATTTCAAAAGACACCATCAAGAACCAGTCCCTGAA<br>GCTGACCTCTGTGACCGCCGCGGACACGGCCGTGTATTACT<br>GTGCCAGAGATGGGGATACGGCGAGAGATACCTCGAATTC<br>TGGGGCCAGGGCGCCCCTGGTCACCGTCTCCTCC | 339 | GCGGCCGAGCTCACACAGTCTCCAGCCTTCGTCTCCTCTGACTCTG<br>AAGGAGAAAGTCACCATCACCTGCCAGGCCAGTCAGAGCATTGGT<br>AGTAGCTTACACTGGTACCAGCAGAAACCGGATCAGTCTCCAAAC<br>TCCTCATCAAGTTGCTTCCAGTCCATTTGCCAGTCCTCCAAG<br>GTTCAGTGGCAGTGGATATGGGACAGATTTCACCTCACTATCAAT<br>AGCCTGCAAGCTGAAGATGCTGCGACGTATTACTGTCAGAGTA<br>GTAGTTTTCCCGTGACGTTCGGCCAAGGGACCAAGGTGGAAATCA<br>AACGA | 307 |
| KP2-18 | GAGGTGCAGCTGCTCGAGTCTGGCCCAGGACTGGTGAGGC<br>CTTCGGAGACCCTGTCCCTCACCTGCACTGTCTCTGGTAACT<br>CCATCAGCAGTGGTTATGGCTGGAGCTGGATCCGCCAGCCC<br>CCAGGGAAGGGGCTGGAGTGGATTGGGTATATCTATTACAGT<br>GGGAGCAACAACTACAATCCCTCCCTCAAGAGTCGAGTCA<br>CCATATTTCAATTCCATGACGTCTGTTATACTG<br>CTGAGGTCTGTGACCGCTGTGGACACGGCCGTGTATTACT<br>GTGCCGCAGAGATTGGGGCTTACAGATACCTTGACTACT<br>GGGGCCAGGGAGTCCTGGTCACCGTCTCCTCA | 340 | GCGGCCGAGCTCACTCAGTCTCCAGCCTTCGTGTCTGACTCTA<br>AAGGAGAAAGTCACCATCACCTGCCAGGCCAGTCAGAGCATTGGT<br>AGTAGCTTACACTGGTACCAGCAGAAACCGGATCAGTCTCCAAAG<br>CTCCTCATCAAGTATGCTTCCAGTCCATCTCAGGGGTCCCCTCAA<br>GGTTCAGTGGCAGTGGATCTGGGACAGATTTCACCCTCACTATCAA<br>TAGCCTGGAAGCTGAAGATGCTGCACGTATTACTGTCAGCAGAG<br>TAGTAGTTTCCCATTCACTTTCGGCCCTGGGACCAAACTGGATATC<br>AAACGA | 308 |
| KP2-19 | GAGGTGCAGCTGCTCGAGTCTGGCCCAGGACTGGTGAAGGCC<br>TTCAGAGACCCTGTCCCTCACCTGCGCTCTCTGGAAGCTC<br>TATCAACGGTGGTTATGACTGGAGTCCGCCAGTCCCC | 341 | GCGGCCGAGCTCACACTCACCAGTCTCCAGCCACCCTGTCTTTG<br>TCTCCAGGGGAAAGAGCCACCCTCTCCTGCAGGGCCAGTCAGAGT<br>GTCAGCAGCTAGCCTGGTACCAGCAGAAACCTGGGCCAAGCT | 309 |

TABLE 6-continued

Anti-Band 3 antibody heavy and light variable chain coding sequences

| Clone | VH | SID | VL | SID |
|---|---|---|---|---|
| | AGGGAAGGGCTGCAGTGTACTATGGTAGTA<br>GGGGACCACCAACTACAACCCGTCCCTGAGGAATCGAGTC<br>ACCATTTCAATAGACACGTCGACGAGGACCAGTTCTCCCTGAGG<br>CTGAGCTCTCTGACCGCTGCGGAACGGCCGTCTATTACTG<br>TGCGAAACAGTCGGCTACGGGCTAACAGCAGTCACTTTGACTACTG<br>GGGCCAGGGAGTCCTGGTCACCGTCTCCTCA | | CCCAGGCTCCTCATTCATTATGATGCATCCAGCAGGGTCACTGGTATC<br>CCAGACAGGTTCAGTGGCAGTGGGTCTGAAGATACAGCAGGACTTCACTCTC<br>ACCATCAGCAGCCTGGAGCCTGAAGATTGTGGAGTTTATCACTGTC<br>AGCAGTATAACGACTTGCTTCCGCTCACTTTCGGCGGAGGGACCA<br>AGGTGGAGATCAAACGA | 310 |
| KP2-20 | GAGGTGCAGCTGCTCGAGTCAGGGCCAGGACTGGTGAAGCC<br>TTCAGAGACCCTGTCCCTCACCTGCGCTGTCTCTGGAGGCTC<br>TATCAGCGGGTGGTTATGACTGACATCCGCCAGTCCC<br>AGGGAAGGGGACTGGAGTGGATTGGTATATATGATGAGCAG<br>GGGGACCACCAACTACAACCCGTCCCTCAAGAAACGGGTCA<br>CCATTTCAATAGACACGTCCAAGAACCAGTTCTCCCTGAAGC<br>TGAGATCTGACCGCCGCGGACACGGCCGTCTATTACTGT<br>GCGAGAGCGAGCCGGCTACGGGCTACTTTGACTACTG<br>GGGCCAGGGAGTCCTGGTCACCGTCTCCTCA | 342 | GCGGCCGAGTCACGGCCAGTCTCCAGCACCTGTCTTTGTCTCCA<br>GGGGAAACAGCCACCCTCTCGCAGGCCAGTCAGAGTGTTGG<br>CAGCAGCTTAGCCTGCTACCAGCAGAAACCTGGACAGGCTCCCAA<br>GCTCCTCGTCTCCATAGTGGTTCGTCAGGGCCACTGGCATCCAGA<br>CAGGTTCAGTGGCAGCGGGTCTAGGACAGATTCACTCTCA<br>CCATTAACAGCCTGGAGCCTGAAGATGTTGGAGTTTATCACTGTCA<br>GCAGCCTGGAGCCTGCTTCCGCTCACTTTCGGCGGAGGGACCAAG<br>TATAACGACTTGCTTCCGCTCACTTTCGGCGGAGGGACCAAG<br>GAGATCAAACGA | 311 |
| KP2-22 | GAGGTGCAGCTGCTCGAGTCGGGCCCAGGACTGGTGAAGC<br>CTTCGAGACCCTGTCCCTCACCTGCGCTGTCTCTGGTGACT<br>CCATCAGCAGTGGTTATGGCTGGAGCTGGATCCGCCAGCC<br>CCAGGGAAGGGGCTGGAGTGGATTGGATACATCGGTAGTAG<br>TAGGGGCAACACCAACTACAACCCCTCCCTCAAGAGTCGAGT<br>CACCATTTCAAAGAGACGTCCAAGAACCAGTTCTCCCTGAA<br>GCTGAGCTCTGTGACCGCCGCGGACACGGCCGTGTATTACT<br>GTGCGAGAGGGCCCCAGGAGTCCTGGTCACCGTCTCCTCA | 343 | GCGGCCGAGTCACACTCACCGACTCCAGCAGCTCCGAGT<br>ATTGGGCACTAACTTAGCCTGGTATCACCAAAACCTGGACAGTCTC<br>CCAAGCTCCTCGTCCATAGTCATATGTCCGGGCACTGGCATCC<br>CAGAGAGGTTCAGTGGCAGCGGGTCTAGGACAGATTCACTCTCA<br>CCATTAACAGCCTGGAGCCTGAAGATGTTGCGTTTATCACTGTCA<br>GCAGTATAACGACTTGCTTCCGCTCACTTTTCGGCGGAGGAACCAA<br>GGTGGAGATCAAACGA | 311 |
| KP2-23 | GAGGTGCAGCTGCTCGAGTCTGGGCCAGGACTGGTGAAGCCT<br>TCGGAGACCCTGTCCCTCACCTGCACTGTCTCTGGTTCCTCCCT<br>CAGCAGTAGTGGTTATGCGGCTGGAACTGGATCCGCCAGCCCCAG<br>GAAGGGGCTGGAGTGGATTGGATCTATCGGTAGTAGGG<br>AATAACACAACTATATCTCCGTCCAAGAGCCGAGTCACCAT<br>TTCAAAGGACACGTCCAAGAACCAGTTCTCCCTGAAGCTGAAG<br>TCTGTGACCGCCGCGGACACGGCCGTCTATTACTGTGCCAGA<br>GGGGTGCTTACGGTTATTTGACTACTGGGGACAGGG<br>AGTCCTGGTCGCCGTCTCCTCA | 344 | GCGGCCGAGTCACACTCACCGCAGTCTCCAGCCACCCTGTCTTTGTC<br>TCCAGGGGAAACAGCCACCCTCTCTGCAGGCCAGTCAGACTGTT<br>GGCAGAAACTTAGCCTGGTACCAGCAGAGGCCTGGCCAGGCTCCC<br>AACCTCCTCGTCCATAGTCATTCAGGGCCACTGGCATCCCGGA<br>CAGGTTCAGTGGCAGCGGGTCTAGGACACTTCACTCTCACCATT<br>AGCAGCCTGGAGCCTGAAGATGCTGGAGTTTATCACTGTCAGCAAT<br>ATAACGACTTGCTTCCGCTCACTTTCGGCGGAGGGACCAAGGTGGA<br>GATCAAACGA | 312 |
| KP2-24 | GAGGTGCAGCTGCTCGAGTCGGGCCCAGGACTGGTGAAGC<br>CTTCGGAGACCCTGTCCCTCACCTGCGCTCTGGTTACT<br>CCATCAGCAGTGGTTATGCGGCTGGATCCGCCAGTCC<br>CCAGGGAAGGGGCTGGAGTGGATTGGCTATTTTGGTGGTAG<br>TAGAGGTAACACCAACTACAACCCCTCCCTCAAGAGTCGAGT<br>CACCATTTCAGACACGTCGAAAGATCAGTTCCCTGAA<br>ACTGAAGTCTGTGACCGCCGCGGACACGCCATTTATTACTACTG<br>CGCCGCGAGACAGCGGTTATTCGCGCGTTGGGTTGACTCCTCA<br>GGGGCCAGGGAGTCCTGGGTCACCGTCCTCCA | 345 | GCGGCCGAGTCACGGCCAGTCTCCAGCACCCTGTCTTTGGCTCCA<br>GGGGAAACAGCCACCCTCTCGCAGGCCAGTCAGAGTGTTGG<br>CACTAACTTAGCCTGTATCACCAGAAACCTGGACAGCTCCCAA<br>GCTCCTCGTCCATAGTGCATATGCCAGGGCCACTGGCATCCCAGA<br>CAGGTTCAGTGGCAGCGGGTCTAGGACAGATTGGCTTTATCACTCTCACCAT<br>TATAACGACTTGCTTCCGCTCACTTTCGGCGGAGGGACCAAGATA<br>GACATCAAACGA | 313 |

TABLE 6-continued

Anti-Band 3 antibody heavy and light variable chain coding sequences

| Clone | VH | SID | VL | SID |
|---|---|---|---|---|
| KP3-01 | GAGGTGCAGCTGCTCGAGTCGGGCCCAGGACTGGTGAAGC<br>CTTTGGAGACCCTGTCCCTCACCTGCGATCTCTGGTTTCT<br>CCATTAGTAGTGATTATGCTGGAGCTGGATCCGCCAGCCC<br>CGGGAAGGGGCTGGAGTTGATTGGGTATATCGGTGGTAGT<br>CGTGGTAACACCAACTATAACCCCTCCCTCAAGAGTCGAGTC<br>ACCATTTCAAGAGACACTTCCGCGAATCAGTTCTCCCTGAAG<br>CTGACCTCTGTGACCGCCGCGGACACGGCCGTCTACTACTG<br>TGCGAGAGATTGGGCTACGGTTATAGGTACTTTGACTTCTG<br>GGGCCAGGGAGTCCTGGTCACCGTCTCCTCA | 346 | GCGGCCGAGCTCACTCAGTCTCCAGCCTTTCGGTCTGTGAGTCTG<br>AAGGAGACAGTCACCTCACCTGCCGGCCAGTCAGAGCGTTGGT<br>AGTAACTTACACTGGTACCAGCAGAAACCGCTCAGTCTCCAAAAC<br>TCCTCATCAAGTATGCTTCCCAGTCCATCTCAGGGGTCCCCTCAAG<br>GTTCAGTGGCACTGGATCTGGGACACAGAGATTTCACCCTCACATCAAT<br>AGTCTGAAGCTGAAGATGCTGACATATTACTGTCAGCAGACTA<br>ATACTTTCCCTGACGTTCGGCCAAGGGACCAAGGGTGAAATCA<br>AGCGA | 314 |
| KP3-02 | GAGGTGCAGCTGCTCGAGTCGGGCCCAGGACTGGTGAAGCCT<br>TCGGAGACCCTGTCCCTCACCTGCGCTGTCTCTGGTTACTCCAT<br>CAGCAGTGGTTATGCTGGCACTGGATCCGCCAGCCCCCAGG<br>GAAGGGGCTGGAGTCGTTGGCCATATCTGGTATAGGG<br>GTAACACCAACTACAACCCCTCCCTCAAGAGTCGAGTCACCAT<br>TTCAACAGACACGTCCAAGAACCAGTTCTCCCTGAAGCTGAGG<br>TCTGTGACCGCCGCGGACACGGCCGTGTATTACTGTGCGAGA<br>GATTCCGGATACAACAAGATACTTTGACTACTGGGGCCAG<br>GGAGTCCTGGTCACCGTCTCCTCA | 347 | GCGGCCGAGCTCACTCAGTCTCCAGCCACCCTGTCTTTGTCTCCAGG<br>GGAAACAGCCACCCTCTCCTGCAGGGCCAGTCAGAGTGTTGGCAGC<br>AACTTAGCCTGGTACCAGCAGAAACCTGGCCAGGCTCCCAAGCTCC<br>TCGTCCATAGTGCATATCTTCAGGGCCACTGGCATCCCAGACAGGTTC<br>AGTGGCAGCGGGTCTAGGACAGACTTCACTCTCACCATTAGCAGCC<br>TGGAGCCTGAAGATGTTGGAGTTTATCACTGTCAGCAGTATAACGA<br>CTTGCTTCCGCTCACTTTCGGCGGAGGGACCAAGGTGGAGATCAAA<br>CGA | 315 |
| KP3-03 | GAGGTGCAGCTGGAGGTGCAGCTGCTCGAGTCTGCCCAG<br>GACTGGTGAAGCCTTCGGAGACCCTGTCTCCTCACCTGCACT<br>GTCTCTGGTTCCCTCAGCGGTGATCTTCAGCAGTGGTGAACTGG<br>ATCCGCCAGCCCCAGGGAAGGGCTGGAGTGGATTGGGT<br>CTATCGGTGGTGTAGGGATAACACCAACTATAATCCCTCCC<br>TCAAGAGTCGAGTCACCATTTCAAGGACACGTCCAAGAACC<br>AGTTCTCCCTGAAGCTGTGACCGCTGCGGCACACG<br>GCTGTCTATTACTGTGCGAGAGGGGTGCTTACGGTTATTCC<br>TATTTTGACTACTGGGGACAGGGAGTCCTGGTCACCGTCTCCTCC | 348 | GCGGCCGAGCTCACGCAGTCTCCAGCCACCCTGTCTTTGTCTCCA<br>GGGGAAACAGCCACCCTCTCCTGCAGGGCCAGTCAGAGTGTTGG<br>CAGCTACTTAGCCTGGTACCAGCAGAAACCTGGCCAGGCTCCCAA<br>GCTCCTCGTCCATGGTGCAGCGGGTCTGGACAGACTTCACTCTCACCAGA<br>CAGGTTCACTGGCAGCGGGGTCTGAAGATGTTGGAATTTATCAGCAG<br>TAGCAGCCTGGAGCCTGCTTCCGCTCACTTTCGGCGGAGGGACCAG<br>TATAACGACTTGCTTCCGCTCACTTTCGGCGGAGGGACCAAGGTG<br>GAGATCAAACGA | 316 |
| KP3-05 | GAGGTGCAGCTGCTCGAGTCGGGCCCAGGACTGGTGAAGC<br>CTTCGGAGACCCTGTCCCTCACTGCACTGTCTCTGGTTCCT<br>CCCTCAGCAGTGCTTATGGTGAACTGGATCCGCCAGCC<br>CCAGGGAAGGGGCTGGAGTGGATTGGGTTATCGGTGGTAG<br>TAGGGATAACAACTATAATCCCTCCCTCAAGAGGGCGAGT<br>CACCATTTCAAAGGACACGTCCAAGAACCAGTTCTCCCTGAA<br>GCTGAAGTCTGTGACCGCCGCGGACACGGCCGTCTATTACT<br>GTGCCAGAGCAGGGAGTGCTTATTACTTATTGGAATACTACT<br>GGGGACAGGGAGTCCTGGTCGCCGTCTCCTCA | 349 | GCGGCCGAGCTCACGCAGTCTCCAGCCACCCTGTCTTTGTCTCCA<br>GGGGAAACAGCCACCCTCTCCTGCAGGGCCAGTCAGAGTGTTGG<br>CAGCTCCTTAGCCTGGTACCAGCAGCAGAAACCTGGCCAGGCTCCAA<br>GCTCCTCGTCCATAGTGCATATCTTCAGGGCCACTGGCATCCAGA<br>CAGGTTCAGTGGCAGCGGGTCTAGGACAGACTTCACTCTCACCAT<br>TAGCAGCCTGGAGCCTGAAGATGTTGGAGTTTATCACTGTCACCAG<br>TATAACGACTTGCTTCCGCTCACTTTCGGCGGAGGGACCAAGGTG<br>GAGATCAAACGA | 317 |

TABLE 6-continued

Anti-Band 3 antibody heavy and light variable chain coding sequences

| Clone | VH | SID | VL | SID |
|---|---|---|---|---|
| KP3-06 | GAGGTGCAGCTGCTCGAGTCGGGCCCAGGACTGGTGAAGGC<br>CTTCGGAGACGCCTGTCTGTCACCTGCGATCTCTGGTGCT<br>CAATCAGCAGTGCTTCCTGAGCTGGAACTCTCTGTAGTGG<br>GGGAAGAGACTGGAGTGGATGGGGATTGGGCTATCTCTGGTAGTGG<br>TAGTCCCACCAACGTCAACCCCTCCCTCAAGAGTCGAGTCAC<br>CCTGTCAGTAGACACGTCCAAGAACCAGTTCTCCCTGAAGTT<br>GAGGTCAATGACCGCCGCGGACACGGCCGTAATAGTAATTACTGTG<br>CAAGACGAGGGGTTACGGTTACGTAGATACTTTGACTATTGGG<br>GCCAGGGAGTCGCGGTCACCGTCTCCTCA | 350 | GCGGCCGAGCTCACGCAGTCTCCAGCCACCCTGTCTTTGTCTCCA<br>GGGGAAACAGCCACCCTCTCCTGCAGGGCCAGTCAGAGTGTTGG<br>CAGCTCCTTAGCCTGGTACCAGCAGAAACCTGGGCAGGCTCCCAA<br>ACTCCTCGTCCATAGTGCATAATTCAGGGCCACTGGACATCTCCAGA<br>CAGTTCAGTGGCAGCGGGTCTAGGACAGATTCACTCTCACCAT<br>TAGCAGCGACTTGCTTCCGCTCACTTTCACTGTCAGCA<br>GTATAACGACTTGCTTCCGCTCACTTTCGGCGGAGGGACCAAGGT<br>GGAGATCAAACGA | 318 |
| KP3-07 | GAGGTGCAGCTGCTCGAGTCGGGCCCAGGACTGGTGAAGC<br>CTTCGGAGACCGCCTGTCTCCCTCACCTGCACTGTCTCGTGGTTCCT<br>CCCTCAGCAGTGCTCTATGGGGTGGAACTGGATCCGCCAGCC<br>CCAGGGAAGGGCTGGAGTGGATTGGGTCTATCGGTGGTAG<br>TAGGGATAACACCAACTATATAACCCCTCGACAGAGGCGAGT<br>CACCATTTCAAAGGACAGCTCCAAGAACCAGTTCTCCCTGAA<br>GCTGAAGTCTGTGACCGCCGCGGACACGGCCGTGTATTACT<br>GTGCGCAGAGGGTGCTTACGGTTATTCCTATTTGACTACT<br>GGGGCCAGGGACGGAGCCTGGTCACCGTCTCCTCA | 351 | GCGGCCGAGCTCGTGATGACACAGTCTCCAGCACCCTGTCTTTG<br>TCTCCAGGGGAAACAGCCACCCTTTCCTGCAGGGCAGTCAGAGT<br>ATTGGCAGCAACTTAGCCTGGTACCAGCAGAAACCTGGGCAGGCT<br>CCCAAGCTCCTCATCTATGGTGCAAACATCAGGGCCACTGGCATC<br>CCAGACAGGTTCATTGGCAGCGGGTCTAGGACAGATTCACTCTC<br>ACCATTAGCAGCCTGAGCCTGAAGATGTTGAGTTTATCACTGTC<br>AGCAGTATAACGACTTCCTTCCGCTCACTTTCGGCGGAGGGACCA<br>AGGTGGAGATCAAACGA | 319 |
| KP3-08 | GAGGTGCAGCTGCTCGAGTCGGGCCCAGGACTGGTGAAGC<br>CTTCGGAGACCGCCTGTCTCACCTGCACTGTCTCTGGTTCCT<br>CCCTCAGCAGTCGTTATGGTGGAACTGGATCCGCCAGCC<br>CCAGGGAAGGGCTGGAGTGGATTGGGTATTCGGTGGTAG<br>TAGGGATAACACCAACTATAATCCCTCGACAGAGGCGAGT<br>CACCATTTCAAAGGACACCTCCAAGAACCAGTTCTCCCTGAA<br>GCTGAAGTCTGTGACCGCCGCGGACACGGCCGTCTATTACT<br>GTGCCCAGAGGGTGCTTACGGTTATTCCTATTTGACTACT<br>GGGGCCAGGGAGTCCTGGTCGCGTCCTCCTCA | 352 | GCGGCCGAGCTCACACTCACGCAGTCTCCAGCCACCCTGTCTTTG<br>TCTCCAGGGGAAACAGCCACCCTCTCCTGCAGGGCCAGTCAGAGT<br>CTTGGCGGCAGCTCCTCATCATATGTGCAGCAGTTAGCAGGCT<br>CCCAAGCTCCTCATCTATGTGCAGCGGGTCTAGGACAGATTCACTCTC<br>ACAGCAGGTTCAGTGGCAGCGGGTCTGAAGATGTTGAGTTTATCACTGTC<br>AGCAGTATAACGACTTCCTTCCGCTCACTTTCGGCGGAGGGACCA<br>AGGTGGAGATCAAACGA | 320 |
| KP3-09 | GAGGTGCAGCTGCTCGAGTCGGGCCCAGGACTGGTGAAGC<br>TTCGGAGAGACCCTGTCCCTCACCTGCGCTCTAGTCTGTC<br>CCTCAGTAGTGGTTTTGCCTGGAGCTGGATCCGCCAGCCC<br>CAGGGAAGGGACTGGAGTTGGATTGGGCTATCGGTGGTAGT<br>CGTCAGCAGGACTCAATTATACCCCTCCCAAGAGCGAGTC<br>ACCATTTCGAAAGACACGTCCAAGAACCAGTTCTCCCTGAGG<br>CTGCGTTCTGTGACGCCGCCCAGCACAGGCCGTGTATTACTG<br>TGTGACCATTCATGGCTACCGGTAACTGGTATCTTGACCACTG<br>GGGCCAGGGAGTCCTGGTCACCGTCTCCACA | 353 | GCGGCCGAGCTCACGCAGTCTCCAGCCATCCTGTCTTTGTCTCCA<br>GGGGAAACAGCCACCCTCTCCTGTAGGGCCAGTCAGAGTATTGGC<br>AGTCCTTAGCCTGGTACCAGCAGAAACTGGGCCAGGCTCCCAAG<br>CTCCTCATCTATAGTGCATCAGGGCCACTGGCATCCCAGAG<br>AGGTTCAGTGGCAGCAGTTAGGGACAGACTTCACTCTCACCATTA<br>GCAGCCTGGAGCCTGAAGATGTTGAGTTATCAGCAGT<br>ATAACGACTTGCTTCCGCTCACTTTCGGCGGAGGGACCAAGGTGG<br>AGATCAAACGA | 321 |
| KP3-12 | GAGGTGCAGCTGCTCGAGTCTGGCCCAGGACTGGTGAAGCC<br>TTCGGAGACCCTGTCCCTCACCTGCGCTGTCTCTGGTAACTC<br>CATCAGCAGCTATGGCTGGCACTGGATCCGCCAGTCC<br>CAGGGAAGGGCTGGAGTGGATTGATGCTTATCGGTGGTAGT | 354 | GCGGCCGAGCTCACGCAGTCTCCAGCCACCCTGTCTTTGGCTCCA<br>GGGGAAACAGCCACCCTCTCCTGCAGGGCCAGTCAGAGTATTGGC<br>ACTAACTTAGCCTGGTATCACCAGAAACCTGGGCAGCCTCCCAAG<br>CTCCTCGTCCATAGTGCATATGTCAGGGCCACTGGCATCCCAAACA | 322 |

TABLE 6-continued

Anti-Band 3 antibody heavy and light variable chain coding sequences

| Clone | VH | SID | VL | SID |
|---|---|---|---|---|
| | AGGGGTACGACCAACTACATCCCCTCCCTCAAGAGTCGAGG<br>CACCATTTCAGAAGACACGTCCGCCCGGACACGGCCGTGTATTCT<br>GCTGAGGTCAGTGTCCGCCCGGACACGGCCGTGTATTCT<br>GTGCGAGAGACAGCGGATATAGTTTCCGTTACTTTGACTTCT<br>GGGGTCGGGGAGTTCTGGTCACCGTCTCCTCA | | GGTTCAGTGGCAGCGGGTCTAGGACAGACTTCACTCTCACCATTA<br>ACACGCTGCAGCCTGAAGATGTTGGCGTTTATCACTGTCAACAGTA<br>CAACGACTTGGTTCCTCTCACTTTCGGCGGAGGGACCAAGATAGA<br>CATCAAACGA | |
| KP3-13 | GAGGTGCAGCTGCTCGAGTCTGGGCCCAGGACTGGTGAAGCC<br>CTTCAGAGACCCTGTCGCTCACCTGCGCTGTCTCCGGCAGTG<br>CTCTCAGCCGGTTGATGACTGGAGCTGGATCCGCCAGTCC<br>CCAAGAAAGGGCTGGAGTGGATTGGCTATATCATGATAGT<br>CGTGGGAGCCAACTACAACCCGTCCAGGAGGCGAGT<br>CACCATTTCAATAGACACGTCCAAGAACCAGTTCTCCCTGAA<br>CCTCAAGTCTGTGACCGCCGCGGACACGGCCGTGTATTATT<br>GTGCGAGACGAGGCGGCTACGGTGCCAGCTACTTTGACTTA<br>TGGGGCCAGGGAGTCCTGGTCACCGTCTCCTCA | 355 | GCGGCCGAGCTCACGCAGTCTCCAGCACCCTGTCTGTGTCTCCA<br>GGGGAAACAGCCACCCTCTCCTGCAGGCCAGTCAGAGTGTTGG<br>CAGCAACTTAGCCTGGTACCAGCAGAAACCTGGGCAGGCTCCCAA<br>GCTCCTCGTCATAGTGCATCCAGGGCCACTGGCATCCCAGA<br>CAGGTTCAGTGGCAGTGGATCAGGACAGACTTCACTCTCACCAT<br>TAGTAGCCTGGAGCCTGAAGATGTTGGAGTTTATCACTGTCAGCAG<br>TATAACGACTTCTTTCCGCTCACTTTCGGCGGAGGGACCAAGGTG<br>GAGATCAAACGA | 323 |
| KP3-15 | GAGGTGCAGCTGCTCGAGTCTGGCCCAGGACTGGTGAAGCC<br>TTCGGAGACCCTGTCCCTCACCTGCACTGTCTCTGGTTCCTC<br>CCTCAGCAGTTATTATGGTGGATCCGCCAGCCCC<br>CAGGGAAGGGGCTGGAGTGGATTGGGTCTATCGGTGGTAAT<br>AGGGATAACACCAACTACAACCCCTCCCTCAAGAGGGCGAGTC<br>ACCATTTCAAAGGACACGTCCAAGAACCAGTTCTCCCTGAAG<br>CTGAGCTCTGTGACCGCCGCGGACACGGCCGTCTATTACTG<br>TGCGAGAGGGGTGCTTACGGTTATTCCTATTTGACTACTG<br>GGGACCAGGGAGTCCTGGTCCCGTCTCCTCA | 356 | GCGGCCGAGCTCACGCAGTCTCCAGCACCCTGTCTGTGTCTCCA<br>GGGGAAGCAGCCACCCTCTCCTGCAGTCAGTCAGAGTGTTGG<br>CAGAAACTTAGCCTGGTACCAGCAGAAGCCTGGCCAGGCTCCCAA<br>GCTCCTCGTCATAGTGCACACTTCAGGGCCACTGGCATCCCGGA<br>CAGGTTCAGTGGCAGCGGGTCTGGGACAGACTTCACTCTCACCAT<br>TAGCAGCCTGGAGCCTGAAATGCTGGAATTTATCACTGTCAGCAA<br>TATAACGACTTGCTTCCGCTCACTTTCGGCCGAGGGACCAAGGTG<br>GAGATCAAACGA | 324 |
| KP3-16 | GAGGTGCAGCTGCTCGAGTCTGGCCCAGGACTGGTGAAGCC<br>TTCGGAGACCCTGTCCCTCACCTGCACTGTCTCTGGTTCCTC<br>CCTCAGCAGCTGCTTATGGGTGGATTCGGCAGCCCC<br>CAGGGAAGGGGCTGGAGTGGATTGGGTCTATCGGTGGTAGT<br>AGGGATAAACACCAACTACAACCCCTCCCTCAAGAGCGAGTC<br>ACCATTTCAAAGGACACGTCCAAGAACCAGTTCTCCCTGAAG<br>CTGAAGTCTGTGACCGCCGCGGACACGGCCGTCTATTACTG<br>TGCCAGAGGGGGTCTTACGGTTATTCCTATTTGACTACTG<br>GGGACCAGGGAGTCCTGGTCCCGTCTCCTCA | 357 | GCGGCCGAGCTCACGCAGTCTCCAGCACCCTGTCTTGTCTCCA<br>GGGGAAACAGCCACCCTCTCCTGCAGGCCAGTCAGAGTCTTGGC<br>AGCAGGTTAGCCTGGTACCAGCAGAAACCTGGCCAGGCTCCCAG<br>GCTCCTCATCTATGGTGCATCCACCAGGGCCACTGGCATCCCAGA<br>CAGGTTCAGTGGCAGCGGGTCTAGGACAGACTTCACTCTCACCAT<br>TAGCAGCCTGGAGCCTGAAAGATGTTGGAGTTTATCACTGTCAGCA<br>GTATAACGACTTCCTTCCGCTCACGTTCGGCCGAGGGACCAAGGT<br>GGAGATCAAACGA | 325 |
| KP3-18 | GAGGTGCAGCTGCTCGAGTCTGGCCCAGGACTGGTGAAGC<br>CATCGGAGACCCTGTCGCTCACCTGCGCTGTCTCTGGTTACT<br>CCCTCAGCAGCTACTTAGCCTGGATCCGCCAGCC<br>CCGGGAAGGGGCTGGAGTGGATTGGGTCTATCGGTGTAG<br>TAGGGATAATAGTCAACTACAACCACTCCCCAGAGGCCGAGT<br>CACCATTTCAAAAGACACGTCCCGGACACCGGCCGTGTATTAT<br>GCTGAGTCTGTGACGGCCGCGGACACGGCCGTGTATTAT<br>GTGTGAGACGCGCGACCTACGGTAACAGCTACTTTGACTCCT<br>GGGGCCAGGGAGTCCAGGTCACCGTCTCTTCA | 358 | GCGGCCGAGCTCACACAGTCTCCAGCCAGTCTCCAGCAGTCTGTCTTG<br>TCTCCAGGGGAAACAGCCACCCTCTCTGCAGGGCCAGTCAGAGT<br>GTTGGCAGCTACTTAGCCTGGTACCAGCAGAAACCTGGGCAGGCT<br>CCCAAGCTCCTCTGCATATGTGCAGCCTCCACACTTGGCACTGGCATC<br>CCAGACAGGTTCAGTGGCAGCGGGTCTAGGACAGACTTCACTCTC<br>ACCATTAGCAGCCTGGAGCCTGAAGATGTTGGAGTTTATCACTGTC<br>AGCAGTATAACGACTTACTTCCCCTCACTTTCGGCGGAGGGACCAA<br>GGTGGAGATCAAACGA | 326 |
| KP3-19 | GAGGTGCAGCTGCTCGAGTCAGGGCCCAGGACTGGTGAAGCC<br>CTCAGAGACCCTGTCCCTCACCTGCGCGCTGTCTCTGGAGGCT<br>CTCTCAGTGGTGGTTATGACTGGAGCTGGATCCGCCAGTCC | 359 | GCGGCCGAGCTCGTGATGACGCAGTCTCCAGCCACCCTGTCTTTG<br>TCTCCAGGGGAAACAGCCACCCTCTCCTGCAGGGCCAGTCAGAGT<br>GTTGGCAGCAACTAGCCTGGTACCAGCAGAAACCTGGGCCAGGCT | 327 |

TABLE 6-continued

Anti-Band 3 antibody heavy and light variable chain coding sequences

| Clone | VH | SID | VL | SID |
|---|---|---|---|---|
|  | CAAGAAAGGGCCTGAGTATATTGTTATATCTATGATAGTC GTGGGACCACCAACTACAACCCGTCCCTCAAGAATCGAGTCA CCATTTCAATAGACACGTCCAAGACCACTTCTCCCTGAACCT CAAGTCTGTGACCGCCGCGGACACGGCCGTGTATTACTGTG CGAGACGAGTCGGGTACGGTGCCACCTATTTGACTTATGGG GCCAGGGAGTCCTGGTCACCGTCTCCTCA |  | CCCAAGCTCCTCGTCCTCCATAGTGCAAACTTCAGGGCCACTGGCATC TCAGACAGGTTCAGTGGCAGCGGGTCTAGGACAGACTTCACTCTC ACCATCAGCAGCCTGGAGCCTGAAGATGTTGGAGTTTATCACTGTC AGCAGTATAACGACTTGCTTCCGCTCACTTTCGGCGGAGGGACCA AGGTGGAGATCAAACGA |  |
| KP3-20 | GAGGTGCAGCTGCTCGAGTCTGGGCCCAAGGACTGGTGAAGCC TTCGGAGACCCTGTCCCTCACCTGCGCTGTCTGTGGTTACTC CATCAGCAGTGGTTTTGCCTGGAACTGGATCCGCCAGACCC CAGGGAAGGGACTGGAGTGGATTGGGTATATCGGTGGTAGT CGTGATAACACCAACTACAACCCCTCCCTCAAGAGTCGAGTC ACCATTTCAAAAGACACGTCCAAGAACCAGTTCTCCCTTAAG CTGACTTCTATGACCGCCGCGGACACGGCCATGTATTACTGT GCGAGAAGGGGGGCCTACGTAACTCCTACTTTGACTTCTG GGGCCAGGGAGTCCCGGTCACCGTCTCCTCA | 360 | GCGGCCGAGTCACACAGTCTCCAGCCACCCTGTCTTTGTCTCCA GGGGAAACAGCCACCCTCTCCTGCAGGGCCAGTCAGAGTGTTGG CAGTAATGTAGCCTGGTACCAGCAGAAACTGGGCAGGCTCCCAA GCTCCTCGTCCATAGTGCATATACAGGGCCACTGCCATCCCAGA CAGGTTCAGTGGCAGCGGGTCTAGGACAGACTTCACTCTCACCAT TAGCAGCCTGGAGCCTGAAGATGTTGGAGTTTATCACTGTCAGCA GTATAACGACTTGCTTCCGCTCACTTTCGGCGGAGGGACCAAGGT GGAGATCAAACGA | 328 |

TABLE 7

| Protein | $K_D$ (95% CI), nM | Bmax (95% CI), copies/RBC × $10^3$ | $k_{off}$ (95% CI), $s^{-1}$ |
|---|---|---|---|
| aRh17 scFv (anti-RhCE) | 41.4 (34.1, 50.2) | 99 (93, 105) | $2.0 \times 10^{-5}$ (1.6, 2.4) |
| aWr$^b$ scFv (anti-Band3/GPA) | 21.3 (17.0, 26.5) | 746 (704, 790) | $2.9 \times 10^{-5}$ (2.0, 3.8) |
| hTM-aRh17 (anti-RhCE) | 45.6 (34.8, 56.5) | 184 (173, 195) | $4.7 \times 10^{-5}$ (3.2, 6.5) |
| hTM-aWr$^b$ (anti-Band3/GPA) | 52.6 (40.1, 65.1) | 904 (848, 961) | $4.8 \times 10^{-5}$ (2.9, 7.0) |

What is claimed is:

1. An antibody or fragment thereof which specifically binds an epitope on an erythrocyte, said antibody or fragment thereof comprising:
   a) a heavy chain variable domain comprising a CDR1 comprising SEQ ID NO: 1, a CDR2 comprising SEQ ID NO: 2, and a CDR3 comprising SEQ ID NO: 3 and light chain variable domain comprising a CDR1 comprising SEQ ID NO: 4, a CDR2 comprising SEQ ID NO: 5, and a CDR3 comprising SEQ ID NO: 6;
   b) a heavy chain variable domain comprising a CDR1 comprising SEQ ID NO: 7, a CDR2 comprising SEQ ID NO: 8, and a CDR3 comprising SEQ ID NO: 9 and light chain variable domain comprising a CDR1 comprising SEQ ID NO: 10, a CDR2 comprising SEQ ID NO: 11, and a CDR3 comprising SEQ ID NO: 12; or
   c) a heavy chain variable domain comprising a CDR1 comprising SEQ ID NO: 13, a CDR2 comprising SEQ ID NO: 14, and a CDR3 comprising SEQ ID NO: 15 and light chain variable domain comprising a CDR1 comprising SEQ ID NO: 16, a CDR2 comprising SEQ ID NO: 17, and a CDR3 comprising SEQ ID NO: 18.

2. The antibody or fragment thereof of claim 1, said antibody or fragment thereof comprising:
   a) the heavy chain variable domain and the light chain variable domain of part a), wherein the heavy chain variable domain comprises SEQ ID NO: 19 and the light chain variable domain comprises SEQ ID NO: 20;
   b) the heavy chain variable domain and the light chain variable domain of part b), wherein the heavy chain variable domain comprises SEQ ID NO: 21 and the light chain variable domain comprises SEQ ID NO: 22; or c) the heavy chain variable domain and the light chain variable domain of part c), wherein the heavy chain variable domain comprises SEQ ID NO: 23 and the light chain variable domain comprises SEQ ID NO: 24.

3. The antibody or fragment thereof of claim 1, which is an scFv.

4. A plasmid comprising a nucleic acid sequence encoding the antibody or fragment thereof of claim 1.

5. A fusion protein comprising the antibody or fragment thereof of claim 1 fused to a pharmacological, therapeutic, prophylactic, imaging or diagnostic agent.

6. The fusion protein of claim 5, wherein the therapeutic or prophylactic agent is an anticoagulant, anti-malarial, anti-hemolytic, or fibrinolytic.

7. A plasmid comprising a nucleic acid sequence encoding the fusion protein of claim 5.

8. A pharmaceutical composition comprising the antibody or fragment thereof of claim 1 and a pharmaceutically acceptable carrier, excipient, diluent, and/or adjuvant.

9. The antibody or fragment thereof of claim 1, which is bound to a pharmacological, therapeutic, prophylactic, imaging or diagnostic agent.

10. The antibody or fragment thereof of claim 9, wherein the therapeutic or prophylactic agent is an anticoagulant, anti-malarial, anti-hemolytic, or fibrinolytic.

11. The antibody or fragment thereof of claim 9, which is an scFv.

12. A pharmaceutical composition comprising the antibody or fragment thereof of claim 9 and a pharmaceutically acceptable carrier, excipient, diluent, and/or adjuvant.

13. The antibody or fragment thereof of claim 1, which is bound to a liposome.

14. The antibody or fragment thereof of claim 13, wherein the liposome is loaded with a pharmacological, therapeutic, prophylactic, imaging, or diagnostic agent.

15. The antibody or fragment thereof of claim 13, which is an scFv.

16. A pharmaceutical composition comprising the antibody or fragment thereof of claim 13 and a pharmaceutically acceptable carrier, excipient, diluent, and/or adjuvant.

17. A plasmid comprising a nucleic acid sequence encoding the antibody or fragment thereof of claim 1 part a), wherein the heavy chain variable domain is encoded by SEQ ID NO: 25 or a sequence sharing at least 70% identity with SEQ ID NO: 25 and the light chain variable domain is encoded by SEQ ID NO: 26 or a sequence sharing at least 70% identity with SEQ ID NO: 26.

18. A plasmid comprising a nucleic acid sequence encoding the antibody or fragment thereof of claim 1 part b), wherein the heavy chain variable domain is encoded by SEQ ID NO: 27 or a sequence sharing at least 70% identity with SEQ ID NO: 27 and the light chain variable domain is encoded by SEQ ID NO: 28 or a sequence sharing at least 70% identity with SEQ ID NO: 28.

19. A plasmid comprising a nucleic acid sequence encoding the antibody or fragment thereof of claim 1 part c), wherein the heavy chain variable domain is encoded by SEQ ID NO: 29 or a sequence sharing at least 70% identity with SEQ ID NO: 29 and the light chain variable domain is encoded by SEQ ID NO: 30 or a sequence sharing at least 70% identity with SEQ ID NO: 30.

20. A fusion protein comprising the antibody or fragment thereof of claim 1 fused to thrombomodulin.

21. A method for treating thrombosis in a subject in need thereof, the method comprising administering the fusion protein of claim 20 to the subject in need thereof.

22. The method of claim 21, wherein the antibody or fragment thereof is an scFv.

23. The method of claim 21, wherein the fusion protein is administered intravenously.

24. A method for treating disseminated intravascular coagulation (DIC) in a subject in need thereof, the method comprising administering the fusion protein of claim 20 to the subject in need thereof.

25. The method of claim 24, wherein the antibody or fragment thereof is an scFv.

26. The method of claim 24, wherein the fusion protein is administered intravenously.

* * * * *